(12) United States Patent
Zhang et al.

(10) Patent No.: US 7,598,237 B2
(45) Date of Patent: Oct. 6, 2009

(54) 7-ARYL 1,5-DIHYDRO-4,1-BENZOXAZEPIN-2(3H)-ONE DERIVATIVES AND THEIR USE AS PROGESTERONE RECEPTOR MODULATORS

(75) Inventors: Puwen Zhang, Audubon, PA (US); Jay Edward Wrobel, Lawrence, NJ (US); Eugene Anthony Terefenko, Quakertown, PA (US); Jeffrey Curtis Kern, Gilbertsville, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/946,408

(22) Filed: Nov. 28, 2007

(65) Prior Publication Data

US 2008/0139530 A1 Jun. 12, 2008

Related U.S. Application Data

(62) Division of application No. 11/087,051, filed on Mar. 22, 2005, now Pat. No. 7,323,455.

(60) Provisional application No. 60/555,945, filed on Mar. 24, 2004.

(51) Int. Cl.
*C07D 267/02* (2006.01)
*C07D 281/02* (2006.01)
*C07D 291/08* (2006.01)
*C07D 498/02* (2006.01)
*C07D 513/02* (2006.01)
*C07D 515/02* (2006.01)
*C07D 243/12* (2006.01)
*C07D 223/16* (2006.01)
*A61K 31/55* (2006.01)
*A61P 5/24* (2006.01)
*A61P 35/00* (2006.01)

(52) U.S. Cl. ........................ 514/212.07; 514/214.02; 514/217.03; 514/221; 540/490; 540/504; 540/523; 540/552; 540/569; 540/593

(58) Field of Classification Search ............... 540/490, 540/504, 523, 552, 569, 593; 514/212.07, 514/214.02, 217.03, 221
See application file for complete search history.

(56) References Cited

U.S. PATENT DOCUMENTS

| | | | |
|---|---|---|---|
| 3,900,501 A | 8/1975 | Ning et al. | 549/452 |
| 4,476,133 A | 10/1984 | Hirai et al. | 514/211.1 |
| 4,916,128 A | 4/1990 | Jonas et al. | 514/213.01 |
| 5,719,136 A | 2/1998 | Chwalisz et al. | 514/170 |
| 6,011,029 A * | 1/2000 | Ding et al. | 514/221 |
| 6,306,851 B1 | 10/2001 | Santilli et al. | 514/230.5 |
| 6,339,098 B1 | 1/2002 | Collins et al. | 514/373 |
| 6,355,648 B1 | 3/2002 | Fensome et al. | 514/275 |
| 6,358,948 B1 | 3/2002 | Zhang et al. | 514/230.5 |
| 6,369,056 B1 | 4/2002 | Zhang et al. | 514/230.5 |
| 6,380,235 B1 | 4/2002 | Zhang et al. | 514/395 |
| 6,391,907 B1 | 5/2002 | Fensome et al. | 514/409 |
| 6,407,101 B1 | 6/2002 | Collins et al. | 514/230.5 |
| 6,417,214 B1 | 7/2002 | Ullrich et al. | 514/378 |
| 6,432,949 B1 | 8/2002 | Brown et al. | 514/232.2 |
| 6,514,965 B1 * | 2/2003 | Tomazic et al. | 514/212.07 |

FOREIGN PATENT DOCUMENTS

| | | |
|---|---|---|
| EP | 0 077 983 A1 | 5/1983 |
| EP | 0 142 361 A2 | 5/1985 |
| EP | 0 294 647 A2 | 12/1988 |
| EP | 0 567 026 A1 | 10/1993 |
| JP | 08-259447 | 10/1996 |
| WO | 86/03749 A1 | 7/1986 |
| WO | 97/48701 A1 | 12/1997 |
| WO | 99/11635 A1 | 3/1999 |
| WO | 99/15524 A1 | 4/1999 |
| WO | 00/66554 A1 | 11/2000 |
| WO | 00/66564 A1 | 11/2000 |
| WO | 00/66570 A1 | 11/2000 |
| WO | 00/66581 A1 | 11/2000 |
| WO | 02/100327 A2 | 12/2002 |

OTHER PUBLICATIONS

Augustine, R. L. et al., "The Synthesis of dl-deethylibogamine," *Journal of Organic Chemsitry*, Apr. 1969, 34(4), 1070-1075.
Chen, R.H.K. et al, "Synthesis and SAR of a Novel Series of Spirobenzothiazepine Derivatives with Antiprogestin Activity," POI-37, 16*th* Int. Cong. Het. Chem., Montana, 1997 (Abstract).
Combs, D. W. et al., "Nonsteroidal Progesterone Receptor Ligands. 2. High-Affinity Ligands with Selectivity for Bone Cell Progesterone Receptors," *J. Med. Chem.*, 38, 4880-4884, 1995.
Hamann, L. G. et al., "Synthesis and and Biological Activity of Novel Nonsteroidal Progesterone Receptor Antagonists," *Ann. N.Y. Acad. Sci.*, 761, 383-387, 1995.
Horwitz, K. B. et al, "Progestins, Progesterone Receptors, and Breast Cancer," *Horm. Cancer*, 283-306, 1996, pub: Birkhaeuser, Boston, Mass., ed. Vedeckis.

(Continued)

*Primary Examiner*—Bruck Kifle
(74) *Attorney, Agent, or Firm*—Paul Carango, Esq.; Howson & Howson LLP

(57) ABSTRACT

This invention provides progesterone receptor modulators having the structure:

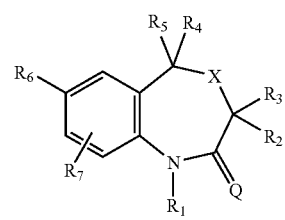

wherein $R^1$ to $R^7$, X, and Q are as defined in the specification; or a pharmaceutically acceptable salt thereof.

45 Claims, No Drawings

OTHER PUBLICATIONS

Kekkonen, R. et al, "Sequential regimen of the antiprogesterone RU486 and synthetic progestin for contraception," *Fertility and Sterility*, 60(4), 610-615, Oct. 1993.

Kettel, L. M. et al., "Endocrine responses to long-term administration of the antiprogesterone RU486 in patients with pelvic endometriosis," *Fertility and Sterility*, 56(3), 402-407, Sep. 1991.

Kurihara, K-I. et. al., "Synthesis of (±)-PF1092A, B, and C; New Nonsteroidal Progesterone Receptor Ligands," *J. Antibiotics*, 50, 360-362, Apr. 1997.

Mangelsdorf, D. J. et al., "The Nuclear Receptor Superfamily: The Second Decade," *Cell*, 83, 835-839, Dec. 15, 1995.

Michna, H. et al, "Differentiation Therapy with Progesterone Antagonists," *Ann. N.Y. Acad. Sci.*, 761, 224-247, 1995.

Murata, M. et al., "Novel Palladium(0)-Catalyzed Coupling Reaction of Dialkoxyborane with Aryl Halides: Convenient Synthetic Route to Arylboronates," *J. Org. Chem.*, 62, 6458-6459, 1997.

Murphy, A. A. et al, "Regression of Uterine Leiomyomata in Response to the Antiprogesterone RU 486," *J. Clin. Endo. Metab.*, 76(2), 513-517, 1993.

Perlman, K. L. et. al., "20-Oxopregnacalciferols: Vitamin D Compounds That Bind The Progesterone Receptor," *Tet. Letters*, 35(15), 2295-2298, 1994.

Robertson, D.W. et al., "Synthesis of a Tritium-Labeled Indolidan Analogue and Its Use as a Radioligand for Phosphodiesterase-Inhibitor Cardiotonic Binding Sites," *J Med Chem*, 1989, 32(7), 1476-1480.

Tegley, C. M. et al., "5-Benzylidene 1,2-Dihydrochromeno[3,4-*f*]quinolines, A Novel Class of Nonsteroidal Human Progesterone Receptor Agonists," *J. Med. Chem.* 41, 4354-4359, 1998.

Ulmann, A. et al., "Clinical Uses of Mifepristone (MFP)," *Ann. N. Y. Acad. Sci.*, 261, 248-260, 1995.

Zhang, P. et al., "The reaction of *o*-amino aryl carboxylic acids with Grignard reagents. The unusual effect of the *N*-protecting group on aryl ketone formation," *Tetrahedron Lett.* (2001), 42(11), 2097-2099.

Zhi, L. et al., 5-Aryl-1,2-Dihydrochromeno[3,4-*f*]quinolines, A Novel Class of Nonsteroidal Human Progesterone Receptor Agonists *J. Med. Chem.*, 41, 291-302, 1998.

Zhi, L. et al., "Nonsteroidal Progesterone Receptor Antagonists Based on 6-Thiophenehydroquinolines," *Bioorg. & Med.Chem. Lett.* 10, 415-418, 2000.

Zhang et al., "7-Aryl 1,5-dihydro-benzo[e][1,4]oxazepin-2-ones and analogs as non-steroidal progesterone receptor antagonists", Bioorg. & Med. Chem., 16(13):6589-6600 (Jul. 1, 2008).

Ramirez et al., "Hormonal therapy for the management of grade 1 endometrial adenocarcinoma: a literature review", Gynecological Oncology, 95(1):133-138 (Oct. 2004).

Maruo et al., "Effects of levonorgestrel-releasing IUS and progesterone receptor modulator PRM CDB-2914 on uterine leiomyomas", Contraception, 75(S6):S99-103 (Mar. 21, 2007 e-publication).

Lamberts et al., "Mifepristone (U486) treatment of meningiomas", J. Neurology and Neurosurgical psychiatry, 55(6):486-490 (Jun. 1992).

Kern et al., "1,5-Dihydro-benzo[e][1,4]oxazepin-2(1H)-ones containing a 7-(5'-cyanopyrrol-2-yl) group as nonsteroidal progesterone receptor modulators", Bioorg. Med. Chem. Lett., 18(18):5015-5017 (Sep. 15, 2008; e-publication Aug. 9, 2008).

* cited by examiner

7-ARYL 1,5-DIHYDRO-4,1-BENZOXAZEPIN-2(3H)-ONE DERIVATIVES AND THEIR USE AS PROGESTERONE RECEPTOR MODULATORS

CROSS-REFERENCE TO RELATED APPLICATIONS

This application is a divisional of U.S. patent application Ser. No. 11/087,051 filed Mar. 22, 2005 and claims benefit of U.S. Application No. 60/555,945, filed on Mar. 24, 2004, the disclosure of which is incorporated by reference herein in its entireties.

FIELD OF THE INVENTION

This invention relates to agonists and antagonists of the progesterone receptor, their preparation and their use as progesterone receptor modulators.

BACKGROUND OF THE INVENTION

Intracellular receptors (IR) form a class of structurally related gene regulators known as "ligand dependent transcription factors" (Mangelsdorf, D. J. etc. *Cell*, 83, 835, 1995). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone. Synthetic compounds, such as medroxyprogesterone acetate or levonorgestrel, can also serve as PR ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and the protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, either along or in the presence of an ER agonist. ER agonists are used to treat the symptoms of menopause, but have been associated with a proliferative effect on the uterus which can lead to an increased risk of uterine cancers. Co-administration of a PR agonist reduces/ablates that risk.

PR antagonists may also be used in contraception. In this context they may be administered alone (Ulmann, et al., *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (U.S. Pat. No. 5,719,136).

PR antagonists may also be useful for the treatment of hormone dependent breast cancers (Horwitz, et al, *Horm. Cancer,* 283, 1996, pub: Birkhaeuser, Boston, Mass., ed. Vedeckis) as well as uterine and ovarian cancers. PR antagonists may also be useful for the treatment of non-malignant chronic conditions such as uterine fibroids (Murphy, et al, *J. Clin. Endo. Metab.*, 76, 513, 1993) and endometriosis (Kettel, et al., *Fertility and Sterility,* 56, 402, 1991).

PR antagonists may also be useful in hormone replacement therapy for post menopausal patients in combination with a partial ER antagonist such as tamoxifen (U.S. Pat. No. 5,719, 136).

PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.,* 761, 224, 1995).

PR ligands have been described, for example, in Zhi, et al, (*Bioorg. & Med. Chem. Lett.* 10, 415, 2000 and *J. Med. Chem.,* 41, 291, 1998), Tegley, et al (*J. Med. Chem.* 41, 4357, 1998), Combs, et al. (*J. Med. Chem.,* 38, 4880, 1995), Perlman, et. al. (*Tet. Letters,* 35, 2295, 1994), Hamann, et al (*Ann. N.Y. Acad. Sci.,* 761, 383, 1995), Chen, et al (Chen, et al, POI-37, 16th Int. Cong. Het. Chem., Montana, 1997), Kurihari, et. al., described the PR ligand 12 (*J. Antibiotics,* 50, 360, 1997).

Zhang, et al., described several PR modulators (U.S. Pat. Nos. 6,432,949, 6,380,235, and 6,358,948). Other PR modulators are described in Fensome, et al. (U.S. Pat. Nos. 6,391, 907 and 6,355,648), Santilli, et al (U.S. Pat. No. 6,306,851), Zhang, et al. (U.S. Pat. No. 6,369,056), Ullrich, et al. (U.S. Pat. No. 6,417,214), and Collins, et al. (U.S. Pat. Nos. 6,407, 101 and 6,339,098).

Certain 4,1-benzoxazepinones are disclosed in the art. PCT Patent Application WO 99/11635 describes the use of some 5,5-disubstituted-1,5-dihydro-4,1-benzoxazepinones as HIV reverse transcriptase inhibitors. PCT Patent Application WO 97/48701 discloses certain squalene synthetase inhibitor 4,1-benzoxazepinones with a linked carboxyl group at position 3. Japanese Patent Application JP 08-259447 and European Patent Application EP 0567026 disclose certain 4,1-benzoxazepinones. U.S. Pat. No. 4,476,133 describe the use of some 5-substituted-4,1-benzoxazepinones as CNS agents. European Patent Application EP 0142361 discloses phospholipase $A_2$ inhibitor benzoxazepinones.

SUMMARY OF THE INVENTION

The present invention relates to agonists and antagonists of the progesterone receptor, their preparation and their use as progesterone receptor modulators. In some aspects, the invention relates to compounds of Formula I:

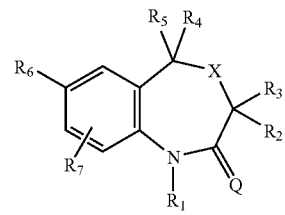

wherein:
$R_1$ is H, $C_{1-3}$ alkyl, or $COR^4$; where $R^4$ is H, $C_{1-4}$ alkyl, $C_{1-4}$ alkoxy, or $C_{1-3}$ aminoalkyl;
$R_2$ and $R_3$ are each independently H, $CF_3$, or $C_{1-3}$ alkyl;
$R_4$ and $R_5$ are each independently H, $C_{1-6}$ alkyl, $C_{2-6}$ alkenyl, $C_{2-6}$ alkynyl, $C_{1-3}$ perfluoroalkyl, $C_{3-6}$ cycloalkyl, aryl, substituted aryl, heterocycle, substituted heterocycle, or together with the carbon atom to which they are attached form a 3 to 6 membered alkylspirocyclic ring comprising $R_4$ and $R_5$, or a 3 to 6 membered heterospirocyclic ring comprising $R_4$ and $R_5$ and containing one to three heteroatoms within the spirocyclic ring, said heteroatoms being O, S, SO, $SO_2$, or N;
$R_6$ is substituted phenyl containing 1 to 3 substituents or a 5 or 6 membered heterocyclic ring containing 1 to 3 heteroatoms and 1 to 3 substituents, said heteroatoms being O, S, SO, $SO_2$ or N and said substituents independently being H, halogen, CN, $NO_2$, OH, amino, and $C_1$ to $C_3$ alkyl, $C_1$ to $C_3$ alkoxy, $C_1$ to $C_3$ aminoalkyl, $C=NOR^C$, $COR^D$, or $NRCOR^D$; or $R^6$ is a benzofused heterocyclic ring of the following formula

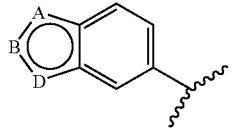

where A, B, and D are each independently CH, N, O, or S;

$R^C$ is H, $C_{1-4}$ alkyl, substituted $C_{1-4}$ alkyl, or $COR^D$;

$R^D$ is H, $C_{1-3}$ alkyl, $C_{1-3}$ alkoxy, or $C_{1-3}$ aminoalkyl;

$R_7$ is H, halogen, CN, $NO_2$, OH, $C_{1-3}$ alkyl, $C_{2-3}$ alkenyl, $C_{2-3}$ alkynyl, $C_{1-3}$ alkoxy, amino, or $C_{1-3}$ aminoalkyl;

Q is O, S, $NR_8$, $CR_9R_{10}$, or $R_{13}R_{14}$;

$R_8$ is CN, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, or substituted heterocyclic, $SO_2CF_3$, $OR_{11}$ or $NR_{11}$, $R_{12}$;

$R_9$ and $R_{10}$ are independently H, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, substituted heterocyclic, $NO_2$, CN, or $CO_2R_{11}$;

or $CR_9R_{10}$ comprises a six membered ring of the structure:

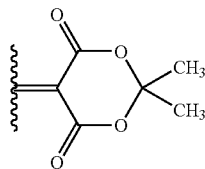

$R_{11}$ and $R_{12}$ are independently each H, $C_{1-6}$ alkyl, substituted $C_{1-6}$ alkyl, aryl, substituted aryl, heterocyclic, substituted heterocyclic, acyl or sulfonyl;

$R_{13}$ and $R_{14}$ are each independently H, $C_{1-3}$ lower alkyl, $C_{1-3}$ lower perfluoroalkyl, aryl, heterocyclic, a 3 to 6 membered alkylspirocyclic ring comprising $R_{13}$ and $R_{14}$, a 3 to 6 membered heterospirocyclic ring comprising $R_{13}$ and $R_{14}$ and containing one to three heteroatoms within the spirocyclic ring, said heteroatoms being O, S, SO, $SO_2$ or N;

X is O, S, $NR^E$, or $CR^ER^F$; where $R^E$ and $R^F$ are each independently H or $C_{1-4}$ alkyl;

or pharmaceutically acceptable salt thereof.

In certain embodiments, when X is O and Q is O or S, then at least one of $R_4$ and $R_5$ is H, $CF_3$, $CF_2CF_3$, $C_{3-6}$ cycloalkyl, aryl, substituted aryl, heterocycle, substituted heterocycle, a 3 to 6 membered alkylspirocyclic ring comprising $R_4$ and $R_5$, or a 3 to 6 membered heterospirocyclic ring comprising $R_4$ and $R_5$ and containing one to three heteroatoms within said spirocyclic ring, said heteroatoms being O, S, SO, $SO_2$, or N. In some embodiments, each of $R_4$ and $R_5$ are selected from the aforementioned atoms or groups.

In yet other embodiments, when X is $NR^E$, Q is O or S, $R_6$ is a 5 or 6 membered heterocyclic ring, and $R_4$ is cyclopropyl or $C_1$ to $C_3$ alkyl, then $R_5$ is H, $CF_3$, $CF_2CF_3$, $C_{3-6}$ cycloalkyl, aryl, substituted aryl, heterocycle, or a substituted heterocycle;

In certain embodiments, when X is O, Q is O or S, and $R_4$ is $CF_3$, then $R_5$ is H, $CF_3$, $CF_2CF_3$, $C_{3-6}$ cycloalkyl, aryl, substituted aryl, heterocycle, substituted heterocycle.

The invention is also directed to pharmaceutical compositions comprising such compounds and the use of such compounds in the treatment of diseases, hormone replacement therapy, or in inducing contraception.

DETAILED DESCRIPTION OF THE INVENTION

In one aspect, the present invention is directed to compounds that act as competitive inhibitors of progesterone binding to the PR and act as agonists and/or antagonists in functional models, either/or in vitro and in vivo. These compounds may be used for contraception, in the treatment of uterine fibroids, endometriosis, dysmenorrhea, breast, uterine, ovarian and prostate cancer, meningloma, and post menopausal hormone replacement therapy.

In one aspect the invention concerns compounds of Formula I:

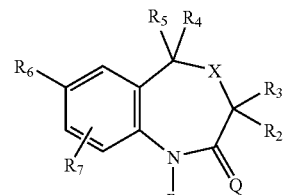

wherein:

$R_1$ is H, $C_{1-3}$ alkyl, or $COR^A$; where $R^A$ is H, $C_{1-4}$ alkyl, $C_{1-4}$ alkoxy, or $C_{1-3}$ aminoalkyl;

$R_2$ and $R_3$ are each independently H, $CF_3$, or $C_{1-3}$ alkyl;

$R_4$ and $R_5$ are each independently H, $C^{1-6}$ alkyl, $C_{2-6}$ alkenyl, $C_{2-6}$ alkynyl, $C_{1-3}$ perfluoroalkyl, $C_{3-6}$ cycloalkyl, aryl, substituted aryl, heterocycle, substituted heterocycle, or together with the carbon atom to which they are attached form a 3 to 6 membered alkylspirocyclic ring comprising $R_4$ and $R_5$, or a 3 to 6 membered heterospirocyclic ring comprising $R_4$ and $R_5$ and containing one to three heteroatoms within the spirocyclic ring, said heteroatoms being O, S, SO, $SO_2$, or N;

$R_6$ is substituted phenyl containing 1 to 3 substituents or a 5 or 6 membered heterocyclic ring containing 1 to 3 heteroatoms and 1 to 3 substituents, said heteroatoms being O, S, SO, $SO_2$ or N and said substituents independently being H, halogen, CN, $NO_2$, OH, amino, and $C_1$ to $C_3$ alkyl, $C_1$ to $C_3$ alkoxy, $C_1$ to $C_3$ aminoalkyl, $C=NOR^C$, $COR^D$, or $NRCOR^D$; or $R_6$ is a benzofused heterocyclic ring of the following formula

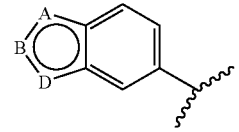

where A, B, and D are each independently CH, N, O, or S;

$R^C$ is H, $C_{1-4}$ alkyl, substituted $C_{1-4}$ alkyl, or $COR^D$;

$R^D$ is H, $C_{1-3}$ alkyl, $C_{1-3}$ alkoxy, or $C_{1-3}$ aminoalkyl;

$R_7$ is H, halogen, CN, $NO_2$, OH, $C_{1-3}$ alkyl, $C_{2-3}$ alkenyl, $C_{2-3}$ alkynyl, $C_{1-3}$ alkoxy, amino, or $C_{1-3}$ aminoalkyl;

Q is O, S, $NR_8$, $CR_9R_{10}$, or $R_{13}R_{14}$;

$R_8$ is CN, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, or substituted heterocyclic, $SO_2CF_3$, $OR_{11}$ or $NR_{11}R_{12}$;

$R_9$ and $R_{10}$ are independently H, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, substituted heterocyclic, $NO_2$, CN, or $CO_2R_{11}$;

or $CR_9R_{10}$ comprises a six membered ring of the structure:

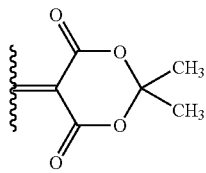

$R_{11}$ and $R_{12}$ are independently each H, $C_{1-6}$ alkyl, substituted $C_{1-6}$ alkyl, aryl, substituted aryl, heterocyclic, substituted heterocyclic, acyl or sulfonyl;

$R_{13}$ and $R_{14}$ are each independently H, $C_{1-3}$ lower alkyl, $C_{1-3}$ lower perfluoroalkyl, aryl, heterocyclic, a 3 to 6 membered alkylspirocyclic ring comprising $R_{13}$ and $R_{14}$, a 3 to 6 membered heterospirocyclic ring comprising $R_{13}$ and $R_{14}$ and containing one to three heteroatoms within the spirocyclic ring, said heteroatoms being O, S, SO, $SO_2$ or N;

X is O, S, $NR^E$, or $CR^ER^F$; where $R^E$ and $R^F$ are each independently H or $C_{1-4}$ alkyl;

provided that when X is O and Q is O or S, then at least one of $R_4$ and $R_5$ is H, $CF_3$, $CF_2CF_3$, $C_{3-6}$ cycloalkyl, aryl, substituted aryl, heterocycle, substituted heterocycle, a 3 to 6 membered alkylspirocyclic ring comprising $R_4$ and $R_5$, or a 3 to 6 membered heterospirocyclic ring comprising $R_4$ and $R_5$ and containing one to three heteroatoms within said spirocyclic ring, said heteroatoms being O, S, SO, $SO_2$, or N;

provided that when $X=NR^E$, $Q=O$ or S, $R_6$ is a 5 or 6 membered heterocyclic ring, and $R_4$ is cyclopropyl or $C_1$ to $C_3$ alkyl, then $R_5$ is H, $CF_3$, $CF_2CF_3$, $C_{3-6}$ cycloalkyl, aryl, substituted aryl, heterocycle, or a substituted heterocycle;

or pharmaceutically acceptable salt thereof.

In some embodiments, $R_1$, $R_2$, and $R_3$ are each H. In other embodiments, $R_4$ is H, $C_{1-6}$ alkyl, $CF_3$, $CF_2CF_3$, $C_{2-6}$ alkenyl, $C_{2-6}$ alkynyl, aryl, substituted aryl, heterocycle, or substituted heterocycle. In yet other embodiments, $R_5$ is aryl, substituted aryl, heterocycle, or substituted heterocycle. In certain embodiments, $R_4$ and $R_5$ are a 3 to 6 membered alkylspirocyclic ring comprising $R_4$ and $R_5$, a 3 to 6 membered heterospirocyclic ring comprising $R_4$ and $R_5$ and containing one to three heteroatoms within the spirocyclic ring, said heteroatoms being O, S, SO, $SO_2$, or N. In still other embodiments, $R_8$ is CN, $C_{1-3}$ alkyl, $SO_2CF_3$, $OR_{11}$ or $NR_{11}R_{12}$. In some embodiments, $R_9$ and $R_{10}$ are each, independently, H, $C_{1-3}$ alkyl, $NO_2$, CN, or $CO_2R_{11}$; or $CR_9R_{10}$ comprise a six membered ring as shown by the structure:

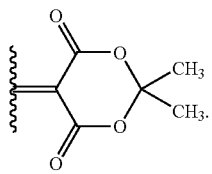

In other embodiments, $R_{11}$ and $R_{12}$ are each, independently, H, $C_{1-3}$ alkyl, acyl (such as alkylcarbonyl) or sulfonyl. In yet other embodiments, $R_{13}$ and $R_{14}$ are each, independently, H, $C_{1-3}$ lower alkyl, or $C_{1-3}$ perfluoroalkyl.

In some aspects, the invention relates to compounds where $R_7$ is H, halogen, CN, or $NO_2$. In other aspects, $R_8$ is selected from the group of CN, $SO_2CF_3$, or $OR_{11}$. In some compositions, $R_9$ and $R_{10}$ are each, independently, $NO_2$, CN, or $CO_2R_{11}$. In other compositions, $R_{11}$ and $R_{12}$ are each, independently, H or $C_{1-3}$ alkyl. In yet other compositions, $R_{13}$ and $R_{14}$ are each, independently, H, $C_{1-3}$ alkyl, or $C_{1-3}$ lower perfluoroalkyl.

In some compounds, $R_6$ is substituted phenyl containing 1 to 2 substituents, where said substituents are halogen, CN, $NO_2$, OH, C=NOH; or $R_5$ is a 5 or 6 membered heterocyclic ring containing 1 to 2 heteroatoms substituted with 1 to 2 substituents from the group including halogen, CN, $NO_2$, OH, and $C_1$ to $C_3$ alkyl, C=NOH, said heteroatoms being O, S, SO, $SO_2$ or N; or $R_6$ is a benzofused heterocyclic ring of the following formula

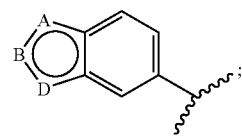

A and D are each independently CH, O, or S; B is N; and X is O.

Certain preferred compounds of the invention are:
4-methyl-5-(5-methyl-2-oxo-5-phenyl-1,2,3,5-tetrahydro-4,1-benzoxazepin-7-yl)thiophene-2-carbonitrile,
tert-butyl 2-cyano-5-(5-methyl-2-oxo-5-thien-2-yl-1,2,3,5-tetrahydro-4,1-benzoxazepin-7-yl)-1H-pyrrole-1-carboxylate,
5-[5-methyl-2-oxo-5-(2-thienyl)-1,2,3,5-tetrahydro-4,1-benzoxazepin-7-yl]-1H-pyrrole-2-carbonitrile,
1-methyl-5-[5-methyl-2-oxo-5-(2-thienyl)-1,2,3,5-tetrahydro-4,1-benzoxazepin-7-yl]-1H-pyrrole-2-carbonitrile,
tert-butyl 2-cyano-5-(5-methyl-2-oxo-5-phenyl-1,2,3,5-tetrahydro-4,1-benzoxazepin-7-yl)-1H-pyrrole-1-carboxylate,
5-(5-methyl-2-oxo-5-phenyl-1,2,3,5-tetrahydro-4,1-benzoxazepin-7-yl)-1H-pyrrole-2-carbonitrile,
1-methyl-5-(5-methyl-2-oxo-5-phenyl-1,2,3,5-tetrahydro-4,1-benzoxazepin-7-yl)-1H-pyrrole-2-carbonitrile,
5-(1,5-dimethyl-2-oxo-5-phenyl-1,2,3,5-tetrahydro-4,1-benzoxazepin-7-yl)-1-methyl-1H-pyrrole-2-carbonitrile,
tert-butyl 2-cyano-5-(5-methyl-2-oxo-1,2,3,5-tetrahydro-4,1-benzoxazepin-7-yl)-1H-pyrrole-1-carboxylate,
5-(5-methyl-2-oxo-1,2,3,5-tetrahydro-4,1-benzoxazepin-7-yl)-1H-pyrrole-2-carbonitrile,
1-methyl-5-(5-methyl-2-oxo-1,2,3,5-tetrahydro-4,1-benzoxazepin-7-yl)-1H-pyrrole-2-carbonitrile,
2'-Cyano-5'-[(2-oxo-1,2,3,5-tetrahydro-benzo[e][1,4]oxazepin-7-yl)-(5-spiro-1''-cyclohexane)]-pyrrole-1'-carboxylic acid tert-butyl ester,
5'-[(2-Oxo-1,2,3,5-tetrahydro-benzo[e][1,4]oxazepin-7-yl)-(5-spiro-1''-cyclohexane)]-1H-pyrrole-2'-carbonitrile,
tert-butyl 2-cyano-5-[5-methyl-2-oxo-5-(1,3-thiazol-2-yl)-1,2,3,5-tetrahydro-4,1-benzoxazepin-7-yl]-1H-pyrrole-1-carboxylate,
tert-butyl 2-cyano-5-[2-oxo-5,5-di(2-thienyl)-1,2,3,5-tetrahydro-4,1-benzoxazepin-7-yl]-1H-pyrrole-1-carboxylate, tert-butyl 2-cyano-5-[5-(2-furyl)-5-methyl-2-oxo-1,2,3,5-tetrahydro-4,1-benzoxazepin-7-yl]-1H-pyrrole-1-carboxylate,
5-[5-methyl-2-oxo-5-(1,3-thiazol-2-yl)-1,2,3,5-tetrahydro-4,1-benzoxazepin-7-yl]-1H-pyrrole-2-carbonitrile,
tert-butyl 2-cyano-5-[5-methyl-2-oxo-5-(3-thienyl)-1,2,3,5-tetrahydro-4,1-benzoxazepin-7-yl]-1H-pyrrole-1-carboxylate,
5-[5-methyl-2-oxo-5-(3-thienyl)-1,2,3,5-tetrahydro-4,1-benzoxazepin-7-yl]-1H-pyrrole-2-carbonitrile,
1-methyl-5-[5-methyl-2-oxo-5-(3-thienyl)-1,2,3,5-tetrahydro-4,1-benzoxazepin-7-yl]-1H-pyrrole-2-carbonitrile,
5-[1,5-dimethyl-2-oxo-5-(1,3-thiazol-2-yl)-1,2,3,5-tetrahydro-4,1-benzoxazepin-7-yl]-1-methyl-1H-pyrrole-2-carbonitrile,
5-(2-oxo-5,5-dithien-2-yl-1,2,3,5-tetrahydro-4,1-benzoxazepin-7-yl)-1H-pyrrole-2-carbonitrile,
1-methyl-5-(2-oxo-5,5-dithien-2-yl-1,2,3,5-tetrahydro-4,1-benzoxazepin-7-yl)-1H-pyrrole-2-carbonitrile,
5-[5-(2-furyl)-5-methyl-2-oxo-1,2,3,5-tetrahydro-4,1-benzoxazepin-7-yl]-1H-pyrrole-2-carbonitrile,
5-[5-(2-furyl)-5-methyl-2-oxo-1,2,3,5-tetrahydro-4,1-benzoxazepin-7-yl]-1-methyl-1H-pyrrole-2-carbonitrile,
5-(1,5-dimethyl-2-oxo-5-thien-2-yl-1,2,3,5-tetrahydro-4,1-benzoxazepin-7-yl)-1-methyl-1H-pyrrole-2-carbonitrile,
7-(3-chlorophenyl)-5-ethyl-5-thien-2-yl-1,5-dihydro-4,1-benzoxazepin-2(3H)-one,
7-(3-chlorophenyl)-5-thien-2-yl-1,5-dihydro-4,1-benzoxazepin-2(3H)-one,
tert-butyl 2-cyano-5-(5-ethyl-2-oxo-5-thien-2-yl-1,2,3,5-tetrahydro-4,1-benzoxazepin-7-yl)-1H-pyrrole-1-carboxylate,
tert-butyl 2-cyano-5-(2-oxo-5-thien-2-yl-1,2,3,5-tetrahydro-4,1-benzoxazepin-7-yl)-1H-pyrrole-1-carboxylate,
5-(5-ethyl-2-oxo-5-thien-2-yl-1,2,3,5-tetrahydro-4,1-benzoxazepin-7-yl)-1H-pyrrole-2-carbonitrile,
5-(2-oxo-5-thien-2-yl-1,2,3,5-tetrahydro-4,1-benzoxazepin-7-yl)-1H-pyrrole-2-carbonitrile,
5-(5-ethyl-2-oxo-5-thien-2-yl-1,2,3,5-tetrahydro-4,1-benzoxazepin-7-yl)-1-methyl-1H-pyrrole-2-carbonitrile,
1-methyl-5-(2-oxo-5-thien-2-yl-1,2,3,5-tetrahydro-4,1-benzoxazepin-7-yl)-1H-pyrrole-2-carbonitrile,
tert-butyl 2-cyano-5-(5-methyl-2-oxo-5-pyridin-2-yl-1,2,3,5-tetrahydro-4,1-benzoxazepin-7-yl)-1H-pyrrole-1-carboxylate,
5-(5-methyl-2-oxo-5-pyridin-2-yl-1,2,3,5-tetrahydro-4,1-benzoxazepin-7-yl)-1H-pyrrole-2-carbonitrile,
1-methyl-5-(5-methyl-2-oxo-5-pyridin-2-yl-1,2,3,5-tetrahydro-4,1-benzoxazepin-7-yl)-1H-pyrrole-2-carbonitrile,
1-methyl-5-(5-methyl-5-thien-3-yl-2-thioxo-1,2,3,5-tetrahydro-4,1-benzoxazepin-7-yl)-1H-pyrrole-2-carbonitrile,
5-(5-methyl-5-thien-3-yl-2-thioxo-1,2,3,5-tetrahydro-4,1-benzoxazepin-7-yl)-1H-pyrrole-2-carbonitrile,
1-benzyl-5-(5-methyl-2-oxo-5-thien-3-yl-1,2,3,5-tetrahydro-4,1-benzoxazepin-7-yl)-1H-pyrrole-2-carbonitrile,
9H-fluoren-9-ylmethyl 7-(5-cyano-1H-pyrrol-2-yl)-5-methyl-5-thien-2-yl-2,3-dihydro-4,1-benzoxazepine-$R_5H$)-carboxylate,
5-[(5S)-5-methyl-2-oxo-5-thien-3-yl-1,2,3,5-tetrahydro-4,1-benzoxazepin-7-yl]-1H-pyrrole-2-carbonitrile,
1-ethyl-5-(5-methyl-2-oxo-5-thien-3-yl-1,2,3,5-tetrahydro-4,1-benzoxazepin-7-yl)-1H-pyrrole-2-carbonitrile,
5-(5-methyl-2-oxo-5-thien-3-yl-1,2,3,5-tetrahydro-4,1-benzoxazepin-7-yl)-1H-pyrrole-1,2-dicarbonitrile,
5-(5-methyl-5-thien-2-yl-1,2,3,5-tetrahydro-4,1-benzoxazepin-7-yl)-1H-pyrrole-2-carbonitrile,
1-methyl-5-(5-methyl-5-thien-2-yl-1,2,3,5-tetrahydro-4,1-benzoxazepin-7-yl)-1H-pyrrole-2-carbonitrile,
7-(3-chloro-4-fluorophenyl)-5-ethyl-5-thien-2-yl-1,5-dihydro-4,1-benzoxazepin-2(3H)-one,
3-(5-ethyl-2-oxo-5-thien-2-yl-1,2,3,5-tetrahydro-4,1-benzoxazepin-7-yl)-5-fluorobenzonitrile,
tert-butyl 2-cyano-5-(5-isopropyl-2-oxo-5-thien-2-yl-1,2,3,5-tetrahydro-4,1-benzoxazepin-7-yl)-1H-pyrrole-1-carboxylate,
5-(5-isopropyl-2-oxo-5-thien-2-yl-1,2,3,5-tetrahydro-4,1-benzoxazepin-7-yl)-1H-pyrrole-2-carbonitrile,
5-(5-isopropyl-2-oxo-5-thien-2-yl-1,2,3,5-tetrahydro-4,1-benzoxazepin-7-yl)-1-methyl-1H-pyrrole-2-carbonitrile,
tert-butyl 2-cyano-5-(2-oxo-5-propyl-5-thien-2-yl-1,2,3,5-tetrahydro-4,1-benzoxazepin-7-yl)-1H-pyrrole-1-carboxylate,
5-(2-oxo-5-propyl-5-thien-2-yl-1,2,3,5-tetrahydro-4,1-benzoxazepin-7-yl)-1H-pyrrole-2-carbonitrile,
5-[(5R)-5-methyl-2-oxo-5-thien-3-yl-1,2,3,5-tetrahydro-4,1-benzoxazepin-7-yl]-1H-pyrrole-2-carbonitrile,
1-methyl-5-(2-oxo-5-propyl-5-thien-2-yl-1,2,3,5-tetrahydro-4,1-benzoxazepin-7-yl)-1H-pyrrole-2-carbonitrile,
tert-butyl 2-cyano-5-(9-fluoro-5-methyl-2-oxo-5-thien-2-yl-1,2,3,5-tetrahydro-4,1-benzoxazepin-7-yl)-1H-pyrrole-1-carboxylate,
7-(3-chloro-4-fluorophenyl)-5-isopropyl-5-thien-2-yl-1,5-dihydro-4,1-benzoxazepin-2(3H)-one,
3-fluoro-5-(5-isopropyl-2-oxo-5-thien-2-yl-1,2,3,5-tetrahydro-4,1-benzoxazepin-7-yl)benzonitrile,
5-(9-fluoro-5-methyl-2-oxo-5-thien-2-yl-1,2,3,5-tetrahydro-4,1-benzoxazepin-7-yl)-1H-pyrrole-2-carbonitrile,
3-fluoro-5-(5-isopropyl-5-thien-2-yl-thioxo-1,2,3,5-tetrahydro-4,1-benzoxazepin-7-yl)benzonitrile,
7-(3-chloro-4-fluorophenyl)-5-propyl-5-thien-2-yl-1,5-dihydro-4,1-benzoxazepin-2(3H)-one,
3-fluoro-5-(5-methyl-2-oxo-5-thien-2-yl-1,2,3,5-tetrahydro-4,1-benzoxazepin-7-yl)benzonitrile,
5-methyl-7-(3-methylphenyl)-5-thien-2-yl-1,5-dihydro-4,1-benzoxazepin-2(3H)-one,
7-(3-aminophenyl)-5-methyl-5-thien-2-yl-1,5-dihydro-4,1-benzoxazepin-2(3H)-one,
7-(3-methoxyphenyl)-5-methyl-5-thien-2-yl-1,5-dihydro-4,1-benzoxazepin-2(3H)-one,
7-(2-chlorophenyl)-5-methyl-5-thien-2-yl-1,5-dihydro-4,1-benzoxazepin-2(3H)-one,
7-(3-chlorophenyl)-5-methyl-5-thien-2-yl-1,5-dihydro-4,1-benzoxazepin-2(3H)-one,
7-(4-chlorophenyl)-5-methyl-5-thien-2-yl-1,5-dihydro-4,1-benzoxazepin-2(3H)-one,
3-(5-methyl-2-oxo-5-thien-2-yl-1,2,3,5-tetrahydro-4,1-benzoxazepin-7-yl)benzonitrile,
7-(3,5-difluorophenyl)-5-methyl-5-thien-2-yl-1,5-dihydro-4,1-benzoxazepin-2(3H)-one,
5-methyl-5,7-dithien-2-yl-1,5-dihydro-4,1-benzoxazepin-2(3H)-one,
5-methyl-5-thien-2-yl-7-thien-3-yl-1,5-dihydro-4,1-benzoxazepin-2(3H)-one,
5-methyl-5-thien-2-yl-7-[3-(trifluoromethyl)phenyl]-1,5-dihydro-4,1-benzoxazepin-2(3H)-one,
5-methyl-7-(3-nitrophenyl)-5-thien-2-yl-1,5-dihydro-4,1-benzoxazepin-2(3H)-one,
7-(3-chloro-4-fluorophenyl)-5-methyl-5-thien-2-yl-1,5-dihydro-4,1-benzoxazepin-2(3H)-one,
7-(2-furyl)-5-methyl-5-thien-2-yl-1,5-dihydro-4,1-benzoxazepin-2(3H)-one,
7-(3-chloro-4-fluorophenyl)-5-ethyl-5-thien-3-yl-1,5-dihydro-4,1-benzoxazepin-2(3H)-one, tert-butyl 2-cyano-5-(5-ethyl-2-oxo-5-thien-3-yl-1,2,3,5-tetrahydro-4,1-benzoxazepin-7-yl)-1H-pyrrole-1-carboxylate,
3-(5-ethyl-2-oxo-5-thien-3-yl-1,2,3,5-tetrahydro-4,1-benzoxazepin-7-yl)-5-fluorobenzonitrile,
7-(3-chloro-4-fluorophenyl)-5-ethyl-5-(2-furyl)-1,5-dihydro-4,1-benzoxazepin-2(3H)-one,
tert-butyl 2-cyano-5-[5-ethyl-5-(2-furyl)-2-oxo-1,2,3,5-tetrahydro-4,1-benzoxazepin-7-yl]-1H-pyrrole-1-carboxylate,
3-[5-ethyl-5-(2-furyl)-2-oxo-1,2,3,5-tetrahydro-4,1-benzoxazepin-7-yl]-5-fluorobenzonitrile,
5-(5-ethyl-2-oxo-5-thien-3-yl-1,2,3,5-tetrahydro-4,1-benzoxazepin-7-yl)-1H-pyrrole-2-carbonitrile,
5-[5-ethyl-5-(2-furyl)-2-oxo-1,2,3,5-tetrahydro-4,1-benzoxazepin-7-yl]-1H-pyrrole-2-carbonitrile,
5-(5-ethyl-2-oxo-5-thien-3-yl-1,2,3,5-tetrahydro-4,1-benzoxazepin-7-yl)-1-methyl-1H-pyrrole-2-carbonitrile,
5-[5-ethyl-5-(2-furyl)-2-oxo-1,2,3,5-tetrahydro-4,1-benzoxazepin-7-yl]-1-methyl-1H-pyrrole-2-carbonitrile,
4-methyl-5-(5-methyl-2-oxo-5-thien-2-yl-1,2,3,5-tetrahydro-4,1-benzoxazepin-7-yl)thiophene-2-carbonitrile,
2-fluoro-5-(5-methyl-2-oxo-5-thien-2-yl-1,2,3,5-tetrahydro-4,1-benzoxazepin-7-yl)benzonitrile,
5-(5-ethyl-2-oxo-5-thien-2-yl-1,2,3,5-tetrahydro-4,1-benzoxazepin-7-yl)-2-fluorobenzonitrile,
4-(5-methyl-2-oxo-5-thien-2-yl-1,2,3,5-tetrahydro-4,1-benzoxazepin-7-yl)-2-furonitrile,
5-(5,5-dimethyl-2-oxo-1,2,3,5-tetrahydro-4,1-benzoxazepin-7-yl)-2-fluorobenzonitrile,
5-(5-ethyl-2-oxo-5-thien-2-yl-1,2,3,5-tetrahydro-4,1-benzoxazepin-7-yl)-4-methylthiophene-2-carbonitrile,
4-(5,5-dimethyl-2-oxo-1,2,3,5-tetrahydro-4,1-benzoxazepin-7-yl)-2-furonitrile,
4-(5-ethyl-2-oxo-5-thien-2-yl-1,2,3,5-tetrahydro-4,1-benzoxazepin-7-yl)-2-furonitrile,
tert-butyl 2-cyano-5-(5-ethyl-1-methyl-2-oxo-5-thien-2-yl-1,2,3,5-tetrahydro-4,1-benzoxazepin-7-yl)-1H-pyrrole-1-carboxylate,
5-(5-ethyl-1-methyl-2-oxo-5-thien-2-yl-1,2,3,5-tetrahydro-4,1-benzoxazepin-7-yl)-1H-pyrrole-2-carbonitrile,
5-(5-ethyl-1-methyl-2-oxo-5-thien-2-yl-1,2,3,5-tetrahydro-4,1-benzoxazepin-7-yl)-1-methyl-H-pyrrole-2-carbonitrile,
4-(5-ethyl-2-oxo-5-thien-2-yl-1,2,3,5-tetrahydro-4,1-benzoxazepin-7-yl)thiophene-2-carbonitrile,
5-(5-ethyl-1-methyl-2-oxo-5-thien-2-yl-1,2,3,5-tetrahydro-4,1-benzoxazepin-7-yl)-2-fluorobenzonitrile,
3-fluoro-5-(2-oxo-5,5-dithien-2-yl-1,2,3,5-tetrahydro-4,1-benzoxazepin-7-yl)benzonitrile,
7-(3-chloro-4-fluorophenyl)-5,5-dithien-2-yl-1,5-dihydro-4,1-benzoxazepin-2(3H)-one,
7-(3-chloro-4-fluorophenyl)-4,5,5-trimethyl-1,3,4,5-tetrahydro-2H-1,4-benzodiazepin-2-one,
1-ethyl-5-(2-oxo-5,5-dithien-2-yl-1,2,3,5-tetrahydro-4,1-benzoxazepin-7-yl)-1H-pyrrole-2-carbonitrile,
1-benzyl-5-(2-oxo-5,5-dithien-2-yl-1,2,3,5-tetrahydro-4,1-benzoxazepin-7-yl)-1H-pyrrole-2-carbonitrile,
3-fluoro-5-(2-oxo-5,5-dithien-3-yl-1,2,3,5-tetrahydro-4,1-benzoxazepin-7-yl)benzonitrile,
tert-butyl 2-cyano-5-(2-oxo-5,5-dithien-3-yl-1,2,3,5-tetrahydro-4,1-benzoxazepin-7-yl)-1H-pyrrole-1-carboxylate,
7-(3-chloro-4-fluorophenyl)-5,5-dithien-3-yl-1,5-dihydro-4,1-benzoxazepin-2(3H)-one,
5-(2-oxo-5,5-dithien-3-yl-1,2,3,5-tetrahydro-4,1-benzoxazepin-7-yl)-1H-pyrrole-2-carbonitrile,
1-methyl-5-(2-oxo-5,5-dithien-3-yl-1,2,3,5-tetrahydro-4,1-benzoxazepin-7-yl)-1H-pyrrole-2-carbonitrile,
3-[5,5-bis(5-chlorothien-2-yl)-2-oxo-1,2,3,5-tetrahydro-4,1-benzoxazepin-7-yl]-5-fluorobenzonitrile,
tert-butyl 2-[5,5-bis(5-bromothien-2-yl)-2-oxo-1,2,3,5-tetrahydro-4,1-benzoxazepin-7-yl]-5-cyano-1H-pyrrole-1-carboxylate,
7-(3-chloro-4-fluorophenyl)-5,5-bis(5-chlorothien-2-yl)-1,5-dihydro-4,1-benzoxazepin-2(3H)-one,
5-[5,5-bis(5-bromothien-2-yl)-2-oxo-1,2,3,5-tetrahydro-4,1-benzoxazepin-7-yl]-1-methyl-1H-pyrrole-2-carbonitrile,
tert-butyl 2-[5,5-bis(5-chlorothien-2-yl)-2-oxo-1,2,3,5-tetrahydro-4,1-benzoxazepin-7-yl]-5-cyano-1H-pyrrole-1-carboxylate,
5-[5,5-bis(5-chlorothien-2-yl)-2-oxo-1,2,3,5-tetrahydro-4,1-benzoxazepin-7-yl]-1H-pyrrole-2-carbonitrile,
7-(3-chloro-4-fluorophenyl)-5,5-di(2-furyl)-1,5-dihydro-4,1-benzoxazepin-2(3H)-one,
tert-butyl 2-cyano-5-[5,5-di(2-furyl)-2-oxo-1,2,3,5-tetrahydro-4,1-benzoxazepin-7-yl]-1H-pyrrole-1-carboxylate,
3-[5,5-bis(4-chlorophenyl)-2-oxo-1,2,3,5-tetrahydro-4,1-benzoxazepin-7-yl]-5-fluorobenzonitrile,
5-[5,5-bis(5-chlorothien-2-yl)-1-methyl-2-oxo-1,2,3,5-tetrahydro-4,1-benzoxazepin-7-yl]-1-methyl-1H-pyrrole-2-carbonitrile,
3-[5,5-di(2-furyl)-2-oxo-1,2,3,5-tetrahydro-4,1-benzoxazepin-7-yl]-5-fluorobenzonitrile,
7-(3-chloro-4-fluorophenyl)-5,5-bis(4-chlorophenyl)-1,5-dihydro-4,1-benzoxazepin-2(3H)-one,
tert-butyl 2-[5,5-bis(4-chlorophenyl)-2-oxo-1,2,3,5-tetrahydro-4,1-benzoxazepin-7-yl]-5-cyano-1H-pyrrole-1-carboxylate,
5-[5,5-bis(4-chlorophenyl)-2-oxo-1,2,3,5-tetrahydro-4,1-benzoxazepin-7-yl]-1H-pyrrole-2-carbonitrile,
7-(3-chloro-4-fluorophenyl)-5,5-diphenyl-1,5-dihydro-4,1-benzoxazepin-2(3H)-one,
5-[5,5-bis(5-chlorothien-2-yl)-2-oxo-1,2,3,5-tetrahydro-4,1-benzoxazepin-7-yl]-1-methyl-1H-pyrrole-2-carbonitrile,
5-[5,5-bis(4-chlorophenyl)-2-oxo-1,2,3,5-tetrahydro-4,1-benzoxazepin-7-yl]-1-methyl-1H-pyrrole-2-carbonitrile,
tert-butyl 2-cyano-5-[(5R)-5-ethyl-2-oxo-5-thien-2-yl-1,2,3,5-tetrahydro-4,1-benzoxazepin-7-yl]-1H-pyrrole-1-carboxylate,
tert-butyl 2-cyano-5-[(5S)-5-ethyl-2-oxo-5-thien-2-yl-1,2,3,5-tetrahydro-4,1-benzoxazepin-7-yl]-1H-pyrrole-1-carboxylate,
5-[5,5-di(2-furyl)-2-oxo-1,2,3,5-tetrahydro-4,1-benzoxazepin-7-yl]-1H-pyrrole-2-carbonitrile,
tert-butyl 2-cyano-5-(2-oxo-5,5-diphenyl-1,2,3,5-tetrahydro-4,1-benzoxazepin-7-yl)-1H-pyrrole-1-carboxylate,
5-(2-oxo-5,5-diphenyl-1,2,3,5-tetrahydro-4,1-benzoxazepin-7-yl)-1H-pyrrole-2-carbonitrile,
tert-butyl 2-[5,5-bis(3-chlorophenyl)-2-oxo-1,2,3,5-tetrahydro-4,1-benzoxazepin-7-yl]-5-cyano-1H-pyrrole-1-carboxylate,
5-[5,5-di(2-furyl)-2-oxo-1,2,3,5-tetrahydro-4,1-benzoxazepin-7-yl]-1-methyl-1H-pyrrole-2-carbonitrile,
7-(3-chloro-4-fluorophenyl)-5,5-bis(3-chlorophenyl)-1,5-dihydro-4,1-benzoxazepin-2(3H)-one,
5-[5,5-bis(5-cyanothien-2-yl)-2-oxo-1,2,3,5-tetrahydro-4,1-benzoxazepin-7-yl]-1H-pyrrole-2-carbonitrile,
5-[5,5-bis(3-chlorophenyl)-2-oxo-1,2,3,5-tetrahydro-4,1-benzoxazepin-7-yl]-1H-pyrrole-2-carbonitrile,
5-[5,5-bis(3-chlorophenyl)-2-oxo-1,2,3,5-tetrahydro-4,1-benzoxazepin-7-yl]-1-methyl-1H-pyrrole-2-carbonitrile, 1-methyl-5-(2-oxo-5,5-diphenyl-1,2,3,5-tetrahydro-4,1-benzoxazepin-7-yl)-1H-pyrrole-2-carbonitrile,
1-methyl-5-(1-methyl-2-oxo-5,5-diphenyl-1,2,3,5-tetrahydro-4,1-benzoxazepin-7-yl)-1H-pyrrole-2-carbonitrile,
7-(3-chloro-4-fluorophenyl)-5,5-bis(4-methoxyphenyl)-1,5-dihydro-4,1-benzoxazepin-2(3H)-one,
3-[5,5-bis(3-chlorophenyl)-2-oxo-1,2,3,5-tetrahydro-4,1-benzoxazepin-7-yl]-5-fluorobenzonitrile,
5-[(5R)-5-ethyl-2-oxo-5-thien-2-yl-1,2,3,5-tetrahydro-4,1-benzoxazepin-7-yl]-1-methyl-1H-pyrrole-2-carbonitrile,
5-[(5S)-5-ethyl-2-oxo-5-thien-2-yl-1,2,3,5-tetrahydro-4,1-benzoxazepin-7-yl]-1-methyl-1H-pyrrole-2-carbonitrile,
5-[5,5-di(3-furyl)-2-oxo-1,2,3,5-tetrahydro-4,1-benzoxazepin-7-yl]-1-methyl-1H-pyrrole-2-carbonitrile,
tert-butyl 2-cyano-5-[5-(4-methoxyphenyl)-5-(4-methoxyphenyl)-2-oxo-1,2,3,5-tetrahydro-4,1-benzoxazepin-7-yl]-1H-pyrrole-1-carboxylate,
3-[5,5-di(3-furyl)-2-oxo-1,2,3,5-tetrahydro-4,1-benzoxazepin-7-yl]-5-fluorobenzonitrile,
5-[5,5-bis(4-methoxyphenyl)-2-oxo-1,2,3,5-tetrahydro-4,1-benzoxazepin-7-yl]-1-methyl-1H-pyrrole-2-carbonitrile,
7-(3,5-dichlorophenyl)-5-ethyl-5-(2-furyl)-1,5-dihydro-4,1-benzoxazepin-2(3H)-one,
5-ethyl-7-(2-fluorophenyl)-5-(2-furyl)-1,5-dihydro-4,1-benzoxazepin-2(3H)-one,
7-(3,4-difluorophenyl)-5-ethyl-5-(2-furyl)-1,5-dihydro-4,1-benzoxazepin-2(3H)-one,
5-ethyl-7-(4-fluorophenyl)-5-(2-furyl)-1,5-dihydro-4,1-benzoxazepin-2(3H)-one,
7-(3-chloro-4-fluorophenyl)-5-(2-furyl)-5-(pentafluoroethyl)-1,5-dihydro-4,1-benzoxazepin-2(3H)-one,
4-[5-ethyl-5-(2-furyl)-2-oxo-1,2,3,5-tetrahydro-4,1-benzoxazepin-7-yl]-2-furonitrile,
7-(2,3-difluorophenyl)-5-ethyl-5-(2-furyl)-1,5-dihydro-4,1-benzoxazepin-2(3H)-one,
7-(4-chloro-3-fluorophenyl)-5-ethyl-5-(2-furyl)-1,5-dihydro-4,1-benzoxazepin-2(3H)-one,
7-(3-chloro-5-fluorophenyl)-5-ethyl-5-(2-furyl)-1,5-dihydro-4,1-benzoxazepin-2(3H)-one,
4-[5-ethyl-5-(2-furyl)-2-oxo-1,2,3,5-tetrahydro-4,1-benzoxazepin-7-yl]-2-fluorobenzonitrile,
7-(3-bromo-5-chlorophenyl)-5-ethyl-5-(2-furyl)-1,5-dihydro-4,1-benzoxazepin-2(3H)-one,
3-chloro-5-[5-ethyl-5-(2-furyl)-2-oxo-1,2,3,5-tetrahydro-4,1-benzoxazepin-7-yl]benzonitrile,
7-(3-bromo-5-fluorophenyl)-5-ethyl-5-(2-furyl)-1,5-dihydro-4,1-benzoxazepin-2(3H)-one,
3-fluoro-5-[5-(2-furyl)-2-oxo-5-(pentafluoroethyl)-1,2,3,5-tetrahydro-4,1-benzoxazepin-7-yl]benzonitrile,
1-methyl-5-(5-methyl-5-thien-3-yl-1,2,3,5-tetrahydro-4,1-benzoxazepin-7-yl)-1H-pyrrole-2-carbonitrile,
5-(5,5-dimethyl-1,2,3,5-tetrahydro-4,1-benzoxazepin-7-yl)-1-methyl-1H-pyrrole-2-carbonitrile, or
5-(1-acetyl-5,5-dimethyl-1,2,3,5-tetrahydro-4,1-benzoxazepin-7-yl)-1-methyl-1H-pyrrole-2-carbonitrile.

The compounds of this invention may contain an asymmetric carbon atom. Some of the compounds may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, other mixtures of the R and S stereoisomers and pharmaceutically acceptable salts thereof. The present invention also includes the pro-drug of compounds of formula I and pharmaceutically acceptable salts thereof.

The term "alkyl" is used herein as a group or part of a group, e.g., alkylamino, to refer to both straight- and branched-chain saturated aliphatic hydrocarbon groups having at least one carbon atoms, e.g., 1 to 6 carbon atoms; "alkenyl" is intended to include both straight- and branched-chain alkyl group with at least one carbon-carbon double bond, e.g., having 2-6 carbon atoms; "alkynyl" group is intended to cover both straight- and branched-chain alkyl group with at least one carbon-carbon triple bond, e.g., having 2-6 carbon atoms.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" as a group or part of a group, e.g., aryloxy, arylthio, is used herein to refer to an aromatic system, e.g., of 6 to 14 carbon atoms, which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, phenanthryl.

The term "substituted aryl" refers to aryl as just defined having one or more, e.g., 1 to 5 or 1-3, substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring, e.g., fused benzene ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one or more substituents selected from the group which includes halogen, CN, OH, $NO_2$, amino, alkyl, substituted alkyl, cycloalkyl, e.g., of 3-8 carbon atoms, alkenyl, substituted alkenyl, alkynyl, alkoxy, aryloxy, substituted alkyloxy, alkylcarbonyl, alkylcarboxy, alkylamino, or arylthio.

The term "alkoxy" is used herein to refer to the OR group, where R is alkyl or substituted alkyl.

The term "aryloxy" is used herein to refer to the OR group, where R is aryl or substituted aryl.

The term "alkylcarbonyl" is used herein to refer to the RCO group, where R is alkyl or substituted alkyl.

The term "alkylcarboxy" is used herein to refer to the COOR group, where R is alkyl or substituted alkyl.

The term "aminoalkyl" refers to both secondary and tertiary amines wherein the alkyl or substituted alkyl groups may be either same or different and the point of attachment is on the nitrogen atom.

The term "halogen" refers to Cl, Br, F, and I.

The term "lower perfluoroalkyl" is used herein to refer to $C_{1-3}$ alkyl groups where each hydrogen atom is replaced with a fluorine atom. Examples include $CF_3$ and $CF_2CF_3$ groups.

The compounds of the present invention can be synthesized following the schemes described below or variations thereof as appreciated by those of skill in the art.

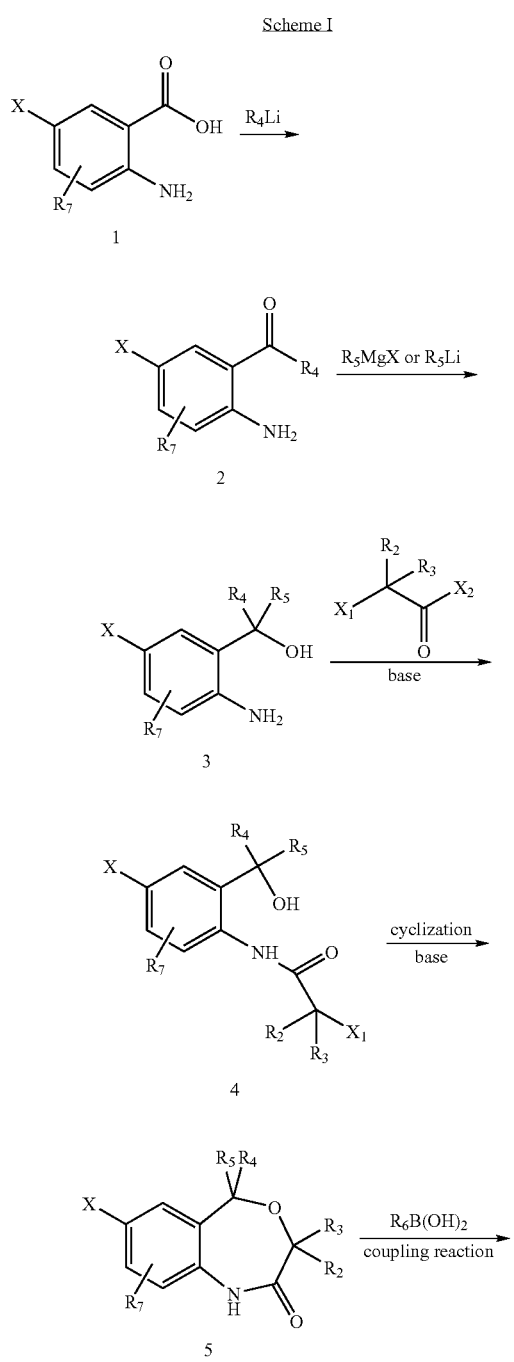

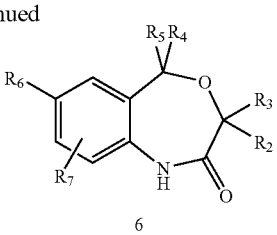

Scheme I illustrates a general synthesis of the compounds of the present invention. The 7-aryl ($R_6$) group was assembled via a coupling reaction such as Suzuki coupling reaction and is critical to the PR activity of compounds in the present invention. As illustrated in Scheme I, access to ketones 2 can be achieved by reaction of an appropriately substituted anthranilic acids 1 with a suitable organo lithium reagent. The reaction can be executed in an aprotic solvent including but not limited to THF or diethyl ether at a suitable temperature such as 0° C. or room temperature under a blanket of inert atmosphere such as nitrogen or argon. To prevent the formation of carbinol side products, a reversing quenching procedure (pouring the reaction mixture to a diluted aqueous acidic solution such as hydrogen chloride solution) is preferred. An alternative way to work up the reaction included but not limited to an addition of trialkylsilyl chloride or equivalent to the reaction before quenching the reaction mixture with a diluted aqueous acidic solution. Treatment of ketones 2 to give carbinols 3 is effected with a suitable organo metallic reagent including but not limited to Grignard or lithium reagents. The reaction can be performed in an aprotic solvent such as diethyl ether or THF at low temperature ranging from –78° C. to room temperature under an inert atmosphere such as argon or nitrogen. Formation of amide 4 can be achieved by treatment of carbinols 3 with an appropriate acylation reagent including but not limited to substituted chloro or bromoacetyl chloride or bromide. A suitable base such as triethyl amine, Hünig's base, potassium carbonate, or sodium carbonate and an aprotic solvent including but not limited to THF or diethyl ether can be used and the reaction temperature ranges from –78° C. to room temperature under an inert atmosphere such as argon or nitrogen. The ring closure to 5 can be effected by treatment of 4 with a suitable base such as sodium hydride, potassium carbonate, or triethyl amine. The reaction can be carried out in an aprotic solvent such as DMF, HMPA, or THF at the temperature ranging from 0° C. to room temperature. The coupling product 6 from 5 can be effected by a number of coupling reactions such as Suzuki and Stille procedures. These reactions are commonly performed in the presence of transition metallic catalyst, e.g., palladium or nickel complex often with phosphino ligands, e.g., $Ph_3P$, dppf, or dppe. Under this catalytic condition, an appropriately substituted nucleophilic reagent, e.g., aryl boronic acid, arylstannane, or aryl zinc compound, can be coupled with 5 to produce the compounds of the present invention, 7-aryl benzoxazepinones 6. The commonly used bases in the reaction include but not limited to sodium bicarbonate, sodium carbonate, potassium phosphate, barium carbonate, cesium fluoride, and potassium acetate. The most commonly used solvents in these reactions include benzene, toluene, DMF, isopropanol, ethanol, DME, and ether. The coupling reaction is generally executed under an inert atmosphere such as nitrogen or argon at temperatures ranging from room temperature to 95° C. In the case when the 7-aryl boronic acid is not available, the 7-halogen of 5 can be converted to the borate or stannane, which can be coupled with an appropriate aryl halide such as aryl bromide or aryl iodide using any coupling reaction described above.

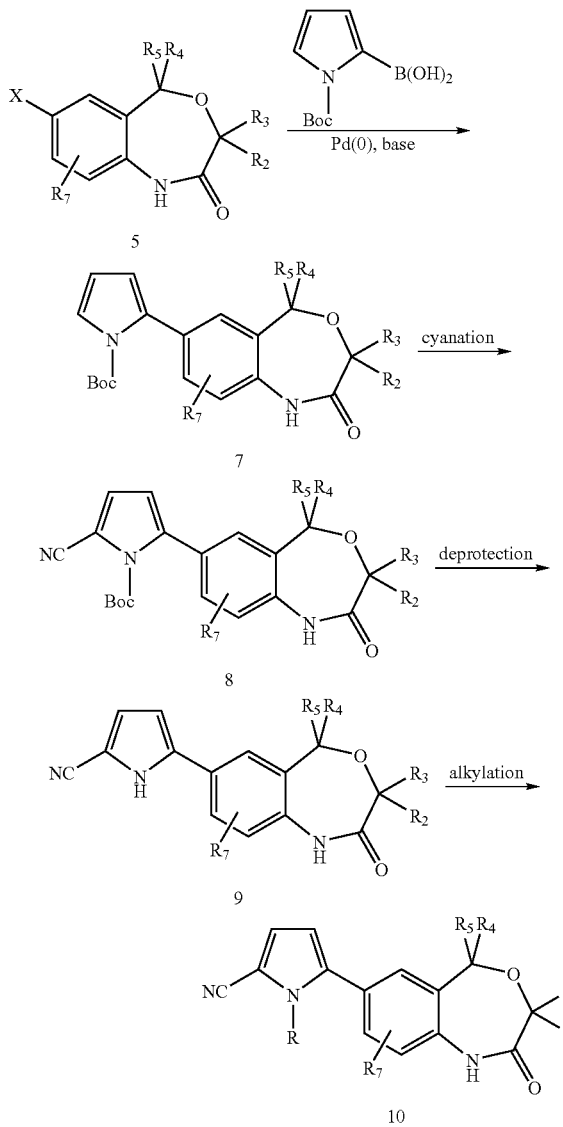

Scheme IA describes a general synthesis of 7-(5-cyanopyrrol-2-yl)benzoxazepinones. An appropriately protected pyrrole moiety was coupled with 5 to yield 7 using the coupling procedure described above. Cyanation of pyrrole moiety at 5'-position can be readily effected by treatment of 7 with a suitable cyanating reagent such as chlorosulfonyl isocyanate in a non-protic solvent including but not limited to THF. When chlorosulfonyl isocyanate is used, the complex was formed and DMF can be used to break up the complex to install cyano moiety on the 5'-position of pyrrole ring. The reaction can be effected at −78° C. under an inert atmosphere such as nitrogen or argon and then treated with DMF to yield 8. There are other means known to those of skill in the art to install cyano moiety on the pyrrole ring including but not limited to a coupling reaction of cyano group to the pyrrole moiety catalyzed by a transition metal. In this procedure, the pyrrole moiety is substituted with bromine, iodine, or triflate serving as a leaving group to effect the coupling with cyano nucleophile. Removal of protecting group from 1'-position of pyrrole can be effected via various means depending on the nature of protecting group by ones of skill in the art. For example, Boc group can be removed by a number of conditions. These include ones such as treatment of 8 with base or acid or by thermo condition of simply heating neat material of 8 under an inert atmosphere such as nitrogen or argon at high temperature such as 165° C. to give the unprotected compounds of the present invention 9. Transformation at the 1'-position of pyrrole moiety included but not limited to alkylation and acylation. The alkylation such as methylation of the 1'-position on the pyrrole moiety to give 10 can be effected by treatment of 9 with an appropriate methylating reagent such as iodomethane. An aprotic solvent such as DMF and a suitable base such as potassium carbonate or potassium bicarbonate are often used and reaction is executed at 0° C. to room temperature.

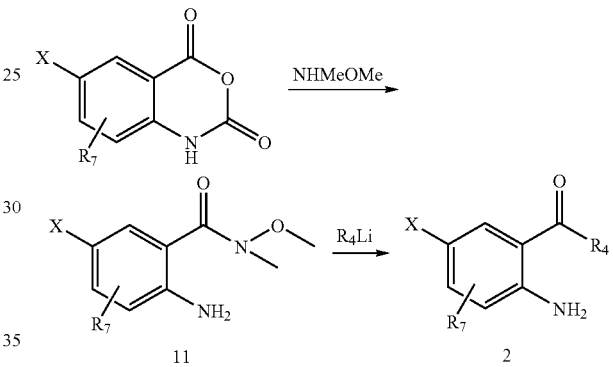

Scheme II described an alternative route leading to ketones 2 by treatment of an appropriately substituted Weinreb amide 11 with organo metallic reagents such as Grignard or lithium reagents. The reaction can be most effectively executed in a suitable nonprotic solvent including but not limited to THF or diethyl ether at the temperature ranging from −78° C. to 0° C. under an inert atmosphere such as nitrogen or argon. The Weinreb amide 11 can be effected by the reaction of an appropriately substituted isatoic anhydride with N,O-dimethylhydroxylamine hydrochloride salt in a protic solvent such as ethanol or methanol at reflux.

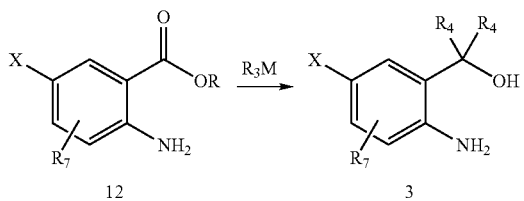

Scheme III illustrates an alternative procedure for preparation of the symmetrical carbinaol 3. The substituted anthranilic acids can be treated with Grignard reagent to give 3. When the ester is used, both Grignard and organo lithium species can be used to effect the formation of carbinols 3 in good yield. The commonly used solvent in this transformation is an aprotic solvent including but not limited to THF and diethyl ether. The reaction can be executed at the temperature ranging from −78° C. to room temperature under an inert atmosphere such as argon or nitrogen.

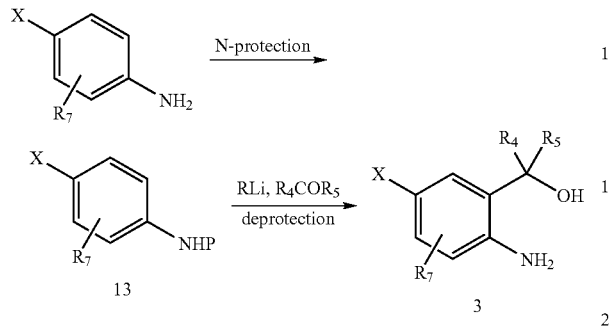

Scheme IV

Amino carbinol 3 can also be effected as illustrated in Scheme IV. A substituted aniline is protected with a suitable protecting group to give 13. The t-butoxylcarbonyl protecting group is preferred but other protecting groups including but not limited to t-butylcarbonyl and acetyl aniline can be used. The protected aniline 13 is treated with a suitable organo lithium base such as n-butyllithium and then quenched with a suitable ketone to afford n-protected amino carbinol. The reaction is executed in an aprotic solvent such as diethyl ether or THF at −78° C. under an inert atmosphere such as argon or nitrogen. Removal of the protecting group to give carbinol 3 can be effected by a number of ways known to those of skill in the art.

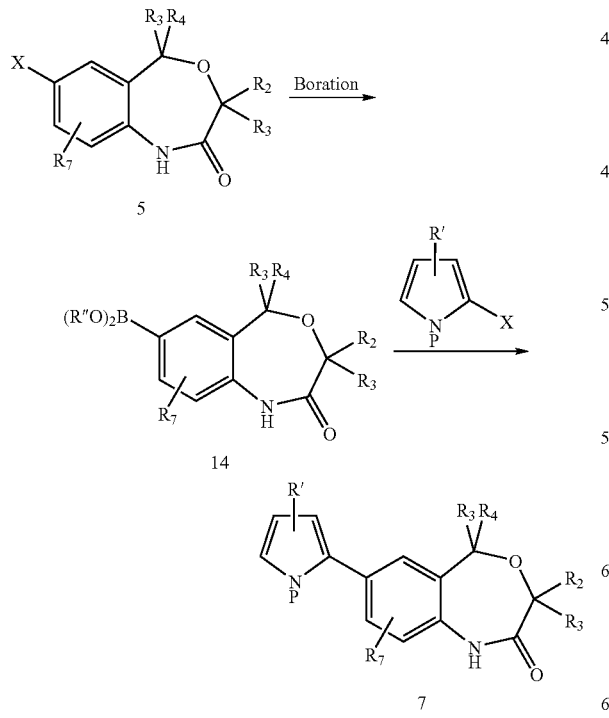

Scheme V

Scheme V depicts an alternative approach for the preparation of 7-pyrrolyl benzoxazepinone 7. A benzoxazepinone 5 is converted into a suitable nucleophile such as borate species by means well known by those of skill in the art. For example, the borate moiety can be effected by a boration procedure catalyzed by a transition metal similar to one reported by Murata et al. (M. Murata et al., *J. Org. Chem.*, 62, 6458-6459, 1997). The borate 14 is then coupled with a suitable pyrrole such as a protected 2-bromo- or 2-iodopyrrole using the procedure described above for the preparation of 7 in Scheme IA.

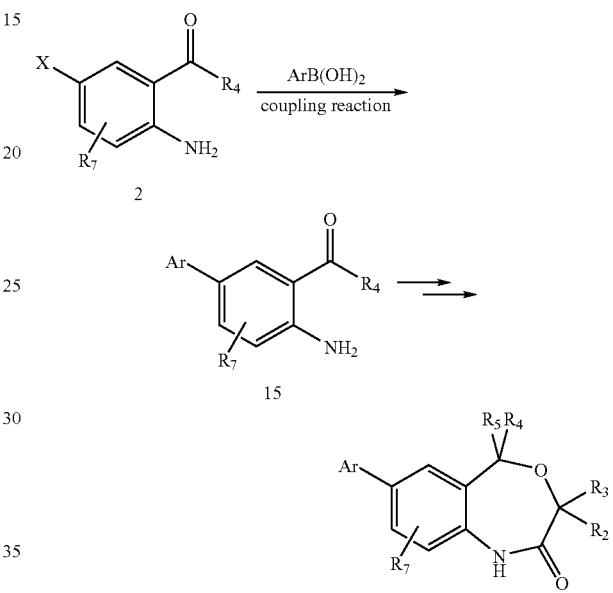

Scheme VI

Scheme VI illustrates another approach for synthesizing compounds in the present invention. Ketone 2 can be coupled with aryl moiety to give 15 using the coupling procedure described above. Following the procedures described in Scheme I, compounds 6 of the present invention can be effected in a multi-step synthesis.

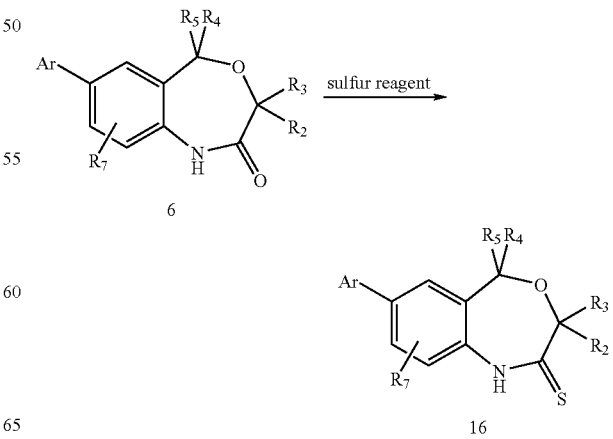

Scheme VII

The preparation of 7-aryl benzoxazepin-2-thione 16, the compounds of present invention, is depicted in Scheme VII. The transformation of 7-aryl benzoxazepinone 6 into 16 can be often effected using a sulfur reagent including but not limited to Lawesson's reagent or phosphorus pentasulfide in a suitable solvent such as toluene, chlorobenzene, or xylene at about 120° C. under nitrogen or argon.

Scheme VIII

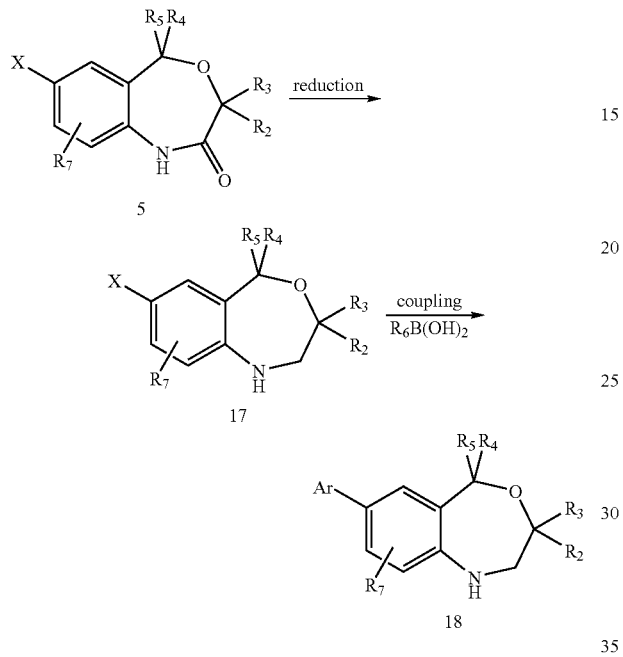

Scheme VIII illustrates a synthesis of 7-aryl benzoxazepines. Benzoxazepinones 5 can be readily reduced to produce 17 by a suitable reducing reagent including but not limit to lithium aluminum hydride in an aprotic solvent such as THF at the ambient temperature under a blanket of inert atmosphere such as nitrogen or argon. Coupling of 17 with various aryl boronic acids using the coupling protocols described in Scheme I can readily effect the compounds of the present invention, 7-aryl benzoxazepines (18). Following the similar procedures described in Scheme IA, benzoxazepines substituted with 7-pyrrole moiety can be prepared.

Scheme IX

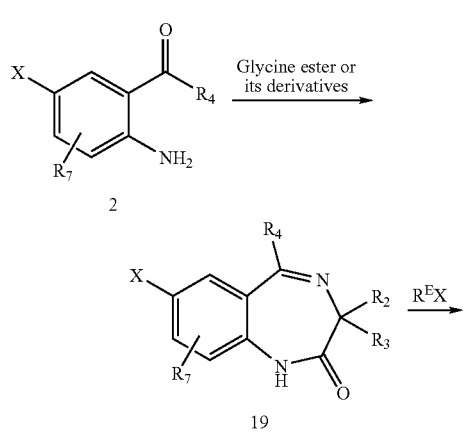

-continued

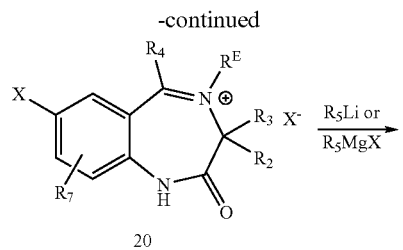

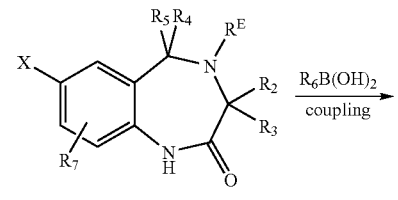

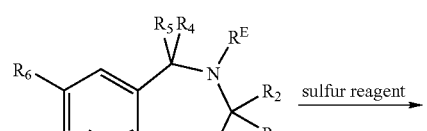

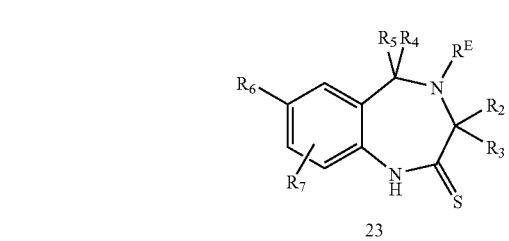

A general synthesis of 7-aryl benzodiazepinones is depicted in Scheme IX. Ring closure of ketone 2 to benzodiazepinones 19 can be effected by condensing 2 with a suitable glycine ester or its derivatives in an aprotic solvent such as pyridine or toluene at reflux under nitrogen or argon. Addition of organo metallic reagent at position-5 can be difficulty without the activation of 4-nitrogen. In this regard, compound 19 can be readily alkylated and activated to give 20 by an appropriate alkylating reagent such as alkyl iodide in a suitable solvent such as acetonitrile under nitrogen or argon. Addition of an appropriate organo metallic reagent such as alkyllithium or Grignard reagent at position-5 to yield 21 can be easily achieved in an aprotic solvent such as diethyl ether or THF from ambient temperature to boiling point of the solvent under nitrogen or argon. In a similar manner as mentioned in Scheme I, the coupling reaction can be most efficiently used to convert 21 to the compounds of the present invention, 7-aryl benzodiazepinones (22). Following the procedure described in Scheme VII, 7-aryl benzodiazepin-2-thiones (23), the compounds of the present invention, can be readily effected.

Scheme X

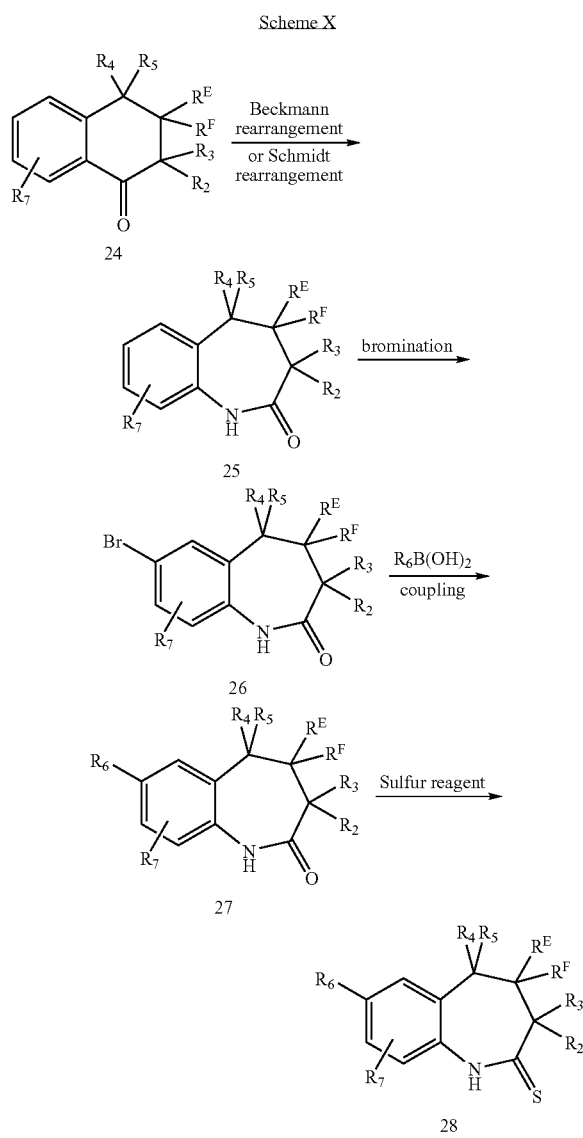

Scheme X describes a synthesis of 7-aryl benzoazepinones. Aryl ketone 24, which can be readily prepared from the appropriately substituted arenes and lactones via Friedel-Crafts reactions, can be converted to benzoazepinones 25 by reacting with hydroxylamine (Beckmann rearrangement) under an acidic condition. Benzoazepinones 25 can also be prepared by treatment of 24 with sodium azide under acidic conditions (Schmidt rearrangement). 7-Bromobenzoazepinones 26 can be effected by treatment of 25 with bromine and a suitable base such as sodium acetate in an acidic solvent such as acetic acid at 0° C. to the ambient temperature. The compounds of present invention, 7-aryl benzoazepinones (27), can be produced most efficiently from 26 and a suitable substituted arene nucleophile by a coupling reaction such as ones described in Scheme I.

Using the procedure illustrated in Scheme VII, 7-aryl benzoazepin-2-thiones (28), claimed in the presentation invention, can be prepared.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions and treatments which comprise administering to a mammal a pharmaceutically effective amount of one or more compounds as described above as antagonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The present invention may be further understood by the following non-limiting examples.

EXAMPLE 1 tert-Butyl 2-cyano-5-(5-methyl-2-oxo-5-thien-2-yl-1,2,3,5-tetrahydro-4,1-benzoxazepin-7-yl)-1H-pyrrole-1-carboxylate 1-(2-Amino-5-bromo-phenyl)-ethanone To a solution of 5-bromo anthranilic acid (50 g, 0.231 mol) in anhydrous THF (500 mL) at 0° C. under nitrogen was added in a dropwise manner methyllithium (1.4 M in diethyl ether, 661 mL, 0.926 mol). After addition, the reaction mixture was slowly allowed to warm to room temperature, stirred overnight, and treated with aqueous saturated ammonium chloride solution (1000 mL). Ethyl acetate (400 mL) was added and organic layer was separated. The aqueous layer was extracted with ethyl acetate (3×200 mL). The combined organic layers were dried ($Mg_2SO_4$) and concentrated. The residue was purified by a flash chromatography on silica gel (hexane:ethyl acetate/9:1) to afford the title compound as a brown solid (29.3 g, 59%). MS (ES) m/z 214/216 ([M+H]$^+$, 100%).

1-(2-Amino-5-bromo-phenyl)-1-thiophen-2-yl-ethanol

To a solution of 1-(2-amino-5-bromo-phenyl)-ethanone (3 g, 14 mmol) in anhydrous THF (50 mL) was added at −78° C. under nitrogen 2-thienyl lithium (1.0 mol in THF, 28 mL, 28 mmol). The reaction mixture was slowly allowed to warm to −20° C., treated with aqueous saturated ammonium chloride solution (50 mL). Ethyl acetate (50 mL) was added and organic layer was separated, dried ($Mg_2SO_4$), and concentrated. The residue was used in next step without further purification. $^1$H-NMR (DMSO-$d_6$) δ 7.4 (d, J=4.9 Hz, 1H), 7.07-7.11 (m, 2H), 6.94 (m, 1H), 6.84 (dd, J=3.5, 0.5 Hz, 1H), 6.55 (d, J=8.2 Hz, 1H), 6.36 (s, 1H), 5.31 (s, 2H), 1.85 (s, 3H).

N-[4-Bromo-2-(1-hydroxy-1-thien-2-ylethyl)phenyl]-2-chloroacetamide

To a solution of 1-(2-amino-5-bromo-phenyl)-1-thiophen-2-yl-ethanol (3.9 g, 13 mmol) in a mixture of anhydrous THF and diethyl ether (20 mL/20 mL) at 0° C. under nitrogen was added triethyl amine (4 mL, 28.7 mmol) and chloroacetyl chloride (1.6 mL, 20 mmol). After addition, the reaction mixture was slowly warmed to room temperature (rt), stirred for 3 h, and treated with a cold 1N hydrogen chloride aqueous solution (70 mL). Ethyl acetate (100 mL) was added and organic layer separated, dried ($Mg_2SO_4$), concentrated to yield the title compound as a white solid (4.7 g, 94%). $^1$H-NMR (DMSO-$d_6$) δ 10.78 (s, 1H), 8.05 (d, J=8.7 Hz, 1H), 7.51 (dd, J=8.7, 2.2 Hz, 1H), 7.43 (d, J=5.0 Hz, 1H), 7.37 (m, 2H), 6.95 (m, 1H), 6.88 (dd, J=3.4, 0.8 Hz, 1H), 4.26 (d, J=6.9 Hz, 2H), 1.94 (s, 3H).

7-Bromo-5-methyl-5-thien-2-yl-1,5-dihydro-4,1-benzoxazepin-2(3H)-one

To a solution of N-[4-bromo-2-(1-hydroxy-1-thien-2-ylethyl)phenyl]-2-chloroacetamide (1.29 g, 3.44 mmol) in anhydrous THF (20 mL) was added at 0 under nitrogen sodium hydride (60% in mineral oil, 0.38 g, 9.5 mmol). After addition, the reaction mixture was stirred for 3 h, treated with an aqueous saturated ammonium chloride solution (30 mL). Ethyl acetate (50 mL) was added and organic layer separated, dried ($Mg_2SO_4$), and concentrated to yield the title compound as a white solid (1.1 g, 96%). $^1$H-NMR (DMSO-$d_6$) δ 10.13 (s, 1H), 7.57 (dd, J=5.0, 1.0 Hz, 1H), 7.47 (dd, J=8.6, 1.4 Hz, 1H), 7.39 (d, J=1.67 Hz, 1H), 7.11 (d, J=8.4 Hz, 1H), 7.00 (m, 1H), 6.88 (dd, J=2.6, 0.9 Hz, 1H), 4.18 (d, J=15.8 Hz, 1H), 4.03 (d, J=16.3 Hz, 1H), 1.99 (s, 3H). MS (ES) m/z 338/340 ([M+H]$^+$, 100%).

A mixture of 7-bromo-5-methyl-5-thien-2-yl-1,5-dihydro-4,1-benzoxazepin-2(3H)-one (1.2 g, 3.55 mmol), 2-borono-1H-pyrrole-1-carboxylic acid, 1-tert-butyl ester (1.2 g, 5.69 mmol), tetrakis(triphenylphosphine) palladium (0) (0.2 g, 0.17 mmol), sodium carbonate (1.2 g, 11.32 mmol) in a mixture of DME and water (20 mL and 5 mL) was degassed to remove air and then heated at 90° C. under nitrogen for 4 h. The mixture was allowed to cool to rt, treated with a saturated aqueous ammonium sulfate solution (50 mL). Ethyl acetate (80 mL) was added and organic layer separated, dried ($Mg_2SO_4$), and concentrated. The residue was purified by a flash chromatography on a silica gel column (Hexane:ethyl acetate/3:1) to give the coupling product as an oil which was used in next step without further purification.

To a solution of the above coupling product in anhydrous THF (30 mL) at −78° C. under nitrogen was added chlorosulfonyl isocyanate (0.46 mL, 5.3 mmol). After kept at −78° C. for 3 h, the reaction solution was treated with anhydrous DMF (5 mL), slowly warmed to rt, and quenched with a saturated aqueous ammonium chloride solution (30 mL). Ethyl acetate (60 mL) was added and organic layer separated, dried ($Mg_2SO_4$), and concentrated. The residue was purified by a flash chromatography on a silica gel column (hexane:THF/3:1) to give tert-butyl 2-cyano-5-(5-methyl-2-oxo-5-thien-2-yl-1,2,3,5-tetrahydro-4,1-benzoxazepin-7-yl)-1H-pyrrole-1-carboxylate as a white solid (0.35 g, 22% for two steps). $^1$H-NMR (DMSO-d$_6$) δ 10.16 (s, 1H), 7.54 (d, J=5.1 Hz, 1H), 7.31-7.36 (m, 2H), 7.29 (dd, J=3.8, 0.7 Hz, 1H), 7.19 (d, J=8.3 Hz, 1H), 6.96 (td, J=4.8, 0.6 Hz, 1H), 6.87 (d, J=3.5 Hz, 1H), 6.43 (dd, J=3.8, 0.5 Hz, 1H), 4.15 (d, J=15.8 Hz, 1H), 4.05 (d, J=15.9 Hz, 1H), 2.00 (s, 3H), 1.39 (s, 9H). MS (ES) m/z 450 ([M+H]$^+$, 100%). Anal. Calc. For C$_{24}$H$_{23}$N$_3$O$_4$S: C, 64.13, H, 5.16; N, 9.35. Found: C, 63.69, H, 5.10; N, 9.14.

EXAMPLE 2

5-[5-Methyl-2-oxo-5-(2-thienyl)-1,2,3,5-tetrahydro-4,1-benzoxazepin-7-yl]-1H-pyrrole-2-carbonitrile A neat tert-butyl 2-cyano-5-(5-methyl-2-oxo-5-thien-2-yl-1,2,3,5-tetrahydro-4,1-benzoxazepin-7-yl)-1H-pyrrole-1-carboxylate (0.25 g, 0.56 mmol) was placed in a flask under nitrogen and heated at 165° C. for 2 minutes until gas evolution ceased. The solid obtained was triturated in small amount of THF and collected on a filter to yield the title compound as a grayish solid (0.18 g, 92%). $^1$H-NMR (DMSO-d$_6$) δ 12.56 (s, 1H), 10.11 (s, 1H), 7.64-7.70 (m, 2H), 7.56 (d, J=5.1 Hz, 1H), 7.17 (d, J=8.4 Hz, 1H), 6.98 (m, 2H), 6.85 (d, J=3.5 Hz, 1H), 6.69 (d, J=3.8 Hz, 1H), 4.13 (d, J=15.8 Hz, 1H), 4.01 (d, J=15.8 Hz, 1H), 2.07 (s, 3H). MS (ES) m/z 348 ([M−H]$^-$, 100%).

EXAMPLE 3

1-Methyl-5-[5-methyl-2-oxo-5-(2-thienyl)-1,2,3,5-tetrahydro-4,1-benzoxazepin-7-yl]-1H-pyrrole-2-carbonitrile To a solution of 5-[5-methyl-2-oxo-5-(2-thienyl)-1,2,3,5-tetrahydro-4,1-benzoxazepin-7-yl]-1H-pyrrole-2-carbonitrile (0.1 g, 0.29 mmol) in anhydrous DMF (5 mL) at rt under nitrogen was added potassium carbonate (1 g, 7.23 mmol) and iodomethane (0.5 mL, 8 mmol). The reaction mixture was stirred for 2 h and treated with brine (30 mL). Ethyl acetate (50 mL) was added and organic layer separated, dried (Mg$_2$SO$_4$), and concentrated. The residue was purified by a flash chromatography on a silica gel column (hexane:ethyl acetate/2:1) to afford the title compound as a white solid (23 mg, 22%): mp 197-198° C.; $^1$H-NMR (DMSO-d$_6$) δ 10.21 (s, 1H), 7.55 (d, J=4.8, 1H), 7.43 (dd, J=8.4, 1.8 Hz, 1H), 7.35 (d, J=1.8 Hz, 1H), 7.27 (d, J=8.4 Hz, 1H), 7.01 (d, J=4.1 Hz, 1H), 6.98 (d, J=4.9 Hz, 1H), 6.93 (d, J=3.0 Hz, 1H), 6.31 (d, J=4.1 Hz, 1H), 4.21 (d, J=15.9 Hz, 1H), 4.07 (d, J=15.9 Hz, 1H), 3.65 (s, 3H), 2.04 (s, 3H). MS (ES) m/z 362 ([M−H]$^-$, 100%).

EXAMPLE 4 tert-Butyl 2-cyano-5-[5-methyl-2-oxo-5-(1,3-thiazol-2-yl)-1,2,3,5-tetrahydro-4,1-benzoxazepin-7-yl]-1H-pyrrole-1-carboxylate 1-(2-Amino-5-bromo-phenyl)-1-thiazol-2-yl-ethanol Prepared from 1-(2-amino-5-bromo-phenyl)-ethanone and 2-thiazolyl lithium generally according to the procedure described in example 1. $^1$H-NMR (DMSO-d$_6$) δ 7.70 (d, J=3.3 Hz, 1H), 7.64 (d, J=3.2 Hz, 1H), 7.28 (d, J=2.4 Hz, 1H), 7.10 (dd, J=8.5, 2.4 Hz, 1H), 6.92 (s, 1H), 6.55 (d, J=8.5 Hz, 1H), 5.50 (s, 2H), 1.90 (s, 3H).

N-{4-Bromo-2-[1-hydroxy-1-(1,3-thiazol-2-yl)ethyl]phenyl}-2-chloroacetamide

Prepared from amino-5-bromo-phenyl)-1-thiazol-2-yl-ethanol and chloro acetyl chloride generally according to the procedure described in example 1. $^1$H-NMR (DMSO-d$_6$) δ 10.88 (s, 1H), 7.91 (d, J=87. Hz, 1H), 7.73 (m, 2H), 7.69, (d, J=3.2 Hz, 1H), 7.59 (d, J=2.3 Hz, 1H), 7.52 (dd, J=8.7, 2.4 Hz, 1H), 4.33 (d, J=5.3 Hz, 2H), 1.95 (s, 3H). Anal. Calc. For C$_{13}$H$_{12}$BrClN$_2$O$_2$S: C, 41.56, H, 3.22; N, 7.46. Found: C, 41.79, H, 3.21; N, 7.04.

7-Bromo-5-methyl-5-(1,3-thiazol-2-yl)-1,5-dihydro-4,1-benzoxazepin-2(3H)-one

Prepared from N-{4-bromo-2-[1-hydroxy-1-(1,3-thiazol-2-yl)ethyl]phenyl}-2-chloroacetamide generally according to the procedure described in example 1. $^1$H-NMR (DMSO-d$_6$) δ 10.12 (s, 1H), 7.79 (d, J=3.24 Hz, 1H), 7.75 (d, J=3.24 Hz, 1H), 7.53 (d, J=2.2 Hz, 1H), 7.48 (dd, J=8.6, 2.3 Hz, 1H), 7.06 (d, J=8.5 Hz, 1H), 4.42 (d, J=15.0 Hz, 1H), 4.20 (d, J=15.0 Hz, 1H), 2.0 (s, 3H). MS (ES) m/z 337/339 ([M−H]$^-$, 100%). Anal. Calc. For C$_{13}$H$_{11}$BrN$_2$O$_2$S: C, 46.03, H, 3.27; N, 8.26. Found: C, 46.19, H, 3.38; N, 8.01.

tert-Butyl 2-[5-methyl-2-oxo-5-(1,3-thiazol-2-yl)-1,2,3,5-tetrahydro-4,1-benzoxazepin-7-yl]-1H-pyrrole-1-carboxylate Prepared from 7-bromo-5-methyl-5-(1,3-thiazol-2-yl)-1,5-dihydro-4,1-benzoxazepin-2(3H)-one and 2-borono-1H-pyrrole-1-carboxylic acid, 1-tert-butyl ester generally according to the procedure described in example 1. $^1$H-NMR (DMSO-d$_6$) δ 10.12 (s, 1H), 7.75 (d, J=3.3 Hz, 1H), 7.70 (d, J=3.1 Hz, 1H), 7.23-7.32 (m, 3H), 7.09 (d, J=8.2 Hz, 1H), 6.24 (t, J=3.3 Hz, 1H), 6.19 (m, 1H), 4.42 (d, J=15.0 Hz, 1H), 4.25 (d, J=14.9 Hz, 1H), 2.01 (s, 3H), 1.31 (s, 9H). MS (ES) m/z 424 ([M−H]$^-$, 100%).

tert-Butyl 2-cyano-5-[5-methyl-2-oxo-5-(1,3-thiazol-2-yl)-1,2,3,5-tetrahydro-4,1-benzoxazepin-7-yl]-1H-pyrrole-1-carboxylate was prepared from tert-butyl 2-[5-methyl-2-oxo-5-(1,3-thiazol-2-yl)-1,2,3,5-tetrahydro-4,1-benzoxazepin-7-yl]-1H-pyrrole-1-carboxylate and chlorosulfonyl isocyanate generally according to the procedure described in example 1. $^1$H-NMR (DMSO-d$_6$) δ 10.22 (s, 1H), 7.73 (d, J=3.2 Hz, 1H), 7.71 (d, J=3.1 Hz, 1H), 7.39 (d, J=2.3 Hz, 1H), 7.32 (dd, J=8.1, 2.3 Hz, 1H), 7.19 (d, J=4.1 Hz, 1H), 7.14, (d, J=8.3 Hz, 1H), 6.42 (d, J=4.2 Hz, 1H), 4.42 (d, J=15.0 Hz, 1H), 4.25 (d, J=14.9 Hz, 1H), 2.02 (s, 3H), 1.32 (s, 9H). MS (ES) m/z 449 ([M−H]$^-$, 100%).

EXAMPLE 5

5-[5-Methyl-2-oxo-5-(1,3-thiazol-2-yl)-1,2,3,5-tetrahydro-4,1-benzoxazepin-7-yl]-1H-pyrrole-2-carbonitrile Prepared from tert-butyl 2-cyano-5-[5-methyl-2-oxo-5-(1,3-thiazol-2-yl)-1,2,3,5-tetrahydro-4,1-benzoxazepin-7-yl]-1H-pyrrole-1-carboxylate generally according to the procedure of example 2. $^1$H-NMR (DMSO-d$_6$) δ 12.65 (s, 1H), 10.12 (s, 1H), 7.78 (d, J=1.9 Hz, 1H), 7.75 (d, J=3.2 Hz, 1H), 7.71 (d, J=3.3 Hz, 1H), 7.64 (dd, J=8.4, 1.9 Hz, 1H), 7.13 (d, J=8.5 Hz, 1H), 6.97 (d, J=3.9 Hz, 1H), 6.65 (d, J=3.9 Hz, 1H), 4.37 (d, J=14.9 Hz, 1H), 4.15 (d, J=14.8 Hz, 1H), 2.10 (s, 3H). MS (ES) m/z 349 ([M−H]⁻, 100%).

EXAMPLE 6 tert-Butyl 2-(5,5-dimethyl-2-oxo-1,2,3,5-tetrahydro-4,1-benzoxazepin-7-yl)-1H-pyrrole-1-carboxylate 2-(2-Amino-5-bromophenyl)propan-2-ol A solution of 2-amino-5-bromobenzoic acid (10 g, 46 mmol) in dry THF (200 mL) was treated at −78° C. under nitrogen with a solution of methylmagnesium bromide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO₄). After removal of solvent in vacuo, the residue was purified by a silica gel flash chromatography (hexane:ethyl acetate/3:2) to give 2-(2-amino-5-bromophenyl)propan-2-ol as off-white solid (6 g, 57%): mp 62-63° C.; $^1$H-NMR (CDCl₃) δ 7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

N-[4-Bromo-2-(1-hydroxy-1-methyl-ethyl)-phenyl]-2-chloro-acetamide

Prepared from 2-(2-amino-5-bromophenyl)propan-2-ol and chloro acetyl chloride generally according to the procedure described in example 1. An off-white solid: mp 133-134° C. $^1$H-NMR (DMSO-d₆) δ 11.21 (s, 1H), 8.12 (d, J=8.6 Hz, 1H), 7.46 (dd, J=8.6, 2.3 Hz, 1H), 7.44 (d, J=2.3 Hz, 1H), 6.28 (s, 1H), 4.43 (s, 2H), 1.53 (s, 6H).

7-Bromo-5,5-dimethyl-1,5-dihydro-4,1-benzoxazepin-2(3H)-one

Prepared from N-[4-bromo-2-(1-hydroxy-1-methyl-ethyl)-phenyl]-2-chloro-acetamide generally according to the procedure described in example 1. An off-white solid: mp 120-121° C. $^1$H-NMR (DMSO-d₆) δ 10.01 (s, 1H), 7.46 (d, J=2.3 Hz, 1H), 7.37 (dd, J=8.6, 2.3 Hz, 1H), 7.04 (d, J=8.6 Hz, 1H), 4.23 (s, 2H), 1.53 (s, 6H).

tert-Butyl 2-(5,5-dimethyl-2-oxo-1,2,3,5-tetrahydro-4,1-benzoxazepin-7-yl)-1H-pyrrole-1-carboxylate was prepared from 7-bromo-5,5-dimethyl-1,5-dihydro-4,1-benzoxazepin-2(3H)-one and 2-borono-1H-pyrrole-1-carboxylic acid, 1-tert-butyl ester generally according to the procedure described in example 1. $^1$H-NMR (DMSO-d₆) δ 9.96 (s, 1H), 7.32 (m, 1H), 7.23 (m, 1H), 7.15 (d, J=8.24 Hz, 1H), 7.07 (d, J=8.3 Hz, 1H), 6.25 (m, 2H), 4.23 (s, 2H), 1.55 (s, 6H), 1.36 (s, 9H); MS (ES) m/z 357 ([M+H]⁺, 100%).

EXAMPLE 7 tert-Butyl-2-cyano-5-(5,5-dimethyl-2-oxo-1,2,3,5-tetrahydro-4,1-benzoxazepin-7-yl)-1H-pyrrole-1-carboxylate Prepared from tert-butyl-2-(5,5-dimethyl-2-oxo-1,2,3,5-tetrahydro-4,1-benzoxazepin-7-yl)-1H-pyrrole-1-carboxylate and chlorosulfonyl isocyanate generally according to the procedure described in example 1. $^1$H-NMR (DMSO-d₆) δ 10.03 (s, 1H), 7.35 (d, J=1.79 Hz, 1H), 7.31 (d, J=3.8 Hz, 1H), 7.23 (dd, J=1.79, 8.31 Hz, 1H), 7.12 (d, J=8.36 Hz, 1H), 6.44 (d, J=3.81 Hz, 1H), 4.25 (s, 2H), 1.55 (s, 6H), 1.39 (s, 9H).

EXAMPLE 8

5-(5,5-Dimethyl-2-oxo-1,2,3,5-tetrahydro-4,1-benzoxazepin-7-yl)-1H-pyrrole-2-carbonitrile Prepared from tert-butyl-2-cyano-5-(5,5-dimethyl-2-oxo-1,2,3,5-tetrahydro-4,1-benzoxazepin-7-yl)-1H-pyrrole-1-carboxylate generally according to the procedure of example 2.

$^1$H-NMR (DMSO-d₆) δ 12.58 (s, 1H), 9.98 (s, 1H), 7.63 (d, J=1.65 Hz, 1H), 7.55 (dd, J=1.62, 8.45 Hz, 1H), 7.12 (d, J=8.43 Hz, 1H), 6.99 (m, 1H), 6.70 (m, 1H), 4.23 (s, 2H), 1.60 (s, 6H); MS (ES) m/z 280 ([M−H]⁻, 100%)

EXAMPLE 9

5-(5,5-Dimethyl-2-oxo-1,2,3,5-tetrahydro-4,1-benzoxazepin-7-yl)-1-methyl-1H-pyrrole-2-carbonitrile Prepared from 5-(5,5-dimethyl-2-oxo-1,2,3,5-tetrahydro-4,1-benzoxazepin-7-yl)-1H-pyrrole-2-carbonitrile and iodomethane generally according to the procedure of example 3. $^1$H-NMR (DMSO-d₆) δ 10.06 (s, 1H), 7.40 (d, J=1.87 Hz, 1H), 7.34 (dd, J=1.87, 8.32 Hz, 1H), 7.20 (d, J=8.38 Hz, 1H), 7.03 (d, J=3.99 Hz, 1H), 6.35 (d, J=4.00, 1H), 4.27 (s, 2H), 3.71 (s, 3H), 1.58 (s, 6H); MS (FI) m/z 294 ([M−H]⁻, 100%)

EXAMPLE 10

5-(5,5-Dimethyl-2-thioxo-1,2,3,5-tetrahydro-4,1-benzoxazepin-7-yl)-1H-pyrrole-2-carbonitrile To a solution of 5-(5,5-dimethyl-2-oxo-1,2,3,5-tetrahydro-4,1-benzoxazepin-7-yl)-1H-pyrrole-2-carbonitrile (0.4 g, 1.4 mmol) in a mixture of toluene (20 mL) and THF (10 mL, help to dissolve the starting material) was added at rt under nitrogen the Lawesson's reagent (0.29 g, 0.71 mmol). The mixture was heated at 100° C. for 10 minutes, cooled to rt, and concentrated. The residue was purified by a flash chromatography on silica gel column (hexane:THF/4:1) to give the title compound as a yellowish solid (0.25 g, 60%). $^1$H-NMR (DMSO-d₆) δ 12.66 (s, 1H), 11.96 (s, 1H), 7.69 (d, J=1.49 Hz, 1H), 7.64 (dd, J=1.48, 8.44 Hz, 1H), 7.35 (d, J=8.51 Hz, 1H), 7.01 (m, 1H), 6.79 (m, 1H), 4.49 (s, 2H), 1.60 (s, 6H); MS (FI) m/z 296 ([M−H]⁻, 100%)

EXAMPLE 11 tert-Butyl 2-cyano-5-(5-methyl-2-oxo-1,2,3,5-tetrahydro-4,1-benzoxazepin-7-yl)-1H-pyrrole-1-carboxylate 1-(2-Amino-5-bromo-phenyl)-ethanol To a solution of 1-(2-amino-5-bromo-phenyl)-ethanone (2.4 g, 11.2 mmol) in anhydrous methanol (50 mL) was added sodium borohydride (1 g, 26 mmol) at rt under nitrogen. The mixture was stirred for 1 h, poured onto ice water, and extracted with ethyl acetate (3×30 mL). The combined organic layers were dried (MgSO₄) and concentrated to yield the title compound as an off-white solid (2.1 g, 86%): mp 95-96° C.

N-[4-bromo-2-(1-hydroxyethyl)phenyl]-2-chloroacetamide

Prepared by from 1-(2-amino-5-bromo-phenyl)-ethanol and chloroacetyl chloride generally according to the procedure described in Example 1. $^1$H-NMR (DMSO-d$_6$) δ 10.11 (s, 1H), 7.64 (d, J=8.63 Hz, 1H), 7.57 (d, J=2.31 Hz, 1H), 7.44 (dd, J=2.34, 8.57 Hz, 1H), 5.77 (d, J=3.88 Hz, 1H), 4.93-4.89 (m, 1H), 4.35, (s, 2H), 1.31 (d, J=6.45 Hz, 3H); MS (ES) m/z 290/292/294 ([M−H]$^−$, 100%).

7-Bromo-5-methyl-1,5-dihydro-4,1-benzoxazepin-2(3H)-one

Prepared from N-[4-bromo-2-(1-hydroxyethyl)phenyl]-2-chloroacetamide generally according to the procedure described in example 1. $^1$H-NMR (DMSO-d$_6$) δ 10.25 (s, 1H), 7.44 (dd, J=2.19, 8.53 Hz, 1H), 7.36 (d, J=2.09 Hz, 1H), 7.07 (d, J=8.54 Hz, 1H), 4.79 (q, J=6.47 Hz, 1H), 4.45 (d, J=16.43 Hz, 1H), 4.33 (d, J=16.46 Hz, 1H), 1.49 (d, J=6.5 Hz, 3H); MS (ES) m/z 256/258 ([M+H]$^+$, 40%); Anal. Calc. For C$_{10}$H$_{10}$BrNO$_2$: C, 46.90; H, 3.94; N, 5.47. Found: C, 49.96; H, 4.01; N, 5.38.

tert-Butyl-2-(5-methyl-2-oxo-1,2,3,5-tetrahydro-4,1-benzoxazepin-7-yl)-1H-pyrrole-1-carboxylate Prepared from 7-bromo-5-methyl-1,5-dihydro-4,1-benzoxazepin-2(3H)-one and 2-borono-1H-pyrrole-1-carboxylic acid, 1-tert-butyl ester according to the coupling procedure described in example 1. $^1$H-NMR (DMSO-d$_6$) δ 10.22 (s, 1H), 7.33 (m, 1H), 7.22 (dd, J=1.83, 8.18 Hz, 1H), 7.15-7.09 (m, 2H), 6.72-6.23 (m, 2H), 4.81 (q, J=6.53 Hz, 1H), 4.43 (d, J=16.17 Hz, 1H), 4.32 (d, J=16.22 Hz, 1H), 1.51 (d, J=6.48 Hz, 3H), 1.34 (s, 9H); MS (ES) m/z 341 ([M−H]$^−$, 100%)

tert-Butyl-2-cyano-5-(5-methyl-2-oxo-1,2,3,5-tetrahydro-4,1-benzoxazepin-7-yl)-1H-pyrrole-1-carboxylate was prepared from tert-butyl-2-(5-methyl-2-oxo-1,2,3,5-tetrahydro-4,1-benzoxazepin-7-yl)-1H-pyrrole-1-carboxylate and chlorosulfonyl isocyanate according to the cyanation procedure described in example 1. $^1$H-NMR (DMSO-d$_6$) δ 10.30 (s, 1H), 7.37-7.25 (m, 3H), 7.16 (d, J=8.26 Hz, 1H), 6.46 (d, J=3.77 Hz, 1H), 4.81 (q, J=6.14 Hz, 1H), 4.47 (d, J=16.42 Hz, 1H), 4.36 (d, J=16.44 Hz, 1H), 1.51 (d, J=6.48 Hz, 3H), 1.37 (s, 9H); MS (ES) m/z 366 ([M−H]$^−$, 100%).

EXAMPLE 12

5-(5-Methyl-2-oxo-1,2,3,5-tetrahydro-4,1-benzoxazepin-7-yl)-1H-pyrrole-2-carbonitrile Prepared from. tert-butyl-2-cyano-5-(5-methyl-2-oxo-1,2,3,5-tetrahydro-4,1-benzoxazepin-7-yl)-1H-pyrrole-1-carboxylate generally according to the procedure of example 2. $^1$H-NMR (DMSO-d$_6$) δ 12.61 (s, 1H), 10.25 (s, 1H), 7.62-7.58 (m, 2H), 7.16 (d, J=8.26 Hz, 1H), 6.99 (m, 1H), 6.68 (m, 1H), 4.82 (q, J=6.52 Hz, 1H), 4.47 (d, J=16.41 Hz, 1H), 4.35 (d, J=16.43 Hz, 1H), 1.58 (d, J=6.48 Hz, 3H); MS (FI) m/z 266 ([M−H]$^−$, 100%).

EXAMPLE 13

1-Methyl-5-(5-methyl-2-oxo-1,2,3,5-tetrahydro-4,1-benzoxazepin-7-yl)-1H-pyrrole-2-carbonitrile Prepared from 5-(5-methyl-2-oxo-1,2,3,5-tetrahydro-4,1-benzoxazepin-7-yl)-1H-pyrrole-2-carbonitrile generally according to the procedure of example 3. $^1$H-NMR (DMSO-d$_6$) δ 10.32 (s, 1H), 7.42-7.39 (m, 1H), 7.32 (bs, 1H), 7.23 (d, J=8.25 Hz, 1H), 7.03 (d, J=3.59 Hz, 1H), 6.35 (d, J=3.61 Hz, 1H), 4.85 (q, J=6.51 Hz, 1H), 4.49 (d, J=16.54 Hz, 1H), 4.37 (d, J=16.55 Hz, 1H), 3.71 (s, 3H), 1.54 (d, J=6.47 Hz, 3H); MS (FI) m/z 280 ([M−H]$^−$, 100%).

EXAMPLE 14 tert-Butyl 2-cyano-5-(5-methyl-2-oxo-5-phenyl-1,2,3,5-tetrahydro-4,1-benzoxazepin-7-yl)-1H-pyrrole-1-carboxylate

1-(2-amino-5-bromophenyl)-1-phenylethanol

Prepared from 1-(2-amino-5-bromo-phenyl)-ethanone and phenyl magnesium bromide generally according to the procedure described in example 1. $^1$H-NMR (DMSO-d$_6$) δ 7.32-7.16 (m, 6H), 7.11 (dd, J=2.03, 8.48 Hz, 1H), 6.49 (d, J=8.55 Hz, 1H), 6.02 (s, 1H), 5.16 (s, 2H), 1.74 (s, 3H); MS (ES) m/z 274/276 ([M+H]$^+$, 100%); Anal. Calc. For C$_{14}$H$_{14}$BrNO: C, 57.55; H, 4.83; N, 4.79. Found: C, 57.67; H, 4.83; N, 4.79.

N-[4-Bromo-2-(1-hydroxy-1-phenylethyl)phenyl]-2-chloroacetamide

Prepared from 1-(2-amino-5-bromophenyl)-1-phenylethanol and chloroacetyl chloride according to the acylation procedure described in example 1. $^1$H-NMR (DMSO-d$_6$) δ 10.42 (s, 1H), 7.93 (d, J=8.71 Hz, 1H), 7.64 (d, J=1.86 Hz, 1H), 7.52 (dd, J=1.77, 8.71 Hz, 1H), 7.33-7.18 (m, 5H), 6.99 (s, 1H), 4.17 (d, J=14.92 Hz, 1H), 3.99 (d, J=14.98 Hz, 1H), 1.84 (s, 3H); MS (ES) m/z 366/368/370 ([M−H]$^−$, 100%); Anal. Calc. For C$_{16}$H$_{15}$BrClNO$_2$: C, 52.13; H, 4.10; N, 3.80. Found: C, 52.18; H, 4.05; N, 3.77.

7-Bromo-5-methyl-5-phenyl-1,5-dihydro-4,1-benzoxazepin-2(3H)-one

Prepared from N-[4-bromo-2-(1-hydroxy-1-phenylethyl)phenyl]-2-chloroacetamide according to the ring closure procedure described in example 1. $^1$H-NMR (DMSO-d$_6$) δ 10.00 (s, 1H), 7.53-7.47 (m, 2H), 7.36-7.27 (m, 3H), 7.25-7.20 (m, 2H), 7.04 (d, J=8.52 Hz, 1H), 4.22 (d, J=14.82 Hz, 1H), 3.98 (d, J=14.82 Hz, 1H), 1.88 (s, 3H); MS (ES) m/z 332/334 ([M+H]$^+$, 100%)

tert-Butyl-2-(5-methyl-2-oxo-5-phenyl-1,2,3,5-tetrahydro-4,1-benzoxazepin-7-yl)-1H-pyrrole-1-carboxylate Prepared from 7-bromo-5-methyl-5-phenyl-1,5-dihydro-4,1-benzoxazepin-2(3H)-one and 2-borono-1H-pyrrole-1-carboxylic acid, 1-tert-butyl ester according to the coupling procedure described in example 1. $^1$H-NMR (DMSO-d$_6$) δ 9.94 (s, 1H), 7.34-7.23 (m, 8H), 7.06 (d, J=7.98 Hz, 1H), 6.27 (d, J=2.44 Hz, 2H), 4.19 (d, J=14.36 Hz, 1H), 3.99, (d, J=14.38 Hz, 1H), 1.86 (s, 3H), 1.36 (s, 9H); MS (ES) m/z 419 ([M+H]$^+$, 30%).

tert-Butyl-2-cyano-5-(5-methyl-2-oxo-5-phenyl-1,2,3,5-tetrahydro-4,1-benzoxazepin-7-yl)-1H-pyrrole-1-carboxylate was prepared from tert-butyl-2-(5-methyl-2-oxo-5-phenyl-1,2,3,5-tetrahydro-4,1-benzoxazepin-7-yl)-1H-pyrrole-1-carboxylate and chlorosulfonyl isocyanate according to the cyanation procedure described in example 1. $^1$H-NMR (DMSO-d$_6$) δ 10.02 (s, 1H), 7.42-7.38 (m, 2H), 7.32-7.10 (m, 7H), 6.49 (d, J=3.80 Hz, 1H), 4.20 (d, J=14.63 Hz, 1H), 3.99, (d, J=14.41 Hz, 1H), 1.87 (s, 3H), 1.39 (s, 9H); MS (ES) m/z 442 ([M−H]⁻, 100%).

EXAMPLE 15

5-(5-Methyl-2-oxo-5-phenyl-1,2,3,5-tetrahydro-4,1-benzoxazepin-7-yl)-1H-pyrrole-2-carbonitrile Prepared from tert-butyl-2-cyano-5-(5-methyl-2-oxo-5-phenyl-1,2,3,5-tetrahydro-4,1-benzoxazepin-7-yl)-1H-pyrrole-1-carboxylate generally according to the procedure of example 2. $^1$H-NMR (DMSO-$d_6$) δ 12.64 (s, 1H), 9.98 (s, 1H), 7.74-7.68 (m, 2H), 7.35-7.22 (m, 5H), 7.13 (d, J=8.35 Hz, 1H), 7.00 (m, 1H), 6.72 (m, 1H), 4.19 (d, J=14.73 Hz, 1H), 3.95, (d, J=14.77 Hz, 1H), 1.97 (s, 3H); MS (ES) m/z 342 ([M−H]⁻, 100%).

EXAMPLE 16

1-Methyl-5-(5-methyl-2-oxo-5-phenyl-1,2,3,5-tetrahydro-4,1-benzoxazepin-7-yl)-1H-pyrrole-2-carbonitrile Prepared from 5-(5-methyl-2-oxo-5-phenyl-1,2,3,5-tetrahydro-4,1-benzoxazepin-7-yl)-1H-pyrrole-2-carbonitrile generally according to the procedure of example 3. $^1$H-NMR (DMSO-$d_6$) δ 10.08 (s, 1H), 7.48-7.42 (m, 2H), 7.36-7.19 (m, 6H), 7.03 (d, J=4.03 Hz, 1H), 6.35 (d, J=4.06 Hz, 1H), 4.27 (d, J=14.95 Hz, 1H), 3.68 (d, J=14.91 Hz, 1H), 3.68, (s, 3H), 1.94 (s, 3H); MS (ES) m/z 358 ([M+H]⁺, 100%).

EXAMPLE 17 tert-Butyl 2-cyano-5-[5-(2-furyl)-5-methyl-2-oxo-1,2,3,5-tetrahydro-4,1-benzoxazepin-7-yl]-1H-pyrrole-1-carboxylate

1-(2-Amino-5-bromophenyl)-1-(2-furyl)ethanol

Prepared from 1-(2-amino-5-bromo-phenyl)-ethanone and 2-furyl lithium generally according to the procedure described in example 1. $^1$H-NMR (DMSO-$d_6$) δ 7.6 (m, 1H), 7.08 (dd, J=2.73, 10.91 Hz, 1H), 6.8 (d, J=2.73 Hz, 1H), 6.56 (d, J=8.18 Hz, 1H), 6.45-6.38 (m, 2H), 6.14 (s, 1H), 5.3 (s, 2H), 1.76 (s, 3H); MS (ES) m/z 280/282 ([M−H]⁻, 30%).

N-{4-Bromo-2-[1-(2-furyl)-1-hydroxyethyl]phenyl}-2-chloroacetamide

Prepared from 1-(2-amino-5-bromophenyl)-1-(2-furyl) ethanol and chloroacetyl chloride generally according to the procedure described in example 1. $^1$H-NMR (DMSO-$d_6$) δ 10.84 (s, 1H), 8.07 (d, J=8.76 Hz, 1H), 7.57 (bs, 1H), 7.50 (dd, J=2.33, 8.76 Hz, 1H), 7.12 (s, 1H), 7.09 (d, J=2.31 Hz, 1H), 6.46-6.42 (m, 2H), 4.35 (d, J=1.69 Hz, 2H), 1.85 (s, 3H); MS (ES) m/z 356/358 ([M−H]⁻, 100%).

7-Bromo-5-(2-furyl)-5-methyl-1,5-dihydro-4,1-benzoxazepin-2(3H)-one

Prepared from N-{4-bromo-2-[1-(2-furyl)-1-hydroxyethyl]phenyl}-2-chloroacetamide generally according to the ring closure procedure described in example 1. $^1$H-NMR (DMSO-$d_6$) δ 10.15 (s, 1H), 7.73 (bs, 1H), 7.47 (dd, J=4.29, 8.57 Hz, 1H), 7.23 (d, J=4.29 Hz, 1H), 7.13 (d, J=8.57 Hz, 1H), 6.49 (m, 1H), 6.30 (d, J=4.29 Hz, 1H), 4.14 (d, J=16.67 Hz, 1H), 4.03 (d, J=16.67 Hz, 1H), 1.87 (s, 3H).

tert-Butyl-2-[5-(2-furyl)-5-methyl-2-oxo-1,2,3,5-tetrahydro-4,1-benzoxazepin-7-yl]-1H-pyrrole-1-carboxylate Prepared from 7-bromo-5-(2-furyl)-5-methyl-1,5-dihydro-4,1-benzoxazepin-2(3H)-one and 2-borono-1H-pyrrole-1-carboxylic acid, 1-tert-butyl ester generally according to the coupling procedure described in example 1. $^1$H-NMR (DMSO-$d_6$) δ 10.10 (s, 1H), 7.70 (bs, 1H), 7.30-7.23 (m, 2H), 7.17-7.14 (m, 1H), 7.02 (m, 1H), 6.43 (m, 1H), 6.28-6.17 (m, 3H), 4.08 (m, 2H), 1.88 (s, 3H), 1.36 (s, 9H); MS (ES) m/z 407 ([M−H]⁻, 30%).

tert-Butyl-2-cyano-5-[5-(2-furyl)-5-methyl-2-oxo-1,2,3,5-tetrahydro-4,1-benzoxazepin-7-yl]-1H-pyrrole-1-carboxylate was prepared from tert-butyl-2-[5-(2-furyl)-5-methyl-2-oxo-1,2,3,5-tetrahydro-4,1-benzoxazepin-7-yl]-1H-pyrrole-1-carboxylate and chlorosulfonyl isocyanate generally according to the cyanation procedure described in example 1. $^1$H-NMR (DMSO-$d_6$) δ 10.17 (s, 1H), 7.71 (d, J=1.46 Hz, 1H), 7.34 (dd, J=1.93, 8.34, Hz, 1H), 7.28 (d, J=3.79 Hz, 1H), 7.21 (d, J=8.42 Hz, 1H), 7.16 (d, J=1.94 Hz, 1H), 6.44-6.41 (m, 2H), 6.24 (d, J=3.18 Hz, 1H), 4.13 (d, J=16.14 Hz, 1H), 4.01 (d, J=16.11 Hz, 1H), 1.89 (s, 3H), 1.38 (s, 9H); MS (ES) m/z 434 ([M+H]⁺, 100%)

EXAMPLE 18

5-[5-(2-Furyl)-5-methyl-2-oxo-1,2,3,5-tetrahydro-4,1-benzoxazepin-7-yl]-1H-pyrrole-2-carbonitrile Prepared from tert-butyl-2-cyano-5-[5-(2-furyl)-5-methyl-2-oxo-1,2,3,5-tetrahydro-4,1-benzoxazepin-7-yl]-1H-pyrrole-1-carboxylate generally according to the procedure of example 2. $^1$H-NMR (DMSO-$d_6$) δ 12.56 (s, 1H), 10.11 (s, 1H), 7.74 (m, 1H), 7.65 (dd, J=1.99, 8.46 Hz, 1H), 7.56 (d, J=1.95 Hz, 1H), 7.21 (d, J=8.56 Hz, 1H), 6.97 (dd, J=2.17, 3.85 Hz, 1H), 6.65 (dd, J=2.51, 3.79 Hz, 1H), 6.45 (dd, J=1.89, 3.32 Hz, 1H), 6.21 (d, J=3.3 Hz, 1H), 4.12 (d, J=16.18 Hz, 1H), 3.96 (d, J=16.22, 1H), 1.97 (s, 3H); MS (ES) m/z 334 ([M+H]⁺, 100%).

EXAMPLE 19

5-[5-(2-Furyl)-5-methyl-2-oxo-1,2,3,5-tetrahydro-4,1-benzoxazepin-7-yl]-1-methyl-1H-pyrrole-2-carbonitrile Prepared from tert-butyl-2-cyano-5-[5-(2-furyl)-5-methyl-2-oxo-1,2,3,5-tetrahydro-4,1-benzoxazepin-7-yl]-1H-pyrrole-1-carboxylate generally according to the procedure of example 3. $^1$H-NMR (DMSO-$d_6$) δ 10.21 (s, 1H), 7.72 (d, J=1.16 Hz, 1H), 7.44 (dd, J=1.99, 8.38 Hz, 1H), 7.29 (d, J=8.45 Hz, 1H), 7.21 (d, J=1.97 Hz, 1H), 7.01 (d, J=4.07 Hz, 1H), 6.45 (dd, J=1.79, 3.26 Hz, 1H), 6.30 (m, 2H), 4.16 (d, J=16.12 Hz, 1H), 4.06 (d, J=16.13 Hz, 1H), 3.64 (s, 3H), 1.93 (s, 3H); MS (ES) m/z 348 ([M+H]⁺, 100%).

EXAMPLE 20 tert-Butyl 2-cyano-5-[5-methyl-2-oxo-5-(3-thienyl)-1,2,3,5-tetrahydro-4,1-benzoxazepin-7-yl]-1H-pyrrole-1-carboxylate

1-(2-amino-5-bromophenyl)-1-thien-3-ylethanol

Prepared from 1-(2-amino-5-bromo-phenyl)-ethanone and 3-thienyllithium generally according to the procedure described in example 1. ¹H-NMR (DMSO-d₆) δ 7.43 (dd, J=2.98, 4.98 Hz, 1H), 7.33 (dd, J=1.27, 2.94 Hz, 1H), 7.07 (dd, J=2.37, 8.47 Hz, 1H), 7.04 (d, J=2.33 Hz, 1H), 6.92 (dd, J=1.26, 4.98 Hz, 1H), 6.52 (d, J=8.38 Hz, 1H), 5.99 (bs, 1H), 5.32 (bs, 2H), 1.78 (s, 3H).

N-{4-Bromo-2-[1-hydroxy-1-(3-thienyl)ethyl]phenyl}-2-chloroacetamide

Prepared from 1-(2-amino-5-bromophenyl)-1-thien-3-ylethanol and chloroacetyl chloride generally according to the procedure described in example 1. ¹H-NMR (DMSO-d₆) δ 10.80 (s, 1H), 8.03 (d, J=7.5 Hz, 1H), 7.52-7.43 (m, 2H), 7.40 (m, 2H), 7.00 (s, 1H), 6.93 (m, 1H), 4.30 (d, J=15.00 Hz, 1H), 4.23 (d, J=15.00 Hz, 1H), 1.90 (s, 3H); MS (ES) m/z 372/374/376 ([M–H]⁻, 100%).

7-Bromo-5-methyl-5-(3-thienyl)-1,5-dihydro-4,1-benzoxazepin-2(3H)-one

Prepared from N-{4-bromo-2-[1-hydroxy-1-(3-thienyl)ethyl]phenyl}-2-chloroacetamide generally according to the procedure described in example 1. ¹H-NMR (DMSO-d₆) δ 10.1 (s, 1H), 7.56 (dd, J=2.95, 5.05 Hz, 1H), 7.45 (dd, J=2.32, 8.65 Hz, 1H), 7.30 (d, J=2.28 Hz, 1H), 7.22 (dd, J=1.31, 2.9 Hz, 1H), 7.11 (d, J=8.71 Hz, 1H), 7.05 (dd, J=1.31, 5.05 Hz, 1H), 4.17 (d, J=16.36 Hz, 1H), 4.01 (d, J=16.36 Hz, 1H), 1.91 (s, 3H); MS (ES) m/z 336/338 ([M–H]⁻, 100%).

tert-Butyl-2-(5-methyl-2-oxo-5-thien-3-yl-1,2,3,5-tetrahydro-4,1-benzoxazepin-7-yl)-1H-pyrrole-1-carboxylate Prepared from 7-bromo-5-methyl-5-(3-thienyl)-1,5-dihydro-4,1-benzoxazepin-2(3H)-one and 2-borono-1H-pyrrole-1-carboxylic acid, 1-tert-butyl ester generally according to the coupling procedure described in example 1. ¹H-NMR (DMSO-d₆) δ 10.03 (s, 1H), 7.53 (dd, J=2.95, 5.04 Hz, 1H), 7.30 (dd, J=1.78, 3.22 Hz, 1H), 7.26-7.21 (m, 2H), 7.14-7.12 (m, 2H), 7.04 (dd, J=1.24, 5.02 Hz, 1H), 6.25-6.20 (m, 2H), 4.13 (d, J=15.58 Hz, 1H), 4.02 (d, J=15.60 Hz, 1H), 1.90 (s, 3H), 1.37 (s, 9H); MS (ES) m/z 425 ([M+H]⁺, 100%).

tert-Butyl-2-cyano-5-[5-methyl-2-oxo-5-(3-thienyl)-1,2,3,5-tetrahydro-4,1-benzoxazepin-7-yl]-1H-pyrrole-1-carboxylate was prepared from tert-butyl-2-(5-methyl-2-oxo-5-thien-3-yl-1,2,3,5-tetrahydro-4,1-benzoxazepin-7-yl)-1H-pyrrole-1-carboxylate and chlorosulfonyl isoyanate generally according to the cyanation procedure described in example 1. ¹H-NMR (DMSO-d₆) δ 10.11 (s, 1H), 7.54 (dd, J=2.96, 5.02 Hz, 1H), 7.33 (dd, J=1.91, 8.30 Hz, 1H), 7.29 (d, J=3.78 Hz, 1H), 7.26-7.17 (m, 3H), 7.05 (dd, J=1.27, 5.01 Hz, 1H), 6.43 (d, J=3.82 Hz, 1H), 4.14 (d, J=15.79 Hz, 1H), 4.01 (d, J=15.78 Hz, 1H), 1.91 (s, 3H), 1.39 (s, 9H); MS (ES) m/z 448 ([M–H]⁻, 20%).

EXAMPLE 21

5-[5-Methyl-2-oxo-5-(3-thienyl)-1,2,3,5-tetrahydro-4,1-benzoxazepin-7-yl]-1H-pyrrole-2-carbonitrile Prepared from tert-butyl-2-cyano-5-[5-methyl-2-oxo-5-(3-thienyl)-1,2,3,5-tetrahydro-4,1-benzoxazepin-7-yl]-1H-pyrrole-1-carboxylate generally according to the procedure of example 2. ¹H-NMR (DMSO-d₆) δ 12.58 (s, 1H), 10.06 (s, 1H), 7.66 (m, 2H), 7.57 (dd, J=2.98, 5.04 Hz, 1H), 7.19 (m, 1H), 7.14 (dd, J=1.22, 2.88 Hz, 1H), 7.08 (dd, J=1.23, 5.03 Hz, 1H), 6.98 (dd, J=2.07, 3.81 Hz, 1H), 6.67 (dd, 2.51, 3.82 Hz, 1H), 4.12 (d, J=15.85 Hz, 1H), 3.95 (d, J=15.85 Hz, 1H), 1.99 (s, 3H); MS (ES) m/z 348 ([M–H]⁻, 20%).

EXAMPLE 22

1-Methyl-5-[5-methyl-2-oxo-5-(3-thienyl)-1,2,3,5-tetrahydro-4,1-benzoxazepin-7-yl]-1H-pyrrole-2-carbonitrile Prepared from 5-[5-methyl-2-oxo-5-(3-thienyl)-1,2,3,5-tetrahydro-4,1-benzoxazepin-7-yl]-1H-pyrrole-2-carbonitrile and iodomethane generally according to the procedure of example 3. ¹H-NMR (DMSO-d₆) δ 10.16 (s, 1H), 7.56 (dd, J=2.92, 5.02 Hz, 1H), 7.42 (dd, J=1.90, 8.42 Hz, 1H), 7.28-7.23 (m, 3H), 7.09 (dd, J=1.06, 4.83 Hz, 1H), 7.01 (d, J=4.06 Hz, 1H), 6.30 (d, J=4.08 Hz, 1H), 4.20 (d, J=15.95 Hz, 1H), 4.05 (d, J=15.93 Hz, 1H), 3.65 (s, 3H), 1.96 (s, 3H); MS (ES) m/z 362 ([M–H]⁻, 100%).

EXAMPLE 23

5'-[(2-Oxo-1,2,3,5,-tetrahydro-benzo[e][1,4]oxazepin-7-yl)-(5-spiro-1"-cyclohexane)]-1H-pyrrole-2'-carbonitrile

N-[4-bromo-2-(1-hydroxycyclohexyl)phenyl]-2-chloroacetamide 1-(2-Amino-5-bromo-phenyl)-cyclohexanol was prepared generally according to the procedure described in Example 6 from 2-amino-5-bromobenzoic acid and pentamethylenebis (magnesium bromide). The crude product was used in the next step without extensive purification and characterization. The title compound was prepared from 1-(2-amino-5-bromophenyl)-cyclohexanol and chloroacetyl chloride generally according to the procedure of Example 1. ¹H-NMR (CDCl₃) δ 10.87 (s, 1H), 8.19 (d, J=8.3 Hz, 1H), 7.41 (m, 2H), 4.15 (s, 2H), 2.27 (s, 1H), 2.07 (d, J=7.3 Hz, 2H), 1.77 (m, 6H), 1.38 (m, 2H); MS (ES) m/z 344 (M–H)⁻; Anal. Calc. For C₁₄H₁₇BrClNO₂: C, 48.51, H, 4.94; N, 4.04. Found: C, 48.63, H, 4.86; N, 4.00.

7-Bromo-1,5-dihydro-(5-spiro-1'-cyclohexane)-benzo[e][1,4]oxazepin-2-one

Prepared from N-[4-bromo-2-(1-hydroxycyclohexyl)phenyl]-2-chloroacetamide generally according to the procedure of Example 1. ¹H-NMR (CDCl₃) δ 7.80 (br s, 1H), 7.38 (d, J=2.4 Hz, 1H), 7.29 (dd, J=8.3, 2.4 Hz, 1H), 6.71 (d, J=8.3 Hz, 1H), 2.08 (d, J=12.7 Hz, 2H), 1.77 (m, 6H), 1.34 (m, 2H), 1.25 (s, 2H); MS (ES) m/z 310 (M+H)⁺; Anal Calc. For C₁₄H₁₆BrNO₂: C, 54.21, H, 5.20; N, 4.52. Found: C, 54.20, H, 5.44; N, 4.20.

2'-[(2-Oxo-1,2,3,5,-tetrahydro-benzo[e][1,4]oxazepin-7-yl)-(5-spiro-1"-cyclohexane)]-pyrrole-1'-carboxylic acid tert-butyl ester Prepared from 7-bromo-1,5-dihydro-(5-spiro-1'-cyclohexane)-benzo[e][1,4]oxazepin-2-one and 2-borono-1H-pyrrole-1-carboxylic acid, 1-tert-butyl ester generally according to the procedure of Example 1. ¹H-NMR (CDCl₃) δ 7.78 (s, 1H), 7.33 (m, 1H), 7.25 (d, J=2.0 Hz, 1H), 7.18 (dd, J=7.9, 1.6 Hz, 1H), 6.80 (d, J=8.3 Hz, 1H), 6.22 (m, 1H), 6.18 (m, 1H), 4.34 (s, 2H), 2.11 (d, J=13.5 Hz, 2H), 1.82 (m, 6H), 1.41 (s, 9H), 1.28 (m, 2H).

2'-Cyano-5'-[(2-oxo-1,2,3,5,-tetrahydro-benzo[e][1,4]oxazepin-7-yl)-(5-spiro-1"-cyclohexane)]-pyrrole-1'-carboxylic acid tert-butyl ester Prepared from 2'-[(2-oxo-1,2,3,5,-tetrahydro-benzo[e][1,4]oxazepin-7-yl)-(5-spiro-1"-cyclohexane)]-pyrrole-1'-carboxylic acid tert-butyl ester and chlorosulfonyl isocyanate generally according to the procedure of Example 1. $^1$H-NMR (DMSO-d$_6$) δ 9.94 (s, 1H), 7.39 (s, 1H), 7.31 (d, J=3.4 Hz, 1H), 7.22 (d, J=8.3 Hz, 1H), 7.10 (d, J=8.8 Hz, 1H), 6.44 (d, J=3.9 Hz, 1H), 4.20 (s, 2H), 1.94 (d, J=13.1 Hz, 2H), 1.87 (m, 2H), 1.62 (m, 4H), 1.38 (s, 9H), 1.35 (m, 2H); MS (ES) m/z 420 (M−H)$^-$.

The title compound was prepared from 2'-cyano-5'-[(2-oxo-1,2,3,5,-tetrahydro-benzo[e][1,4]oxazepin-7-yl)-(5-spiro-1"-cyclohexane)]-pyrrole-1'-carboxylic acid tert-butyl ester generally according to the procedure of Example 1. $^1$H-NMR (DMSO-d$_6$) δ 12.59 (s, 1H), 9.88 (s, 1H), 7.67 (d, J=2.7 Hz, 1H), 7.57 (dd, J=8.2, 2.7 Hz, 1H), 7.12 (d, J=8.2 Hz, 1H), 6.98 (d, J=5.5 Hz, 1H), 6.79 (d, J=2.7 Hz, 1H), 4.20 (s, 2H), 2.00 (m, 4H), 1.70 (m, 6H); MS (ES) m/z 320 (M−H)$^-$

EXAMPLE 24 tert-Butyl 2-cyano-5-[2-oxo-5,5-di(2-thienyl)-,1,2,3,5-tetrahydro-4,1-benzoxazepin-7-yl]-1H-pyrrole-1-carboxylate (2-Amino-5-bromophenyl)(dithien-2-yl)methanol Prepared from methyl 2-amino-5-bromobenzoate and 2-thienyllithium using the procedure similar to example 6. $^1$H-NMR (CDCl$_3$) δ 7.35 (dd, J=5.3, 1.1 Hz, 2H), 7.26 (dd, J=8.4, 2.3 Hz, 1H), 6.98 (m, 2H), 6.82 (d, J=2.3 Hz, 1H), 6.79 (m, 2H), 6.62 (d, J=8.4 Hz, 1H), 5.45 (br s, 1H), 3.86 (br s, 2H); Anal. Calc. For C$_{15}$H$_{12}$BrNOS$_2$: C, 49.18, H, 3.30; N, 3.82. Found: C, 49.62, H, 3.47; N, 3.60.

2-Bromo-N-{4-bromo-2-[hydroxy(dithien-2-yl)methyl]phenyl}acetamide

Prepared from (2-amino-5-bromophenyl)(dithien-2-yl)methanol and bromoacetyl chloride using the procedure described in example 1. $^1$H-NMR (DMSO-d$_6$) δ 10.22 (s, 1H), 8.42 (s, 1H), 8.05 (d, J=9.0 Hz, 1H) 7.59 (m, 3H), 7.05 (m, 2H), 6.87 (m, 2H), 6.78 (d, J=3 Hz, 1H), 3.92 (s, 2H); MS (ES) m/z 484 (M−H)$^-$.

7-Bromo-5,5-dithien-2-yl-1,5-dihydro-4,1-benzoxazepin-2(3H)-one

Prepared from 2-bromo-N-{4-bromo-2-[hydroxy(dithien-2-yl)methyl]phenyl}acetamide using the similar procedure described in example 1. $^1$H-NMR (CDCl$_3$) δ 8.08 (br s, 1H), 7.40 (d, J=4.0 Hz, 2H), 7.37 (d, J=2.1 Hz, 1H), 7.14 (d, J=2.2 Hz, 1H), 6.99 (m, 2H), 6.89 (d, J=3.6 Hz, 2H), 6.83 (d, J=8.5 Hz, 1H), 4.35 (s, 1H); MS (ES) m/z 404 (M−H)$^-$; Anal Calc. For C$_{17}$H$_{12}$BrNO$_2$S$_2$: C, 50.25, H, 2.98; N, 3.45. Found: C, 50.57, H, 3.01; N, 3.25.

tert-Butyl 2-[2-oxo-5,5-di(2-thienyl)-1,2,3,5-tetrahydro-4,1-benzoxazepin-7-yl]-1H-pyrrole-1-carboxylate Prepared from 7-bromo-5,5-dithien-2-yl-1,5-dihydro-4,1-benzoxazepin-2(3H)-one and 2-borono-1H-pyrrole-1-carboxylic acid, 1-tert-butyl ester generally according to the procedure described in example 1. $^1$H-NMR (CDCl$_3$) δ 7.70 (br s, 1H), 7.38 (m, 2H), 7.27 (m, 2H), 7.09 (d, J=1.5 Hz, 1H), 6.96 (m, 4H), 6.88 (d, J=9.0 Hz, 1H), 6.19 (t, J=3.0 Hz, 1H), 6.06 (m, 1H), 4.36 (s, 2H), 1.41 (s, 9H); MS (ES) m/z 491 (M−H)$^-$; Anal. Calc. For C$_{26}$H$_{24}$N$_2$O$_4$S$_2$: C, 63.39, H, 4.91; N, 5.69. Found: C, 62.59, H, 4.99; N, 5.35.

The title compound was prepared from tert-butyl 2-[2-oxo-5,5-di(2-thienyl)-1,2,3,5-tetrahydro-4,1-benzoxazepin-7-yl]-1H-pyrrole-1-carboxylate and chlorosulfonyl isocyanate generally according to the procedure described in example 1. $^1$H-NMR (CDCl$_3$) δ 7.87 (br s, 1H), 7.38 (dd, J=5.0, 1.2 Hz, 2H), 7.25 (dd, J=8.4, 2.0 Hz, 1H), 7.06 (d, J=2.0 Hz, 1H), 6.96 (m, 6H), 6.08 (d, J=3.7 Hz, 1H), 4.37 (s, 2H), 1.50 (s, 9H); MS (ES) m/z 516 (M−H)$^-$.

EXAMPLE 25

5-(2-Oxo-5,5-dithien-2-yl-1,2,3,5-tetrahydro-4,1-benzoxazepin-7-yl)-1H-pyrrole-2-carbonitrile Prepared from tert-butyl 2-cyano-5-[2-oxo-5,5-di(2-thienyl)-,1,2,3,5-tetrahydro-4,1-benzoxazepin-7-yl]-1H-pyrrole-1-carboxylate generally according to the procedure of example 2. $^1$H-NMR (DMSO-d$_6$) δ 12.57 (s, 1H), 10.21 (s, 1H), 7.66 (m, 1H), 7.62 (dd, J=5.0, 1.2 Hz, 2H), 7.42 (d, J=2.0 Hz, 1H), 7.21 (d, J=8.5 Hz, 1H) 7.05 (m, 4H), 6.93 (d, J=3.8 Hz, 1H), 6.41 (d, J=3.9 Hz, 1H), 4.15 (s, 2H); MS (ES) m/z 418 (M+H)$^+$.

EXAMPLE 26

1-Methyl-5-(2-oxo-5,5-dithien-2-yl-1,2,3,5-tetrahydro-4,1-benzoxazepin-7-yl)-1H-pyrrole-2-carbonitrile Prepared from 5-(2-oxo-5,5-dithien-2-yl-1,2,3,5-tetrahydro-4,1-benzoxazepin-7-yl)-1H-pyrrole-2-carbonitrile and iodomethane generally according to the procedure of example 3. $^1$H-NMR (DMSO-d$_6$) δ 10.33 (s, 1H), 7.63 (dd, J=5.0, 1.1 Hz, 2H), 7.50 (dd, J=8.3, 2.1 Hz, 1H), 7.29 (d, J=8.4 Hz, 1H), 7.03 (m, 4H), 6.89 (dd, J=3.6, 1.1 Hz, 2H), 6.18 (d, J=4.0 Hz, 1H), 4.25 (s, 2H), 3.49 (s, 3H); MS (ES) m/z 432 (M+H)$^+$.

EXAMPLE 27

3-(5,5-dimethyl-2-oxo-1,2,3,5-tetrahydro-4,1-benzoxazepin-7-yl)-5-fluorobenzonitrile Prepared from 7-bromo-5,5-dimethyl-1,5-dihydro-4,1-benzoxazepin-2(3H)-one and 3-cyano-5-fluorophenyl boronic acid generally according to the coupling procedure described in example 1. A white solid: mp 238-239° C.; $^1$H NMR (DMSO-d$_6$): δ 10.1 (s, 1H), 8.14 (t, J=1.5 Hz, 1H), 7.98 (m, 1H), 7.80 (m, 1H), 7.69 (d, J=1.9 Hz, 1H), 7.64 (dd, J=8.3, 2.0 Hz, 1H), 7.19 (d, J=8.3 Hz, 1H), 4.27 (s, 2H), 1.63 (s, 6H). MS m/z 309 ([M−H]$^-$); Anal. calcd for C$_{18}$H$_{15}$FN$_2$O$_2$: C, 69.67; H, 4.87; N, 9.03. Found: C, 69.51; H, 4.63; N, 9.07

EXAMPLE 28

7-(3-Chlorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 3-chlorophenyl boronic acid generally according to the coupling procedure described in example 1. A white solid: mp 152-153° C.; ¹H NMR (DMSO-d₆): δ 10.02 (s, 1H), 7.76 (s, 1H), 7.65 (d, J=7.7 Hz, 1H), 7.38-7.58 (m, 4H), 7.18 (d, J=8.3 Hz, 1H), 4.28 (s, 2H), 1.64 (s, 6H); MS m/z 300, ([M−H]−); Anal. calcd for $C_{17}H_{16}ClNO_2$: C, 67.66; H, 5.34; N, 4.64. Found: C, 66.79; H, 5.23; N, 4.50.

EXAMPLE 29

7-(3-Chlorophenyl)-3,5,5-trimethyl-1,5-dihydro-4,1-benzoxazepin-2(H)-one

7-Bromo-3,5,5-trimethyl-1,5-dihydro-4,1-benzoxazepin-2(H)-one

Prepared from 2-(2-amino-5-bromophenyl)propan-2-ol and 2-bromopropylonyl chloride in two steps generally according to the procedure described in example 1. A white solid: ¹H NMR (DMSO-d₆): δ 9.88 (s, 1H), 7.48 (d, J=2.3 Hz, 1H), 7.36 (dd, J=8.6, 2.3 Hz, 1H), 6.99 (d, J=8.6 Hz, 1H), 4.34, (q, J=6.4 Hz, 1H), 1.65 (s, 3H), 1.39 (s, 3H), 1.18 (d, J=6.5 Hz, 3H); MS (ESI) m/z 284/286 ([M+H]⁺); MS (ESI) m/z 282/284

([M−H]−); Anal. calcd for $C_{12}H_{14}BrNO_2$: C, 50.72; H, 4.97; N, 4.93. Found: C, 50.44; H, 4.84; N, 4.95.

The title compound was prepared from 7-bromo-3,5,5-trimethyl-1,5-dihydro-4,1-benzoxazepin-2(H)-one and 3-chlorophenyl boronic acid generally according to the coupling procedure described in example 1. white solid: mp 169-170° C.; ¹H NMR (DMSO-d₆): δ 9.91 (s, 1H), 7.74 (d, J=1.7 Hz, 1H), 7.64 (d, J=7.7 Hz, 1H), 7.57 (d, J=2.0 Hz, 1H), 7.53 (dd, J=8.4, 2.0 Hz, 1H), 7.46 (t, J=7.7 Hz, 1H), 7.38, (d, J=8.0 Hz, 1H), 7.14 (d, J=8.4 Hz, 1H), 4.37 (q, J=6.5 Hz, 1H), 1.74 (s, 3H), 1.47 (s, 3H), 1.21 (d, J=6.5 Hz, 3H). MS m/z 314/316 ([M−H]−). Anal. calcd for $C_{18}H_{18}ClNO_2$: C, 68.46; H, 5.75; N, 4.44. Found: C, 68.32; H, 5.60; N, 4.24.

EXAMPLE 30

5-[1,5-dimethyl-2-oxo-5-(1,3-thiazol-2-yl)-1,2,3,5-tetrahydro-4,1-benzoxazepin-7-yl]-1-methyl-H-pyrrole-2-carbonitrile Prepared from 5-[5-methyl-2-oxo-5-(1,3-thiazol-2-yl)-1,2,3,5-tetrahydro-4,1-benzoxazepin-7-yl]-1H-pyrrole-2-carbonitrile and iodomethane generally according to the procedure described in example 3. A white solid: ¹H NMR (DMSO-d₆): δ 7.75 (d, J=1.9 Hz, 1H), 7.71 (dd, J=8.3, 1.9 Hz, 1H), 7.65 (d, J=7.3 Hz, 1H), 7.57 (d, J=8.3 Hz, 1H), 7.50 (d, J=8.3 Hz, 1H), 7.09 (d, J=4.1 Hz, 1H), 6.52 (d, J=4.1 Hz, 1H), 4.09 (m, 2H), 3.81 (s, 3H), 2.72 (s, 3H), 1.92 (s, 3H). MS m/z 379 ([M+H]+).

EXAMPLE 31 tert-Butyl 2-cyano-5-(3,5,5-trimethyl-2-oxo-1,2,3,5-tetrahydro-4,1-benzoxazepin-7-yl)-H-pyrrole-1-carboxylate tert-Butyl 2-(3,5,5-trimethyl-2-oxo-1,2,3,5-tetrahydro-4,1-benzoxazepin-7-yl)-H-pyrrole-1-carboxylate Prepared from 7-bromo-3,5,5-trimethyl-1,5-dihydro-4,1-benzoxazepin-2(H)-one and 2-borono-1H-pyrrole-1-carboxylic acid, 1-tert-butyl ester generally according to the coupling procedure described in example 1. ¹H NMR (DMSO-d₆): δ 9.85 (s, 1H), 7.32 (m, 1H), 7.24 (d, J=1.8 Hz, 1H), 7.13 (dd, J=8.3, 1.9 Hz, 1H), 7.03 (d, J=8.4 Hz, 1H), 6.20-6.27 (m, 2H), 4.32 (q, J=6.4 Hz, 1H), 1.68 (s, 3H), 1.41 (s, 3H), 1.38 (s, 9H), 1.22 (d, J=6.5 Hz, 3H). MS (ESI) m/z 371 ([M+H]+); MS (ESI) m/z 369 ([M−H]−); Anal. calcd for $C_{21}H_{26}N_2O_4$: C, 68.09; H, 7.07 N, 7.56. Found: C, 67.80; H, 6.85 N, 7.18.

The title compound was prepared from tert-butyl 2-(3,5,5-trimethyl-2-oxo-1,2,3,5-tetrahydro-4,1-benzoxazepin-7-yl)-H-pyrrole-1-carboxylate and chlorosulfonyl isocyanate generally according to the procedure described in example 1. ¹H NMR (DMSO-d₆): δ 9.92 (s, 1H), 7.38 (d, J=1.8 Hz, 1H), 7.32 (d, J=3.8 Hz, 1H), 7.25 (dd, J=8.3, 1.9 Hz, 1H), 7.07 (d, J=8.4 Hz, 1H), 5.94 (d, J=3.8 Hz, 1H), 4.32 (q, J=6.3 Hz, 1H), 1.65 (s, 3H), 1.41 (s, 3H), 1.38 (s, 9H), 1.21 (d, J=6.5 Hz, 3H); MS (ESI) m/z 394 ([M−H]−).

EXAMPLE 32

5-(3,5,5-Trimethyl-2-oxo-1,2,3,5-tetrahydro-4,1-benzoxazepin-7-yl)-H-pyrrole-2-carbonitrile Prepared from tert-butyl 2-cyano-5-(3,5,5-trimethyl-2-oxo-1,2,3,5-tetrahydro-4,1-benzoxazepin-7-yl)-H-pyrrole-1-carboxylate generally according to the procedure of example 2. ¹H NMR (DMSO-d₆): δ 12.58 (s, 1H), 9.88 (s, 1H), 7.63 (d, J=1.8 Hz, 1H), 7.54 (dd, J=8.5, 1.9 Hz, 1H), 7.08 (d, J=8.5 Hz, 1H), 6.98 (m, 1H), 4.34 (q, J=6.6 Hz, 1H), 1.72 (s, 3H), 1.45 (s, 3H), 1.22 (d, J=6.5 Hz, 3H); MS (ESI) m/z 296 ([M+H]+).

EXAMPLE 33

5-(1,5-Dimethyl-2-oxo-5-thien-2-yl-1,2,3,5-tetrahydro-4,1-benzoxazepin-7-yl)-1-methyl-H-pyrrole-2-carbonitrile Prepared from 5-[5-methyl-2-oxo-5-(1,3-thiazol-2-yl)-1,2,3,5-tetrahydro-4,1-benzoxazepin-7-yl]-1H-pyrrole-2-carbonitrile and iodomethane generally according to the procedure of example 3. ¹H NMR (DMSO-d₆): δ 7.72 (s, 1H), 7.70 (dd, J=8.2, 1.9 Hz, 1H), 7.51 (d, J=9.0 Hz, 1H), 7.33 (dd, J=5.0, 1.1 Hz, 1H), 7.08 (d, J=4.1 Hz, 1H), 6.88 (m, 1H), 6.60 (dd, 3.5, 1.2 Hz, 1H), 6.51 (d, J=4.1 Hz, 1H), 4.03 (q, J=2.3 Hz, 1H), 3.81 (s, 3H), 2.81 (s, 3H), 1.93 (s, 3H); MS (ESI) m/z 422 ([M+FORMATE).

EXAMPLE 34 tert-Butyl 2-cyano-5-(2-oxo-5-propyl-5-thien-2-yl-1,2,3,5-tetrahydro-4,1-benzoxazepin-7-yl)-H-pyrrole-1-carboxylate N-[4-Bromo-2-(1-hydroxy-1-thien-2-ylbutyl)phenyl]-2-chloroacetamide Prepared from the 5-bromo anthranilic acid in multiple steps generally according to the procedure described in example 1. ¹H NMR (DMSO-d₆): δ 10.93 (s, 1H), 8.06 (d, J=8.5 Hz, 1H), 7.47 (dd, J=8.8, 2.3 Hz, 1H), 7.41 (m, 2H), 7.15 (s, 1H), 6.94 (m, 2H), 4.28 (m, 2H), 2.15-2.40 (m, 2H), 1.25-1.40 (m, 2H), 0.88 (t, J=7.3 Hz, 3H). MS (ESI) m/z 400/402/404 ([M−H]−); Anal. calcd for C16H17BrClNO2S: C, 47.72%, 4.25; N, 3.48. Found: C, 47.76; H, 4.39; N, 3.46.

7-Bromo-5-propyl-5-thien-2-yl-1,5-dihydro-4,1-benzoxazepin-2(H)-one

Prepared from N-[4-bromo-2-(1-hydroxy-1-thien-2-ylbutyl)phenyl]-2-chloroacetamide generally according to the procedure described in example 1. A white solid, ¹H NMR (DMSO-d$_6$): δ 10.06 (s, 1H), 7.58 (dd, J=5.1, 1.1 Hz, 1H), 7.45 (dd, J=8.7, 2.2 Hz, 1H), 7.36 (d, J=2.3 Hz, 1H), 7.12 (d, J=8.7 Hz, 1H), 7.03 (dd, J=5.1, 3.6 Hz, 1H), 6.92 (dd, J=3.6, 1.1 Hz, 1H), 4.08 (d, J=15.4 Hz, 1H), 3.91 (d, J=15.3 Hz, 1H), 2.32 (m, 2H), 1.43 (m, 1H), 0.92 (m, 1H), 08.84 (t, J=7.2 Hz, 3H); MS (ESI) m/z 366/368 ([M+H]+); MS (ESI) m/z 364/366 ([M–H]–); Anal. calcd for C$_{16}$H$_{16}$BrNO$_2$S: C, 52.47; H, 4.40; N, 3.82. Found: C, 52.37; H, 4.21; N, 3.77.

tert-Butyl 2-(2-oxo-5-propyl-5-thien-2-yl-1,2,3,5-tetrahydro-4,1-benzoxazepin-7-yl)-H-pyrrole-1-carboxylate Prepared from 7-bromo-5-propyl-5-thien-2-yl-1,5-dihydro-4,1-benzoxazepin-2(H)-one and 2-borono-1H-pyrrole-1-carboxylic acid, 1-tert-butyl ester using the coupling procedure described in example 1. $^1$H NMR (DMSO-d$_6$): δ 10.01 (s, 1H), 7.54 (dd, J=5.0, 1.2 Hz, 1H), 7.31 (dd, J=3.2, 1.7 Hz, 1H), 7.24 (dd, J=8.3, 1.9 Hz, 1H), 7.12 (m, 2H), 6.90-7.00 (m, 2H), 6.23 (t, J=3.3 Hz, 1H), 6.19 (m, 1H), 4.12 (d, J=15.2 Hz, 1H), 3.87 (d, J=15.2 Hz, 1H), 2.31 (m, 2H), 1.45 (m, 1H), 1.42 (s, 9H), 1.12 (m, 1H), 0.83 (t, J=7.2 Hz, 3H); MS (ESI) m/z 453 ([M+H]+); MS (ESI) m/z 451 ([M–H]–); Anal. calcd for C$_{25}$H$_{28}$N$_2$O$_4$S: C, 66.35; H, 6.24; N, 6.19. Found: C, 65.89; H, 6.13; N, 5.89.

The title compound was prepared from tert-butyl 2-(2-oxo-5-propyl-5-thien-2-yl-1,2,3,5-tetrahydro-4,1-benzoxazepin-7-yl)-H-pyrrole-1-carboxylate and chlorosulfonyl isocyanate using the similar procedure described in example. A white solid: mp 163-164° C.; $^1$H NMR (DMSO-d$_6$): δ 10.08 (s, 1H), 7.57 (dd, J=5.0, 1.0 Hz, 1H), 7.33 (dd, J=8.1, 1.9 Hz, 1H), 7.28 (m, 2H), 7.18 (d, J=8.4 Hz, 1H), 6.97 (dd, J=5.0, 3.6 Hz, 1H), 6.89 (dd, J=3.6, 1.1 Hz, 1H), 6.41 (d, J=3.9 Hz, 1H), 4.12 (d, J=15.3 Hz, 1H), 3.92 (d, J=15.3 Hz, 1H), 2.43 (m, 2H), 1.43 (s, 9H), 1.42 (m, 1H), 1.01 (m, 1H), 0.86 (t, J=7.1 Hz, 3H); MS m/z 00-1894-IMS; Anal. calcd for C$_{26}$H$_{27}$N$_3$O$_4$S: C, 65.39; H, 5.70; N, 8.80. Found: C, 65.32; H, 5.74; N, 8.45.

EXAMPLE 35

5-(2-Oxo-5-propyl-5-thien-2-yl-1,2,3,5-tetrahydro-4,1-benzoxazepin-7-yl)-H-pyrrole-2-carbonitrile Prepared from tert-butyl 2-cyano-5-(2-oxo-5-propyl-5-thien-2-yl-1,2,3,5-tetrahydro-4,1-benzoxazepin-7-yl)-H-pyrrole-1-carboxylate generally according to the procedure of example 2. A off-white solid: mp 245-246° C.; $^1$H NMR (DMSO-d$_6$): δ 12.56 (s, 1H), 10.04 (s, 1H), 7.65 (m, 2H), 7.57 (dd, J=5.0, 1.0 Hz, 1H), 7.21 (d, J=9.2 Hz, 1H), 6.95-7.02 (m, 2H), 6.92 (dd, J=3.6, 1.1 Hz, 1H), 6.68 (, dd, J=3.8, 2.5 Hz, 1H), 4.05 Z (d, J=15.5 Hz, 1H), 3.89 (d, J=15.4 Hz, 1H), 2.43 (m, 2H), 1.48 (m, 1H), 0.95 (m, 1H), 0.83 (t, J=6.9 Hz, 3H); MS m/z 00-1901-IMS; Anal. calcd for C$_{21}$H$_{19}$N$_3$O$_2$S: C, 66.82; H, 5.07; N, 11.13. Found: C, 66.09; H, 5.01; N, 10.82.

EXAMPLE 36

1-Methyl-5-(2-oxo-5-propyl-5-thien-2-yl-1,2,3,5-tetrahydro-4,1-benzoxazepin-7-yl)-H-pyrrole-2-carbonitrile Prepared from 5-(2-oxo-5-propyl-5-thien-2-yl-1,2,3,5-tetrahydro-4,1-benzoxazepin-7-yl)-H-pyrrole-2-carbonitrile and iodomethane using the procedure of example 3. A white solid, $^1$H NMR (DMSO-d$_6$): δ 10.13 (s, 1H), 7.56 (dd, J=4.9, 1.1 Hz, 1H), 7.42 (dd, J=8.3, 1.8 Hz, 1H), 7.35 (d, J=1.8 Hz, 1H), 7.28 (d, J=8.5 Hz, 1H), 6.95-7.05 (m, 3H), 6.31 (d, J=4.1 Hz, 1H), 4.12 (d, J=15.4 Hz, 1H), 3.98 (d, J=15.4 Hz, 1H), 3.66 (s, 3H), 2.37 (m, 2H), 1.48 (m, 1H), 1.04 (m, 1H), 0.88 (t, J=7.4 Hz, 3H); MS (ESI) m/z 392 ([M+H]–); MS (ESI) m/z 390 ([M–H]–); Anal. calcd for C$_{22}$H$_{21}$N$_3$O$_2$S: C, 67.50; H, 5.41; N, 10.73. Found: C, 66.73; H, 5.30; N, 10.48.

EXAMPLE 37

7-(3-Chloro-4-fluorophenyl)-5-propyl-5-thien-2-yl-1,5-dihydro-4,1-benzoxazepin-2(H)-one Prepared from 7-bromo-5-propyl-5-thien-2-yl-1,5-dihydro-4,1-benzoxazepin-2(H)-one and 3-chloro-4-fluorophenyl boronic acid using the procedure described in example 1. A white solid: mp 183-184° C.; $^1$H NMR (DMSO-d$_6$): δ 10.07 (s, 1H), 7.83 (dd, J=7.1, 2.2 Hz, 1H), 7.51-7.68 (m, 4H), 7.47 (t, J=9.0 Hz, 1H), 7.24 (d, J=8.5 Hz, 1H), 7.02 (t, J=5.0 Hz, 1H), 6.96 (dd, J=3.5, 1.0 Hz, 1H), 4.09 (d, J=15.3 Hz, 1H), 3.90 (d, J=15.3 Hz, 1H), 2.45 (m, 2H), 1.48 (m, 1H), 0.98 (m, 1H), 0.86 (t, J=7.2 Hz, 3H); Anal. calcd for C$_{22}$H$_{19}$ClFNO$_2$S: C, 63.53; H, 4.60; N, 3.37. Found: C, 61.60; H, 4.32; N, 3.25.

EXAMPLE 38

7-(3-Chloro-4-fluorophenyl)-4,5-dimethyl-2-oxo-2,3-dihydro-H-1,4-benzodiazepin-4-ium

7-Bromo-5-methyl-1,3-dihydro-benzo[e][1,4]diazepin-2-one

A mixture of 1-(2-amino-5-bromo-phenyl)-ethanone (8 g, 37 mmol) and glycine ethyl ester hydrogen chloride (6.7 g, 48 mmol) in pyridine was heated at reflux for 24 hrs under nitrogen. The reaction mixture was cooled, solvent removed, and residue was treated with a saturated aqueous ammonium chloride solution (200 mL). Ethyl acetate (300 mL) was added and organic layer was separated, dried (MgSO$_4$), concentrated, and the residue purified on silica gel column (hexane:ethyl acetate/1:1) to give 7-bromo-5-methyl-1,3-dihydro-benzo[e][1,4]diazepin-2-one as a brown solid (1.51 g, 16%). $^1$H NMR (DMSO-d$_6$): δ 10.49 (s, 1H), 7.92 (d, J=2.0 Hz, 1H), 7.66 (dd, J=8.7, 2.1 Hz, 1H), 7.08 (d, J=8.7 Hz, 1H), 3.91 (s, 2H), 2.39 (s, 3H). MS (ESI) m/z 253/255 ([M+H]+); Anal. calcd for C$_{10}$H$_9$BrN$_2$O: C, 47.46; H, 3.58; N, 11.07. Found: C, 47.58; H, 3.52; N, 10.95.

7-(3-Chloro-4-fluorophenyl)-5-methyl-1,3-dihydro-H-1,4-benzodiazepin-2-one

Prepared from 7-bromo-5-methyl-1,3-dihydro-benzo[e][1,4]diazepin-2-one and 3-chloro-4-fluorophenyl boronic acid using the coupling procedure described in example 1. $^1$H NMR (DMSO-d$_6$): δ 10.52 (s, 1H), 8.02 (d, J=2.2 Hz, 1H), 7.99 (d, J=2.1 Hz, 1H), 7.83 (dd, J=8.5, 2.2 Hz, 1H), 7.76 (m, 1H), 7.52 (t, J=8.76 Hz, 1H), 7.20 (d, J=8.5 Hz, 1H), 3.91 (s, 2H), 2.48 (s, 3H); MS (ESI) m/z 303/305 ([M+H]+); MS (ESI) m/z 301/303 ([M–H]–); Anal. calcd for C$_{16}$H$_{12}$ClFN$_2$O: C, 63.48; H, 4.00; N, 9.25 Found: C, 63.16; H, 4.02; N, 8.85.

A mixture of 7-(3-chloro-4-fluorophenyl)-5-methyl-1,3-dihydro-H-1,4-benzodiazepin-2-one (0.4 g, 1.32 mmol) and iodomethane (0.125 mL, 2 mmol) in anhydrous acetonitrile (20 mL) was heated at 50° C. under nitrogen for 24 hrs. The solvent was removed and residue triturated in ethyl acetate to give the title compound as greenish solid (60 mg, 14%). $^1$H NMR (DMSO-d$_6$): δ 11.52 (s, 1H), 8.24 (d, J=2.0 Hz, 1H), 8.13 (dd, J=5.2, 2.2 Hz, 1H), 8.06 (dd, J=7.0, 2.3 Hz, 1H), 7.81 (m, 1H), 7.58 (t, J=9.0 Hz, 1H), 7.39 (d, J=8.7 Hz, 1H), 4.48 (bs, 2H), 3.84 (s, 3H), 2.98 (s, 3H). MS (ESI) m/z 317/319 ([M]+); Anal. calcd for $C_{17}H_{15}ClFN_2O$ I: C, 45.92; H, 3.40; N, 6.30. Found: C, 45.50; H, 3.39; N, 6.55.

EXAMPLE 39

7-(3-chloro-4-fluorophenyl)-4,5,5-trimethyl-1,3,4,5-tetrahydro-H-1,4-benzodiazepin-2-one A mixture of 7-(3-chloro-4-fluorophenyl)-4,5-dimethyl-2-oxo-2,3-dihydro-H-1,4-benzodiazepin-4-ium (0.2 g, 0.63 mmol) and methyl magnesium bromide (11 mL in diethyl ether, 3M, 3 mmol) in anhydrous diethyl ether (20 mL) was heated at reflux under nitrogen for 3 hrs. The reaction mixture was treated with a saturated aqueous ammonium chloride solution (30 mL). The organic layer was separated and aqueous layer was extracted with ethyl acetate (3×30 mL). The organic extracts were combined, dried ($MgSO_4$), concentrated, and residue purified on a silica gel column (hexane: ethyl acetate/3:1) to give the title compound as a white solid (11 mg, 5.2%). $^1H$ NMR (DMSO-$d_6$): δ 10.06 (s, 1H), 7.92 (dd, J=7.1, 2.2 Hz, 1H), 7.68 (m, 1H), 7.45-7.53 (m, 3H), 7.26 (d, J=8.2 Hz, 1H), 3.78 (s, 2H), 2.18 (s, 3H), 1.52 (s, 6H). MS (ESI) m/z 333/335 ([M+H]+).

EXAMPLE 40

3-[5,5-Bis(5-chlorothien-2-yl)-2-oxo-1,2,3,5-tetrahydro-4,1-benzoxazepin-7-yl]-5-fluorobenzonitrile 7-Bromo-5,5-bis(5-chlorothien-2-yl)-1,5-dihydro-4,1-benzoxazepin-2(H)-one Prepared from 2-amino-5-bromobenzoic acid in multiple steps following the procedure described in example 6. $^1H$ NMR (DMSO-$d_6$): δ 10.15 (s, 1H), 7.91 (dd, J=8.8, 2.4 Hz, 1H), 7.18 (d, J=8.8 HZ, 1H), 7.10 (d, J=2.6 Hz, 1H), 7.06 (d, J=3.9 Hz, 2H), 6.78 (d, J=3.9 Hz, 2H), 4.22 (s, 2H). MS (ESI) m/z 472/474/476 ([M–H]–); Anal. calcd for $C_{17}H_{10}BrCl_2NO_2S_2$: C, 42.97; H, 2.12; N, 2.95. Found: C, 43.34; H, 2.17; N, 2.78.

The title compound was prepared from 7-bromo-5,5-bis(5-chlorothien-2-yl)-1,5-dihydro-4,1-benzoxazepin-2(H)-one and 3-cyano-5-fluorophenyl boronic acid generally according to the coupling procedure of example 1. $^1H$ NMR (DMSO-$d_6$): δ 10.32 (s, 1H), 7.89 (t, J=1.5 Hz, 1H), 7.73-7.82 (m, 3H), 7.48 (d, J=2.5 Hz, 1H), 7.29 (d, J=8.3 Hz, 1H), 7.07 (d, J=3.9 Hz, 2H), 6.98 (d, J=3.9 Hz, 2H), 4.22 (s, 2H); MS (ESI) m/z 513/515/517 ([M–H]–); Anal. calcd for $C_{24}H_{13}Cl_2FN_2O_2S_2$: C, 55.93; H, 2.54; N, 5.44. Found: C, 56.34; H, 2.64; N, 5.36.

EXAMPLE 41

7-(3-Chloro-4-fluorophenyl)-5,5-bis(5-chlorothien-2-yl)-1,5-dihydro-4,1-benzoxazepin-2(H)-one Prepared from 7-bromo-5,5-bis(5-chlorothien-2-yl)-1,5-dihydro-4,1-benzoxazepin-2(H)-one and 3-chloro-4-fluorophenyl boronic acid generally according to the coupling procedure of example 1. $^1H$ NMR (DMSO-$d_6$): δ 10.30 (s, 1H), 7.71 (t, J=1.9 Hz, 1H), 7.69 (d, J=2.0 Hz, 1H), 7.44-7.50 (m, 2H), 7.29 (d, J=2.4 Hz, 1H), 7.26 (d, J=8.3 Hz, 1H), 7.05 (d, J=3.9 Hz, 2H), 6.89 (d, J=3.9 Hz, 2H), 4.24 (s, 2H); MS (ESI) m/z 522/524/526 ([M–H]–).

EXAMPLE 42 tert-Butyl 2-[5,5-bis(5-chlorothien-2-yl)-2-oxo-1,2,3,5-tetrahydro-4,1-benzoxazepin-7-yl]-5-cyano-H-pyrrole-1-carboxylate tert-Butyl 2-[5,5-bis(5-chlorothien-2-yl)-2-oxo-1,2,3,5-tetrahydro-4,1-benzoxazepin-7-yl]-H-pyrrole-1-carboxylate Prepared from 7-bromo-5,5-bis(5-chlorothien-2-yl)-1,5-dihydro-4,1-benzoxazepin-2(H)-one and 2-borono-1H-pyrrole-1-carboxylic acid, 1-tert-butyl ester generally according to the coupling procedure of example 1. $^1H$ NMR (DMSO-$d_6$): δ 10.23 (s, 1H), 7.35 (dd, J=8.3, 2.4 Hz, 1H), 7.29 (m, 1H), 7.14 (d, J=8.3 Hz, 1H), 7.01 (d, J=4.0 Hz, 2H), 6.96 (d, J=2.0 Hz, 1H), 6.72 (d, J=3.9 Hz, 2H), 6.23 (t, J=3.4 Hz, 1H), 6.13 (m, 1H), 4.24 (s, 2H), 1.38 (s, 9H); MS (ESI) m/z 561/563 ([M+H]+); MS (ESI) m/z 559/561 ([M–H]–); Anal. calcd for $C_{26}H_{22}Cl_2N_2O_4S_2$: C, 55.62; H, 3.95; N, 4.99. Found: C, 56.61; H, 4.18; N, 4.40.

The title compound was prepared from tert-butyl 2-[5,5-bis(5-chlorothien-2-yl)-2-oxo-1,2,3,5-tetrahydro-4,1-benzoxazepin-7-yl]-H-pyrrole-1-carboxylate and chlorosulfonyl isocyanate using the procedure described in example 1. $^1H$ NMR (DMSO-$d_6$): δ 10.31 (s, 1H), 7.43 (dd, J=8.3, 2.4 Hz, 1H), 7.27 (d, J=3.9 Hz, 1H), 7.20 (d, J=8.3 Hz, 1H), 7.07 (d, J=2.4 Hz, 1H), 7.03 (d, J=3.9 Hz, 2H), 6.77 (d, J=3.9 Hz, 2H), 6.34 (d, J=3.9 Hz, 1H), 4.23 (s, 2H), 1.38 (s, 9H); MS (ESI) m/z [M+H]$^+$ (586/588); MS (ESI) m/z [M–H]-(584/586); Anal. calcd for $C_{27}H_{21}Cl_2N_3O_4S_2$: C, 55.29; H, 3.61; N, 7.16. Found: C, 55.52; H, 3.63; N, 6.97.

EXAMPLE 43

5-[5,5-Bis(5-chlorothien-2-yl)-2-oxo-1,2,3,5-tetrahydro-4,1-benzoxazepin-7-yl]-H-pyrrole-2-carbonitrile Prepared from tert-butyl 2-[5,5-bis(5-chlorothien-2-yl)-2-oxo-1,2,3,5-tetrahydro-4,1-benzoxazepin-7-yl]-5-cyano-H-pyrrole-1-carboxylate generally according to the procedure of example 2. $^1H$ NMR (DMSO-$d_6$): δ 12.5 (br s, 1H), 10.23 (s, 1H), 7.70 (dd, J=8.5, 2.2 Hz, 1H), 7.50 (d, J=2.0 Hz, 1H), 7.20 (d, J=8.5 Hz, 1H), 7.09 (d, J=3.9 Hz, 2H), 6.96 (d, J=3.9 Hz, 1H), 6.94 (d, J=3.9 Hz, 2H), 6.54 (d, J=3.8 Hz, 1H), 4.21 (s, 2H). MS (ES) m/z 484/486 ([M–H]–); Anal. calcd for $C_{22}H_{13}Cl_2N_3O_2S_2$: C, 54.33; H, 2.69; N, 8.64. Found: C, 52.62; H, 3.30; N, 7.95.

EXAMPLE 44

5-[5,5-Bis(5-chlorothien-2-yl)-2-oxo-1,2,3,5-tetrahydro-4,1-benzoxazepin-7-yl]-1-methyl-H-pyrrole-2-carbonitrile Prepared from 5-[5,5-bis(5-chlorothien-2-yl)-2-oxo-1,2,3,5-tetrahydro-4,1-benzoxazepin-7-yl]-H-pyrrole-2-carbonitrile and iodomethane generally according to the procedure of example 3. $^1H$ NMR (DMSO-$d_6$): δ 10.04 (s, 1H), 7.53 (dd, J=8.3, 2.4 Hz, 1H), 7.27 (d, J=8.3 Hz, 1H), 7.11 (d, J=4.2 Hz, 1H), 7.05 (d, J=3.8 Hz, 2H), 6.99 (d, J=3.9 Hz, 1H), 6.83 (d, J=3.9 Hz, 2H), 6.23 (d, J=4.4 Hz, 1H), 4.27 (s, 2H), 3.56 (s, 3H); MS (ESI) m/z 498/500 ([M–H]–).

EXAMPLE 45

7-(3-Chloro-4-fluorophenyl)-5-(2-furyl)-5-(pentafluoroethyl)-1,5-dihydro-4,1-benzoxazepin-2(H)-one

1-(2-Amino-5-bromophenyl)-2,2,3,3,3-pentafluoropropan-1-one

A solution of BOC protected aniline (14 g, 72 mmol) in anhydrous ether (150 mL) at −15° C. under nitrogen was treated with a solution of t-butyllithium (1.7 M in pentane, 106 mL, 183 mmol). The reaction mixture was stirred at −15° C. for 4 hrs, cooled to −78° C., and treated with ethyl pentafluoropropionate (13 mL, 88 mmol). The mixture was allowed to slowly warm to rt and brine (500 mL) was added. The organic layer was separated, dried ($MgSO_4$), and concentrated. The residue was taken up in methylene chloride (100 mL) and treated with TFA (5 mL) at 0° C. under nitrogen. After 1.5 hrs, the solution was treated with a cold sodium bicarbonate solution (3N, 100 mL) and organic layer was separated, dried ($MgSO_4$), and concentrated. The crude residue (5 g, 21 mmol) was then taken up in methylene chloride (80 mL) and treated with NBS (3.6 g, 20 mmol) in portions at rt under nitrogen. After 1 hr, the solution was washed with aqueous 3N sodium bicarbonate solution (3×20 mL), dried ($MgSO_4$), and concentrated to give 1-(2-amino-5-bromophenyl)-2,2,3,3,3-pentafluoropropan-1-one as a yellow solid (6 g, 25% in three steps). $^1$H NMR (DMSO-$d_6$): δ 7.97 (s, 2H), 7.67 (d, J=2.3 Hz, 1H), 7.56 (dd, J=9.2, 2.2 Hz, 1H), 6.94 (d, J=9.3 Hz, 1H); MS (ESI) m/z 318/320 ([M+H]$^+$); MS (ESI) m/z 316/318 ([M−H]−); Anal. calcd for $C_9H_5BrF_5NO$: C, 33.99; H, 1.58; N, 4.40. Found: C, 34.27; H, 1.75; N, 4.22.

N-{4-Bromo-2-[2,2,3,3,3-pentafluoro-1-(2-furyl)-1-hydroxypropyl]phenyl}-2-chloroacetamide To a solution of furan (13 g, 190 mmol) in anhydrous THF (150 mL) was added n-butyllithium (2.5 M in hexane, 40 mL, 100 mmol) at 0° C. under nitrogen. The solution was stirred at 0° C. for 30 minutes, cooled to −78° C., and treated with a solution of 1-(2-amino-5-bromophenyl)-2,2,3,3,3-pentafluoropropan-1-one. The mixture was allowed to warm to −30° C., a saturated ammonium chloride solution (100 mL) was added and mixture was warmed to rt. Ethyl acetate (300 mL) was added and organic layer separated, dried ($MgSO_4$), and concentrated. The residue was dissolved in anhydrous THF. The resultant solution was cooled to 0° C., treated with triethylamine followed by addition of chloroacetyl chloride following the procedure described in example 1 to give N-{4-bromo-2-[2,2,3,3,3-pentafluoro-1-(2-furyl)-1-hydroxypropyl]phenyl}-2-chloroacetamide as a white solid. $^1$H NMR (DMSO-$d_6$): δ 10.54 (s, 1H), 9.11 (s, 1H), 8.18 (d, J=9.0 Hz, 1H), 7.79 (m, 1H), 7.64 (dd, J=8.8, 2.4 Hz, 1H), 7.21 (d, J=1.7 Hz, 1H), 6.71 (s, 1H), 6.58 (m, 1H), 4.35 (d, J=1.5 Hz, 2H). MS (ESI) m/z 462/464 ([M+H]+); MS (ESI) m/z 460/462 ([M−H]−).

7-Bromo-5-(2-furyl)-5-(pentafluoroethyl)-1,5-dihydro-4,1-benzoxazepin-2(H)-one Prepared from N-{4-bromo-2-[2,2,3,3,3-pentafluoro-1-(2-furyl)-1-hydroxypropyl]phenyl}-2-chloroacetamide using the procedure described in example 1. $^1$H NMR (DMSO-$d_6$): δ 10.33 (s, 1H), 7.93 (s, 1H), 7.68 (dd, J=8.6, 2.0 Hz, 1H), 7.49 (s, 1H), 7.20 (d, J=8.7 Hz, 1H), 6.75 (d, J=2.9 Hz, 1H), 6.64 (m, 1H), 4.49 (d, J=14.8 Hz, 1H), 4.14 (d, J=14.9 hz, 1H); MS (ESI) m/z 426/428 ([M+H]+); MS (ESI) m/z 424/426 ([M−H]−).

The title compound was prepared from 7-bromo-5-(2-furyl)-5-(pentafluoroethyl)-1,5-dihydro-4,1-benzoxazepin-2 (H)-one and 3-chloro-4-fluorophenyl boronic acid generally according to the coupling procedure described in example 1. $^1$H NMR (DMSO-$d_6$): δ 10.36 (s, 1H), 7.93 (d, J=1.3 Hz, 1H), 7.82 (dd, J=8.5, 2.1 Hz, 1H), 7.72 (dd, J=7.8, 1.8 Hz, 1H), 7.45-7.58 (m, 3H), 7.36 (d, J=8.6 Hz, 1H), 6.78 (d, J=3.4 Hz, 1H), 6.63 (dd, J=3.5, 1.8 Hz, 1H), 4.49 (d, J=14.8 Hz, 1H), 4.12 (d, J=14.8 Hz, 1H); MS (ESI) m/z 474/476 ([M−H]−).

EXAMPLE 46

3-Fluoro-5-[5-(2-furyl)-2-oxo-5-(pentafluoroethyl)-1,2,3,5-tetrahydro-4,1-benzoxazepin-7-yl]benzonitrile Prepared from 7-bromo-5-(2-furyl)-5-(pentafluoroethyl)-1,5-dihydro-4,1-benzoxazepin-2(H)-one and 3-cyano-5-fluorophenyl boronic acid generally according to the coupling procedure described in example 1. $^1$H NMR (DMSO-$d_6$): δ 10.41 (s, 1H), 7.84-7.94 (m, 4H), 7.76 (td, J=10.1, 2.1 Hz, 1H), 7.68 (d, J=1.7 Hz, 1H), 7.36 (d, J=8.6 Hz, 1H), 6.84 (d, J=3.4 Hz, 1H), 6.64 (dd, J=3.4, 1.8 Hz, 1H), 4.45 (d, J=14.9 Hz, 1H), 4.14 (d, J=14.8 Hz, 1H); MS (ESI) m/z 467 ([M+H]+); MS (ESI) m/z 465 ([M−H]−); Anal. calcd for $C_{22}H_{12}F_6N_2O_3$: C, 56.66; H, 2.59; N, 6.01. Found: C, 56.64; H, 2.85; N, 5.61.

EXAMPLE 47

7-(3-Chloro-4-fluorophenyl)-5,5-dimethyl-1,5-dihydro-4,1-benzoxazepin-2(H)-one Prepared from 7-bromo-5,5-dimethyl-1,5-dihydro-4,1-benzoxazepin-2(H)-one and 3-chloro-4-fluorophenyl boronic acid generally according to the coupling procedure described in example 1. A white solid: mp 170-171° C.; $^1$H NMR (DMSO-$d_6$): δ 10.01 (s, 1H), 7.93 (dd, J=8.1, 2.3 Hz, 1H), 7.68 (m, 1H), 7.44-7.59 (m, 3H), 7.18 (d, J=8.4 Hz, 1H), 4.25 (s, 2H), 1.63 (s, 6H). MS (ESI) m/z 318 ([M−H]−); Anal. calcd for $C_{17}H_{15}ClFNO_2$: C, 63.86; H, 4.73; N, 4.38. Found: C, 63.54; H, 4.72; N, 4.11.

EXAMPLE 48

7-(3-Fluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(H)-one and 3-fluorophenyl boronic acid generally according to the coupling procedure described in example 1. A white solid: mp 196-197° C.; $^1$H NMR (DMSO-$d_6$): δ 9.98 (s, 1H), 7.43-7.58 (m, 5H), 7.12-7.20 (m, 2H), 4.23 (s, 2H), 1.63 (s, 6H). MS (ESI) m/z 286 ([M+H]+); Anal. calcd for $C_{17}H_{16}FNO_2$: C, 71.56; H, 5.65; N, 4.91. Found: C, 71.54; H, 5.77; N, 4.82.

EXAMPLE 49

H-Fluoren-9-ylmethyl 7-(5-cyano-H-pyrrol-2-yl)-5-methyl-5-thien-2-yl-2,3-dihydro-4,1-benzoxazepine-1(H)-carboxylate

7-Bromo-5-methyl-5-thien-2-yl-1,2,3,5-tetrahydro-4,1-benzoxazepine

To a solution of 7-bromo-5-methyl-5-thien-2-yl-1,5-dihydro-4,1-benzoxazepin-2(3H)-one (5 g, 14.6 mmol) in anhydrous THF (100 mL) was added lithium aluminum hydride (0.2 g, 5.2 mmol) at rt under nitrogen. After addition, the mixture was stirred for 3 hrs and treated with aqueous ammonium chloride solution (200 mL). Ethyl acetate (300 mL) was added. Organic layer was separated, dried (MgSO$_4$), and concentrated to afford 7-bromo-5-methyl-5-thien-2-yl-1,2,3,5-tetrahydro-4,1-benzoxazepine as an oil (4 g, 85%). A white solid as a HCl salt: $^1$H NMR (DMSO-d$_6$): δ 7.52 (dd, J=5.0, 0.8 Hz, 1H), 7.31 (dd, J=8.5, 2.1 Hz, 1H), 7.12 (d, J=2.1 Hz, 1H), 6.95-7.04 (m, 2H), 6.78 (dd, J=3.5, 0.9 Hz, 1H), 3.61-3.85 (m, 4H), 3.12 (m, 2H), 2.93 (s, 3H); MS (ESI) m/z 324/326 ({M+H}+); Anal. calcd for C$_{14}$H$_{14}$BrNOS HCl: C, 46.62; H, 4.19; N, 3.88. Found: C, 46.70; H, 3.99; N, 3.83.

tert-Butyl 2-(5-methyl-5-thien-2-yl-1,2,3,5-tetrahydro-4,1-benzoxazepin-7-yl)-H-pyrrole-1-carboxylate Prepared from 7-bromo-5-methyl-5-thien-2-yl-1,2,3,5-tetrahydro-4,1-benzoxazepine and 2-borono-1H-pyrrole-1-carboxylic acid, 1-tert-butyl ester using the coupling procedure described in example 1. $^1$H NMR (DMSO-d$_6$): δ 7.46 (dd, J=5.0, 0.8 Hz, 1H), 7.23 (dd, J=3.2, 1.8 Hz, 1H), 7.02 (dd, J=8.1, 1.9 Hz, 1H), 6.91 (dd, J=5.0, 3.6 Hz, 1H), 6.87 (m, 2H), 6.72 (dd, J=3.4, 0.8 Hz, 1H), 6.18 (t, J=3.3 Hz, 1H), 6.08 (dd, J=3.2, 1.7 Hz, 1H), 5.68 (m, 1H), 3.85 (m, 1H), 3.72 (m, 1H), 3.02 (m, 2H), 1.94 (m, 3H), 1.35 (s, 9H); MS (ESI) m/z 411 ([M+H]+); Anal. calcd for C$_{23}$H$_{26}$N$_2$O$_3$S: C, 67.29; H, 6.38; N, 6.82. Found: C, 67.20; H, 6.32; N, 6.74.

H-Fluoren-9-ylmethyl 7-(5-cyano-H-pyrrol-2-yl)-5-methyl-5-thien-2-yl-2,3-dihydro-4,1-benzoxazepine-1(H)-carboxylate A mixture of tert-butyl 2-(5-methyl-5-thien-2-yl-1,2,3,5-tetrahydro-4,1-benzoxazepin-7-yl)-H-pyrrole-1-carboxylate (4 g, 9.74 mmol), 9-fluorenylmethyl chloroformate (3.8, 15 mmol), and a saturated sodium bicarbonate solution (50 mL) in dioxane (50 mL) was stirred for 3 hrs. A saturated aqueous ammonium chloride solution (100 mL) and ethyl acetate (200 mL) were added. Organic layer was separated, dried (MgSO$_4$), and concentrated. The residue obtained was dissolved in anhydrous THF and treated with chlorosulfonyl isocyanate following the procedure described in example 1. Using the deprotection procedure described in example 1, the BOC group of cyanation product was removed to afford H-fluoren-9-ylmethyl 7-(5-cyano-H-pyrrol-2-yl)-5-methyl-5-thien-2-yl-2,3-dihydro-4,1-benzoxazepine-1(H)-carboxylate as off-white solid: MS (ESI) m/z 558 ([M+H]+); MS (ESI) m/z 556 ([M−H]−).

EXAMPLE 50

1-Methyl-5-(5-methyl-5-thien-2-yl-1,2,3,5-tetrahydro-4,1-benzoxazepin-7-yl)-H-pyrrole-2-carbonitrile Methylation of H-fluoren-9-ylmethyl 7-(5-cyano-H-pyrrol-2-yl)-5-methyl-5-thien-2-yl-2,3-dihydro-4,1-benzoxazepine-1(H)-carboxylate was effected generally according to the procedure described in example 3. The crude methylation product (0.2 g, 0.035 mmol) was dissolved in DMF (16 mL) and piperidine (4 mL) was added at rt under nitrogen. The reaction solution was stirred at rt under nitrogen for 50 minutes. A saturated aqueous sodium bicarbonate solution (20 mL) and ethyl acetate (50 mL) were added. The organic layer was separated, dried (MgSO$_4$), and concentrated. The residue was purified on a silica gel column (hexane:ethyl acetate/3:1) to give the title compound as a white solid (25 mg, 20%). $^1$H NMR (DMSO-d$_6$): δ 7.49 (dd, J=5.0, 0.9 Hz, 1H), 7.18 (dd, J=8.2, 2.0 Hz, 1H), 7.03 (d, J=2.0 Hz, 1H), 6.96 (m, 3H), 6.78 (dd, J=3.4, 0.9 Hz, 1H), 6.18 (d, J=4.0 Hz, 1H), 5.96 (s, 1H), 3.86 (m, 1H), 3.75 (m, 1H), 3.61 (s, 3H), 3.02 (m, 2H), 1.95 (s, 3H); MS (ESI) m/z 350 ([M+H]−).

EXAMPLE 51

5-(5-Methyl-5-thien-2-yl-1,2,3,5-tetrahydro-4,1-benzoxazepin-7-yl)-H-pyrrole-2-carbonitrile Prepared from H-fluoren-9-ylmethyl 7-(5-cyano-H-pyrrol-2-yl)-5-methyl-5-thien-2-yl-2,3-dihydro-4,1-benzoxazepine-1(H)-carboxylate using the deprotection procedure described in example 50. $^1$H NMR (DMSO-d$_6$): δ 12.38 (s, 1H), 7.41-7.54 (m, 3H), 6.85-6.94 (m, 3H), 6.63 (dd, J=3.4, 1.1 Hz, 1H), 6.45 (dd, J=3.6, 2.5 Hz, 1H), 3.72 (m, 1H), 3.61 (m, 1H), 2.91-3.13 (m, 2H), 2.01 (s, 3H). MS (ESI) m/z 336 ([M+H]$^+$); MS (ESI) m/z 334, ([M−H]−).

EXAMPLE 52 tert-Butyl 2-cyano-5-(5-ethyl-2-oxo-5-thien-2-yl-1,2,3,5-tetrahydro-4,1-benzoxazepin-7-yl)-1H-pyrrole-1-carboxylate (2-Amino-5-bromophenyl)(2-thienyl)methanone Prepared from 5-bromo anthranilic acid using the procedure described in example 1. $^1$H-NMR (CDCl$_3$) δ 7.86 (d, J=2.3 Hz, 1H), 7.71 (dd, J=5.0, 1.0 Hz, 1H), 7.59 (dd, J=3.8, 1.0 Hz, 1H), 7.39 (dd, J=8.8, 2.4 Hz, 1H), 7.19 (m, 1H), 6.66 (d, J=8.8 Hz, 1H), 5.71 (s, 2H); MS (ES) m/z 280 (M−H)$^-$.

N-[4-Bromo-2-(1-hydroxy-1-thien-2-ylpropyl)phenyl]-2-chloroacetamide 1-(2-Amino-5-bromophenyl)-1-thiophen-2-yl-propan-1-ol was prepared from (2-amino-5-bromophenyl)(2-thienyl)methanone using the procedure described in example 1.

The title compound was prepared from 1-(2-amino-5-bromophenyl)-1-thiophen-2-yl-propan-1-ol and chloroacetyl chloride using the procedure described in example 1. $^1$H-NMR (CDCl$_3$) δ 10.23 (s, 1H), 8.11 (d, J=8.7 Hz, 1H), 7.46 (dd, J=8.7, 2.3 Hz, 1H), 7.37 (d, J=2.3 Hz, 1H), 7.29 (dd, J=5.1, 1.0 Hz, 1H), 6.97 (m, 1H), 6.90 (dd, J=3.5, 1.0 Hz, 1H), 4.09 (m, 2H), 2.80 (s, 1H), 2.43 (m, 2H), 1.03 (t, J=7.3 Hz, 3H); MS (ES) m/z 386 (M−H)$^-$; Anal Calc. For C$_{15}$H$_{15}$BrClNO$_2$S: C, 46.35, H, 3.89; N, 3.60. Found: C, 46.67, H, 3.80; N, 3.52.

7-Bromo-5-ethyl-5-thien-2-yl-1,5-dihydro-4,1-benzoxazepin-2(3H)-one

Prepared from N-[4-bromo-2-(1-hydroxy-1-thien-2-yl-propyl)phenyl]-2-chloroacetamide using the procedure described in example 1. $^1$H-NMR (CDCl$_3$) δ 7.80 (br s, 1H), 7.39 (m, 3H), 6.97 (m, 1H), 6.81 (m, 2H), 4.19 (d, J=16.0 Hz, 1H), 4.05 (d, J=16.0 Hz, 1H), 2.58 (m, 2H), 2.31 (m, 1H), 0.87 (t, J=7.2 Hz, 3H); MS (ES) m/z 350 (M−H)$^-$.

tert-Butyl 2-(5-ethyl-2-oxo-5-thien-2-yl-1,2,3,5-tetrahydro-4,1-benzoxazepin-7-yl)-1H-pyrrole-1-carboxylate Prepared from 7-bromo-5-ethyl-5-thien-2-yl-1,5-dihydro-4,1-benzoxazepin-2(3H)-one and 2-borono-1H-pyrrole-1-carboxylic acid, 1-tert-butyl ester using the procedure described in example 1. $^1$H-NMR (CDCl$_3$) δ 7.58 (br s, 1H), 7.34 (t, J=3.1 Hz, 1H), 7.29 (m, 3H), 6.91 (d, J=3.1 Hz, 2H), 6.85 (d, J=8.1 Hz, 1H), 6.20 (t, J=3.3 Hz, 1H), 6.16 (m, 1H), 4.22 (d, J=15.8 Hz, 1H), 4.06 (d, J=15.8 Hz, 1H), 2.54 (m, 1H), 2.30 (m, 1H), 1.46 (s, 9H), 0.89 (t, J=7.2 Hz, 3H); MS (ES) m/z 437 (M–H)⁻; Anal Calc. For $C_{24}H_{26}N_2O_4S$: C, 65.73, H, 5.98; N, 6.39. Found: C, 65.64, H, 5.81; N, 6.36.

The title compound was prepared from tert-butyl 2-(5-ethyl-2-oxo-5-thien-2-yl-1,2,3,5-tetrahydro-4,1-benzoxazepin-7-yl)-1H-pyrrole-1-carboxylate using the procedure described in example 1. ¹H-NMR (CDCl₃) δ 7.68 (br s, 1H), 7.36 (d, J=4.9 Hz, 1H), 7.27 (m, 1H), 7.22 (d, J=1.8 Hz, 1H), 6.95 (d, J=3.7 Hz, 1H), 6.92 (m, 3H), 6.23 (d, J=3.7 Hz, 1H), 4.21 (d, J=16.1 Hz, 1H), 4.07 (d, J=16.1 Hz, 1H), 2.56 (m, 1H), 2.28 (m, 1H), 1.57 (s, 9H), 0.88 (t, J=7.2 Hz, 3H); MS (ES) m/z 462 (M–H)⁻; Anal. Calc. For $C_{25}H_{25}N_3O_4S$: C, 64.78, H, 5.44; N, 9.06. Found: C, 64.88, H, 5.40; N, 8.89.

EXAMPLE 53

5-(5-Ethyl-2-oxo-5-thien-2-yl-1,2,3,5-tetrahydro-4,1-benzoxazepin-7-yl)-1H-pyrrole-2-carbonitrile Prepared from tert-butyl 2-cyano-5-(5-ethyl-2-oxo-5-thien-2-yl-1,2,3,5-tetrahydro-4,1-benzoxazepin-7-yl)-1H-pyrrole-1-carboxylate using the procedure described in example 2. ¹H-NMR (DMSO-d₆) δ 12.57 (s, 1H), 10.05 (s, 1H), 7.67 (m, 2H), 7.58 (d, J=5.0 Hz, 1H), 7.20 (d, J=4.5 Hz, 1H), 7.01 (m, 2H), 6.90 (d, J=3.2 Hz, 1H), 6.69 (d, J=3.8 Hz, 1H), 4.08 (d, J=15.5 Hz, 1H), 3.98 (d, J=15.5 Hz, 1H), 2.50 (m, 2H), 0.78 (t, J=7.0 Hz, 3H); MS (ES) m/z 362 (M–H)⁻.

EXAMPLE 54

5-(5-Ethyl-2-oxo-5-thien-2-yl-1,2,3,5-tetrahydro-4,1-benzoxazepin-7-yl)-1-methyl-1H-pyrrole-2-carbonitrile Prepared from 5-(5-ethyl-2-oxo-5-thien-2-yl-1,2,3,5-tetrahydro-4,1-benzoxazepin-7-yl)-1H-pyrrole-2-carbonitrile using the procedure described in example 3. ¹H-NMR (DMSO-d₆) δ 10.14 (s, 1H), 7.56 (d, J=4.8 Hz, 1H), 7.44 (dd, J=8.3, 1.6 Hz, 1H), 7.33 (s, 1H), 7.28 (d, J=8.5 Hz, 1H), 7.01 (m, 3H), 6.30 (d, J=4.0 Hz, 1H), 4.14 (d, J=15.4 Hz, 1H), 4.00 (d, J=15.4 Hz, 1H), 3.65 (s, 3H), 2.50 (m, 2H), 0.79 (t, J=7.0 Hz, 3H); MS (ES) m/z 376 (M–H)⁻.

EXAMPLE 55

7-(3-Chloro-4-fluoro-phenyl)-5-ethyl-5-thiophen-2-yl-1,5-dihydro-benzo[e][1,4]oxazepin-2-one Prepared from 7-bromo-5-ethyl-5-thien-2-yl-1,5-dihydro-4,1-benzoxazepin-2(3H)-one and 3-chloro-4-fluorobenzeneboronic acid using the coupling procedure described in example 1. ¹H-NMR (DMSO-d₆) δ 10.08 (s, 1H), 7.85 (dd, J=7.1, 2.2 Hz, 1H), 7.65 (m, 2H), 7.57 (dd, J=5.0, 1.0 Hz, 1H), 7.52 (m, 2H), 7.26 (d, J=8.5 Hz, 1H), 7.01 (m, 2H), 4.11 (d, J=15.4 Hz, 1H), 3.95 (d, J=15.4 Hz, 1H), 2.41 (m, 2H), 0.78 (t, J=7.0 Hz, 3H); MS (ES) m/z 400 (M–H)⁻.

EXAMPLE 56

3-(5-ethyl-2-oxo-5-thiophen-2-yl-1,2,3,5-tetrahydro-benzo[e][1,4]oxazepin-7-yl)-5-fluoro-benzonitrile Prepared from 7-bromo-5-ethyl-5-thien-2-yl-1,5-dihydro-4,1-benzoxazepin-2(3H)-one and 5-fluoro-3-cyanobenzeneboronic acid using the coupling procedure described in example 1. ¹H-NMR (DMSO-d₆) δ 10.12 (s, 1H), 8.07 (s, 1H), 7.95 (dt, J=10.3, 2.0 Hz, 1H), 7.81 (m, 2H), 7.69 (d, J=2.0 Hz, 1H), 7.57 (dd, J=5.0, 0.9 Hz, 1H), 7.29 (d, J=8.5 Hz, 1H), 7.01 (m, 1H), 6.95 (m, 1H), 4.10 (d, J=15.5 Hz, 1H), 4.01 (d, J=15.5 Hz, 1H), 2.65 (m, 2H), 0.78 (t, J=7.0 Hz, 3H); MS (ES) m/z 391 (M–H)⁻.

EXAMPLE 57 tert-Butyl 2-cyano-5-(2-oxo-5-thien-2-yl-1,2,3,5-tetrahydro-4,1-benzoxazepin-7-yl)-1H-pyrrole-1-carboxylate (2-Amino-5-bromophenyl)(2-thienyl)methanol Prepared from (2-amino-5-bromophenyl)(2-thienyl)methanone using the procedure described in example 11. ¹H-NMR (CDCl₃) δ 7.33 (m, 2H), 7.25 (dd, J=8.5, 2.4 Hz, 1H), 7.00 (m, 1H), 6.92 (d, J=2.5 Hz, 1H), 6.59 (d, J=8.4 Hz, 1H), 6.0 (s, 1H), 3.95 (br s, 2H), 2.75 (br s, 1H); MS (ES) m/z 266 (M–H₂O)⁺; Anal. Calc. For $C_{11}H_{10}BrNOS$: C, 46.49, H, 3.55; N, 4.93. Found: C, 46.77, H, 3.54; N, 4.68.

7-Bromo-5-thien-2-yl-1,5-dihydro-4,1-benzoxazepin-2(3H)-one

Prepared from (2-amino-5-bromophenyl)(2-thienyl)methanol in two steps using the procedure described in example 1. ¹H-NMR (CDCl₃) δ 8.30 (s, 1H), 7.42 (m, 2H), 7.14 (d, J=2.2 Hz, 1H), 7.05 (m, 1H), 6.90 (d, J=3.6 Hz, 1H), 6.87 (d, J=8.5 Hz, 1H), 6.09 (s, 1H), 4.53 (m, 2H); MS (ES) m/z 322 (M–H)⁻.

tert-Butyl 2-(2-oxo-5-thien-2-yl-1,2,3,5-tetrahydro-4,1-benzoxazepin-7-yl)-1H-pyrrole-1-carboxylate Prepared from 7-bromo-5-thien-2-yl-1,5-dihydro-4,1-benzoxazepin-2(3H)-one and 2-borono-1H-pyrrole-1-carboxylic acid, 1-tert-butyl ester using the procedure described in example 1. ¹H-NMR (CDCl₃) δ 8.05 (s, 1H), 7.37 (dd, J=5.0, 1.0 Hz, 1H), 7.30 (m, 2H), 7.01 (m, 2H), 6.93 (m, 2H), 6.19 (t, J=3.3 Hz, 1H), 6.14 (s, 1H), 6.12 (m, 1H), 4.56 (m, 2H), 1.41 (s, 9H); MS (ES) m/z 409 (M–H)⁻; Anal. Calcd. For $C_{22}H_{22}N_2O_4S$: C, 64.37, H, 5.4; N, 6.82. Found: C, 64.05, H, 5.4; N, 6.7.

The title compound was prepared from tert-butyl 2-(2-oxo-5-thien-2-yl-1,2,3,5-tetrahydro-4,1-benzoxazepin-7-yl)-1H-pyrrole-1-carboxylate using the procedure described in example 1. ¹H-NMR (CDCl₃) δ 8.27 (s, 1H), 7.40 (dd, J=5.0, 1.0 Hz, 1H), 7.29 (m, 1H), 7.02 (m, 3H), 6.94 (d, J=3.7 Hz, 2H), 6.18 (d, J=3.7 Hz, 1H), 6.14 (s, 1H), 4.58 (m, 2H), 1.49 (s, 9H); MS (ES) m/z 434 (M–H)⁻.

EXAMPLE 58

5-(2-Oxo-5-thien-2-yl-1,2,3,5-tetrahydro-4,1-benzoxazepin-7-yl)-1H-pyrrole-2-carbonitrile Prepared from tert-butyl 2-cyano-5-(2-oxo-5-thien-2-yl-1,2,3,5-tetrahydro-4,1-benzoxazepin-7-yl)-1H-pyrrole-1-carboxylate using the procedure described in example 2. ¹H-NMR (DMSO-d₆) δ 12.56 (s, 1H), 10.34 (s, 1H), 7.65 (m, 2H), 7.41 (d, J=1.8 Hz, 1H), 7.24 (d, J=8.5 Hz, 1H), 7.07 (m, 1H), 6.97 (m, 2H), 6.50 (d, J=3.8 Hz, 1H), 6.30 (s, 1H), 4.48 (d, J=16.3 Hz, 1H), 4.20 (d, J=16.3 Hz, 1H); MS (ES) m/z 334 (M−H)−.

EXAMPLE 59

1-Methyl-5-(2-oxo-5-thien-2-yl-1,2,3,5-tetrahydro-4,1-benzoxazepin-7-yl)-1H-pyrrole-2-carbonitrile Prepared from 5-(2-oxo-5-thien-2-yl-1,2,3,5-tetrahydro-4,1-benzoxazepin-7-yl)-1H-pyrrole-2-carbonitrile using the procedure described in example 3. $^1$H-NMR (DMSO-$d_6$) δ 10.44 (s, 1H), 7.62 (d, J=5.0 Hz, 1H), 7.47 (dd, J=8.3, 2.0 Hz, 1H), 7.30 (d, J=8.3 Hz, 1H), 7.08 (m, 1H), 7.04 (m, 2H), 6.33 (s, 1H), 6.22 (d, J=4.0 Hz, 1H), 4.56 (d, J=16.5 Hz, 1H), 4.32 (d, J=16.5 Hz, 1H), 3.61 (s, 3H); MS (ES) m/z 348 (M−H)−.

EXAMPLE 60

7-(3-Chlorophenyl)-5-thien-2-yl-1,5-dihydro-4,1-benzoxazepin-2(3H)-one

Prepared from 7-bromo-5-thien-2-yl-1,5-dihydro-4,1-benzoxazepin-2(3H)-one and 3-chlorobenzeneboronic acid generally according to the procedure described in example 1. $^1$H-NMR (CDCl$_3$) δ 8.26 (br s, 1H), 7.51 (dd, J=8.3, 2.1 Hz, 1H), 7.45 (d, J=0.9 Hz, 1H), 7.42 (dd, J=5.1, 0.9 Hz, 1H), 7.36 (m, 3H), 7.24 (d, J=2.0 Hz, 1H), 7.05 (m, 2H), 6.93 (d, J=3.5 Hz, 1H), 6.24 (s, 1H), 4.56 (d, J=17.0 Hz, 1H), 4.47 (d, J=17.0 Hz, 1H); MS (ES) m/z 356 (M+H)+; Anal. Calc. For C$_{19}$H$_{14}$ClNO$_2$S: C, 64.13, H, 3.97; N, 3.94. Found: C, 64.1, H, 3.83; N, 3.99.

EXAMPLE 61 tert-Butyl 2-cyano-5-(5-methyl-2-oxo-5-pyridin-2-yl-1,2,3,5-tetrahydro-4,1-benzoxazepin-7-yl)-1H-pyrrole-1-carboxylate 1-(2-Amino-5-bromophenyl)-1-pyridin-2-ylethanol Prepared from 2-amino-5-bromophenyl methyl ketone and 2-pyridyllithium generally according to the procedure described in example 1. $^1$H NMR (DMSO-$d_6$): δ 8.5 (d, J=3.99 Hz, 1H), 7.77 (dt, J=7.77, 1.79 Hz, 1H), 7.64 (d, J=7.96 Hz, 1H), 7.30 (d, J=2.37 Hz, 1H), 7.21-7.25 (m, 1H), 7.06 (dd, J=8.49, 2.36 Hz, 1H), 6.47 (d, J=8.51 Hz, 1H), 6.18 (s, 1H), 5.26 (s, 2H), 1.8 (s, 3H); MS (ESI) m/z 293/295, 1 Br pattern ([M+H]+).

N-[4-Bromo-2-(1-hydroxy-1-pyridin-2-ylethyl)phenyl]-2-chloroacetamide

Prepared from 1-(2-amino-5-bromophenyl)-1-pyridin-2-ylethanol using the procedure described in example 1. $^1$H-NMR (CDCl$_3$) δ 10.00 (s, 1H), 8.58 (d, J=4.9 Hz, 1H), 7.93 (d, J=8.7 Hz, 1H), 7.63 (m, 2H), 7.52 (dd, J=8.7, 2.2 Hz, 1H), 7.26 (m, 1H), 6.91 (d, J=7.8 Hz, 1H), 6.05 (s, 1H), 3.97 (d, J=15.2 Hz, 1H), 3.66 (d, J=15.2 Hz, 1H), 1.87 (s, 3H); MS (ES) m/z 367 (M−H)−.

7-Bromo-5-methyl-5-pyridin-2-yl-1,5-dihydro-4,1-benzoxazepin-2(3H)-one

Prepared from N-[4-bromo-2-(1-hydroxy-1-pyridin-2-ylethyl)phenyl]-2-chloroacetamide using the procedure described in example 1. $^1$H-NMR (CDCl$_3$) δ 8.50 (dt, J=4.8, 0.8 Hz, 1H), 7.72 (td, J=7.5, 1.6 Hz, 1H), 7.63 (d, J=7.4 Hz, 1H), 7.55 (m, 2H), 7.42 (dd, J=8.4, 2.1 Hz, 1H), 7.20 (m, 1H), 6.79 (d, J=8.5 Hz, 1H), 4.37 (d, J=14.5 Hz, 1H), 4.30 (d, J=14.5 Hz, 1H), 1.97 (s, 3H); MS (ES) m/z 333 (M−H)+; Anal. Calc. For C$_{15}$H$_{13}$BrN$_2$O$_2$: C, 54.07, H, 3.93; N, 8.14. Found: C, 53.96, H, 4.02; N, 8.14.

tert-Butyl 2-(5-methyl-2-oxo-5-pyridin-2-yl-1,2,3,5-tetrahydro-4,1-benzoxazepin-7-yl)-1H-pyrrole-1-carboxylate Prepared from 7-bromo-5-methyl-5-pyridin-2-yl-1,5-dihydro-4,1-benzoxazepin-2(3H)-one and 2-borono-1H-pyrrole-1-carboxylic acid, 1-tert-butyl ester using the coupling procedure described in example 1. $^1$H-NMR (CDCl$_3$) δ 8.52 (d, J=0.6 Hz, 1H), 7.69 (td, J=7.9, 1.8 Hz, 1H), 7.60 (m, 1H), 7.35 (m, 3H), 7.26 (m, 1H), 7.18 (m, 1H), 6.86 (d, J=8.2 Hz, 1H), 6.22 (m, 1H), 6.18 (m, 1H), 4.36 (s, 2H), 2.01 (s, 3H), 1.41 (s, 9H); MS (ES) m/z 418 (M−H)−.

The title compound was prepared from tert-butyl 2-(5-methyl-2-oxo-5-pyridin-2-yl-1,2,3,5-tetrahydro-4,1-benzoxazepin-7-yl)-1H-pyrrole-1-carboxylate using the procedure described in example 1. $^1$H-NMR (DMSO-$d_6$) δ 10.05 (s, 1H), 8.46 (d, J=1.3 Hz, 1H), 7.80 (td, J=2.7, 1.6 Hz, 1H), 7.55 (d, J=4.0 Hz, 1H), 7.35 (m, 4H), 7.11 (d, 8.2 Hz, 1H), 6.45 (d, J=4.0 Hz, 1H), 4.35 (d, J=14.3 Hz, 1H), 4.18 (d, J=14.3 Hz, 1H), 1.9 (s, 3H), 1.39 (s, 9H); MS (ES) m/z 443 (M−H)−.

EXAMPLE 62

5-(5-Methyl-2-oxo-5-pyridin-2-yl-1,2,3,5-tetrahydro-4,1-benzoxazepin-7-yl)-1H-pyrrole-2-carbonitrile Prepared from tert-butyl 2-cyano-5-(5-methyl-2-oxo-5-pyridin-2-yl-1,2,3,5-tetrahydro-4,1-benzoxazepin-7-yl)-1H-pyrrole-1-carboxylate using the procedure described in example 2. $^1$H-NMR (DMSO-$d_6$) δ 12.64 (s, 1H), 9.94 (s, 1H), 8.47 (d, J=3.9 Hz, 1H), 7.81 (td, J=7.7, 1.8 Hz, 1H), 7.70 (d, J=1.8 Hz, 1H), 7.65 (dd, J=8.3, 1.9 Hz, 1H), 7.54 (d, J=8.0 Hz, 1H), 7.29 (m, 1H), 7.09 (d, J=8.4 Hz, 1H), 6.99 (d, J=3.8 Hz, 1H), 6.66 (d, J=3.8 Hz, 1H), 4.30 (d, J=14.4 Hz, 1H), 4.10 (d, J=14.4 Hz, 1H), 1.99 (s, 3H); MS (ES) m/z 343 (M−H)−.

EXAMPLE 63

1-Methyl-5-(5-methyl-2-oxo-5-pyridin-2-yl-1,2,3,5-tetrahydro-4,1-benzoxazepin-7-yl)-1H-pyrrole-2-carbonitrile Prepared from 5-(5-methyl-2-oxo-5-pyridin-2-yl-1,2,3,5-tetrahydro-4,1-benzoxazepin-7-yl)-1H-pyrrole-2-carbonitrile using the procedure described in example 3. $^1$H-NMR (DMSO-$d_6$) δ 10.07 (s, 1H), 8.50 (d, J=4.7 Hz, 1H), 7.82 (td, J=7.8, 1.8 Hz, 1H), 7.58 (d, J=8.0 Hz, 1H), 7.42 (m, 2H), 7.30 (m, 1H), 7.18 (d, J=8.2 Hz, 1H), 7.02 (d, J=4.1 Hz, 1H), 6.30 (d, J=4.1 Hz, 1H), 4.38 (d, J=14.7 Hz, 1H), 4.20 (d, J=14.7 Hz, 1H), 3.65 (s, 3H), 1.99 (s, 3H); MS (ES) m/z 357 (M−H)−.

EXAMPLE 64 tert-Butyl 2-cyano-5-(9-fluoro-5-methyl-2-oxo-5-thien-2-yl-1,2,3,5-tetrahydro-4,1-benzoxazepin-7-yl)-1H-pyrrole-1-carboxylate tert-Butyl 2-acetyl-4-bromo-6-fluorophenylcarbamate Prepared from 5-bromo-2-[(tert-butoxycarbonyl)amino]-3-fluorobenzoic acid generally according to the procedure described in the literature (Zhang et al. *Tetrahedron Lett.* (2001), 42(11), 2097-2099). $^1$H-NMR (DMSO-d$_6$) δ 9.18 (s, 1H), 7.80 (dd, J=9.5, 2.2 Hz, 1H), 7.63 (d, J=1.6 Hz, 1H), 2.46 (s, 3H), 1.44 (s, 9H); MS (ES) m/z 332 (M+H)$^+$.

1-(2-Amino-5-bromo-3-fluorophenyl) ethnanone

Prepared from tert-butyl 2-acetyl-4-bromo-6-fluorophenylcarbamate by treatment with TFA in methylene chloride. $^1$H-NMR (DMSO-d$_6$) δ 7.75 (s, 1H), 7.58 (dd, J=9.5, 2.2 Hz, 1H), 7.09 (br s, 2H), 2.55 (s, 3H); MS (ES) m/z 390 (M–H)$^-$ N-[4-Bromo-2-fluoro-6-(1-hydroxy-1-thien-2-yl-ethyl)phenyl]-2-chloroacetamide Prepared from 1-(2-amino-5-bromo-3-fluorophenyl)ethnanone in two steps using the procedure described in example 1. $^1$H-NMR (DMSO-d$_6$) δ 9.27 (s, 1H), 7.63 (dd, J=9.3, 2.1 Hz, 1H), 7.53 (s, 1H), 7.40 (dd, J=5.1, 1.1 Hz, 1H), 6.90 (m, 1H), 6.81 (s, 1H), 6.76 (dd, J=3.5, 1.1 Hz, 1H), 4.13 (d, J=14.3 Hz, 1H), 4.04 (d, J=14.3 Hz, 1H), 1.89 (s, 3H); MS (ES) m/z 390 (M–H)$^-$; Anal. Calc. For C$_{14}$H$_{12}$BrClFNO$_2$S: C, 42.82, H, 3.08; N, 3.57. Found: C, 42.76, H, 3.03; N, 3.41.

7-Bromo-9-fluoro-5-methyl-5-thien-2-yl-1,5-dihydro-4,1-benzoxazepin-2(3H)-one

Prepared from N-[4-bromo-2-fluoro-6-(1-hydroxy-1-thien-2-ylethyl)phenyl]-2-chloroacetamide using the procedure described in example 1. $^1$H-NMR (DMSO-d$_6$) δ 9.66 (s, 1H), 7.65 (dd, J=10.0, 2.2 Hz, 1H), 7.53 (dd, J=5.0, 1.1 Hz, 1H), 7.34 (m, 1H), 6.99 (m, 1H), 6.90 (m, 1H), 4.23 (d, J=14.8 Hz, 1H), 4.11 (d, J=14.8 Hz, 1H), 1.98 (s, 3H); MS (ES) m/z 354 (M–H)$^-$; Anal. Calc. For C$_{14}$H$_{11}$BrFNO$_2$S: C, 47.21, H, 3.11, N, 3.93. Found: C, 47.03, H, 3.07; N, 3.82.

tert-Butyl 2-(9-fluoro-5-methyl-2-oxo-5-thien-2-yl-1,2,3,5-tetrahydro-4,1-benzoxazepin-7-yl)-1H-pyrrole-1-carboxylate Prepared from 7-bromo-9-fluoro-5-methyl-5-thien-2-yl-1,5-dihydro-4,1-benzoxazepin-2(3H)-one and 2-borono-1H-pyrrole-1-carboxylic acid, 1-tert-butyl ester using the coupling procedure described in example 1. $^1$H-NMR (DMSO-d$_6$) δ 9.63 (s, 1H), 7.50 (dd, J=5.0, 1.1 Hz, 1H), 7.35 (m, 2H), 7.12 (s, 1H), 6.95 (m, 1H), 6.89 (dd, J=3.6, 1.2 Hz, 1H), 6.31 (m, 1H), 6.27 (m, 1H), 4.20 (d, J=14.6 Hz, 1H), 4.12 (d, J=14.6 Hz, 1H), 1.98 (s, 3H), 1.38 (s, 9H); MS (ES) m/z 441 (M–H)$^-$; Anal. Calc. For C$_{23}$H$_{23}$FN$_2$O$_4$S: C, 62.43, H, 5.24; N, 6.33. Found: C, 62.08, H, 5.33; N, 6.15.

The title compound was prepared from tert-butyl 2-(9-fluoro-5-methyl-2-oxo-5-thien-2-yl-1,2,3,5-tetrahydro-4,1-benzoxazepin-7-yl)-1H-pyrrole-1-carboxylate generally according to the procedure described in example 1. $^1$H-NMR (DMSO-d$_6$) δ 9.70 (s, 1H), 7.51 (m, 2H), 7.32 (d, J=3.8 Hz, 1H), 7.25 (s, 1H), 6.96 (dd, J=5.0, 3.6 Hz, 1H), 6.87 (dd, J=3.5, 1.1 Hz, 1H), 6.50 (d, J=3.8 Hz, 1H), 4.21 (d, J=14.7 Hz, 1H), 4.12 (d, J=14.7 Hz, 1H), 1.99 (s, 3H), 1.40 (s, 9H); MS (ES) m/z 466 (M–H)$^-$; Anal. Calc. For C$_{24}$H$_{22}$FN$_3$O$_4$S: C, 61.66, H, 4.74; N, 8.99. Found: C, 61.62, H, 4.6; N, 8.65.

EXAMPLE 65

5-(9-Fluoro-5-methyl-2-oxo-5-thien-2-yl-1,2,3,5-tetrahydro-4,1-benzoxazepin-7-yl)-1H-pyrrole-2-carbonitrile Prepared from tert-butyl 2-cyano-5-(9-fluoro-5-methyl-2-oxo-5-thien-2-yl-1,2,3,5-tetrahydro-4,1-benzoxazepin-7-yl)-1H-pyrrole-1-carboxylate using the procedure described in example 2. $^1$H-NMR (DMSO-d$_6$) δ 12.7 (s, 1H), 9.61 (s, 1H), 7.73 (dd, J=11.9, 1.8 Hz, 1H), 7.60 (s, 1H), 7.52 (dd, J=5.0, 1.0 Hz, 1H), 7.0 (d, J=3.9 Hz, 1H), 6.97 (m, 1H), 6.87 (dd, J=3.5, 1.0 Hz, 1H), 6.81 (d, J=3.9 Hz, 1H), 4.20 (d, J=14.8 Hz, 1H), 4.12 (d, J=14.8 Hz, 1H), 2.06 (s, 3H); MS (ES) m/z 366 (M–H)$^-$.

EXAMPLE 66 tert-Butyl 2-cyano-5-(5-isopropyl-2-oxo-5-thien-2-yl-1,2,3,5-tetrahydro-4,1-benzoxazepin-7-yl)-1H-pyrrole-1-carboxylate N-[4-Bromo-2-(1-hydroxy-2-methyl-1-thien-2-yl-propyl)phenyl]-2-chloroacetamide Prepared from (2-amino-5-bromophenyl)(2-thienyl)methanone in two steps using the procedure described in example 1. $^1$H-NMR (DMSO-d$_6$) δ 11.25 (s, 1H), 8.14 (d, J=8.8 Hz, 1H), 7.50 (d, J=2.3 Hz, 1H), 7.46 (dd, J=8.8, 2.3 Hz, 1H), 7.40 (dd, J=5.0, 1.1 Hz, 1H), 7.02 (d, J=3.5, 1.1 Hz, 1H), 6.96 (m, 2H), 4.36 (d, J=15.0 Hz, 1H), 4.30 (d, J=15.0 Hz, 1H), 2.86 (m, 1H), 0.94 (dd, J=22.0, 6.6 Hz, 6H); MS (ES) m/z 400 (M–H)$^-$; Anal. Calc. For C$_{16}$H$_{17}$BrClNO$_2$S: C, 47.72, H, 4.25; N, 3.48. Found: C, 47.89, H, 4.14; N, 3.37.

7-Bromo-5-isopropyl-5-thien-2-yl-1,5-dihydro-4,1-benzoxazepin-2(3H)-one

Prepared from N-[4-bromo-2-(1-hydroxy-2-methyl-1-thien-2-ylpropyl)phenyl]-2-chloroacetamide using the procedure described in example 1. $^1$H-NMR (DMSO-d$_6$) δ 10.01 (s, 1H), 7.56 (dd, J=4.9, 1.0 Hz, 1H), 7.52 (dd, J=8.6, 2.2 Hz, 1H), 7.44 (d, J=2.2 Hz, 1H), 7.10 (d, J=8.6 Hz, 1H), 7.03 (m, 2H), 4.22 (d, J=14.4 Hz, 1H), 3.87 (d, J=14.4 Hz, 1H), 2.69 (m, 1H), 0.93 (dd, J=17.8, 6.8 Hz, 6H); MS (ES) m/z 364 (M–H)$^-$.

tert-Butyl 2-(5-isopropyl-2-oxo-5-thien-2-yl-1,2,3,5-tetrahydro-4,1-benzoxazepin-7-yl)-1H-pyrrole-1-carboxylate Prepared from 7-bromo-5-isopropyl-5-thien-2-yl-1,5-dihydro-4,1-benzoxazepin-2(3H)-one and 2-borono-1H-pyrrole-1-carboxylic acid, 1-tert-butyl ester using the coupling procedure described in example 1. $^1$H-NMR (DMSO-d$_6$) δ 9.97 (s, 1H), 7.53 (dd, J=5.0, 0.9 Hz, 1H), 7.32 (dd, J=3.2, 1.7 Hz, 1H), 7.30 (m, 2H), 7.13 (d, J=8.9 Hz, 1H), 7.01 (dd, J=3.5, 1.0 Hz, 1H), 6.98 (m, 1H), 6.26 (t, J=3.3 Hz, 1H), 6.20 (m, 1H), 4.19 (d, J=14.3 Hz, 1H), 3.85 (d, J=14.3 Hz, 1H), 2.64 (m, 1H), 1.38 (s, 9H), 0.89 (d, J=6.8 Hz, 3H), 0.84 (d, J=6.5 Hz, 3H); MS (ES) m/z 453 (M+H)$^+$; Anal. Calc. for C$_{25}$H$_{28}$N$_2$O$_4$S: C, 66.35, H, 6.24; N, 6.19. Found: C, 66.41, H, 5.95; N, 6.07.

The title compound was prepared from tert-butyl 2-(5-isopropyl-2-oxo-5-thien-2-yl-1,2,3,5-tetrahydro-4,1-benzoxazepin-7-yl)-1H-pyrrole-1-carboxylate using the procedure described in example 1. $^1$H-NMR (DMSO-d$_6$) δ 10.04 (s, 1H), 7.52 (dd, J=4.6, 1.5 Hz, 1H), 7.38 (m, 2H), 7.30 (d, J=3.8 Hz, 1H), 7.17 (m, 1H), 6.99 (m, 2H), 6.41 (d, J=3.8 Hz, 1H), 4.19 (d, J=14.4 Hz, 1H), 3.89 (d, J=14.4 Hz, 1H), 2.67 (m, 1H), 1.42 (s, 9H), 0.89 (d, J=6.8 Hz, 3H), 0.84 (d, J=6.5 Hz, 3H); MS (ES) m/z 478 (M+H)$^+$; Anal. Calc. for C$_{26}$H$_{27}$N$_3$O$_4$S: C, 65.39, H, 5.70; N, 8.80. Found: C, 65.05, H, 5.39; N, 8.68.

EXAMPLE 67

5-(5-Isopropyl-2-oxo-5-thien-2-yl-1,2,3,5-tetrahydro-4,1-benzoxazepin-7-yl)-1H-pyrrole-2-carbonitrile Prepared from tert-butyl 2-cyano-5-(5-isopropyl-2-oxo-5-thien-2-yl-1,2,3,5-tetrahydro-4,1-benzoxazepin-7-yl)-1H-pyrrole-1-carboxylate using the procedure described in example 2. $^1$H-NMR (DMSO-d$_6$) δ 12.64 (s, 1H), 9.97 (s, 1H), 7.77 (d, J=1.8 Hz, 1H), 7.69 (dd, J=8.4, 1.9 Hz, 1H), 7.51 (dd, J=4.9, 1.2 Hz, 1H), 7.16 (d, J=8.5 Hz, 1H), 7.01 (m, 3H), 6.65 (d, J=3.9 Hz, 1H), 4.16 (d, J=14.4 Hz, 1H), 3.92 (d, J=14.4 Hz, 1H), 2.79 (m, 1H), 0.93 (m, 6H); MS (ES) m/z 378 (M+H)$^+$.

EXAMPLE 68

5-(5-Isopropyl-2-oxo-5-thien-2-yl-1,2,3,5-tetrahydro-4,1-benzoxazepin-7-yl)-1-methyl-1H-pyrrole-2-carbonitrile Prepared from 5-(5-isopropyl-2-oxo-5-thien-2-yl-1,2,3,5-tetrahydro-4,1-benzoxazepin-7-yl)-1H-pyrrole-2-carbonitrile using the procedure described in example 3. $^1$H-NMR (DMSO-d$_6$) δ 10.08 (s, 1H), 7.52 (dd, J=4.9, 1.2 Hz, 1H), 7.49 (dd, J=8.3, 1.9 Hz, 1H), 7.43 (d, J=1.8 Hz, 1H), 7.24 (d, J=8.3 Hz, 1H), 7.02 (m, 3H), 6.30 (d, J=4.1 Hz, 1H), 4.24 (d, J=14.4 Hz, 1H), 3.93 (d, J=14.4 Hz, 1H), 3.70 (s, 3H), 2.70 (m, 1H), 0.90 (m, 6H); MS (ES) m/z 390 (M−H)$^-$.

EXAMPLE 69

7-(3-Chloro-4-fluorophenyl)-5-isopropyl-5-thien-2-yl-1,5-dihydro-4,1-benzoxazepin-2(3H)-one Prepared from 7-bromo-5-isopropyl-5-thien-2-yl-1,5-dihydro-4,1-benzoxazepin-2(3H)-one and 3-chloro-4-fluorobenzeneboronic acid using the coupling procedure described in example 1. $^1$H-NMR (DMSO-d$_6$) δ 10.02 (s, 1H), 7.83 (dd, J=7.1, 2.2 Hz, 1H), 7.67 (dd, J=8.4, 2.0 Hz, 1H), 7.60 (m, 2H), 7.53 (m, 1H), 7.52 (m, 1H), 7.23 (d, J=8.5 Hz, 1H), 7.05 (dd, J=3.6, 1.3 Hz, 1H), 7.02 (dd, J=5.0, 3.7 Hz, 1H), 4.21 (d, J=14.4 Hz, 1H), 3.90 (d, J=14.4 Hz, 1H), 2.81 (m, 1H), 0.91 (m, 6H); Anal. Calc. for C$_{22}$H$_{19}$ClFNO$_2$S: C, 63.53, H, 4.60; N, 3.37. Found: C, 63.34, H, 4.92; N, 2.97.

EXAMPLE 70

3-Fluoro-5-(5-isopropyl-2-oxo-5-thien-2-yl-1,2,3,5-tetrahydro-4,1-benzoxazepin-7-yl)benzonitrile Prepared from 7-bromo-5-isopropyl-5-thien-2-yl-1,5-dihydro-4,1-benzoxazepin-2(3H)-one and 3-cyano-5-fluorobenzeneboronic acid using the coupling procedure described in example 1. $^1$H-NMR (DMSO-d$_6$) δ 10.07 (s, 1H), 8.03 (s, 1H), 7.90 (m, 1H), 7.84 (m, 1H), 7.77 (m, 2H), 7.51 (dd, J=5.0, 1.2 Hz, 1H), 7.24 (d, J=8.5 Hz, 1H), 7.04 (m, 2H), 4.20 (d, J=14.4 Hz, 1H), 3.96 (d, J=14.4 Hz, 1H), 2.90 (m, 1H), 0.92 (t, J=6.4 Hz, 6H); MS (ES) m/z 407 (M+H)$^+$.

EXAMPLE 71

3-Fluoro-5-(5-isopropyl-5-thien-2-yl-2-thioxo-1,2,3,5-tetrahydro-4,1-benzoxazepin-7-yl)benzonitrile Prepared by heating a mixture of 3-fluoro-5-(5-isopropyl-2-oxo-5-thien-2-yl-1,2,3,5-tetrahydro-4,1-benzoxazepin-7-yl)benzonitrile and Lawesson's reagent at reflux in toluene generally according to example 10. $^1$H-NMR (DMSO-d$_6$) δ 12.09 (s, 1H), 8.1 (s, 1H), 7.96 (d, J=10.1 Hz, 1H), 7.88 (m, 2H), 7.83 (dd, J=8.5, 1.8 Hz, 1H), 7.48 (dd, J=4.9, 0.66 Hz, 1H), 7.40 (d, J=8.5 Hz, 1H), 7.03 (d, J=2.6 Hz, 1H), 7.00 (m, 1H), 4.48 (d, J=14.1 Hz, 1H), 4.37 (d, J=14.1 Hz, 1H), 2.96 (m, 1H), 0.93 (d, J=6.7 Hz, 3H), 0.87 (d, J=6.5 Hz, 3H); MS (ES) m/z 421 (M−H)$^-$.

EXAMPLE 72 tert-Butyl 2-cyano-5-(5-ethyl-2-oxo-5-thien-3-yl-1,2,3,5-tetrahydro-4,1-benzoxazepin-7-yl)-1H-pyrrole-1-carboxylate N-[4-Bromo-2-(1-hydroxy-1-thien-3-ylpropyl)phenyl]-2-chloroacetamide Prepared from 1-(2-amino-5-bromophenyl)-propan-1-one using the procedure described in example 1. $^1$H-NMR (DMSO-d$_6$) δ 10.95 (s, 1H), 8.05 (dd, J=6.8, 2.9 Hz, 1H), 7.47 (m, 2H), 7.42 (m, 1H), 7.40 (m, 1H), 6.88 (dd, J=4.9, 1.0 Hz, 1H), 6.74 (s, 1H), 4.32 (d, J=31.7, 1H), 4.25 (d, J=31.7 Hz, 1H), 2.30 (m, 2H), 0.82 (t, J=7.3 Hz, 3H); MS (ES) m/z 386 (M+H)$^+$; Anal. Calc. for C$_{15}$H$_{15}$BrClNO$_2$S: C, 46.35, H, 3.89; N, 3.60. Found: C, 46.03, H, 3.73; N, 3.55.

7-Bromo-5-ethyl-5-thien-3-yl-1,5-dihydro-4,1-benzoxazepin-2(3H)-one

Prepared from N-[4-bromo-2-(1-hydroxy-1-thien-3-yl-propyl)phenyl]-2-chloroacetamide using the procedure described in example 1. $^1$H-NMR (DMSO-d$_6$) δ 10.03 (s, 1H), 7.57 (dd, J=4.9, 3.0 Hz, 1H), 7.45 (dd, J=8.5, 2.2 Hz, 1H), 7.28 (d, J=2.2 Hz, 1H), 7.26 (dd, J=2.7, 1.4 Hz, 1H), 7.12 (dd, J=5.2, 1.4 Hz, 1H), 7.10 (d, J=8.5 Hz, 1H), 4.05 (d, J=15.4 Hz, 1H), 3.93 (d, J=15.4 Hz, 1H), 2.51 (m, 1H), 2.20 (m, 1H), 0.73 (t, J=7.1 Hz, 3H); MS (ES) m/z 352 (M+H)$^+$; Anal. Calc. for C$_{15}$H$_{14}$BrNO$_2$S: C, 51.15, H, 4.01; N, 3.98. Found: C, 51.38, H, 4.09; N, 3.82.

tert-Butyl 2-(5-ethyl-2-oxo-5-thien-3-yl-1,2,3,5-tetrahydro-4,1-benzoxazepin-7-yl)-1H-pyrrole-1-carboxylate Prepared from 7-bromo-5-ethyl-5-thien-3-yl-1,5-dihydro-4,1-benzoxazepin-2(3H)-one and 2-borono-1H-pyrrole-1-carboxylic acid, 1-tert-butyl ester one using the coupling procedure described in example 1. $^1$H-NMR (DMSO-d$_6$) δ 9.97 (s, 1H), 7.55 (dd, J=4.9, 2.9 Hz, 1H), 7.29 (m, 1H), 7.25 (m, 2H), 7.14 (m, 3H), 6.24 (m, 1H), 6.21 (m, 1H), 4.03 (d, J=15.1 Hz, 1H), 3.90 (d, J=15.1 Hz, 1H), 2.42 (m, 1H), 2.14 (m, 1H), 1.39 (s, 9H), 0.75 (t, J=7.3 Hz, 3H); MS (ES) m/z 439 (M+H)$^+$.

The title compound was prepared from tert-butyl 2-(5-ethyl-2-oxo-5-thien-3-yl-1,2,3,5-tetrahydro-4,1-benzoxazepin-7-yl)-1H-pyrrole-1-carboxylate using the procedure described in example 1. $^1$H-NMR (DMSO-d$_6$) δ 10.05 (s, 1H), 7.55 (dd, J=5.4, 2.9 Hz, 1H), 7.34 (dd, J=8.3, 2.0 Hz, 1H), 7.29 (d, J=3.9 Hz, 1H), 7.23 (d, J=2.0 Hz, 1H), 7.21 (dd, J=2.9, 1.0 Hz, 1H), 7.19 (d, J=8.8 Hz, 1H), 7.11 (dd, J=5.4, 1.5 Hz, 1H), 6.42 (d, J=3.9 Hz, 1H), 4.02 (d, J=15.1 Hz, 1H), 3.93 (d, J=15.1 Hz, 1H), 2.44 (m, 1H), 2.18 (m, 1H), 1.39 (s, 9H), 0.74 (t, J=6.8 Hz, 3H); MS (ES) m/z 464 (M+H)$^+$.

EXAMPLE 73

5-(5-Ethyl-2-oxo-5-thien-3-yl-1,2,3,5-tetrahydro-4,1-benzoxazepin-7-yl)-1H-pyrrole-2-carbonitrile Prepared from tert-butyl 2-cyano-5-(5-ethyl-2-oxo-5-thien-3-yl-1,2,3,5-tetrahydro-4,1-benzoxazepin-7-yl)-1H-pyrrole-1-carboxylate using the procedure described in example 2. $^1$H-NMR (DMSO-$d_6$) δ 12.57 (s, 1H), 10.00 (s, 1H), 7.65 (dd, J=8.5, 1.9 Hz, 1H), 7.61 (d, J=2.2 Hz, 1H), 7.58 (dd, J=4.9, 2.7 Hz, 1H), 7.19 (m, 2H), 7.16 (dd, J=5.2, 1.4 Hz, 1H), 6.97 (d, J=3.8 Hz, 1H), 6.68 (d, J=3.8 Hz, 1H), 3.99 (d, J=15.4 Hz, 1H), 3.91 (d, J=15.4 Hz, 1H), 2.53 (m, 1H), 2.32 (m, 1H), 0.75 (t, J=7.1 Hz, 3H); MS (ES) m/z 364 (M+H)$^+$.

EXAMPLE 74

5-(5-Ethyl-2-oxo-5-thien-3-yl-1,2,3,5-tetrahydro-4,1-benzoxazepin-7-yl)-1-methyl-1H-pyrrole-2-carbonitrile Prepared from 5-(5-ethyl-2-oxo-5-thien-3-yl-1,2,3,5-tetrahydro-4,1-benzoxazepin-7-yl)-1H-pyrrole-2-carbonitrile using the procedure described in example 3. $^1$H-NMR (DMSO-$d_6$) δ 10.09 (s, 1H), 7.56 (dd, J=4.9, 2.9 Hz, 1H), 7.41 (dd, J=8.3, 2.0 Hz, 1H), 7.27 (m, 3H), 7.16 (dd, J=5.4, 1.5 Hz, 1H), 7.00 (d, J=3.9 Hz, 1H), 6.30 (d, J=3.9 Hz, 1H), 4.07 (d, J=15.1 Hz, 1H), 3.98 (d, J=15.1 Hz, 1H), 3.64 (s, 3H), 2.51 (m, 1H), 2.25 (m, 1H), 0.76 (t, J=7.3 Hz, 3H); MS (ES) m/z 378 (M+H)$^+$.

EXAMPLE 75

3-(5-Ethyl-2-oxo-5-thien-3-yl-1,2,3,5-tetrahydro-4,1-benzoxazepin-7-yl)-5-fluorobenzonitrile Prepared from 7-bromo-5-ethyl-5-thien-3-yl-1,5-dihydro-4,1-benzoxazepin-2(3H)-one and 3-cyano-5-fluorobenzeneboronic acid using the coupling procedure described in example 1. $^1$H-NMR (DMSO-$d_6$) δ 10.07 (s, 1H), 8.07 (t, J=1.5 Hz, 1H), 7.94 (dt, J=10.3, 2.0 Hz, 1H), 7.80 (m, 1H), 7.73 (dd, J=8.3, 2.0 Hz, 1H), 7.63 (d, J=2.4 Hz, 1H), 7.57 (dd, J=4.9, 2.9 Hz, 1H), 7.27 (m, 2H), 7.17 (dd, J=4.9, 1.5 Hz, 1H), 4.02 (d, J=15.6 Hz, 1H), 3.96 (d, J=15.6 Hz, 1H), 2.54 (m, 1H), 2.49 (m, 1H), 0.74 (t, J=7.3 Hz, 3H); MS (ES) m/z 393 (M+H)$^+$.

EXAMPLE 76

7-(3-Chloro-4-fluorophenyl)-5-ethyl-5-thien-3-yl-1,5-dihydro-4,1-benzoxazepin-2(3H)-one Prepared from 7-bromo-5-ethyl-5-thien-3-yl-1,5-dihydro-4,1-benzoxazepin-2(3H)-one and 3-chloro-4-fluorobenzeneboronic acid using the coupling procedure described in example 1. $^1$H-NMR (DMSO-$d_6$) δ 10.03 (s, 1H), 7.84 (dd, J=6.9, 2.2 Hz, 1H), 7.62 (m, 2H), 7.56 (dd, J=5.2, 3.0 Hz, 1H), 7.48 (m, 2H), 7.27 (m, 1H), 7.24 (d, J=8.5 Hz, 1H), 7.16 (dd, J=5.2, 1.4 Hz, 1H), 4.04 (d, J=15.4 Hz, 1H), 3.94 (d, J=15.4 Hz, 1H), 2.53 (m, 1H), 2.35 (m, 1H), 0.75 (t, J=7.1 Hz, 3H); MS (ES) m/z 402 (M+H)$^+$;

EXAMPLE 77 tert-Butyl 2-cyano-5-[5-ethyl-5-(2-furyl)-2-oxo-1,2,3,5-tetrahydro-4,1-benzoxazepin-7-yl]-H-pyrrole-1-carboxylate N-{4-Bromo-2-[1-(2-furyl)-1-hydroxypropyl]phenyl}-2-chloroacetamide Prepared from 1-(2-amino-5-bromophenyl)-propan-1-one in two steps using the procedure described in example 1. $^1$H-NMR (DMSO-$d_6$) δ 10.96 (s, 1H), 8.11 (d, J=8.8 Hz, 1H), 7.60 (d, J=1.0 Hz, 1H), 7.49 (dd, J=8.8, 2.4 Hz, 1H), 7.11 (d, J=2.0 Hz, 1H), 6.95 (s, 1H), 6.47 (m, 2H), 4.35 (s, 2H), 2.23 (q, 7.3 Hz, 2H), 0.82 (t, J=7.3 Hz, 3H); MS (ES) m/z 372 (M−H)$^-$.

7-Bromo-5-ethyl-5-(2-furyl)-1,5-dihydro-4,1-benzoxazepin-2(H)-one

Prepared from N-{4-bromo-2-[1-(2-furyl)-1-hydroxypropyl]phenyl}-2-chloroacetamide using the procedure described in example 1. $^1$H-NMR (DMSO-$d_6$) δ 10.08 (s, 1H), 7.72 (t, J=1.0 Hz, 1H), 7.47 (dd, J=8.8, 2.4 Hz, 1H), 7.17 (d, J=2.4 Hz, 1H), 7.12 (d, J=8.8 Hz, 1H), 6.48 (dd, J=2.4, 1.0 Hz, 1H), 6.34 (d, J=2.4 Hz, 1H), 4.21 (d, J=15.1 Hz, 1H), 3.95 (d, J=15.1 Hz, 1H), 2.45 (m, 1H), 2.10 (m, 1H), 0.73 (t, J=7.3 Hz, 3H); MS (ES) m/z 336 (M+H)$^+$.

tert-Butyl 2-[5-ethyl-5-(2-furyl)-2-oxo-1,2,3,5-tetrahydro-4,1-benzoxazepin-7-yl]-H-pyrrole-1-carboxylate Prepared from 7-bromo-5-ethyl-5-(2-furyl)-1,5-dihydro-4,1-benzoxazepin-2(H)-one and 2-borono-1H-pyrrole-1-carboxylic acid, 1-tert-butyl ester using the coupling procedure described in example 1. $^1$H-NMR (DMSO-$d_6$) δ 10.02 (s, 1H), 7.69 (dd, J=1.9, 0.8 Hz, 1H), 7.29 (dd, J=3.3, 1.6 Hz, 1H), 7.26 (dd, J=8.2, 1.9 Hz, 1H), 7.15 (d, J=8.5 Hz, 1H), 6.97 (d, J=2.2 Hz, 1H), 6.43 (dd, J=3.3, 1.9 Hz, 1H), 6.32 (dd, J=3.3, 0.8 Hz, 1H), 6.23 (m, 1H), 6.16 (dd, J=3.3, 1.9 Hz, 1H), 4.20 (d, J=15.4 Hz, 1H), 3.93 (d, J=15.4 Hz, 1H), 2.43 (m, 1H), 2.07 (m, 1H), 1.37 (s, 9H), 0.75 (t, J=7.1 Hz, 3H); Anal. Calc. for $C_{24}H_{26}N_2O_5$: C, 68.23, H, 6.20; N, 6.63. Found: C, 68.06, H, 6.24; N, 6.30.

The title compound was prepared from tert-butyl 2-[5-ethyl-5-(2-furyl)-2-oxo-1,2,3,5-tetrahydro-4,1-benzoxazepin-7-yl]-H-pyrrole-1-carboxylate using the procedure described in example 1. $^1$H-NMR (DMSO-$d_6$) δ 10.10 (s, 1H), 7.70 (s, 1H), 7.35 (dd, J=8.5, 1.9 Hz, 1H), 7.28 (d, J=3.8 Hz, 1H), 7.20 (d, J=8.5 Hz, 1H), 7.09 (d, J=1.9 Hz, 1H), 6.43 (m, 1H), 6.39 (d, J=3.8 Hz, 1H), 6.28 (d, J=3.0 Hz, 1H), 4.17 (d, J=15.4 Hz, 1H), 3.95 (d, J=15.4 Hz, 1H), 2.46 (m, 1H), 2.11 (m, 1H), 1.41 (s, 9H), 0.74 (t, J=7.1 Hz, 3H); MS (ES) m/z 448 (M+H)$^+$; Anal. Calc. for $C_{25}H_{25}N_3O_5$: C, 67.10, H, 5.63; N, 9.39. Found: C, 66.98, H, 5.47; N, 9.30.

EXAMPLE 78

5-[5-Ethyl-5-(2-furyl)-2-oxo-1,2,3,5-tetrahydro-4,1-benzoxazepin-7-yl]-H-pyrrole-2-carbonitrile Prepared from tert-butyl 2-cyano-5-[5-ethyl-5-(2-furyl)-2-oxo-1,2,3,5-tetrahydro-4,1-benzoxazepin-7-yl]-H-pyrrole-1-carboxylate using the procedure described in example 2. $^1$H-NMR (DMSO-$d_6$) δ 12.55 (s, 1H), 10.04 (s, 1H), 7.72 (d, J=1.1 Hz, 1H), 7.65 (dd, J=8.5, 1.9 Hz, 1H), 7.51 (d, J=2.2 Hz, 1H), 7.20 (d, J=8.5 Hz, 1H), 6.96 (d, J=3.6 Hz, 1H), 6.63 (d, J=3.8 Hz, 1H), 6.46 (m, 1H), 6.26 (d, J=3.3 Hz, 1H), 4.11 (d, J=15.6 Hz, 1H), 3.93 (d, J=15.6 Hz, 1H), 2.55 (m, 1H), 2.25 (m, 1H), 0.75 (t, J=7.4 Hz, 3H); MS (ES) m/z 348 (M+H)$^+$.

EXAMPLE 79

5-[5-Ethyl-5-(2-furyl)-2-oxo-1,2,3,5-tetrahydro-4,1-benzoxazepin-7-yl]-1-methyl-H-pyrrole-2-carbonitrile Prepared from 5-[5-ethyl-5-(2-furyl)-2-oxo-1,2,3,5-tetrahydro-4,1-benzoxazepin-7-yl]-H-pyrrole-2-carbonitrile using the procedure described in example 3. $^1$H-NMR (DMSO-d$_6$) δ 10.14 (s, 1H), 7.71 (s, 1H), 7.44 (d, J=8.3 Hz, 1H), 7.28 (d, J=8.3 Hz, 1H), 7.16 (s, 1H), 7.00 (d, J=3.9 Hz, 1H), 6.46 (m, 1H), 6.34 (d, J=3.4 Hz, 1H), 6.28 (d, J=3.9 Hz, 1H), 4.23 (d, J=15.1 Hz, 1H), 3.98 (d, 15.1 Hz, 1H), 3.62 (s, 3H), 2.47 (m, 1H), 2.18 (m, 1H), 0.75 (t, J=7.3 Hz, 3H); MS (ES) m/z 362 (M+H)$^+$.

EXAMPLE 80

7-(3-Chloro-4-fluorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 3-chloro-4-fluorobenzeneboronic acid using the procedure described in example 1. $^1$H-NMR (DMSO-d$_6$) δ 10.08 (s, 1H), 8.32 (s, 1H), 7.81 (dd, J=7.1, 2.5 Hz, 1H), 7.72 (s, 1H), 7.63 (dd, J=8.5, 2.2 Hz, 1H), 7.47 (t, J=9.0 Hz, 1H), 7.33 (d, J=2.2 Hz, 1H), 7.25 (d, J=8.5 Hz, 1H), 6.47 (m, 1H), 6.32 (d, J=3.3 Hz, 1H), 4.19 (d, J=15.4 Hz, 1H), 3.95 (d, J=15.4 Hz, 1H), 2.52 (m, 1H), 2.26 (m, 1H), 0.75 (t, J=7.1 Hz, 3H); MS (ES) m/z 386 (M+H)$^+$.

EXAMPLE 81

3-[5-Ethyl-5-(2-furyl)-2-oxo-1,2,3,5-tetrahydro-4,1-benzoxazepin-7-yl]-5-fluorobenzonitrile Prepared from 7-bromo-5-ethyl-5-(2-furyl)-1,5-dihydro-4,1-benzoxazepin-2(H)-one and 3-cyano-5-fluorobenzeneboronic acid generally according to the coupling procedure described in example 1. $^1$H-NMR (DMSO-d$_6$) δ 10.13 (s, 1H), 8.03 (s, 1H), 7.90 (dt, J=10.5, 2.2 Hz, 1H), 7.80 (m, 1H), 7.74 (m, 2H), 7.52 (d, J=2.2 Hz, 1H), 7.28 (d, J=8.5 Hz, 1H), 6.46 (m, 1H), 6.29 (d, J=3.3 Hz, 1H), 4.14 (d, J=15.6 Hz, 1H), 3.96 (d, J=15.6 Hz, 1H), 2.54 (m, 1H), 2.49 (m, 1H), 0.75 (t, J=7.4 Hz, 3H); MS (ES) m/z 753 (2M+H)$^+$.

EXAMPLE 82

7-(3-Bromo-5-fluorophenyl)-5-ethyl-5-(2-furyl)-1,5-dihydro-4,1-benzoxazepin-2(H)-one 5-Ethyl-5-(2-furyl)-7-(4,4,5,5-tetramethyl-1,3,2-dioxaborolan-2-yl)-1,5-dihydro-4,1-benzoxazepin-2(H)-one To a stirred solution of 7-bromo-5-ethyl-5-(2-furyl)-1,5-dihydro-4,1-benzoxazepin-2(H)-one (5.0 g, 14.8 mmol) in DMF (100 mL) was added potassium acetate (4.5 g, 44.4 mmol), bis(pinacolato)diboron (7.5 g, 29.6 mmol), and [1,1'-bis(diphenylphosphino)-ferrocene]dichloropalladium (II) (0.6 g, 0.8 mmol) at rt under nitrogen. The mixture was heated at reflux under nitrogen overnight. The solution was allowed to cool to room temperature and partitioned between ammonium chloride solution (sat.) (100 mL) and ethyl acetate (150 mL). The aqueous layer was extracted with ethyl acetate (3×50 mL). The organic layers were combined, dried over magnesium sulfate, filtered through silica gel and triturated with ether to give 5-ethyl-5-(2-furyl)-7-(4,4,5,5-tetramethyl-1,3,2-dioxaborolan-2-yl)-1,5-dihydro-4,1-benzoxazepin-2(H)-one as a white solid (2.9 g, 50%). $^1$H-NMR (DMSO-d$_6$) δ 10.08 (s, 1H), 7.71 (s, 1H), 7.53 (d, J=8.0 Hz, 1H), 7.33 (s, 1H), 7.16 (d, J=8.1 Hz, 1H), 6.48 (d, J=3.2 Hz, 1H), 6.30 (d, J=3.2 Hz, 1H), 4.21 (d, J=15.4 Hz, 1H), 4.04 (d, J=15.4 Hz, 1H), 2.45 (m, 1H), 2.00 (m, 1H), 1.25 (s, 8H), 0.71 (t, J=7.1 Hz, 3H); MS (ES) m/z 384 (M+H)$^+$; Anal. Calc. for C$_{21}$H$_{26}$BNO$_5$: C, 65.81; H, 6.84; N, 3.65. Found: C, 65.51; H, 6.96; N, 3.51.

The title compound was prepared from 5-ethyl-5-(2-furyl)-7-(4,4,5,5-tetramethyl-1,3,2-dioxaborolan-2-yl)-1,5-dihydro-4,1-benzoxazepin-2(H)-one and 1,3-dibromo-5-fluorobenzene using the coupling procedure described in example 1. $^1$H-NMR (DMSO-d$_6$) δ 10.05 (s, 1H), 7.68 (s, 1H), 7.63 (m, 2H), 7.46 (d, J=9.8 Hz, 2H), 7.35 (s, 1H), 7.23 (d, J=8.6 Hz, 1H), 6.44 (m, 1H), 6.28 (m, 1H), 4.15 (d, J=15.3 Hz, 1H), 3.93 (d, J=15.3 Hz, 1H), 2.47 (m, 1H), 2.29 (m, 1H), 0.72 (t, J=7.1 Hz, 3H); MS (ES) m/z 430 (M+H)$^+$; Anal. Calc. for C$_{21}$H$_{17}$BrFNO$_3$: C, 58.62; H, 3.98; N, 3.26. Found: C, 58.26; H, 3.87; N, 2.95.

EXAMPLE 83

7-(3-Bromo-5-chlorophenyl)-5-ethyl-5-(2-furyl)-1,5-dihydro-4,1-benzoxazepin-2(H)-one Prepared from 5-ethyl-5-(2-furyl)-7-(4,4,5,5-tetramethyl-1,3,2-dioxaborolan-2-yl)-1,5-dihydro-4,1-benzoxazepin-2(H)-one and 1,3-dibromo-5-chlorobenzene using the coupling procedure described in example 1. $^1$H-NMR (DMSO-d$_6$) δ 10.08 (s, 1H), 7.75 (m, 1H), 7.71 (m, 1H), 7.65 (m, 3H), 7.39 (d, J=2.3 Hz, 1H), 7.27 (d, J=8.6 Hz, 1H), 6.47 (m, 1H), 6.32 (d, J=3.3 Hz, 1H), 4.18 (d, J=15.4 Hz, 1H), 4.04 (d, J=15.4 Hz, 1H), 2.51 (m, 1H), 2.35 (m, 1H), 0.76 (t, J=7.0 Hz, 3H); MS (ES) m/z 448 (M+H)$^+$; Anal. Calc. for C$_{21}$H$_{17}$BrClNO$_3$: C, 56.46; H, 3.84; N, 3.14. Found: C, 56.87; H, 3.95; N, 3.05.

EXAMPLE 84

3-Chloro-5-[5-ethyl-5-(2-furyl)-2-oxo-1,2,3,5-tetrahydro-4,1-benzoxazepin-7-yl]benzonitrile To a stirred solution of 7-(3-bromo-5-chlorophenyl)-5-ethyl-5-(2-furyl)-1,5-dihydro-4,1-benzoxazepin-2(H)-one (0.6 g, 1.3 mmol) in DMF (15 mL) was added zinc cyanide (0.19 g, 1.6 mmol), tris(dibenzylideneacetone)dipalladium (0.06 g, 0.07 mmol), and diphenylphosphinoferrocene (0.04 g, 0.07 mmol). The resulting solution was heated for 2 hr. at 120° C. The solution was allowed to cool to room temperature and partitioned between ammonium chloride solution (sat.) and ethyl acetate. The organic layer was dried over magnesium sulfate, concentrated and purified using silica gel flash column (25% ethyl acetate/hexane) to give 0.23 g of the title compound as an off-white solid (45%). $^1$H-NMR (DMSO-d$_6$) δ 10.10 (s, 1H), 8.12 (t, J=1.5 Hz, 1H), 8.03 (t, J=2.0 Hz, 1H), 7.97 (d, J=2.0, 1.5 Hz, 1H), 7.74 (m, 2H), 7.51 (d, J=2.4 Hz, 1H), 7.29 (d, J=8.5 Hz, 1H), 6.47 (dd, J=3.4, 2.0 Hz, 1H), 6.30 (dd, J=3.2, 0.7 Hz, 1H), 4.15 (d, J=15.6 Hz, 1H), 3.97 (d, J=15.6 Hz, 1H), 2.56 (m, 1H), 2.48 (m, 1H), 0.76 (t, J=7.3 Hz, 3H); MS (ES) m/z 393 (M+H)$^+$; Anal. Calc. for C$_{22}$H$_{17}$ClN$_2$O$_3$: C, 67.26; H, 4.36; N, 7.13. Found: C, 67.18; H, 4.05; N, 6.87.

EXAMPLE 85

4-[5-Ethyl-5-(2-furyl)-2-oxo-1,2,3,5-tetrahydro-4,1-benzoxazepin-7-yl]-2-fluorobenzonitrile Prepared from 5-ethyl-5-(2-furyl)-7-(4,4,5,5-tetramethyl-1,3,2-dioxaborolan-2-yl)-1,5-dihydro-4,1-benzoxazepin-2 (H)-one and 4-bromo-2-fluorobenzonitrile using the coupling procedure described in example 1. $^1$H-NMR (DMSO-d$_6$) δ 10.15 (s, 1H), 7.97 (m, 1H), 7.83 (dd, J=11.2, 1.7 Hz, 1H), 7.76 (dd, J=8.5, 2.2 Hz, 1H), 7.72 (m, 1H), 7.68 (m, 1H), 7.49 (d, J=2.2 Hz, 1H), 7.31 (d, J=8.5 Hz, 1H), 6.47 (m, 1H), 6.32 (dd, J=3.4, 1.0 Hz, 1H), 4.19 (d, J=15.4 Hz, 1H), 3.98 (d, J=15.4 Hz, 1H), 2.56 (m, 1H), 2.34 (m, 1H), 0.76 (t, J=7.3 Hz, 3H); MS (ES) m/z 377 (M+H)$^+$; Anal. Calc. for C$_{22}$H$_{17}$FN$_2$O$_3$: C, 70.21; H, 4.55; N, 7.44. Found: C, 69.30; H, 4.39; N, 7.13.

EXAMPLE 86

7-(3-Chloro-5-fluorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 3-chloro-5-fluorobenzeneboronic acid using the coupling procedure described in example 1. $^1$H-NMR (DMSO-d$_6$) δ 10.09 (s, 1H), 7.72 (m, 1H), 7.68 (dd, J=8.3, 2.2 Hz, 1H), 7.52 (m, 1H), 7.48 (m, 1H), 7.40 (m, 2H), 7.27 (d, J=8.5 Hz, 1H), 6.47 (m, 1H), 6.32 (dd, J=3.4, 1.0 Hz, 1H), 4.19 (d, J=15.4 Hz, 1H), 3.97 (d, J=15.4 Hz, 1H), 2.53 (m, 1H), 2.33 (m, 1H), 0.76 (t, J=7.3 Hz, 3H); MS (ES) m/z 386 (M+H)$^+$; Anal. Calc. for C$_{21}$H$_{17}$ClFNO$_3$: C, 65.38; H, 4.44; N, 3.63. Found: C, 64.76; H, 4.44; N, 3.42.

EXAMPLE 87

7-(4-Chloro-3-fluorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 3-chloro-4-fluorobenzeneboronic acid using the coupling procedure described in example 1. $^1$H-NMR (DMSO-d$_6$) δ 10.08 (s, 1H), 8.34 (s, 1H), 7.71 (m, 3H), 7.45 (dd, J=8.4, 2.1 Hz, 1H), 7.38 (d, J=2.1 Hz, 1H), 7.28 (dd, J=8.7, 2.0 Hz, 1H), 6.47 (m, 1H), 6.33 (m, 1H), 4.20 (d, J=15.3 Hz, 1H), 3.97 (d, J=15.3 Hz, 1H), 2.51 (m, 1H), 2.28 (m, 1H), 0.76 (t, J=7.1 Hz, 3H); MS (ES) m/z 368 (M+H)$^+$; Anal. Calc. for C$_{21}$H$_{17}$ClFNO$_3$: C, 65.38; H, 4.44; N, 3.63. Found: C, 61.12; H, 4.05; N, 2.49.

EXAMPLE 88

7-(2,3-Difluorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 2,3-difluorobenzeneboronic acid using the coupling procedure described in example 1. $^1$H-NMR (DMSO-d$_6$) δ 10.11 (s, 1H), 7.71 (s, 1H), 7.64 (m, 1H), 7.57 (m, 1H), 7.51 (d, J=8.3 Hz, 1H), 7.43 (m, 1H), 7.28 (m, 2H), 6.47 (dd, J=3.6, 1.8 Hz, 1H), 6.35 (d, J=3.6 Hz, 1H), 4.25 (d, J=14.9 Hz, 1H), 3.97 (d, J=14.9 Hz, 1H), 2.52 (m, 1H), 2.14 (m, 1H), 0.76 (t, J=7.1 Hz, 3H); MS (ES) m/z 370 (M+H)$^+$; Anal. Calc. for C$_{21}$H$_{17}$F$_2$NO$_3$: C, 68.29; H, 4.64; N, 3.79. Found: C, 66.40; H, 4.43; N, 3.33.

EXAMPLE 89

4-[5-Ethyl-5-(2-furyl)-2-oxo-1,2,3,5-tetrahydro-4,1-benzoxazepin-7-yl]-2-furonitrile Prepared from 5-ethyl-5-(2-furyl)-7-(4,4,5,5-tetramethyl-1,3,2-dioxaborolan-2-yl)-1,5-dihydro-4,1-benzoxazepin-2 (H)-one and 4-bromo-furan-2-carbonitrile using the coupling procedure described in example 1. $^1$H-NMR (DMSO-d$_6$) δ 10.02 (s, 1H), 8.55 (d, J=2.2 Hz, 1H), 8.10 (d, J=2.0 Hz, 1H), 7.71 (d, J=1.9 Hz, 1H), 7.58 (m, 1H), 7.41 (s, 1H), 7.24 (dd, J=8.4, 2.7 Hz, 1H), 6.45 (s, 1H), 6.25 (d, J=2.7 Hz, 1H), 4.11 (d, J=15.6 Hz, 1H), 3.96 (d, J=15.6 Hz, 1H), 2.50 (m, 1H), 2.33 (m, 1H), 0.75 (m, 3H); MS (ES) m/z 349 (M+H)$^+$; Anal. Calc. for C$_{20}$H$_{16}$N$_2$O$_4$: C, 68.96; H, 4.63; N, 8.04. Found: C, 68.38; H, 4.73; N, 7.84.

EXAMPLE 90

7-(3,4-Difluorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 3,4-difluorobenzeneboronic acid using the coupling procedure described in example 1. $^1$H-NMR (DMSO-d$_6$) δ 10.06 (s, 1H), 7.73 (s, 1H), 7.71 (m, 1H), 7.53 (m, 3H), 7.33 (s, 1H), 7.26 (d, J=8.4 Hz, 1H), 6.47 (m, 1H), 6.33 (s, 1H), 4.21 (d, J=15.4 Hz, 1H), 3.96 (d, J=15.4 Hz, 1H), 2.51 (m, 1H), 2.27 (m, 1H), 0.76 (t, J=7.0 Hz, 3H); MS (ES) m/z 370 (M+H)$^+$; Anal. Calc. for C$_{21}$H$_{17}$F$_2$NO$_3$: C, 68.29; H, 4.64; N, 3.79. Found: C, 66.29; H, 4.49; N, 3.33.

EXAMPLE 91

5-Ethyl-7-(4-fluorophenyl)-5-(2-furyl)-1,5-dihydro-4,1-benzoxazepin-2(H)-one

Prepared from 7-bromo-5-ethyl-5-(2-furyl)-1,5-dihydro-4,1-benzoxazepin-2(H)-one and 4-fluorobenzeneboronic acid using the coupling procedure described in example 1. $^1$H-NMR (DMSO-d$_6$) δ 10.04 (s, 1H), 7.71 (s, 1H), 7.58 (m, 3H), 7.31 (m, 4H), 6.47 (dd, J=3.2, 1.8 Hz, 1H), 6.35 (m, 1H), 4.24 (d, J=15.2 Hz, 1H), 3.96 (d, J=15.2 Hz, 1H), 2.51 (m, 1H), 2.24 (m, 1H), 0.75 (t, J=6.0 Hz, 3H); MS (ES) m/z 352 (M+H)$^+$; Anal. Calc. for C$_{21}$H$_{18}$FNO$_3$: C, 71.78; H, 5.16; N, 3.99. Found: C, 70.73; H, 4.93; N, 3.77.

EXAMPLE 92

5-Ethyl-7-(2-fluorophenyl)-5-(2-furyl)-1,5-dihydro-4,1-benzoxazepin-2(H)-one

Prepared from 7-bromo-5-ethyl-5-(2-furyl)-1,5-dihydro-4,1-benzoxazepin-2(H)-one and 2-fluorobenzeneboronic acid using the coupling procedure described in example 1. $^1$H-NMR (DMSO-d$_6$) δ 10.08 (s, 1H), 7.70 (s, 1H), 7.64 (m, 1H), 7.51 (m, 3H), 7.28 (m, 3H), 6.47 (dd, J=3.3, 1.9 Hz, 1H), 6.35 (dd, J=3.2, 0.7 Hz, 1H), 4.27 (d, J=15.2 Hz, 1H), 3.97 (d, J=15.2 Hz, 1H), 2.51 (m, 1H), 2.13 (m, 1H), 0.77 (t, J=7.3 Hz, 3H); MS (ES) m/z 352 (M+H)+; Anal. Calc. for $C_{21}H_{18}FNO_3$: C, 71.78; H, 5.16; N, 3.99. Found: C, 68.53; H, 4.91; N, 3.35.

EXAMPLE 93

7-(3,5-Dichlorophenyl)-5-ethyl-5-(2-furyl)-1,5-dihydro-4,1-benzoxazepin-2(H)-one Prepared from 7-bromo-5-ethyl-5-(2-furyl)-1,5-dihydro-4,1-benzoxazepin-2(H)-one and 3,5-dichlorobenzeneboronic acid using the coupling procedure described in example 1. $^1$H-NMR (DMSO-$d_6$) δ 10.09 (s, 1H), 7.71 (d, J=0.7 Hz, 1H), 7.68 (dd, J=8.4, 2.1 Hz, 1H), 7.64 (d, J=1.9 Hz, 2H), 7.57 (m, 1H), 7.43 (d, J=4.6 Hz, 1H), 7.27 (d, J=8.6 Hz, 1H), 6.47 (m, 1H), 6.32 (dd, J=3.2, 0.6 Hz, 1H), 4.18 (d, J=15.5 Hz, 1H), 3.92 (d, J=15.5 Hz, 1H), 2.51 (m, 1H), 2.35 (m, 1H), 0.76 (t, J=7.1 Hz, 3H); MS (ES) m/z 402 (M+H)+; Anal. Calc. for $C_{21}H_{17}Cl_2NO_3$: C, 62.70; H, 4.26; N, 3.48. Found: C, 61.70; H, 4.46; N, 3.02.

EXAMPLE 94 tert-Butyl 2-cyano-5-(5-ethyl-1-methyl-2-oxo-5-thien-2-yl-1,2,3,5-tetrahydro-4,1-benzoxazepin-7-yl)-H-pyrrole-1-carboxylate Prepared from 2-(5-ethyl-1-methyl-2-oxo-5-thiophen-2-yl-1,2,3,5-tetrahydro-4,1-benzoxazepin-7-yl)-pyrrole-1-carboxylic acid tert-butyl ester and chlorosulfonyl isocyanate using the procedure described in example 1. $^1$H-NMR (DMSO-$d_6$) δ 7.64 (d, J=1.8 Hz, 1H), 7.60 (dd, J=8.3, 1.8 Hz, 1H), 7.45 (d, J=8.3 Hz, 1H), 7.36 (m, 2H), 6.92 (dd, J=5.0, 3.6 Hz, 1H), 6.62 (dd, J=3.5, 1.2 Hz, 1H), 6.59 (d, J=3.8 Hz, 1H), 4.07 (d, J=12.3 Hz, 1H), 4.00 (d, J=12.3 Hz, 1H), 2.75 (s, 3H), 2.31 (m, 1H), 2.18 (m, 1H), 1.40 (s, 9H), 0.83 (t, J=7.2 Hz, 3H); MS (ES) m/z 478 (M+H)+.

EXAMPLE 95

5-(5-Ethyl-1-methyl-2-oxo-5-thien-2-yl-1,2,3,5-tetrahydro-4,1-benzoxazepin-7-yl)-H-pyrrole-2-carbonitrile Prepared from tert-butyl 2-cyano-5-(5-ethyl-1-methyl-2-oxo-5-thien-2-yl-1,2,3,5-tetrahydro-4,1-benzoxazepin-7-yl)-H-pyrrole-1-carboxylate using the procedure described in example 2. $^1$H-NMR (DMSO-$d_6$) δ 12.82 (s, 1H), 7.97 (d, J=1.8 Hz, 1H), 7.89 (dd, J=8.4, 1.9 Hz, 1H), 7.44 (d, J=8.4 Hz, 1H), 7.34 (dd, J=5.0, 1.1 Hz, 1H), 7.05 (d, J=3.8 Hz, 1H), 6.91 (dd, J=5.0, 3.6, Hz, 1H), 6.83 (d, J=3.9 Hz, 1H), 6.63 (dd, J=3.5, 1.1 Hz, 1H), 4.04 (s, 2H), 2.71 (s, 3H), 2.45 (m, 1H), 2.29 (m, 1H), 0.87 (t, J=7.1 Hz, 3H); MS (ES) m/z 378 (M+H)+.

EXAMPLE 96

5-(5-Ethyl-1-methyl-2-oxo-5-thien-2-yl-1,2,3,5-tetrahydro-4,1-benzoxazepin-7-yl)-1-methyl-H-pyrrole-2-carbonitrile Prepared from 5-(5-ethyl-1-methyl-2-oxo-5-thien-2-yl-1,2,3,5-tetrahydro-4,1-benzoxazepin-7-yl)-H-pyrrole-2-carbonitrile using the procedure described in example 3. $^1$H-NMR (DMSO-$d_6$) δ 7.67 (m, 2H), 7.50 (d, J=8.0 Hz, 1H), 7.36 (d, J=5.0 Hz, 1H), 7.08 (d, J=4.0 Hz, 1H), 6.93 (t, J=4.7 Hz, 1H), 6.66 (d, J=3.5 Hz, 1H), 6.48 (d, J=4.0 Hz, 1H), 4.05 (s, 2H), 3.76 (s, 3H), 2.79 (s, 3H), 2.38 (m, 1H), 2.29 (m, 1H), 0.86 (t, J=7.0 Hz, 3H); MS (ES) m/z 392 (M+H)+; Anal. Calc. for $C_{22}H_{21}N_3O_2S$: C, 67.50, H, 5.41; N, 10.73. Found: C, 67.34, H, 5.46; N, 10.41.

EXAMPLE 97

1-Ethyl-5-(2-oxo-5,5-dithien-2-yl-1,2,3,5-tetrahydro-4,1-benzoxazepin-7-yl)-H-pyrrole-2-carbonitrile Prepared from 5-(2-oxo-5,5-dithien-2-yl-1,2,3,5-tetrahydro-4,1-benzoxazepin-7-yl)-1H-pyrrole-2-carbonitrile and iodoethane using the procedure described in example 3. $^1$H-NMR (DMSO-$d_6$) δ 10.33 (s, 1H), 7.62 (dd, J=5.4, 1.5 Hz, 2H), 7.43 (dd, J=8.3, 2.0 Hz, 1H), 7.27 (d, J=8.3 Hz, 1H), 7.01 (dd, J=4.9, 3.4, 2H), 6.98 (d, J=3.9 Hz, 1H), 6.93 (d, J=2.4 Hz, 1H), 6.86 (dd, J=3.9, 1.5 Hz, 2H), 6.17 (dd, J=3.9 Hz, 1H), 4.24 (s, 2H), 3.86 (q, J=7.3 Hz, 2H), 1.17 (t, J=7.3 Hz, 3H); MS (ES) m/z 446 (M+H)+.

EXAMPLE 98

1-Benzyl-5-(2-oxo-5,5-dithien-2-yl-1,2,3,5-tetrahydro-4,1-benzoxazepin-7-yl)-H-pyrrole-2-carbonitrile Prepared from 5-(2-oxo-5,5-dithien-2-yl-1,2,3,5-tetrahydro-4,1-benzoxazepin-7-yl)-1H-pyrrole-2-carbonitrile and benzyl bromide using the procedure described in example 3. $^1$H-NMR (DMSO-$d_6$) δ 10.28 (s, 1H), 7.58 (dd, J=4.9, 1.0 Hz, 2H), 7.40 (dd, J=8.3, 2.0 Hz, 1H), 7.26 (m, 4H), 7.11 (d, J=3.9 Hz, 1H), 6.94 (dd, J=4.9, 3.4 Hz, 2H), 6.90 (d, J=2.0 Hz, 1H), 6.66 (dd, J=7.3, 1.0 Hz, 2H), 6.52 (dd, J=3.4, 1.0 Hz, 2H), 6.31 (d, J=3.9 Hz, 1H), 5.16 (s, 2H), 4.13 (s, 2H); MS (ES) m/z 508 (M+H)+.

EXAMPLE 99

7-(3-Chloro-4-fluorophenyl)-5,5-dithien-2-yl-1,5-dihydro-4,1-benzoxazepin-2(H)-one Prepared from 7-bromo-5,5-dithien-2-yl-1,5-dihydro-4,1-benzoxazepin-2(3H)-one and 3-chloro-4-fluorobenzeneboronic acid using the coupling procedure described in example 1. $^1$H-NMR (DMSO-$d_6$) δ 10.27 (s, 1H), 7.68 (m, 4H), 7.48 (t, J=8.8 Hz, 1H), 7.38 (m, 1H), 7.27 (d, J=8.5 Hz, 1H), 7.16 (d, J=2.1 Hz, 1H), 7.04 (dd, J=5.0, 3.6 Hz, 2H), 6.93 (dd, J=3.6, 1.2 Hz, 2H), 4.22 (s, 2H); MS (ES) m/z 456 (M+H)+; Anal. Calc. For $C_{23}H_{15}ClFNO_2S_2$: C, 60.59, H, 3.32; N, 3.07. Found: C, 60.35, H, 3.28; N, 2.91.

EXAMPLE 100

3-Fluoro-5-(2-oxo-5,5-dithien-2-yl-1,2,3,5-tetrahydro-4,1-benzoxazepin-7-yl)benzonitrile Prepared from 7-bromo-5,5-dithien-2-yl-1,5-dihydro-4,1-benzoxazepin-2(3i)-one and 5-fluoro-3-cyanobenzeneboronic acid using the coupling procedure described in example 1. $^1$H-NMR (DMSO-$d_6$) δ 10.32 (s, 1H), 7.81 (m, 3H), 7.63 (m, 3H), 7.30 (m, 2H), 7.05 (m, 4H), 4.21 (s, 2H); MS (ES) m/z 445 (M−H)−.

EXAMPLE 101 tert-Butyl 2-[5,5-bis(5-bromothien-2-yl)-2-oxo-1,2,3,5-tetrahydro-4,1-benzoxazepin-7-yl]-5-cyano-H-pyrrole-1-carboxylate To a stirred mixture of tert-butyl 2-cyano-5-[2-oxo-5,5-di(2-thienyl)-,1,2,3,5-tetrahydro-4,1-benzoxazepin-7-yl]-1H- pyrrole-1-carboxylate (0.5 g, 0.97 mmol) and potassium acetate (0.38 g, 3.7 mmol) in glacial acetic acid (12 mL) was added bromine (0.1 mL, 1.9 mmol) at room temperature. After 1 hr, reaction mixture was slowly quenched with sodium bicarbonate solution (sat.) and extracted with ethyl acetate (3×40 mL). The combined organic layers were washed with water, brine and dried over magnesium sulfate. The solvent was removed in vacuo and residue purified on silica gel column (30% ethyl acetate in hexane) to give the title compound as yellowish solid (0.16 g, 25%). $^1$H-NMR (DMSO-$d_6$) δ 10.29 (s, 1H), 7.43 (dd, J=8.3, 2.0 Hz, 1H), 7.26 (d, J=3.9 Hz, 1H), 7.20 (d, J=8.3 Hz, 1H), 7.12 (d, J=3.9 Hz, 2H), 7.05 (d, J=2.0 Hz, 1H), 6.73 (d, J=3.9 Hz, 2H), 6.33 (d, J=3.4 Hz, 1H), 4.23 (s, 2H), 1.37 (s, 9H); MS (ES) m/z 674 (M–H)$^-$; Anal. Calc. for $C_{27}H_{21}Br_2N_3O_4S_2$: C, 48.01; H, 3.13; N, 6.22. Found: C, 47.94; H, 3.16; N, 5.92.

EXAMPLE 102

5-[5,5-Bis(5-bromothien-2-yl)-2-oxo-1,2,3,5-tetrahydro-4,1-benzoxazepin-7-yl]-1-methyl-H-pyrrole-2-carbonitrile Prepared from tert-butyl 2-[5,5-bis(5-bromothien-2-yl)-2-oxo-1,2,3,5-tetrahydro-4,1-benzoxazepin-7-yl]-5-cyano-H-pyrrole-1-carboxylate in two steps using the procedure described in examples 2 and 3. $^1$H-NMR (DMSO-$d_6$) δ 10.38 (s, 1H), 7.62 (dd, J=5.0, 1.0 Hz, 2H), 7.46 (dd, J=8.3, 1.9 Hz, 1H), 7.34 (d, J=8.5 Hz, 1H), 7.05 (m, 3H), 6.88 (d, J=2.4 Hz, 2H), 4.26 (s, 2H), 3.49 (s, 3H); MS (ES) m/z 588 (M–H)$^-$; Anal. Calc. for $C_{23}H_{15}Br_2N_3O_2S_2$: C, 46.88; H, 2.57; N, 7.13. Found: C, 47.23; H, 2.60; N, 7.10.

EXAMPLE 103

5-[5,5-Bis(5-cyanothien-2-yl)-2-oxo-1,2,3,5-tetrahydro-4,1-benzoxazepin-7-yl]-H-pyrrole-2-carbonitrile Prepared from 5-[5,5-Bis-(5-bromo-thiophen-2-yl)-2-oxo-1,2,3,5-tetrahydro-benzo[e][1,4]oxazepin-7-yl]-1H-pyrrole-2-carbonitrile generally according to example 84. $^1$H-NMR (DMSO-$d_6$) δ 12.55 (s, 1H), 10.30 (s, 1H), 7.93 (d, J=3.8 Hz, 2H), 7.78 (dd, J=8.2, 2.2 Hz, 1H), 7.46 (d, J=2.2 Hz, 1H), 7.21 (m, 3H), 6.97 (dd, J=3.8, 2.2 Hz, 1H), 6.58 (dd, J=3.8, 2.7 Hz, 1H), 4.28 (s, 2H); MS (ES) m/z 466 (M–H)$^-$.

EXAMPLE 104

7-(3-Chloro-4-fluorophenyl)-5,5-dimethyl-1,3,4,5-tetrahydro-H-1-benzazepin-2-one 5,5-Dimethyl-1,3,4,5-tetrahydro-H-1-benzazepin-2-one To a stirred solution of levulinic acid (2.8 g, 19.5 mmol) in 65 mL of ether at 0° C. was slowly added methyl magnesium bromide (3M, 13 mL, 39 mmol). The resulting solution was allowed to stir overnight at room temperature. The solution was cooled to 0° C., decomposed with 50% sulfuric acid, extracted with ether, dried over magnesium sulfate, and concentrated to give 5,5-dimethyl-dihydro-furan-2-one (400 mg, 18%) as a brown oil.

To a stirred solution of aluminum chloride (25.5 g, 191.7 mmol) in benzene (100 mL) at 0° C. was added a solution of above brown oil (7.3 g, 63.9 mmol) in 50 mL of benzene. The resulting solution was then heated to reflux 3 h. The solution was then cooled to rt, quenched slowly in 1N HCl and ice. The benzene layer was successively washed with dilute 1N HCl, water, sodium carbonate solution, dried over magnesium sulfate, and concentrated to give 4,4-dimethyl-3,4-dihydro-2H-naphthalen-1-one (8.4 g 75%).

A mixture of 4,4-dimethyl-3,4-dihydro-2H-naphthalen-1-one (0.5 g, 2.9 mmol), sodium azide (0.32 g, 4.9 mmol), and polyphosphoric acid (50 mL) was stirred via a mechanical stirrer at 60° C. overnight. The solution was then poured on ammonium hydroxide with cooling and extracted with ethyl acetate. The organic layer was dried ($MgSO_4$), concentrated, and purified on a silica gel flash column (ethyl acetate:hexane/2:5) to give the title compound (0.07 g, 13%). $^1$H-NMR (DMSO-$d_6$) δ 9.52 (s, 1H), 7.38 (d, J=7.8 Hz, 1H), 7.22 (t, J=7.4 Hz, 1H), 7.11 (t, J=7.6 Hz, 1H), 6.97 (d, J=7.7 Hz, 1H), 2.19 (t, J=6.8 Hz, 2H), 2.00 (t, J=7.3 Hz, 2H), 1.32 (s, 6H); MS (ES) m/z 190 (M+H)$^+$; Anal. Calc. For $C_{12}H_{15}NO$: C, 76.16, H, 7.99; N, 7.40. Found: C, 76.07, H, 8.09; N, 7.43.

7-Bromo-5,5-dimethyl-1,3,4,5-tetrahydro-2H-1-benzazepin-2-one

To a mixture of glacial acetic acid (6 mL) and potassium acetate (0.2 g, 2.1 mmol) was added 5,5-dimethyl-1,3,4,5-tetrahydro-H-1-benzazepin-2-one (0.1 g, 0.5 mmol). Bromine (0.1 mL, 1.9 mmol) was added and the solution was allowed to stir overnight at room temperature. The solution was partitioned between brine and ethyl acetate. The organic layer was separated, dried over magnesium sulfate, and concentrated. The product was crystallized from ether to give 7-bromo-5,5-dimethyl-1,3,4,5-tetrahydro-2H-1-benzazepin-2-one as an off-white solid (0.07 g, 50%). $^1$H-NMR (DMSO-$d_6$) δ 9.62 (s, 1H), 7.45 (d, J=2.4 Hz, 1H), 7.41 (dd, J=8.8, 2.4 Hz, 1H), 6.92 (d, J=8.3 Hz, 1H), 2.20 (t, J=6.8 Hz, 2H), 2.00 (t, J=7.8 Hz, 2H), 1.33 (s, 6H); MS (ES) m/z 268 (M+H)$^+$; Anal. Calc. For $C_{12}H_{14}BrNO$: C, 53.75, H, 5.26; N, 5.22. Found: C, 49.14, H, 4.57; N, 4.68.

The title compound was prepared from 5,5-dimethyl-1,3,4,5-tetrahydro-H-1-benzazepin-2-one and 3-chloro-4-fluorobenzeneboronic acid generally according to the coupling procedure described in example 1. $^1$H-NMR (DMSO-$d_6$) δ 9.65 (s, 1H), 7.89 (dd, J=7.3, 2.4 Hz, 1H), 7.69 (m, 1H), 7.59 (d, J=2.0 Hz, 1H), 7.53 (m, 2H), 7.05 (d, J=7.8 Hz, 1H), 2.25 (t, J=6.8 Hz, 2H), 2.03 (t, J=7.3 Hz, 2H), 1.39 (s, 6H); MS (ES) m/z 318 (M+H)$^+$.

EXAMPLE 105

3-(5,5-Dimethyl-2-oxo-2,3,4,5-tetrahydro-H-1-benzazepin-7-yl)-5-fluorobenzonitrile Prepared from 5,5-dimethyl-1,3,4,5-tetrahydro-H-1-benzazepin-2-one and 5-fluoro-3-cyanobenzeneboronic acid generally according to the coupling procedure described in example 1. $^1$H-NMR (DMSO-$d_6$) δ 9.70 (s, 1H), 8.10 (t, J=1.5 Hz, 1H), 7.97 (dt, J=10.3, 2.0 Hz, 1H), 7.82 (d, J=8.3 Hz, 1H), 7.70 (d, J=2.0 Hz, 1H), 7.64 (dd, J=7.8, 2.0 Hz, 1H), 7.08 (d, J=8.3 Hz, 1H), 2.26 (t, J=7.3 Hz, 2H), 2.03 (t, J=7.3 Hz, 2H), 1.40 (s, 6H); MS (ES) m/z 309 (M+H)$^+$.

EXAMPLE 106

7-(3-Chloro-4-fluorophenyl)-5-methyl-5-thien-2-yl-1,5-dihydro-4,1-benzoxazepin-2(H)-one Prepared from 7-bromo-5-methyl-5-thien-2-yl-1,5-dihydro-4,1-benzoxazepin-2(3H)-one and 3-chloro-4-fluorobenzeneboronic acid generally according to the coupling procedure described in example 1. ¹H-NMR (DMSO-d₆) δ 10.13 (s, 1H), 7.86 (dd, J=6.8, 2.0 Hz, 1H), 7.64 (m, 2H), 7.55 (m, 2H), 7.48 (t, J=8.8 Hz, 1H), 7.25 (d, J=8.3 Hz, 1H), 6.99 (dd, J=4.9, 3.4 Hz, 1H), 6.91 (dd, J=3.4, 1.0 Hz, 1H), 4.16 (d, J=16.1 Hz, 1H), 4.06 (d, J=16.1 Hz, 1H), 2.08 (s, 3H); MS (ES) m/z 388 (M+H)⁺; Anal. Calc. For $C_{20}H_{15}ClFNO_2S$: C, 61.93, H, 3.90; N, 3.61. Found: C, 61.88, H, 3.99; N, 3.35.

EXAMPLE 107

3-Fluoro-5-(5-methyl-2-oxo-5-thien-2-yl-1,2,3,5-tetrahydro-4,1-benzoxazepin-7-yl)benzonitrile Prepared from 7-bromo-5-methyl-5-thien-2-yl-1,5-dihydro-4,1-benzoxazepin-2(3H)-one and 5-fluoro-3-cyanobenzeneboronic acid generally according to the coupling procedure described in example 1. ¹H-NMR (DMSO-d₆) δ 10.18 (s, 1H), 8.09 (s, 1H), 7.96 (dt, J=9.8, 2.4 Hz, 1H), 7.80 (dt, J=8.3, 1.5 Hz, 1H), 7.76 (dd, J=8.3, 2.0 Hz, 1H), 7.72 (d, J=2.0 Hz, 1H), 7.55 (dd, J=5.4, 1.5 Hz, 1H), 7.28 (d, J=8.3 Hz, 1H), 6.99 (dd, J=4.9, 3.4 Hz, 1H), 6.89 (dd, J=3.4, 1.5 Hz, 1H), 4.17 (d, J=16.1 Hz, 1H), 4.04 (d, J=16.1 Hz, 1H), 2.12 (s, 3H); MS (ES) m/z 379 (M+H)⁺.

EXAMPLE 108

4-Methyl-5-(5-methyl-2-oxo-5-thien-2-yl-1,2,3,5-tetrahydro-4,1-benzoxazepin-7-yl)thiophene-2-carbonitrile Prepared from 7-bromo-5-methyl-5-thien-2-yl-1,5-dihydro-4,1-benzoxazepin-2(3H)-one and 5-bromo-4-methylthiophene-2-carbonitrile generally according to the coupling procedure described in examples 82 and 1. ¹H-NMR (DMSO-d₆) δ 10.26 (s, 1H), 7.83 (s, 1H), 7.56 (dd, J=4.9, 1.1 Hz, 1H), 7.47 (dd, J=8.5, 2.2 Hz, 1H), 7.32 (d, J=2.2 Hz, 1H), 7.29 (d, J=8.5 Hz, 1H), 7.00 (m, 1H), 6.96 (m, 1H), 4.23 (d, J=15.9 Hz, 1H), 4.13 (d, J=15.9 Hz, 1H), 2.19 (s, 3H), 2.03 (s, 3H); MS (ES) m/z 381 (M+H)⁺; Anal. Calc. For $C_{20}H_{16}N_2O_2S_2$: C, 63.14, H, 4.24; N, 7.36. Found: C, 62.85, H, 4.16; N, 7.09.

EXAMPLE 109

2-Fluoro-5-(5-methyl-2-oxo-5-thien-2-yl-1,2,3,5-tetrahydro-4,1-benzoxazepin-7-yl)benzonitrile Prepared from 7-bromo-5-methyl-5-thien-2-yl-1,5-dihydro-4,1-benzoxazepin-2(3H)-one and 5-bromo-2-fluorobenzonitrile generally according to the coupling procedure described in examples 82 and 1. ¹H-NMR (DMSO-d₆) δ 10.14 (s, 1H), 8.27 (dd, J=5.6, 2.4 Hz, 1H), 8.06 (m, 1H), 7.68 (dd, J=8.8, 2.4 Hz, 1H), 7.63 (d, J=2.0 Hz, 1H), 7.60 (t, J=9.3 Hz, 1H), 7.55 (dd, J=5.4, 1.5 Hz, 1H), 7.27 (d, J=8.8 Hz, 1H), 6.98 (m, 1H), 6.89 (dd, J=3.9, 1.5 Hz, 1H), 4.16 (d, J=15.6 Hz, 1H), 4.05 (d, J=15.6 Hz, 1H), 2.10 (s, 3H); MS (ES) m/z 379 (M+H)⁺.

EXAMPLE 110

4-(5-Methyl-2-oxo-5-thien-2-yl-1,2,3,5-tetrahydro-4,1-benzoxazepin-7-yl)-2-furonitrile Prepared from 7-bromo-5-methyl-5-thien-2-yl-1,5-dihydro-4,1-benzoxazepin-2(3H)-one and 4-bromofuran-2-carbonitrile generally according to the coupling procedure described in examples 82 and 1. ¹H-NMR (DMSO-d₆) δ 10.09 (s, 1H), 8.60 (s, 1H), 8.16 (s, 1H), 7.61 (m, 2H), 7.54 (dd, J=4.9, 1.0 Hz, 1H), 7.22 (d, J=8.3 Hz, 1H), 6.97 (dd, J=5.4, 3.9 Hz, 1H), 6.84 (dd, J=3.4, 1.0 Hz, 1H), 4.16 (d, J=15.6 Hz, 1H), 4.00 (d, J=15.6 Hz, 1H), 2.07 (s, 3H); MS (ES) m/z 351 (M+H)⁺.

EXAMPLE 111

5-(5,5-Dimethyl-2-oxo-1,2,3,5-tetrahydro-4,1-benzoxazepin-7-yl)-2-fluorobenzonitrile Prepared from 7-bromo-5,5-dimethyl-1,5-dihydro-4,1-benzoxazepin-2(3H)-one and 5-bromo-2-fluorobenzonitrile generally according to the coupling procedure described in examples 82 and 1. ¹H-NMR (DMSO-d₆) δ 10.02 (s, 1H), 8.32 (dd, J=6.3, 2.4 Hz, 1H), 8.11 (m, 1H), 7.62 (m, 1H), 7.58 (m, 2H), 7.19 (d, J=8.8 Hz, 1H), 4.26 (s, 2H), 1.62 (s, 6H); MS (ES) m/z 311 (M+H)⁺.

EXAMPLE 112

4-(5,5-Dimethyl-2-oxo-1,2,3,5-tetrahydro-4,1-benzoxazepin-7-yl)-2-furonitrile

Prepared from 7-bromo-5,5-dimethyl-1,5-dihydro-4,1-benzoxazepin-2(3H)-one and 4-bromofuran-2-carbonitrile generally according to the coupling procedure described in examples 82 and 1. ¹H-NMR (DMSO-d₆) δ 9.96 (s, 1H), 8.61 (s, 1H), 8.19 (s, 1H), 7.56 (d, J=1.9 Hz, 1H), 7.50 (dd, J=8.3, 2.0 Hz, 1H), 7.14 (d, J=8.4 Hz, 1H), 4.24 (s, 2H), 1.59 (s, 6H); MS (ES) m/z 283 (M+H)⁺.

EXAMPLE 113 tert-Butyl 2-cyano-5-(2-oxo-5,5-dithien-3-yl-1,2,3,5-tetrahydro-4,1-benzoxazepin-7-yl)-H-pyrrole-1-carboxylate 2-Bromo-N-{4-bromo-2-[hydroxy(dithien-3-yl)methyl]phenyl}acetamide Prepared from methyl 2-amino-5-bromobenzoate in two steps generally according to the procedures described in example 24. ¹H-NMR (DMSO-d₆) δ 10.26 (s, 1H), 8.03 (d, J=5.3 Hz, 1H), 7.73 (s, 1H), 7.59 (m, 3H), 7.09 (m, 2H), 6.98 (dd, J=5.0, 1.3 Hz, 2H), 6.72 (d, J=2.4 Hz, 1H), 3.91 (s, 2H); MS (ES) m/z 486 (M−H)⁻; Anal. Calc. For $C_{17}H_{13}Br_2NO_2S_2$: C, 41.91, H, 2.69; N, 2.87. Found: C, 41.62, H, 2.71; N, 2.72.

7-Bromo-5,5-dithien-3-yl-1,5-dihydro-4,1-benzoxazepin-2(H)-one

Prepared from 2-bromo-N-{4-bromo-2-[hydroxy(dithien-3-yl)methyl]phenyl}acetamide generally according to the procedure described in example 1. ¹H-NMR (DMSO-d₆) δ 10.21 (s, 1H), 7.60 (dd, J=4.9, 2.9 Hz, 2H), 7.50 (dd, J=8.8, 2.4 Hz, 1H), 7.15 (d, J=8.8 Hz, 1H), 7.08 (dd, J=3.4, 1.5 Hz, 2H), 6.90 (dd, J=4.9, 1.5 Hz, 2H), 6.75 (d, J=2.4 Hz, 1H), 4.19 (s, 2H); MS (ES) m/z 408 (M+H)⁺.

tert-Butyl 2-(2-oxo-5,5-dithien-3-yl-1,2,3,5-tetrahydro-4,1-benzoxazepin-7-yl)-H-pyrrole-1-carboxylate Prepared from 7-bromo-5,5-dithien-3-yl-1,5-dihydro-4,1-benzoxazepin-2(H)-one and 2-borono-1H-pyrrole-1-carboxylic acid, 1-tert-butyl ester generally according to the coupling procedure described in example 1. ¹H-NMR (DMSO-d$_6$) δ 10.13 (s, 1H), 7.55 (dd, J=4.9, 2.9 Hz, 2H), 7.27 (m, 2H), 7.16 (d, J=8.3 Hz, 1H), 7.07 (dd, J=2.9, 1.5 Hz, 2H), 6.89 (dd, J=4.9, 1.5 Hz, 2H), 6.70 (d, J=2.4 Hz, 1H), 6.19 (m, 1H), 6.06 (m, 1H), 4.17 (s, 2H), 1.36 (s, 9H); MS (ES) m/z 493 (M+H)$^+$.

The title compound was prepared from tert-butyl 2-(2-oxo-5,5-dithien-3-yl-1,2,3,5-tetrahydro-4,1-benzoxazepin-7-yl)-H-pyrrole-1-carboxylate and chlorosulfonyl isocyanate steps generally according to the procedure described in example 1. $^1$H-NMR (DMSO-d$_6$) δ 10.20 (s, 1H), 7.56 (dd, J=4.9, 2.9 Hz, 2H), 7.35 (dd, J=8.3, 2.0 Hz, 1H), 7.23 (m, 2H), 7.07 (dd, J=2.9, 1.5 Hz, 2H), 6.89 (dd, J=5.4, 1.5 Hz, 2H), 6.74 (d, J=2.0 Hz, 1H), 6.26 (d, J=3.4 Hz, 1H), 4.18 (s, 2H), 1.38 (s, 9H); MS (ES) m/z 518 (M+H)$^+$.

EXAMPLE 114

5-(2-Oxo-5,5-dithien-3-yl-1,2,3,5-tetrahydro-4,1-benzoxazepin-7-yl)-H-pyrrole-2-carbonitrile Prepared from tert-butyl 2-cyano-5-(2-oxo-5,5-dithien-3-yl-1,2,3,5-tetrahydro-4,1-benzoxazepin-7-yl)-H-pyrrole-1-carboxylate generally according to the procedure described in example 2. $^1$H-NMR (DMSO-d$_6$) δ 12.49 (s, 1H), 10.14 (s, 1H), 7.61 (dd, J=8.5, 2.2 Hz, 1H), 7.57 (dd, J=5.2, 3.0 Hz, 2H), 7.23 (d, J=8.5 Hz, 1H), 7.16 (m, 3H), 6.96 (dd, J=5.2, 1.4 Hz, 2H), 6.91 (d, J=3.8 Hz, 1H), 6.30 (d, J=3.8 Hz, 1H), 4.12 (s, 2H); MS (ES) m/z 418 (M+H)$^+$.

EXAMPLE 115

1-Methyl-5-(2-oxo-5,5-dithien-3-yl-1,2,3,5-tetrahydro-4,1-benzoxazepin-7-yl)-H-pyrrole-2-carbonitrile Prepared from 5-(2-oxo-5,5-dithien-3-yl-1,2,3,5-tetrahydro-4,1-benzoxazepin-7-yl)-H-pyrrole-2-carbonitrile and iodomethane generally according to the procedure described in example 3. $^1$H-NMR (DMSO-d$_6$) δ 10.26 (s, 1H), 7.59 (dd, J=5.2, 3.0 Hz, 2H), 7.45 (dd, J=8.2, 2.2 Hz, 1H), 7.30 (d, J=8.2 Hz, 1H), 7.10 (dd, J=3.0, 1.4 Hz, 2H), 6.95 (m, 3H), 6.79 (d, J=2.2 Hz, 1H), 6.14 (d, J=4.1 Hz, 1H), 4.20 (s, 2H), 3.45 (s, 3H); MS (ES) m/z 432 (M+H)$^+$.

EXAMPLE 116

3-Fluoro-5-(2-oxo-5,5-dithien-3-yl-1,2,3,5-tetrahydro-4,1-benzoxazepin-7-yl)benzonitrile Prepared from 7-bromo-5,5-dithien-3-yl-1,5-dihydro-4,1-benzoxazepin-2(H)-one and 5-fluoro-3-cyanobenzeneboronic acid generally according to the coupling procedure described in example 1. $^1$H-NMR (DMSO-d$_6$) δ 10.25 (s, 1H), 7.78 (m, 1H), 7.73 (m, 2H), 7.59 (m, 3H), 7.31 (d, J=8.3 Hz, 1H), 7.18 (dd, J=2.9, 1.5 Hz, 2H), 7.06 (d, J=2.4 Hz, 1H), 6.97 (dd, J=4.9, 1.5 Hz, 2H), 4.18 (s, 2H); MS (ES) m/z 447 (M+H)$^+$.

EXAMPLE 117

7-(3-Chloro-4-fluorophenyl)-5,5-dithien-3-yl-1,5-dihydro-4,1-benzoxazepin-2(H)-one Prepared from 7-bromo-5,5-dithien-3-yl-1,5-dihydro-4,1-benzoxazepin-2(H)-one and 3-chloro-4-fluorobenzeneboronic acid generally according to the coupling procedure described in example 1. $^1$H-NMR (DMSO-d$_6$) δ 10.20 (s, 1H), 7.62 (dd, J=8.3, 2.0 Hz, 1H), 7.58 (m, 3H), 7.45 (t, J=8.8 Hz, 1H), 7.34 (m, 1H), 7.28 (d, J=8.3 Hz, 1H), 7.13 (dd, J=2.9, 1.5 Hz, 2H), 6.95 (d, J=1.0 Hz, 1H), 6.94 (d, J=1.5 Hz, 2H), 4.18 (s, 2H); MS (ES) m/z 456 (M+H)$^+$.

EXAMPLE 118 tert-Butyl 2-[5,5-bis(3-chlorophenyl)-2-oxo-1,2,3,5-tetrahydro-4,1-benzoxazepin-7-yl]-5-cyano-H-pyrrole-1-carboxylate N-{2-[Bis(3-chlorophenyl)(hydroxy)methyl]-4-bromophenyl}-2-bromoacetamide Prepared from Prepared from methyl 2-amino-5-bromobenzoate in two steps generally according to the procedure described in example 24. $^1$H-NMR (DMSO-d$_6$) δ 9.89 (s, 1H), 8.01 (s, 1H), 7.94 (d, J=8.8 Hz, 1H), 7.61 (dd, J=8.8, 2.4 Hz, 1H), 7.43 (m, 4H), 7.35 (t, J=1.5 Hz, 2H), 7.05 (dt, J=7.3, 1.5 Hz, 2H), 6.60 (d, J=2.4 Hz, 1H), 3.82 (s, 2H); MS (ES) m/z 542 (M–H)$^-$; Anal. Calc. for C$_{21}$H$_{15}$Br$_2$Cl$_2$NO$_2$: C, 46.36; H, 2.78; N, 2.57. Found: C, 46.63; H, 2.77; N, 2.57.

7-Bromo-5,5-bis(3-chlorophenyl)-1,5-dihydro-4,1-benzoxazepin-2(H)-one

Prepared from N-{2-[bis(3-chlorophenyl)(hydroxy)methyl]-4-bromophenyl}-2-bromoacetamide generally according to the procedure described in example 1. $^1$H-NMR (DMSO-d$_6$) δ 10.13 (s, 1H), 7.62 (dd, J=8.8, 2.4 Hz, 1H), 7.47 (m, 4H), 7.21 (t, J=2.0 Hz, 2H), 7.10 (d, J=8.3 Hz, 1H), 7.02 (dt, J=7.3, 1.5 Hz, 2H), 6.61 (d, J=2.4 Hz, 1H), 4.28 (s, 2H); MS (ES) m/z 464 (M+H)$^+$; Anal. Calc. for C$_{21}$H$_{14}$BrCl$_2$NO$_2$: C, 54.46; H, 3.05; N, 3.02. Found: C, 54.54; H, 3.49; N, 2.67.

tert-Butyl 2-[5,5-bis(3-chlorophenyl)-2-oxo-1,2,3,5-tetrahydro-4,1-benzoxazepin-7-yl]-H-pyrrole-1-carboxylate Prepared from 7-bromo-5,5-bis(3-chlorophenyl)-1,5-dihydro-4,1-benzoxazepin-2(H)-one and 2-borono-1H-pyrrole-1-carboxylic acid, 1-tert-butyl ester generally according to the coupling procedure described in example 1. $^1$H-NMR (DMSO-d$_6$) δ 10.10 (s, 1H), 7.43 (m, 5H), 7.25 (dd, J=2.9, 1.5 Hz, 1H), 7.20 (t, J=1.5 Hz, 2H), 7.14 (d, J=8.3 Hz, 1H), 7.06 (dt, J=7.3, 1.5 Hz, 2H), 6.50 (d, J=2.0 Hz, 1H), 6.20 (t, J=3.4 Hz, 1H), 6.08 (dd, J=3.4, 2.0 Hz, 1H), 4.29 (s, 2H), 1.35 (s, 9H); MS (ES) m/z 547 (M–H)$^-$; Anal. Calc. for C$_{30}$H$_{26}$Cl$_2$N$_2$O$_4$: C, 65.58; H, 4.77; N, 5.10. Found: C, 64.81; H, 4.92; N, 4.53.

The title compound was prepared from tert-butyl 2-[5,5-bis(3-chlorophenyl)-2-oxo-1,2,3,5-tetrahydro-4,1-benzoxazepin-7-yl]-H-pyrrole-1-carboxylate and chlorosulfonyl isocyanate generally according to the procedure described in example 1. $^1$H-NMR (DMSO-d$_6$) δ 10.20 (s, 1H), 7.47 (dd, J=8.2, 2.2 Hz, 1H), 7.44 (m, 4H), 7.24 (d, J=3.8 Hz, 1H), 7.20 (m, 3H), 7.06 (dt, J=7.7, 1.1 Hz, 2H), 6.56 (d, J=2.2 Hz, 1H), 6.28 (d, J=3.8 Hz, 1H), 4.28 (s, 2H), 1.37 (s, 9H); MS (ES) m/z 574 (M+H)$^+$; Anal. Calc. for C$_{31}$H$_{25}$Cl$_2$N$_3$O$_4$: C, 64.82; H, 4.39; N, 7.31. Found: C, 64.56; H, 4.62; N, 7.00.

EXAMPLE 119

5-[5,5-Bis(3-chlorophenyl)-2-oxo-1,2,3,5-tetrahydro-4,1-benzoxazepin-7-yl]-H-pyrrole-2-carbonitrile Prepared from tert-butyl 2-[5,5-bis(3-chlorophenyl)-2-oxo-1,2,3,5-tetrahydro-4,1-benzoxazepin-7-yl]-5-cyano-H- pyrrole-1-carboxyl at generally according to the procedure described in example 2. $^1$H-NMR (DMSO-$d_6$) δ 12.53 (s, 1H), 10.14 (s, 1H), 7.70 (dd, J=8.2, 2.2 Hz, 1H), 7.46 (m, 4H), 7.27 (d, J=1.6 Hz, 2H), 7.21 (d, J=8.2 Hz, 1H), 7.16 (dt, J=6.6, 2.2 Hz, 2H), 7.03 (d, J=1.6 Hz, 1H), 6.92 (d, J=3.8 Hz, 1H), 6.30 (d, J=3.8 Hz, 1H), 4.19 (s, 2H); MS (ES) m/z 472 (M−H)$^-$; Anal. Calc. for $C_{26}H_{17}Cl_2N_3O_2$: C, 65.84; H, 3.61; N, 8.86. Found: C, 65.60; H, 3.50; N, 8.78.

EXAMPLE 120

5-[5,5-Bis(3-chlorophenyl)-2-oxo-1,2,3,5-tetrahydro-4,1-benzoxazepin-7-yl]-1-methyl-H-pyrrole-2-carbonitrile Prepared from 5-[5,5-bis(3-chlorophenyl)-2-oxo-1,2,3,5-tetrahydro-4,1-benzoxazepin-7-yl]-H-pyrrole-2-carbonitrile and iodomethane generally according to the procedure described in example 3. $^1$H-NMR (DMSO-$d_6$) δ 10.22 (s, 1H), 7.55 (dd, J=8.2, 2.2 Hz, 1H), 7.45 (m, 4H), 7.27 (m, 3H), 7.09 (dt, J=7.1, 1.6 Hz, 2H), 6.96 (d, J=3.8 Hz, 1H), 6.67 (d, J=2.2 Hz, 1H), 6.17 (d, J=3.8 Hz, 1H), 4.28 (s, 2H), 3.48 (s, 3H); MS (ES) m/z 486 (M−H)$^-$; Anal. Calc. for $C_{27}H_{19}Cl_2N_3O_2$: C, 66.40; H, 3.92; N, 8.60. Found: C, 66.07; H, 4.32; N, 7.86.

EXAMPLE 121

5-[5,5-Bis(3-chlorophenyl)-1-methyl-2-oxo-1,2,3,5-tetrahydro-4,1-benzoxazepin-7-yl]-1-methyl-H-pyrrole-2-carbonitrile Prepared from 5-[5,5-bis(3-chlorophenyl)-2-oxo-1,2,3,5-tetrahydro-4,1-benzoxazepin-7-yl]-H-pyrrole-2-carbonitrile and iodomethane generally according to the procedure described in example 3. $^1$H-NMR (DMSO-$d_6$) δ 7.76 (dd, J=8.2, 2.2 Hz, 1H), 7.60 (d, J=8.2 Hz, 1H), 7.42 (m, 4H), 7.37 (s, 2H), 7.09 (m, 2H), 6.99 (d, J=3.8 Hz, 1H), 6.58 (d, J=2.2 Hz, 1H), 6.24 (d, J=3.8 Hz, 1H), 4.25 (s, 2H), 3.58 (s, 3H), 2.65 (s, 3H); MS (ES) m/z 504 (M+H)$^+$; Anal. Calc. for $C_{28}H_{21}Cl_2N_3O_2$: C, 66.94; H, 4.21; N, 8.36. Found: C, 66.38; H, 4.44; N, 8.15.

EXAMPLE 122

3-[5,5-Bis(3-chlorophenyl)-2-oxo-1,2,3,5-tetrahydro-4,1-benzoxazepin-7-yl]-5-fluorobenzonitrile Prepared from 7-bromo-5,5-bis(3-chlorophenyl)-1,5-dihydro-4,1-benzoxazepin-2(H)-one and 5-fluoro-3-cyanobenzeneboronic acid generally according to the coupling procedure described in example 1. $^1$H-NMR (DMSO-$d_6$) δ 10.23 (s, 1H), 7.80 (dd, J=6.6, 2.2 Hz, 1H), 7.78 (m, 1H), 7.62 (dt, J=9.9, 2.7 Hz, 1H), 7.46 (m, 5H), 7.29 (m, 3H), 7.17 (dt, J=7.1, 1.6 Hz, 2H), 6.96 (d, J=2.2 Hz, 1H), 4.25 (s, 2H); MS (ES) m/z 501 (M−H)$^-$; Anal. Calc. for $C_{28}H_{17}Cl_2FN_2O_2$: C, 66.81; H, 3.40; N, 5.57. Found: C, 66.47; H, 3.31; N, 5.40.

EXAMPLE 123

7-(3-Chloro-4-fluoro-phenyl)-5,5-bis-(3-chloro-phenyl)-1,5-dihydro-benzo[e][1,4]oxazepin-2-one Prepared from 7-bromo-5,5-bis(3-chlorophenyl)-1,5-dihydro-4,1-benzoxazepin-2(H)-one and 3-chloro-4-fluorobenzeneboronic acid generally according to the coupling procedure described in example 1. $^1$H-NMR (DMSO-$d_6$) δ 10.17 (s, 1H), 7.73 (dd, J=8.2, 2.2 Hz, 1H), 7.60 (dd, J=7.1, 2.7 Hz, 1H), 7.46 (m, 5H), 7.33 (m, 1H), 7.27 (t, J=1.6 Hz, 2H), 7.24 (d, J=8.2 Hz, 1H), 7.11 (dt, J=7.1, 1.6 Hz, 2H), 6.80 (d, J=2.2 Hz, 1H), 4.28 (s, 2H); MS (ES) m/z 510 (M−H)$^-$; Anal. Calc. for $C_{27}H_{17}Cl_3FNO_2$: C, 63.24; H, 3.34; N, 2.73. Found: C, 60.08; H, 3.00; N, 2.28.

EXAMPLE 124 tert-Butyl 2-[5,5-bis(4-chlorophenyl)-2-oxo-1,2,3,5-tetrahydro-4,1-benzoxazepin-7-yl]-5-cyano-H-pyrrole-1-carboxylate N-{2-[Bis(4-chlorophenyl)(hydroxy)methyl]-4-bromophenyl}-2-bromoacetamide Prepared from methyl 2-amino-5-bromobenzoate in two steps generally according to the procedure described in example 24. $^1$H-NMR (DMSO-$d_6$) δ 10.01 (s, 1H), 7.98 (d, J=8.8 Hz, 1H), 7.94 (s, 1H), 7.59 (dd, J=8.8, 2.4 Hz, 1H), 7.44 (m, 4H), 7.19 (m, 4H), 6.58 (d, J=2.4 Hz, 1H), 3.84 (s, 2H); MS (ES) m/z 542 (M−H)$^-$; Anal. Calc. for $C_{21}H_{15}Br_2Cl_2NO_2$: C, 46.36; H, 2.78; N, 2.57. Found: C, 46.59; H, 2.82; N, 2.36.

7-Bromo-5,5-bis(4-chlorophenyl)-1,5-dihydro-4,1-benzoxazepin-2(H)-one

Prepared from N-{2-[bis(4-chlorophenyl)(hydroxy)methyl]-4-bromophenyl}-2-bromoacetamide generally according to the procedure described in example 1. $^1$H-NMR (DMSO-$d_6$) δ 10.13 (s, 1H), 7.58 (dd, J=8.3, 2.0 Hz, 1H), 7.46 (m, 4H), 7.14 (m, 4H), 7.10 (d, J=8.3 Hz, 1H), 6.60 (d, J=2.4 Hz, 1H), 4.24 (s, 2H); MS (ES) m/z 462 (M−H)$^-$; Anal. Calc. for $C_{21}H_{14}BrCl_2NO_2$: C, 54.46; H, 3.05; N, 3.02. Found: C, 54.54; H, 3.00; N, 2.78.

tert-Butyl 2-[5,5-bis(4-chlorophenyl)-2-oxo-1,2,3,5-tetrahydro-4,1-benzoxazepin-7-yl]-H-pyrrole-1-carboxylate Prepared from 7-bromo-5,5-bis(4-chlorophenyl)-1,5-dihydro-4,1-benzoxazepin-2(H)-one and 2-borono-1H-pyrrole-1-carboxylic acid, 1-tert-butyl ester generally according to the coupling procedure described in example 1. $^1$H-NMR (DMSO-$d_6$) δ 10.08 (s, 1H), 7.42 (m, 4H), 7.35 (dd, J=8.3, 2.4 Hz, 1H), 7.25 (dd, J=2.9, 1.5 Hz, 1H), 7.16 (m, 5H), 6.51 (d, J=2.0 Hz, 1H), 6.19 (t, J=3.4 Hz, 1H), 6.08 (dd, J=3.4, 2.0 Hz, 1H), 4.24 (s, 2H), 1.35 (s, 9H); MS (ES) m/z 547 (M−H)$^-$; Anal. Calc. for $C_{30}H_{26}Cl_2N_2O_4$: C, 65.58; H, 4.77; N, 5.10. Found: C, 64.81; H, 4.80; N, 4.80.

The title compound was prepared from tert-butyl 2-[5,5-bis(4-chlorophenyl)-2-oxo-1,2,3,5-tetrahydro-4,1-benzoxazepin-7-yl]-H-pyrrole-1-carboxylate and chlorosulfonyl isocyanate generally according to the procedure described in example 1. $^1$H-NMR (DMSO-$d_6$) δ 10.18 (s, 1H), 7.43 (m, 5H), 7.23 (d, J=3.9 Hz, 1H), 7.19 (d, J=8.3 Hz, 1H), 7.15 (m, 4H), 6.58 (d, J=2.0 Hz, 1H), 6.26 (d, J=3.9 Hz, 1H), 4.23 (s, 2H), 1.35 (s, 9H); MS (ES) m/z 572 (M−H)$^-$; Anal. Calc. for $C_{31}H_{25}Cl_2N_3O_4$: C, 64.82; H, 4.39; N, 7.31. Found: C, 63.79; H, 4.52; N, 7.31.

EXAMPLE 125

5-[5,5-Bis(4-chlorophenyl)-2-oxo-1,2,3,5-tetrahydro-4,1-benzoxazepin-7-yl]-H-pyrrole-2-carbonitrile Prepared from tert-butyl 2-[5,5-bis(4-chlorophenyl)-2-oxo-1,2,3,5-tetrahydro-4,1-benzoxazepin-7-yl]-5-cyano-H-pyrrole-1-carboxylate generally according to the procedure described in example 2. $^1$H-NMR (DMSO-d$_6$) δ 12.49 (s, 1H), 10.14 (s, 1H), 7.67 (dd, J=8.2, 1.9 Hz, 1H), 7.46 (m, 4H), 7.25 (m, 4H), 7.20 (d, J=8.5 Hz, 1H), 7.01 (d, J=1.9 Hz, 1H), 6.92 (d, J=3.8 Hz, 1H), 6.30 (d, J=3.8 Hz, 1H), 4.15 (s, 2H); MS (ES) m/z 472 (M−H)$^-$; Anal. Calc. for C$_{26}$H$_{17}$Cl$_2$N$_3$O$_2$: C, 65.84; H, 3.61; N, 8.86. Found: C, 65.14; H, 4.56; N, 7.41.

EXAMPLE 126

5-[5,5-Bis(4-chlorophenyl)-2-oxo-1,2,3,5-tetrahydro-4,1-benzoxazepin-7-yl]-1-methyl-H-pyrrole-2-carbonitrile Prepared from 5-[5,5-bis(4-chlorophenyl)-2-oxo-1,2,3,5-tetrahydro-4,1-benzoxazepin-7-yl]-H-pyrrole-2-carbonitrile and iodomethane generally according to the procedure described in example 3. $^1$H-NMR (DMSO-d$_6$) δ 10.23 (s, 1H), 7.52 (dd, J=8.3, 2.0 Hz, 1H), 7.45 (m, 4H), 7.26 (d, J=8.3 Hz, 1H), 7.19 (m, 4H), 6.95 (d, J=3.9 Hz, 1H), 6.63 (d, J=2.0 Hz, 1H), 6.14 (d, J=4.4 Hz, 1H), 4.25 (s, 2H), 3.46 (s, 3H); MS (ES) m/z 486 (M−H)$^-$; Anal. Calc. for C$_{27}$H$_{19}$Cl$_2$N$_3$O$_2$: C, 66.40; H, 3.92; N, 8.60. Found: C, 65.97; H, 4.40; N, 7.85.

EXAMPLE 127

3-[5,5-Bis(4-chlorophenyl)-2-oxo-1,2,3,5-tetrahydro-4,1-benzoxazepin-7-yl]-5-fluorobenzonitrile Prepared from 7-bromo-5,5-bis(4-chlorophenyl)-1,5-dihydro-4,1-benzoxazepin-2(H)-one and 5-fluoro-3-cyanobenzeneboronic acid generally according to the coupling procedure described in example 1. $^1$H-NMR (DMSO-d$_6$) δ 10.24 (s, 1H), 7.79 (m, 3H), 7.59 (dt, J=9.8, 2.0 Hz, 1H), 7.46 (m, 4H), 7.28 (d, J=8.3 Hz, 1H), 7.26 (m, 4H), 6.93 (d, J=2.0 Hz, 1H), 4.20 (s, 2H); MS (ES) m/z 501 (M−H)$^-$; Anal. Calc. for C$_{28}$H$_{17}$Cl$_2$FN$_2$O$_2$: C, 66.81; H, 3.40; N, 5.57. Found: C, 66.46; H, 3.43; N, 5.48.

EXAMPLE 128

7-(3-Chloro-4-fluorophenyl)-5,5-bis(4-chlorophenyl)-1,5-dihydro-4,1-benzoxazepin-2(H)-one Prepared from 7-bromo-5,5-bis(4-chlorophenyl)-1,5-dihydro-4,1-benzoxazepin-2(H)-one and 3-chloro-4-fluorobenzeneboronic acid generally according to the coupling procedure described in example 1. $^1$H-NMR (DMSO-d$_6$) δ 10.17 (s, 1H), 7.69 (dd, J=8.3, 2.4 Hz, 1H), 7.58 (dd, J=6.8, 2.4 Hz, 1H), 7.46 (m, 5H), 7.31 (m, 1H), 7.24 (d, J=8.3 Hz, 1H), 7.22 (m, 4H), 6.78 (d, J=2.0 Hz, 1H), 4.23 (s, 2H); MS (ES) m/z 510 (M−H)$^-$; Anal. Calc. for C$_{27}$H$_{17}$Cl$_3$FNO$_2$: C, 63.24; H, 3.34; N, 2.73. Found: C, 62.75; H, 3.58; N, 2.72.

EXAMPLE 129

7-(3,5-Difluorophenyl)-5,5-dimethyl-1,5-dihydro-4,1-benzoxazepin-2(3H)-one

Prepared from 7-bromo-5,5-dimethyl-1,5-dihydro-4,1-benzoxazepin-2(3H)-one and 3,5-difluorobenzene boronic acid generally according to the coupling procedure described in example 1. $^1$H-NMR (DMSO-d$_6$) δ 10.04 (s, 1H), 7.61-7.57 (m, 2H), 7.52-7.45 (m, 2H), 7.23-7.17 (m, 2H), 4.72 (s, 2H), 1.60 (s, 6H); MS (FI) m/z 304 [M+H]$^+$.

EXAMPLE 130

7-(3,5-Difluorophenyl)-5,5-dimethyl-1,5-dihydro-4,1-benzoxazepin-2(3H)-thione

Prepared from 7-(3,5-difluorophenyl)-5,5-dimethyl-1,5-dihydro-4,1-benzoxazepin-2(3H)-one and Lawesson's Reagent using the procedure of example 10. $^1$H-NMR (DMSO-d$_6$) δ 12.01 (s, 1H), 7.70-7.63 (m, 2H), 7.59-7.48 (m, 2H), 7.41 (d, J=8.82 Hz, 1H), 7.28-7.18 (m, 1H), 4.51 (s, 2H), 1.62 (s, 6H); MS (FI) m/z 318 [M−H]$^-$.

EXAMPLE 131

5-(5,5-Dimethyl-2-oxo-1,2,3,5-tetrahydro-4,1-benzoxazepin-7-yl)-4-methylthiophene-2-carbonitrile Prepared from 7-bromo-5,5-dimethyl-1,5-dihydro-4,1-benzoxazepin-2(3H)-one and 5-bromo-4-methyl-thiophene-2-carbonitrile using the coupling procedures in examples 82 and 1. $^1$H-NMR (DMSO-d6) δ 10.13 (s, 1H), 7.87 (s, 1H), 7.41-7.36 (m, 2H), 7.22 (d, J=8.32 Hz, 1H), 4.29 (s, 2H), 2.29 (s, 3H), 1.58 (s, 6H); MS (FI) m/z 311 ([M−H]$^-$, 20%).

EXAMPLE 132

4-Methyl-5-(5-methyl-2-oxo-5-phenyl-1,2,3,5-tetrahydro-4,1-benzoxazepin-7-yl)thiophene-2-carbonitrile Prepared from 7-bromo-5-methyl-5-phenyl-1,5-dihydro-4,1-benzoxazepin-2(3H)-one and 5-bromo-4-methyl-thiophene-2-carbonitrile using the coupling procedures of examples 82 and 1. $^1$H-NMR (DMSO-d6) δ 10.15 (s, 1H), 7.85 (s, 1H), 7.49 (m, 1H), 7.38-7.21 (m, 7H), 4.29 (d, J=15.19 Hz, 1H), 4.04 (d, J=15.05 Hz, 1H), 2.22, (s, 3H), 1.93 (s, 3H); MS (ES) m/z 375 ([M+H]$^+$, 100%).

EXAMPLE 133

5-(1,5-Dimethyl-2-oxo-5-phenyl-1,2,3,5-tetrahydro-4,1-benzoxazepin-7-yl)-1-methyl-1H-pyrrole-2-carbonitrile Prepared from 5-(5-methyl-2-oxo-5-phenyl-1,2,3,5-tetrahydro-4,1-benzoxazepin-7-yl)-1H-pyrrole-2-carbonitrile generally according to procedure of example 3. $^1$H-NMR (DMSO-d$_6$) δ 7.84 (d, J=1.71 Hz, 1H), 7.71 (dd, J=8.32, 1.54 Hz, 1H), 7.47 (d, J=8.25 Hz, 1H), 7.19-7.28 (m, 3H), 7.06-7.11 (m, 3H), 6.56 (d, J=3.77 Hz, 1H), 3.99 (s, 2H), 3.83 (s, 3H), 2.42, (s, 3H), 1.77 (s, 3H); Anal. Calc. For C$_{23}$H$_{21}$N$_3$O$_2$: C, 74.37; H, 5.70; N, 11.31. Found: C, 74.29; H, 5.56; N, 11.06.

EXAMPLE 134

1-Methyl-5-(5-methyl-5-thien-3-yl-2-thioxo-1,2,3,5-tetrahydro-4,1-benzoxazepin-7-yl)-1H-pyrrole-2-carbonitrile Prepared from 1-methyl-5-[5-methyl-2-oxo-5-(3-thienyl)-1,2,3,5-tetrahydro-4,1-benzoxazepin-7-yl]-1H-pyrrole-2-carbonitrile and Lawesson's reagent generally according to example 10. $^1$H NMR (DMSO-d$_6$): δ 12.11 (s, 1H), 7.45-7.54 (m, 3H), 7.37 (d, J=1.62 Hz, 1H), 7.29 (dd, J=2.87, 1.3 Hz, 1H), 7.06 (dd, J=5.02, 1.28 Hz, 1H), 7.03 (d, J=4.09 Hz, 1H), 6.37 (d, J=4.09 Hz, 1H), 4.46 (d, J=15.33 Hz, 1H), 4.35 (d, J=15.33 Hz, 1H), 3.70 (s, 3H), 1.99 (s, 3H); MS (ESI) m/z 378 ([M−H]−); Anal. calcd for C$_{20}$H$_{17}$N$_3$OS$_2$: C, 63.3; H, 4.52; N, 11.07. Found: C, 63.06; H, 4.76; N, 10.29.

EXAMPLE 135

5-(5-Methyl-5-thien-3-yl-2-thioxo-1,2,3,5-tetrahydro-4,1-benzoxazepin-7-yl)-1H-pyrrole-2-carbonitrile Prepared from 5-[5-methyl-2-oxo-5-(3-thienyl)-1,2,3,5-tetrahydro-4,1-benzoxazepin-7-yl]-1H-pyrrole-2-carbonitrile and Lawesson's reagent generally according to example 10. $^1$H NMR (DMSO-d$_6$): δ 12.67 (s, 1H), 12.01 (s, 1H), 7.71-7.74 (m, 2H), 7.54 (dd, J=5.08, 2.99 Hz, 1H), 7.41 (d, J=9.2 Hz, 1H), 7.2 (dd, J=2.87, 1.3 Hz, 1H), 7.05 (dd, J=5.04, 1.31 Hz, 1H), 7.00 (dd, J=3.84, 2.1 Hz, 1H), 6.76 (dd, J=3.79, 2.51 Hz, 1H), 4.4 (d, J=15.34 Hz, 1H), 4.27 (d, J=15.33 Hz, 1H), 1.98 (s, 3H); MS (ESI) m/z 366 ([M+H]$^+$); MS (ESI) m/z 364 ([M−H]−). Anal. calcd for C$_{19}$H$_{15}$N$_3$OS$_2$: C, 62.44; H, 4.14; N, 11.5. Found: C, 61.9; H, 4.14; N, 11.27.

EXAMPLE 136

1-Ethyl-5-(5-methyl-2-oxo-5-thien-3-yl-1,2,3,5-tetrahydro-4,1-benzoxazepin-7-yl)-H-pyrrole-2-carbonitrile Prepared from 5-[5-methyl-2-oxo-5-(3-thienyl)-1,2,3,5-tetrahydro-4,1-benzoxazepin-7-yl]-1H-pyrrole-2-carbonitrile generally according to the procedure described in example 3. An off-white solid: mp 179-180° C.; $^1$H NMR (DMSO-d$_6$): δ 10.19 (s, 1H), 7.56 (dd, J=5.04, 2.94 Hz, 1H), 7.37 (dd, J=8.35, 1.94 Hz, 1H), 7.66-7.22 (m, 2H), 7.16 (d, J=1.91 Hz, 1H), 7.08 (dd, J=5.14, 1.28 Hz, 1H), 7.03 (d, J=4.02 Hz, 1H), 6.26 (d, J=4.02 Hz, 1H), 4.20 (d, J=15.95 Hz, 1H), 4.09 (d, J=15.98 Hz, 1H), 3.98 (q, J=7.28 Hz, 2H), 1.95 (s, 3H), 1.16 (t, J=7.16 Hz, 3H); MS (ESI) m/z 378 ([M+H]+); MS (ESI) m/z 755 ([2M+H]$^+$); Anal. calcd for C$_{21}$H$_{19}$N$_3$O$_2$S: C, 66.82; H, 5.07; N, 11.13. Found: C, 66.38; H, 4.94; N, 10.71.

EXAMPLE 137

5-(5-Methyl-2-oxo-5-thien-3-yl-1,2,3,5-tetrahydro-4,1-benzoxazepin-7-yl)-H-pyrrole-1,2-dicarbonitrile Prepared from 5-[5-methyl-2-oxo-5-(3-thienyl)-1,2,3,5-tetrahydro-4,1-benzoxazepin-7-yl]-1H-pyrrole-2-carbonitrile and cyanogenbromide using the similar procedure of example 3. An off-white solid: mp 226-227° C.; $^1$H NMR (DMSO-d$_6$): δ 10.25 (s, 1H), 7.62-7.65 (m, 2H), 7.57 (dd, J=5.03, 2.93 Hz, 1H), 7.52 (d, J=4.03 Hz, 1H), 7.32 (d, J=9.04 Hz, 1H), 7.19 (dd, J=2.85, 1.25 Hz, 1H), 7.09 (dd, J=5.05, 1.23 Hz, 1H), 6.83 (d, J=4.04 Hz, 1H), 4.17 (d, J=16.03 Hz, 1H), 4.02 (d, J=16.06 Hz, 1H), 1.96 (s, 3H); MS (ESI) m/z [M−H]-(373); MS (ESI) m/z [M+H]$^+$ (375); MS (ESI) m/z [2M+H]$^+$ (749); Anal. calcd for C$_{20}$H$_{14}$N$_4$O$_2$S: C, 64.16; H, 3.77; N, 14.96. Found: C, 62.78; H, 3.75; N, 13.94.

EXAMPLE 138

7-(2-Furyl)-5-methyl-5-thien-2-yl-1,5-dihydro-4,1-benzoxazepin-2(H)-one

Prepared from 7-bromo-5-methyl-5-thien-2-yl-1,5-dihydro-4,1-benzoxazepin-2(3H)-one and 2-furylboronic acid generally according to the procedure described in example 1. $^1$H NMR (DMSO-d$_6$): δ 10.14 (s, 1H), 7.56-6.89 (m, 9H), 4.17 (d, J=15.62 Hz, 1H), 4.05 (d, J=15.62 Hz, 1H), 2.0 (s, 3H).

EXAMPLE 139

5-(5-Ethyl-2-oxo-5-thien-2-yl-1,2,3,5-tetrahydro-4,1-benzoxazepin-7-yl)-2-fluorobenzonitrile Prepared from 7-bromo-5-ethyl-5-thien-2-yl-1,5-dihydro-4,1-benzoxazepin-2(3H)-one and 5-bromo-2-fluorobenzonitrile generally according to the procedures described in examples 82 and 1. An off-white solid: mp 197-199° C.; $^1$H NMR (DMSO-d$_6$): δ 10.09 (s, 1H), 8.25 (dd, J=6.35, 2.44 Hz, 1H), 8.02-8.05 (m, 1H), 7.68 (dd, J=8.3, 1.95 Hz, 1H), 7.61 (d, J=1.95 Hz, 1H), 7.7 (dd, J$_{HF}$=9.28 Hz, J$_{HH}$=9.28 Hz, 1H), 7.56 (dd, J=5.37, 1.47 Hz, 1H), 7.27 (d, J=8.79 Hz, 1H), 7.0 (dd, J=4.88, 3.42 Hz, 1H), 6.95 (dd, J=3.9, 1.47 Hz, 1H), 4.08 (d, J=15.62 Hz, 1H), 3.94 (d, J=15.13 Hz, 1H), 2.46-2.57 (m, 2H), 0.76 (t, J=6.83 Hz, 3H); MS (ESI) m/z 393 ([M+H]$^+$); MS (ESI) m/z 391 ([M−H]−); Anal. calcd for C$_{22}$H$_{17}$FN$_2$O$_2$S: C, 67.33; H, 4.37; N, 7.14. Found: C, 67.26; H, 4.38; N, 6.90.

EXAMPLE 140

5-(5-Ethyl-2-oxo-5-thien-2-yl-1,2,3,5-tetrahydro-4,1-benzoxazepin-7-yl)-4-methylthiophene-2-carbonitrile Prepared from 7-bromo-5-ethyl-5-thien-2-yl-1,5-dihydro-4,1-benzoxazepin-2(3H)-one and 5-bromo-4-methylthiophene-2-carbonitrile generally according to the procedures described in examples 82 and 1. An off-white solid: mp 182-184° C.; $^1$H NMR (DMSO-d$_6$): δ 10.19 (s, 1H), 7.83 (s, 1H), 7.57 (dd, J=4.88, 0.98 Hz, 1H), 7.46 (dd, J=8.3, 1.95 Hz, 1H), 7.33 (d, J=1.95 Hz, 1H), 7.29 (d, J=8.3 Hz, 1H), 7.07 (dd, J=4.88, 3.42 Hz, 1H), 6.98 (dd, J=3.42, 0.98 Hz, 1H), 4.14 (d, J=15.6 Hz, 1H), 3.98 (d, J=15.13 Hz, 1H), 2.47 (m, 1H), 2.35 (m, 1H), 2.21 (s, 3H), 0.77 (t, J=6.84 Hz, 3H); MS (ESI) m/z 395 ([M+H]$^+$); MS (ESI) m/z 393 ([M−H]$^−$); Anal. calcd for C$_{21}$H$_{18}$N$_2$O$_2$S$_2$: C, 63.93; H, 4.60; N, 7.10. Found: C, 60.33; H, 4.13; N, 6.65.

EXAMPLE 141

4-(5-Ethyl-2-oxo-5-thien-2-yl-1,2,3,5-tetrahydro-4,1-benzoxazepin-7-yl)-2-furonitrile Prepared from 7-bromo-5-ethyl-5-thien-2-yl-1,5-dihydro-4,1-benzoxazepin-2(3H)-one and 4-bromo-2-cyanofuran generally according to the procedures described in examples 82 and 1. A white solid: mp 99-100° C.; $^1$H NMR (DMSO-d$_6$): δ 10.04 (s, 1H), 8.60 (s, 1H), 8.17 (s, 1H), 7.54-7.61 (m, 3H), 7.22 (d, J=8.45 Hz, 1H), 6.99 (dd, J=4.99, 3.60 Hz, 1H), 6.90 (dd, J=3.48, 1.02 Hz, 1H), 4.40 (d, J=15.42 Hz, 1H), 3.94 (d, J=15.47 Hz, 1H), 2.5 (m, 2H), 0.76 (t, J=7.02 Hz, 3H); MS (ESI) m/z 365 ([M+H]$^+$); MS (ESI) m/z 363 ([M−H]−); Anal. calcd for C$_{20}$H$_{16}$N$_2$O$_3$S: C, 65.92; H, 4.43; N, 7.69. Found: C, 64.84; H, 4.59; N, 6.98.

EXAMPLE 142

5-(5-Ethyl-1-methyl-2-oxo-5-thien-2-yl-1,2,3,5-tetrahydro-4,1-benzoxazepin-7-yl)-2-fluorobenzonitrile Prepared from 5-(5-ethyl-2-oxo-5-thien-2-yl-1,2,3,5-tetrahydro-4,1-benzoxazepin-7-yl)-2-fluorobenzonitrile generally according to example 3. $^1$H NMR (DMSO-$d_6$): δ 8.43 (dd, J=5.86, 2.44 Hz, 1H), 8.18-8.21 (m, 1H), 7.91 (d, J=1.95 Hz, 1H), 7.88 (dd, J=8.3, 1.95 Hz, 1H), 7.66 (t, J=8.79 Hz, 1H), 7.49 (d, J=8.3 Hz, 1H), 7.34 (dd, J=4.88, 1.46 Hz, 1H), 6.91 (dd, J=4.88, 3.42 Hz, 1H), 6.65 (dd, J=3.42, 0.98 Hz, 1H), 4.05 (s, 2H), 2.75 (s, 3H), 2.46 (m, 1H), 2.35 (m, 1H), 0.85 (t, J=7.32 Hz, 3H); MS (ESI) m/z 407 ([M+H]$^+$).

EXAMPLE 143

4-(5-Ethyl-2-oxo-5-thien-2-yl-1,2,3,5-tetrahydro-4,1-benzoxazepin-7-yl)thiophene-2-carbonitrile Prepared from 7-bromo-5-ethyl-5-thien-2-yl-1,5-dihydro-4,1-benzoxazepin-2(3H)-one and 4-bromo-2-cyanothiophene generally according to the procedures described in examples 82 and 1. A yellowish solid: mp 202-204° C.; $^1$H NMR (DMSO-$d_6$): δ 10.06 (s, 1H), 8.48 (s, 1H), 8.33 (s, 1H), 7.64-7.7 (m, 2H), 7.55 (d, J=5.0 Hz, 1H), 7.23 (d, J=8.48 Hz, 1H), 6.92-7.03 (m, 2H), 4.06 (d, J=15.52 Hz, 1H), 3.94 (d, J=15.44 Hz, 1H), 3.37 (m, 1H), 2.5 (m, 1H), 0.76 (t, J=6.79 Hz, 1H); MS (ESI) m/z 381 ([M+H]$^+$); MS (ESI) m/z 379 ([M−H]−); Anal. calcd for $C_{20}H_{16}N_2O_2S_2$: C, 63.14; H, 4.24; N, 7.36. Found: C, 62.53; H, 4.25; N, 7.12.

EXAMPLE 144

1-Benzyl-5-(5-methyl-2-oxo-5-thien-3-yl-1,2,3,5-tetrahydro-4,1-benzoxazepin-7-yl)-H-pyrrole-2-carbonitrile Prepared from 5-[5-methyl-2-oxo-5-(3-thienyl)-1,2,3,5-tetrahydro-4,1-benzoxazepin-7-yl]-1H-pyrrole-2-carbonitrile and benzylbromide generally according to example 3. $^1$H NMR (DMSO-$d_6$): δ 10.12 (s, 1H), 7.53 (dd, J=5.03, 2.97 Hz, 1H), 7.36 (dd, J=8.33, 1.78 Hz, 1H), 7.24-7.28 (m, 3H), 7.20 (d, J=8.42 Hz, 1H), 7.15 (d, J=4.03 Hz, 1H), 7.05 (d, J=1.84 Hz, 1H), 6.93-6.98 (m, 2H), 6.76-6.79 (m, 2H), 6.42 (d, J=4.04 Hz, 1H), 5.27 (s, 2H), 4.11 (d, J=15.9 Hz, 1H), 3.96 (d, J=15.9 Hz, 1H), 1.66 (s, 3H); MS (ESI) m/z 440 ([M+H]$^+$); MS (ESI) m/z 438 ([M−H]$^-$).

EXAMPLES 145-156

The following examples were prepared from 7-bromo-5-methyl-5-thien-2-yl-1,5-dihydro-4,1-benzoxazepin-2(3H)-one and corresponding aryl boronic acid generally according to the procedure described in example 1. The compound was purified on HPLC using YMC combi pro C18 Column (5 micron, 12 nm, 50×4.4 mm).

Mobile Phase A: acetonitrile with 0.1% TFA

Mobile Phase B: Water with 0.1% TFA

Conditions: 1 mL/min., 10% A to 100% A 10 minute linear gradient, 100% A for 3 minutes.

UV detection at 220 and 254 nm.

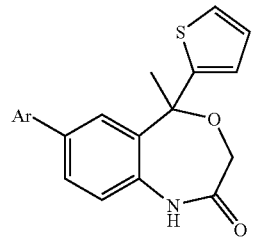

| Compounds | R | Retention Time | MS (ES) m/z |
|---|---|---|---|
| 5-Methyl-5-thiophen-2-yl-7-m-tolyl-1,5-dihydro-benzo[e][1,4]oxazepin-2-one | 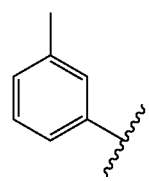 | 9.88 | 349 |
| 7-(3-Amino-phenyl)-5-methyl-5-thiophen-2-yl-1,5-dihydro-benzo[e][1,4]oxazepin-2-one | 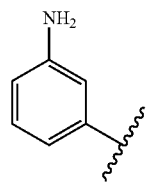 | 5.49 | 350 |

-continued

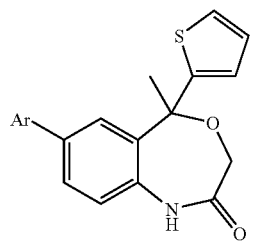

| Compounds | R | Retention Time | MS (ES) m/z |
|---|---|---|---|
| 7-(3-Methoxy-phenyl)-5-methyl-5-thiophen-2-yl-1,5-dihydro-benzo[e][1,4]oxazepin-2-one | 3-methoxyphenyl | 7.36 | 365 |
| 7-(2-Chloro-phenyl)-5-methyl-5-thiophen-2-yl-1,5-dihydro-benzo[e][1,4]oxazepin-2-one | 2-chlorophenyl | 9.84 | 369 |
| 7-(3-Chloro-phenyl)-5-methyl-5-thiophen-2-yl-1,5-dihydro-benzo[e][1,4]oxazepin-2-one | 3-chlorophenyl | 10.23 | 369 |
| 7-(4-Chloro-phenyl)-5-methyl-5-thiophen-2-yl-1,5-dihydro-benzo[e][1,4]oxazepin-2-one | 4-chlorophenyl | 10.28 | 369 |
| 3-(5-Methyl-2-oxo-5-thiophen-2-yl-1,2,3,5-tetrahydro-benzo[e][1,4]oxazepin-7-yl)-benzonitrile | 3-cyanophenyl | 8.66 | 360 |
| 7-(3,5-Difluoro-phenyl)-5-methyl-5-thiophen-2-yl-1,5-dihydro-benzo[e][1,4]oxazepin-2-one | 3,5-difluorophenyl | 10.00 | 371 |
| 5-Methyl-5,7-di-thiophen-2-yl-1,5-dihydro-benzo[e][1,4]oxazepin-2-one | thiophen-2-yl | 9.09 | 341 |

-continued

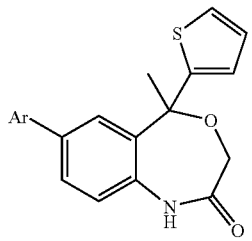

| Compounds | R | Retention Time | MS (ES) m/z |
|---|---|---|---|
| 5-Methyl-5-thiophen-2-yl-7-thiophen-3-yl-1,5-dihydro-benzo[e][1,4]oxazepin-2-one | thiophen-3-yl | 9.05 | 341 |
| 5-Methyl-5-thiophen-2-yl-7-(3-trifluoromethyl-phenyl)-1,5-dihydro-benzo[e][1,4]oxazepin-2-one | 3-CF₃-phenyl | 10.42 | 403 |
| 5-Methyl-7-(3-nitro-phenyl)-5-thiophen-2-yl-1,5-dihydro-benzo[e][1,4]oxazepin-2-one | 3-NO₂-phenyl | 9.30 | 380 |

EXAMPLE 157 tert-Butyl 2-cyano-5-[5,5-di(2-furyl)-2-oxo-1,2,3,5-tetrahydro-4,1-benzoxazepin-7-yl]-H-pyrrole-1-carboxylate N-(4-Bromo-2-[di(2-furyl)(hydroxy)methyl]phenyl}-2-chloroacetamide Prepared from methyl 2-amino-5-bromobenzoate in two step generally according to the procedure described in example 24. $^1$H-NMR (DMSO-d$_6$) δ 10.4 (s, 1H), 8.06 (d, J=8.79 Hz, 1H), 8.04 (s, 1H), 7.70-7.71 (m, 2H), 7.55 (dd, J=8.79, 2.44 Hz, 1H), 6.67 (d, J=2.44 Hz, 1H), 6.49-6.50 (m, 2H), 6.23-6.24 (m, 2H), 4.23 (s, 2H); MS (ES) m/z 408/410/412 ([M–H]⁻, 100%).

7-Bromo-5,5-di(2-furyl)-1,5-dihydro-4,1-benzoxazepin-2(3H)-one

Prepared from N-(4-bromo-2-[di(2-furyl)(hydroxy)methyl]phenyl}-2-chloroacetamide using the procedure described in example 1. $^1$H-NMR (DMSO-d$_6$) δ 10.27 (s, 1H), 7.78 (d, J=0.98 Hz, 2H), 7.52 (dd, J=8.79, 2.44 Hz, 1H), 7.18 (d, J=8.79 Hz, 1H), 6.73 (d, J=2.44 Hz, 1H), 6.51 (dd, J=3.42, 1.95 Hz, 2H), 6.24 (dd, J=3.42, 0.98 Hz, 2H), 4.1 (s, 2H); MS (ES) m/z 372/374 ([M–H]⁻, 100%); MS (ES) m/z 374/376 ([M+H]⁺, 100%).

tert-Butyl 2-[5,5-di(2-furyl)-2-oxo-1,2,3,5-tetrahydro-4,1-benzoxazepin-7-yl]-H-pyrrole-1-carboxylate Prepared from 7-bromo-5,5-di(2-furyl)-1,5-dihydro-4,1-benzoxazepin-2(3H)-one and 2-borono-1H-pyrrole-1-carboxylic acid, 1-tert-butyl ester generally according to the coupling procedure of example 1. $^1$H NMR (DMSO-d$_6$): δ 10.21 (s, 1H), 7.73 (m, 2H), 7.30 (dd, J=8.3, 1.95 Hz, 1H), 7.26 (dd, J=3.42, 1.47 Hz, 1H), 7.21 (d, J=8.3 Hz, 1H), 6.63 (d, J=1.95 Hz, 1H), 6.47 (dd, J=3.42, 1.95 Hz, 2H), 6.19-6.20 (m, 3H), 6.06 (dd, J=3.42, 1.95 Hz, 1H), 4.15 (s, 2H), 1.35 (s, 9H); MS (ESI) m/z 461 ([M+H]⁺); MS (ESI) m/z 459 ([M–H]–).

The title compound was prepared from tert-butyl 2-[5,5-di(2-furyl)-2-oxo-1,2,3,5-tetrahydro-4,1-benzoxazepin-7-yl]-H-pyrrole-1-carboxylate and chlorosulfonyl isocyanate generally according to the procedure of example 1. $^1$H NMR (DMSO-d$_6$): δ 10.29 (s, 1H), 7.74 (dd, J=1.95, 0.98 Hz, 2H), 7.40 (dd, J=8.3, 1.95 Hz, 1H), 7.26 (d, J=8.3 Hz, 1H), 7.24 (d, J=3.91 Hz, 1H), 6.67 (d, J=1.95 Hz), 1H, 6.48 (d, J=1.95 Hz, 1H), 6.48 (dd, J=3.42, 1.95 Hz, 2H), 6.20 (dd, J=3.42, 0.98 Hz, 2H), 4.16 (s, 2H), 1.37 (s, 9H); MS (ESI) m/z 486 ([M+H]+); MS (ESI) m/z 484 ([M–H]–).

EXAMPLE 158

7-(3-Chloro-4-fluorophenyl)-5,5-di(2-furyl)-1,5-dihydro-4,1-benzoxazepin-2(H)-one Prepared from 7-bromo-5,5-di(2-furyl)-1,5-dihydro-4,1-benzoxazepin-2(3H)-one and 3-chloro-4-fluoro benzeneboronic acid generally according to the coupling procedure of example 1. $^1$H NMR (DMSO-d$_6$): δ 10.28 (s, 1H), 7.77 (dd, J=1.95, 0.98 Hz, 2H), 7.66 (dd, J=8.3, 1.95 Hz, 1H), 7.59 (dd, J=7.32, 2.44 Hz, 1H), 7.45 (dd, J$_{HF}$=J$_{HH}$=8.79 Hz, 1H), 7.33-7.36 (m, 1H), 7.32 (d, J=8.79 Hz, 1H), 6.89 (d, J=2.44 Hz, 1H), 6.51 (dd, J=3.42, 1.95 Hz, 2H), 6.27 (dd, J=3.42, 0.98 Hz, 2H), 4.17 (s, 2H); MS (ESI) m/z 422/424 ([M−H]−); Anal. calcd for C$_{23}$H$_{15}$ClFNO$_4$: C, 65.18; H, 3.57; N, 3.30. Found: C, 64.16; H, 3.66; N, 2.78.

EXAMPLE 159

3-[5,5-Di(2-furyl)-2-oxo-1,2,3,5-tetrahydro-4,1-benzoxazepin-7-yl]-5-fluorobenzonitrile Prepared from 7-bromo-5,5-di(2-furyl)-1,5-dihydro-4,1-benzoxazepin-2(3H)-one and 3-cyano-5-fluorobenzeneboronic acid generally according to the coupling procedure of example 1. $^1$H NMR (DMSO-d$_6$): δ 10.34 (s, 1H), 7.73-7.87 (m, 5H), 7.59 (dt, J=10.25, 1.95 Hz, 1H), 7.35 (d, J=8.3 Hz, 1H), 6.98 (d, J=1.95 Hz, 1H), 1H, 6.52 (dd, J=3.42, 1.95 Hz, 2H), 6.29 (dd, J=3.42, 0.98 Hz, 2H), 4.16 (s, 2H); MS (ESI) m/z 415 ([M+H]+); MS (ESI) m/z 413 ([M−H]−); Anal. calcd for C$_{24}$H$_{15}$FN$_2$O$_4$: C, 69.56; H, 3.65; N, 6.76. Found: C, 67.60; H, 3.77; N, 5.81.

EXAMPLE 160

5-[5,5-Di(2-furyl)-2-oxo-1,2,3,5-tetrahydro-4,1-benzoxazepin-7-yl]-H-pyrrole-2-carbonitrile Prepared from tert-butyl 2-cyano-5-[5,5-di(2-furyl)-2-oxo-1,2,3,5-tetrahydro-4,1-benzoxazepin-7-yl]-H-pyrrole-1-carboxylate generally according to example 2. $^1$H NMR (DMSO-d$_6$): δ 12.61 (s, 1H), 10.3 (s, 1H), 7.84 (dd, J=1.92, 0.82 Hz, 2H), 7.72 (dd, J=8.51, 2.20 Hz, 1H), 7.33 (d, J=8.51 Hz, 1H), 7.15 (d, J=2.20 Hz, 1H), 6.99 (d, J=3.85 Hz, 1H), 6.57 (dd, J=3.30, 1.92 Hz, 2H), 6.40 (d, J=3.85 Hz, 1H), 6.32 (dd, J=3.30, 0.82 Hz, 2H), 4.18 (s, 2H); MS (ESI) m/z 386 ([M+H]+); MS (ESI) m/z 384 ([M−H]−); Anal. calcd for C$_{22}$H$_{15}$N$_3$O$_4$: C, 68.57; H, 3.92; N, 10.90. Found: C, 65.05; H, 3.97; N, 9.41.

EXAMPLE 161

5-[5,5-Di(2-furyl)-2-oxo-1,2,3,5-tetrahydro-4,1-benzoxazepin-7-yl]-1-methyl-H-pyrrole-2-carbonitrile Prepared from 5-[5,5-di(2-furyl)-2-oxo-1,2,3,5-tetrahydro-4,1-benzoxazepin-7-yl]-H-pyrrole-2-carbonitrile generally according to example 3. $^1$H NMR (DMSO-d$_6$): δ 10.34 (s, 1H), 7.77 (m, 2H), 7.49 (dd, J=8.3, 2.44 Hz, 1H), 7.33 (d, J=8.30 Hz, 1H), 6.97 (d, J=3.91 Hz, 1H), 6.76 (d, J=1.95 Hz, 1H), 6.50 (dd, J=3.42, 1.95 Hz, 2H), 6.25 (dd, J=3.42, 0.98 Hz, 2H), 6.16 (d, J=3.91 Hz, 1H), 4.18 (s, 2H), 3.54 (s, 3H); MS (ESI) m/z 400 ([M+H]+); MS (ESI) m/z 398 ([M−H]−); Anal. calcd for C$_{23}$H$_{17}$N$_3$O$_4$: C, 69.17; H, 4.29; N, 10.52. Found: C, 68.09; H, 4.45; N, 10.09.

EXAMPLE 162

7-(4-Fluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 4-fluoro benzeneboronic acid generally according to the coupling procedure described in example 1. $^1$H NMR (DMSO-d$_6$): δ 9.92 (s, 1H), 7.64-7.67 (m, 2H), 7.41-7.46 (m, 2H), 7.17-7.25 (m, 2H), 7.12 (s, J=2.26 Hz, 1H), 4.21 (s, 2H), 1.57 (s, 6H); MS (ESI) m/z 286 ([M+H]+); MS (ESI) m/z 284 ([M−H]−).

EXAMPLE 163

7-(2-Fluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 2-fluoro benzeneboronic acid generally according to the coupling procedure described in example 1. $^1$H NMR (DMSO-d$_6$): δ 10.01 (s, 1H), 7.63 (m, 1H), 7.51-7.57 (m, 1H), 7.36-7.43 (m, 2H), 7.25-7.30 (m, 2H), 7.19 (d, J=8.32 Hz, 1H), 4.27 (s, 2H), 1.59 (s, 6H); MS (ESI) m/z 286 ([M+H]+); MS (ESI) m/z 284 ([M−H]−).

EXAMPLE 164

7-(3,4-Difluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 3,4-difluoro benzeneboronic acid generally according to the coupling procedure described in example 1. $^1$H NMR (DMSO-d$_6$): δ 9.98 (s, 1H), 7.76-7.83 (m, 1H), 7.60-7.67 (m, 1H), 7.49-7.56 (m, 3H), 7.17 (d, J=8.32 Hz, 1H), 4.26 (s, 2H), 1.61 (s, 6H); MS (ESI) m/z 304 ([M+H]+); MS (ESI) m/z 302 ([M−H]−).

EXAMPLE 165

7-(3,5-Dichlorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 3,5-dichloro benzeneboronic acid generally according to the coupling procedure described in example 1. $^1$H NMR (DMSO-d$_6$): δ 10.02 (s, 1H), 7.76 (s, 2H), 7.55-7.64 (m, 3H), 7.18 (d, J=8.45 Hz, 1H), 4.26 (s, 2H), 1.62 (s 6H); MS (ESI) m/z 336/338/340 ([M+H]+); MS (ESI) m/z 334/336/338 ([M−H]−).

EXAMPLE 166

7-(2,3-Difluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 2,3-difluoro benzeneboronic acid generally according to the coupling procedure described in example 1. $^1$H NMR (DMSO-d$_6$): δ 10.04 (s, 1H), 7.2-7.45 (m, 6H), 4.28 (s, 2H), 1.59 (s, 6H); MS (ESI) m/z 304 ([M+H]+); MS (ESI) m/z 302 ([M−H]−).

EXAMPLE 167

7-(4-Chloro-3-fluorophenyl)-5,5-dimethyl-1,5-dihydro-4,1-benzoxazepin-2(H)-one Prepared from 7-bromo-5,5-dimethyl-1,5-dihydro-4,1-benzoxazepin-2(3H)-one and 4-chloro-3-fluoro benzeneboronic acid generally according to the coupling procedure described in example 1. $^1$H NMR (DMSO-d$_6$): δ 10.01 (s, 1H), 7.79 (dd, J=11.23, 1.95 Hz, 1H), 7.54-7.65 (m, 4H), 7.18

(d, J=8.3 Hz, 1H), 4.26 (s, 2H), 1.61 (s, 6H); MS (ESI) m/z 320/322 ([M+H]+); MS (ESI) m/z 318/320 ([M−H]−).

EXAMPLE 168

4-(5,5-Dimethyl-2-oxo-1,2,3,5-tetrahydro-4,1-benzoxazepin-7-yl)-2-fluorobenzonitrile Prepared from 7-bromo-5,5-dimethyl-1,5-dihydro-4,1-benzoxazepin-2(3H)-one and 3-bromo-2-fluorobenzonitrile generally according to the coupling procedure described in examples 82 and 1. $^1$H NMR (DMSO-d$_6$): δ 10.08 (s, 1H), 7.92-7.99 (m, 2H), 7.77-7.79 (m, 1H), 7.64-7.69 (m, 2H), 7.22 (d, J=8.39 Hz, 1H), 4.28 (s, 2H), 1.62 (s, 6H). MS (ESI) m/z 311 ([M+H]+); MS (ESI) m/z 309 ([M−H]−).

EXAMPLE 169

7-(3-Bromo-5-fluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 1,3-dibromo-5-fluorobenzene generally according to the coupling procedure described in examples 82 and 1. $^1$H NMR (DMSO-d$_6$): δ 10.0 (s, 1H), 7.6 (m, 1H), 7.56-7.63 (m, 3H), 7.48-7.51 (m, 1H), 7.18 (d, J=8.3 Hz, 1H), 4.27 (s, 2H), 1.53 (s, 6H); MS (ESI) m/z 364/366 ([M+H]+); MS (ESI) m/z 362/364 ([M−H]−).

EXAMPLE 170

7-(3-Chloro-5-fluorophenyl)-5,5-dimethyl-1,5-dihydro-4,1-benzoxazepin-2(H)-one

Prepared from 7-bromo-5,5-dimethyl-1,5-dihydro-4,1-benzoxazepin-2(3H)-one and 3-bromo-5-chloro-1-fluorobenzene generally according to the coupling procedure described in examples 82 and 1. $^1$H NMR (DMSO-d$_6$): δ 10.01 (s, 1H), 7.61-7.65 (m, 4H), 7.36-7.39 (m, 1H), 7.18 (d, J=8.54 Hz, 1H), 4.26 (s, 2H), 1.62 (s, 6H); MS (ESI) m/z 320/322 ([M+H]+); MS (ESI) m/z 318/320 ([M−H]−). Anal. calcd for C$_{17}$H$_{15}$ClFNO$_2$: C, 63.86; H, 4.73; N, 4.38. Found: C, 62.53; H, 4.55; N, 3.50.

EXAMPLE 171

3-Chloro-5-(5,5-dimethyl-2-oxo-1,2,3,5-tetrahydro-4,1-benzoxazepin-7-yl)benzonitrile Prepared from 7-(3-bromo-5-chlorophenyl)-5,5-dimethyl-1,5-dihydro-4,1-benzoxazepin-2(H)-one and zinc cyanide generally according to example 84. $^1$H NMR (DMSO-d$_6$): δ 10.03 (s, 1H), 8.22 (m, 1H), 8.14 (m, 1H), 7.97 (m, 1H), 7.69 (m, 1H), 7.64 (dd, J=8.54, 2.44 Hz, 1H), 7.20 (d, J=8.54 Hz, 1H), 4.27 (s, 2H), 1.63 (s, 6H); MS (ESI) m/z 327/329 ([M+H]+); MS (ESI) m/z 325/327 ([M−H]−).

EXAMPLE 172 tert-Butyl 2-cyano-5-(2-oxo-5,5-diphenyl-1,2,3,5-tetrahydro-4,1-benzoxazepin-7-yl)-H-pyrrole-1-carboxylate N-{4-Bromo-2[hydroxyl(diphenyl)methyl]phenyl}-2-chloroacetamide Prepared from methyl 2-amino-5-bromobenzoate in two step generally according to the procedure described in example 24. $^1$H NMR (DMSO-d$_6$): δ 10.28 (s, 1H), 8.00 (d, J=8.79 Hz, 1H), 7.78 (s, 1H), 7.54 (dd, J=8.79, 2.44 Hz, 1H), 7.29-7.37 (m, 6H), 7.17-7.19 (m, 4H), 6.56 (d, J=2.44 Hz, 1H), 3.93 (s, 2H); MS (ESI) m/z 428/430/432 ([M−H]−).

7-Bromo-5,5-diphenyl-1,5-dihydro-4,1-benzoxazepin-2(3H)-one

Prepared from N-{4-bromo-2-[hydroxyl(diphenyl)methyl]phenyl}-2-chloroacetamide generally according to the procedure described in example 1. $^1$H NMR (DMSO-d$_6$): δ 10.13 (s, 1H), 7.53 (dd, J=8.3, 1.95 Hz, 1H), 7.35-7.40 (m, 6H), 7.09-7.12 (m, 5H), 6.58 (d, J=2.44 Hz, 1H), 4.26 (s, 2H). MS (ESI) m/z 394 ([M+H]+); MS (ESI) m/z 398 ([M−H]−).

tert-Butyl 2-(2-oxo-5,5-diphenyl-1,2,3,5-tetrahydro-4,1-benzoxazepin-7-yl)-H-pyrrole-1-carboxylate Prepared from 7-bromo-5,5-diphenyl-1,5-dihydro-4,1-benzoxazepin-2(3H)-one and 2-borono-1H-pyrrole-1-carboxylic acid, 1-tert-butyl ester generally according to the coupling procedure described in example 1. $^1$H NMR (DMSO-d$_6$): δ 10.07 (s, 1H), 7.36-7.38 (m, 7H), 7.22 (dd, J=3.42, 1.95 Hz, 1H), 7.12-7.14 (m, 5H), 6.49 (d, J=2.44 Hz, 1H), 6.16 (t, J=3.42 Hz, 1H), 5.99 (dd, J=2.93, 1.46 Hz, 1H), 4.26 (s, 2H), 1.35 (s, 9H); MS (ESI) m/z 481 ([M+H]+); MS (ESI) m/z 479 ([M−H]−).

The title compound was prepared from tert-butyl 2-(2-oxo-5,5-diphenyl-1,2,3,5-tetrahydro-4,1-benzoxazepin-7-yl)-H-pyrrole-1-carboxylate and chlorosulfonyl isocyanate generally according to the procedure described in example 1. $^1$H NMR (DMSO-d$_6$): δ 10.17 (s, 1H), 7.32-7.4 (m, 7H), 7.19-7.20 (m, 2H), 7.13-7.14 (m, 4H), 6.52 (d, J=1.95 Hz, 1H), 6.19 (d, J=3.42 Hz, 1H), 4.26 (s, 2H), 1.39 (s, 9H); MS (ESI) m/z 506 ([M+H]+); MS (ESI) m/z 504 ([M−H]−). Anal. calcd for C$_{31}$H$_{27}$N$_3$O$_4$: C, 73.65; H, 5.38; N, 8.31. Found: C, 70.80; H, 5.27; N, 7.99.

EXAMPLE 173

5-(2-Oxo-5,5-diphenyl-1,2,3,5-tetrahydro-4,1-benzoxazepin-7-yl)-H-pyrrole-2-carbonitrile Prepared from tert-butyl 2-cyano-5-(2-oxo-5,5-diphenyl-1,2,3,5-tetrahydro-4,1-benzoxazepin-7-yl)-H-pyrrole-1-carboxylate generally according to example 2. $^1$H NMR (DMSO-d$_6$): δ 12.5 (s, 1H), 10.13 (s, 1H), 7.62 (dd, J=8.79, 2.20 Hz, 1H), 7.33-7.40 (m, 6H), 7.20-7.22 (m, 5H), 6.95 (d, J=1.65 Hz, 1H), 6.88 (dd, J=3.85, 2.20 Hz, 1H), 6.14 (dd, J=3.85, 2.75 Hz, 1H), 4.17 (s, 2H). MS (ESI) m/z 406 ([M+H]+); MS (ESI) m/z 404 ([M−H]−); Anal. calcd for C$_{26}$H$_{19}$N$_3$O$_2$: C, 77.02; H, 4.72; N, 10.36. Found: C, 75.34; H, 4.80; N, 9.84.

EXAMPLE 174

1-Methyl-5-(2-oxo-5,5-diphenyl-1,2,3,5-tetrahydro-4,1-benzoxazepin-7-yl)-H-pyrrole-2-carbonitrile Prepared from 5-(2-oxo-5,5-diphenyl-1,2,3,5-tetrahydro-4,1-benzoxazepin-7-yl)-H-pyrrole-2-carbonitrile generally according to example 3. $^1$H NMR (DMSO-d$_6$): δ 10.23 (s, 1H), 7.48 (dd, J=8.24, 2.20 Hz, 1H), 7.35-7.39 (m, 6H), 7.27 (d, J=8.24 Hz, 1H), 7.15-7.17 (m, 4H), 6.93 (d, J=4.39 Hz, 1H), 6.59 (d, J=2.20 Hz, 1H), 6.10 (d, J=4.39 Hz, 1H), 4.28 (s, 2H), 3.39 (s, 3H); MS (ESI) m/z 420 ([M+H]+); MS (ESI) m/z 418 ([M−H]−).

EXAMPLE 175

1-Methyl-5-(1-methyl-2-oxo-5,5-diphenyl-1,2,3,5-tetrahydro-4,1-benzoxazepin-7-yl)-H-pyrrole-2-carbonitrile Prepared from 5-(2-oxo-5,5-diphenyl-1,2,3,5-tetrahydro-4,1-benzoxazepin-7-yl)-H-pyrrole-2-carbonitrile generally according to example 3. $^1$H NMR (DMSO-d$_6$): δ 7.70 (dd, J=8.24, 2.20 Hz, 1H), 7.55 (d, J=8.24 Hz, 1H), 7.29-7.37 (m, 6H), 7.19 (d, J=7.69 Hz, 4H), 6.97 (d, J=4.39 Hz, 1H), 6.56 (d, J=2.20 Hz, 1H), 6.19 (d, J=3.85 Hz, 1H), 4.26 (s, 2H), 3.53, (s, 3H), 2.60 (s, 3H); MS (ESI) m/z 434 ([M+H]+).

EXAMPLE 176

7-(3-Chloro-4-fluorophenyl)-5,5-diphenyl-1,5-dihydro-4,1-benzoxazepin-2(H)-one

Prepared from 7-bromo-5,5-diphenyl-1,5-dihydro-4,1-benzoxazepin-2(3H)-one and 3-chloro-4-fluoro benzeneboronic acid generally according to the coupling procedure described in example 1. $^1$H NMR (DMSO-d$_6$): δ 10.17 (s, 1H), 7.65 (dd, J=8.3, 2.44 Hz, 1H), 7.50 (dd, J=7.32, 2.44 Hz, 1H), 7.34-7.43 (m, 7H), 7.25 (d, J=8.3 Hz, 1H), 7.22-7.24 (m, 1H), 7.16-7.19 (m, 4H), 6.75 (d, 1.95 Hz, 1H), 4.26 (s, 2H); MS (ESI) m/z 442/444 ([M–H]–); Anal. calcd for C$_{27}$H$_{19}$ClFNO$_2$: C, 73.06; H, 4.31; N, 3.16. Found: C, 72.67; H, 4.36; N, 2.89.

EXAMPLE 177

2-[5,5-Bis-(4-methoxy-phenyl)-2-oxo-1,2,3,5-tetrahydro-benzo[e][1,4]oxazepin-7-yl]-5-cyano-pyrrole-1-carboxylic acid tert-butyl ester N-(4-Bromo-2-{hydroxy[bis(4-methoxyphenyl]methyl}phenyl)-2-chloroacetamide Prepared from methyl 2-amino-5-bromobenzoate in two steps generally according to the procedures described in example 24. $^1$H NMR (DMSO-d$_6$): δ 10.45 (s, 1H), 8.07 (d, J=8.24 Hz, 1H), 7.58 (s, 1H), 7.53 (dd, J=8.24, 2.20 Hz, 1H), 7.07 (d, J=7.14 Hz, 4H), 6.90 (d, J=8.79 Hz, 4H), 6.60 (d, J=2.75 Hz, 1H), 4.03 (s, 2H), 3.75 (s, 6H); MS (ESI) m/z 488/490/492 ([M–H]–).

7-Bromo-5,5-bis(4-methoxyphenyl)-1,5-dihydro-4,1-benzoxazepin-2(3H)-one

Prepared from N-(4-bromo-2-{hydroxy[bis(4-methoxyphenyl]methyl}phenyl)-2-chloroacetamide following the procedure described in example 1. $^1$H NMR (DMSO-d$_6$): δ 10.13 (s, 1H), 7.49 (dd, J=8.79, 2.20 Hz, 1H), 7.11 (d, J=8.79 Hz, 1H), 6.92-7.0 (m, 8H), 6.59 (d, J=2.20 Hz, 1H), 4.21 (s, 2H), 3.76 (s, 6H); MS (ESI) m/z 454/456 ([M+H]$^+$); MS (ESI) m/z 452/454 ([M–H]–).

tert-Butyl 2-[5,5-bis(4-methoxyphenyl)-2-oxo-1,2,3,5-tetrahydro-4,1-benzoxazepin-7-yl]-H-pyrrole-1-carboxylate Prepared from 7-bromo-5,5-bis(4-methoxyphenyl)-15-dihydro-4,1-benzoxazepin-2(H)-one and 2-borono-1H-pyrrole-1-carboxylic acid, 1-tert-butylester generally according to the coupling procedure described in example 1. $^1$H NMR (DMSO-d$_6$): δ 10.68 (s, 1H), 7.25 (dd, J=8.24, 2.20 Hz, 1H), 7.22 (dd, J=3.30, 1.65 Hz, 1H), 7.13 (d, J=8.24 Hz, 1H), 7.02 (d, J=9.34 Hz, 4H), 6.88 (d, J=9.34 Hz, 4H), 6.51 (d, J=1.65 Hz, 1H), 6.17 (m, 1H), 6.00 (m, 1H), 4.2 (s, 2H), 3.73 (s, 6H), 1.35 (s, 9H); MS (ESI) m/z 541 ([M+H]+).

The title compound was prepared from tert-butyl 2-[5,5-bis(4-methoxyphenyl)-2-oxo-1,2,3,5-tetrahydro-4,1-benzoxazepin-7-yl]-H-pyrrole-1-carboxylate generally according to the procedure described in example 1. $^1$H NMR (DMSO-d$_6$): δ 11.8 (s, 1H), 10.2 (s, 1H), 7.35 (dd, J=8.30, 2.05 Hz, 1H), 7.18-7.23 (m, 1H), 7.02 (d, J=8.88 Hz, 4H), 6.90 (d, J=8.93 Hz, 4H), 6.54 (d, J=1.98 Hz, 1H), 6.20 (d, J=3.80 Hz, 1H), 4.21 (s, 2H), 3.75 (s, 6H), 1.37 (s, 9H); MS (ESI) m/z 564 ([M–H]–).

EXAMPLE 178

7-(3-Chloro-4-fluorophenyl)-5,5-bis(4-methoxyphenyl)-1,5-dihydro-4,1-benzoxazepin-2(H)-one Prepared from 7-bromo-5,5-bis(4-methoxyphenyl)-15-dihydro-4,1-benzoxazepin-2(H)-one and 3-chloro-4-fluoro benzeneboronic acid generally according to the coupling procedure described in example 1. $^1$H NMR (DMSO-d$_6$): δ 10.16 (s, 1H), 7.60-7.62 (m, 1H), 7.49-7.52 (m, 1H), 7.42 (m, 1H), 7.25 (m, 2H), 7.07 (d, J=4.94 Hz, 4H), 6.93 (d, J=4.94 Hz, 4H), 6.77 (d, J=2.20 Hz, 1H), 4.20 (s, 2H), 3.75 (s, 6H); MS (ESI) m/z 504/506 ([M+H]+); MS (ESI) m/z 502/504 ([M–H]–).

EXAMPLE 179

5-[5,5-Bis-(4-methoxy-phenyl)-2-oxo-1,2,3,5-tetrahydro-benzo[e][1,4]oxazepin-7-yl]-1H-pyrrole-2-carbonitrile Prepared from 2-[5,5-Bis-(4-methoxy-phenyl)-2-oxo-1,2,3,5-tetrahydro-benzo[e][1,4]oxazepin-7-yl]-5-cyano-pyrrole-1-carboxylic acid tert-butyl ester following example 2. $^1$H NMR (DMSO-d$_6$): δ 12.5 (s, 1H), 10.14 (s, 1H), 7.59 (dd, J=8.41, 1.99 Hz, 1H), 6.90-7.22 (m, 3H), 7.16 (d, J=8.81 Hz, 4H), 6.93 (d, J=8.92 Hz, 4H), 6.20 (d, J=3.59 Hz, 1H), 4.11 (s, 2H), 3.76 (s, 6H); MS (ESI) m/z 466 ([M+H]+); MS (ESI) m/z 464 ([M–H]–).

EXAMPLE 180

5-[5,5-Bis(4-methoxyphenyl)-2-oxo-1,2,3,5-tetrahydro-4,1-benzoxazepin-7-yl]-1-methyl-H-pyrrole-2-carbonitrile Prepared from 2-cyano-5-[5-(4-methoxyphenyl)-5-(4-methoxyphenyl)-2-oxo-1,2,3,5-tetrahydro-4,1-benzoxazepin-7-yl]-H-pyrrole generally according to example 3. $^1$H NMR (DMSO-d$_6$): δ 10.21 (s, 1H), 7.44 (dd, J=8.23, 1.97 Hz, 1H), 7.27 (d, J=8.46 Hz, 1H), 7.05 (d, J=8.92 Hz, 4H), 6.92 (d, J=8.92 Hz, 4H), 6.94 (s, 1H), 6.61 (s, 1H), 6.11 (d, J=4.06 Hz, 1H), 4.22 (s, 2H), 3.75 (s, 6H), 3.42 (s, 3H); MS (ESI) m/z 480 ([M+H]+).

EXAMPLE 181

5-[5,5-Di(3-furyl)-2-oxo-1,2,3,5-tetrahydro-4,1-benzoxazepin-7-yl]-1-methyl-H-pyrrole-2-carbonitrile (2-Amino-5-bromophenyl)[di(3-furyl)]methanol Prepared from methyl 2-amino-5-bromobenzoate and 3-furyl lithium following the procedure described in example 24. ¹H NMR (DMSO-d₆): δ 7.6 (t, J=1.73 Hz, 2H), 7.25 (q, J=1.51, 0.81 Hz, 2H), 7.10 (q, J=8.46, 2.43 Hz, 1H), 6.79 (d, J=2.43 Hz, 1H), 6.56 (d, J=8.46 Hz, 1H), 6.46 (d, J=8.46 Hz, 1H), 6.39 (q, J=1.73, 0.81 Hz, 2H), 5.35 (s, 2H); MS (ESI) m/z 332/334 ([M−H]−).

N-{4-Bromo-2-[di(3-furyl)(hydroxy)methyl]phenyl}-2-chloroacetamide

Prepared from (2-amino-5-bromophenyl)[di(3-furyl)]methanol and chloroacetyl chloride generally according to procedure of described in example 1. ¹H NMR (DMSO-d₆): δ 10.69 (s, 1H), 8.14 (d, J=8.74 Hz, 1H), 7.69 (t, J=1.68 Hz, 2H), 7.54 (q, J=8.74 Hz, 1H), 7.51 (s, 1H), 7.32 (s, 2H), 7.02 (d, J=2.37 Hz, 1H), 6.43 (d, J=1.03 Hz, 1H), 4.26 (s, 2H); MS (ESI) m/z 408/410/412 ([M−H]−).

7-Bromo-5,5-di(3-furyl)-1,5-dihydro-4,1-benzoxazepin-2(3H)-one

Prepared from N-{4-bromo-2-[di(3-furyl)(hydroxy)methyl]phenyl}-2-chloroacetamide following the procedure described in example 1. ¹H NMR (DMSO-d₆): δ 10.2 (s, 1H), 7.74 (s, 2H), 7.47 (dd, J=8.63, 2.27 Hz, 1H), 7.36 (s, 2H), 7.14 (d, J=8.67 Hz, 1H), 7.01 (d, J=2.2 Hz, 1H), 6.40 (s, 2H), 4.20 (s, 2H); MS (ESI) m/z 374/376 ([M+H]+); MS (ESI) m/z 372/374 ([M−H]−).

The title compound was prepared from 7-bromo-5-di(3-furyl)benzoxazepinone and 5-cyano-1-methyl-1H-pyrrol-2-ylboronic acid generally according to the coupling procedure described in example 1. ¹H NMR (DMSO-d₆): δ 10.27 (s, 1H), 7.72 (t, J=1.62 Hz, 2H), 7.43 (dd, J=8.37, 1.99 Hz, 1H), 7.38 (s, 2H), 7.29 (d, J=8.42 Hz, 1H), 7.03 (d, J=1.92 Hz, 1H), 6.98 (d, J=4.09 Hz, 1H), 6.43 (d, J=0.93 Hz, 2H), 6.19 (d, J=4.09 Hz, 1H), 4.22 (s, 2H), 3.55 (s, 3H); MS (ESI) m/z 400 ([M+H]+); MS (ESI) m/z 398 ([M−H]−); Anal. calcd for C₂₃H₁₇N₃O₄: C, 69.17; H, 4.29; N, 10.52. Found: C, 68.72; H, 4.42; N, 10.27.

EXAMPLE 182

3-[5,5-Di(3-furyl)-2-oxo-1,2,3,5-tetrahydro-4,1-benzoxazepin-7-yl]-5-fluorobenzonitrile Prepared from 7-bromo-5-di(3-furyl)benzoxazepinone and 3-cyano-5-fluoro benzeneboronic acid generally according to the coupling procedure described in example 1. ¹H NMR (DMSO-d₆): δ 10.22 (s, 1H), 7.28-7.83 (m, 1H), 6.45 (s, 1H), 4.19 (s, 2H); MS (ESI) m/z 415 ([M+H]+); MS (ESI) m/z 413 ([M−H]−).

EXAMPLE 183

7-(3-Chloro-4-fluorophenyl)-5,5-di(3-furyl)-1,5-dihydro-4,1-benzoxazepin-2(H)-one Prepared from 7-bromo-5-di(3-furyl)benzoxazepinone and 3-chloro-4-fluoro benzeneboronic acid generally according to the coupling procedure described in example 1. ¹H NMR (DMSO-d₆): δ 10.18 (s, 1H), 7.71 (m, 2H), 7.59-7.66 (m, 2H), 7.40-7.45 (m, 4H), 7.28 (d, J=8.46 Hz, 1H), 7.19 (s, 1H), 6.43 (m, 2H), 4.19 (s, 2H); MS (ESI) m/z 424/426 ([M+H]+); MS (ESI) m/z 422/424 ([M−H]−).

EXAMPLE 184

Assay Tests

The compounds of this invention were tested in the relevant assay as described below and their potency are in the range of 0.01 nM to 5 µM in the in vitro assays and 0.001 to 300 mg/kg in the in vivo assays.

TABLE 1

Potency of selected 5,5-dimethyl 7-aryl benzoxazepinones as PR modulators in some in vitro and in vivo assays

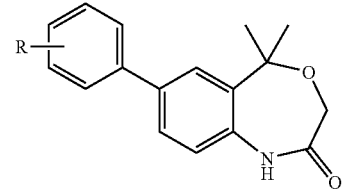

| Compound | R | Alk. Phos. IC₅₀ (nM) | Decidualization IC₅₀ (mg/kg) |
|---|---|---|---|
| 1 | 3'-Cl, 4'-F | 30.5 | >3 |
| 2 | 3'-F | 14.9 | ND* |
| 3 | 3'-CN, 5'-F | 22.5 | 40% @ 3 |
| 4 | 3'-F, 5'-F | 30.0 | >3 |
| 5 | 3'-Cl | 120.5 | ND |
| 6 | 3'-CN, 4'-F | 42.1 | ND |
| 7 | 4'-F | 100.0 | ND |
| 8 | 2'-F | 62.1 | ND |
| 9 | 3'-F, 4'-F | 29.3 | ND |
| 10 | 3'-Cl, 5'-Cl | 29.1 | ND |
| 11 | 2'-F, 3'-F | 15.7 | ND |
| 12 | 4'-Cl, 3'-F | 33.1 | ND |
| 13 | 3'-CN, 5'-Cl | 34.6 | ND |

*ND: not determined.

TABLE 2

Potency of selected 5-(-benzoxazepin-7-yl)-pyrrole-2-carbonitrileas
PR modulators in some in vitro and in vivo assays

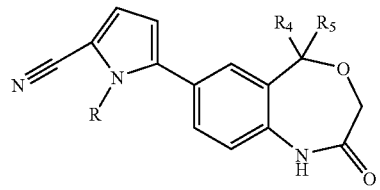

| Compound | R | R₄ | R₅ | Alk. Phos. EC₅₀ (nM) | Alk. Phos. IC₅₀ (nM) |
|---|---|---|---|---|---|
| 1 | BOC | Me | Me | 4.8 | |
| 2 | H | Me | Me | 3.3 | |
| 3 | Me | Me | Me | 3.3 | |
| 4 | BOC | Me | 2-thienyl | 1.45 | |
| 5 | H | Me | 2-thienyl | 0.8 | |
| 6 | Me | Me | 2-thienyl | 0.8 | |
| 7 | BOC | Me | Phenyl | 15.8 | |
| 8 | H | Me | Phenyl | 11.2 | |
| 9 | Me | Me | Phenyl | 247.5 | |
| 10 | BOC | H | Me | 149.2 | |
| 11 | H | H | Me | 245.8 | |
| 12 | Me | H | Me | 137.7 | |
| 13 | H | 2-thienyl | 2-thienyl | | 43.9 |

TABLE 2-continued

Potency of selected 5-(-benzoxazepin-7-yl)-pyrrole-2-carbonitrileas PR modulators in some in vitro and in vivo assays

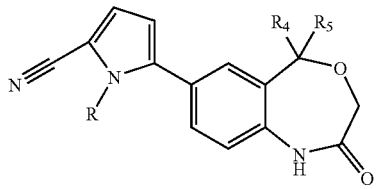

| Compound | R | $R_4$ | $R_5$ | Alk. Phos. $EC_{50}$ (nM) | Alk. Phos. $IC_{50}$ (nM) |
|---|---|---|---|---|---|
| 14 | Me | 2-thienyl | 2-thienyl | | 11.3 |
| 15 | BOC | Phenyl | Phenyl | | 532 |
| 16 | H | Phenyl | Phenyl | | 51 |
| 17 | Me | Phenyl | Phenyl | | 11.5 |
| 18 | H | Et | 2-thienyl | | 78.1 |
| 19 | Me | Et | 2-thienyl | | 14.6 |

Pharmacology (1) T47D Cell Proliferation Assay

Objective:

Determination of progestational and antiprogestational potency by using a cell proliferation assay in T47D cells. A compound's effect on DNA synthesis in T47D cells is measured.

Methods:

A. Reagents:

Growth medium: DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

Treatment medium: Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

B. Cell Culture:

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

C. Cell Proliferation Assay:

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10-20 min depending upon the potency of tested compounds. Then 25 µl of 1 M sulfuric acid is added to each well to stop color reaction and optical density is read in a plate reader at 450 nm within 5 min.

Analysis of Results:

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

Reference Compounds:

Trimegestone and medroxyprogesterone acetate (MPA) were reference progestins and RU486 is the reference antiprogestin. All reference compounds were run in full dose-response curves and the $EC_{50}$ or $IC_{50}$ values were calculated.

TABLE 1

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |
| | 3 | 0.019 | 0.001 | 0.016 | 0.024 |
| MPA | 1 | 0.019 | 0.001 | 0.013 | 0.027 |
| | 2 | 0.017 | 0.001 | 0.011 | 0.024 |

TABLE 2

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
| | 2 | 0.016 | 0.001 | 0.014 | 0.020 |
| | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE (2) Rat Decidualization Assay Objective:

This procedure was used to evaluate the effect of progestins and antiprogestins on rat uterine decidualization and compare the relative potencies of various test compounds.

Methods:

A. Reagents

Test compounds were dissolved in 100% ethanol and mixed with corn oil (vehicle). Stock solutions of the test compounds in oil (Mazola™) were then prepared by heating (~80° C.) the mixture to evaporate ethanol. Test compounds were subsequently diluted with 100% corn oil or 10% ethanol in corn oil prior to the treatment of animals. No difference in decidual response was found when these two vehicles were compared.

B. Animals (RACUC Protocol #5002)

Ovariectomized mature female Sprague-Dawley rats (~60-day old and 230 g) were obtained from Taconic (Taconic Farms, N.Y.) following surgery. Ovariectomy was performed at least 10 days prior to treatment to reduce circulating sex steroids. Animals were housed under 12 hr light/dark cycle and given standard rat chow and water ad libitum.

C. Treatment

Rats were weighed and randomly assigned to groups of 4 or 5 before treatment. Test compounds in 0.2 mL vehicle were administered by subcutaneous injection in the nape of the neck or by gavage using 0.5 ml. The animals were treated once daily for seven days. For testing antiprogestins, animals were given the test compounds and a $EC_{50}$ dose of progesterone (5.6 mg/kg) during the first three days of treatment. Following decidual stimulation, animals continued to receive progesterone until necropsy four days later.

D. Dosing

Doses were prepared based upon mg/kg mean group body weight. In all studies, a control group receiving vehicle was included. Determination of dose-response curves was carried out using doses with half log increases (e.g. 0.1, 0.3, 1.0, 3.0 mg/kg . . . ).

E. Decidual Induction

Approximately 24 hr after the third injection, decidualization was induced in one of the uterine horns by scratching the antimesometrial luminal epithelium with a blunt 21 G needle. The contralateral horn was not scratched and served as an unstimulated control. Approximately 24 hr following the final treatment, rats were sacrificed by $CO_2$ asphyxiation and body weight measured. Uteri were removed and trimmed of fat. Decidualized (D-horn) and control (C-horn) uterine horns were weighed separately.

Analysis of Results:

The increase in weight of the decidualized uterine horn was calculated by D-horn/C-horn and logarithmic transformation was used to maximize normality and homogeneity of variance. The Huber M-estimator was used to down weight the outlying transformed observations for both dose-response curve fitting and one-way analysis of variance. JMP software (SAS Institute, Inc.) was used for both one-way ANOVA and non-linear dose-response analyses.

Reference Compounds:

All progestin reference compounds were run in full dose-response curves and the $EC_{50}$ for uterine wet weight was calculated.

TABLE 3

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
| | 2 | 6.21 | 1.12 | 4.41 | 8.76 |
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |

TABLE 3-continued

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.05 | 0.22 | 0.67 |
| | 3 | 0.39 | 0.04 | 0.25 | 0.61 |

TABLE 4

Estimated average $EC_{50}$, standard error, and 95% confidence intervals for dose-response curves of 3 reference compounds

| Compound | EC50 (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 5

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
| | 2 | 0.14 | 0.02 | 0.08 | 0.27 |

Concentration: Compound Concentration in Assay (Default-mg/kg Body Weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: [(D−C)/C]×100%

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

(3) PRE-Luciferase Assay in CV-1 Cells

Objective:

To determine a compound's progestational or antiprogestational potency based on its effect on PRE-luciferase reporter activity in CV-1 cells co-transfected with human PR and PRE-luciferase plasmids.

Methods:

A. Reagents:

Culture Medium:

Growth medium: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL).

Experimental medium: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

Cell culture, transfection, treatment, and luciferase assay

Stock CV-1 cells were maintained in growth medium. Co-transfection was done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation was carried out at 260 V and 1,000 mF in a Biorad Gene Pulser II. After electroporation, cells were resuspended in growth medium and plated in 96-well plate at 40,000 cells/well in 200 µl. Following overnight incubation, the medium was changed to experimental medium. Cells were then treated with reference or test compounds in experimental medium. Compounds were tested for antiprogestational activity in the presence of 3 nM progesterone. Twenty-four hr. after treatment, the medium was discarded, cells were washed three times with D-PBS (GIBCO, BRL). Fifty ml of cell lysis buffer (Promega, Madison, Wis.) was added to each well and the plates were shaken for 15 min in a Titer Plate Shaker (Lab Line Instrument, Inc.). Luciferase activity was measured using luciferase reagents from Promega.

Analysis of Results:

Each treatment consists of at least 4 replicates. Log transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear response analyses.

Reference Compounds:

Progesterone and trimegestone were reference progestins and RU486 was the reference antiprogestin. All reference compounds were run in full dose-response curves and the $EC_{50}$ or $IC_{50}$ values were calculated.

TABLE 6

Estimated $EC_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 7

Estimated $IC_{50}$, standard error (SE), and 95% confident interval (CI) for the antiprogestin, RU486 from three individual studies

| Compound | Exp. | IC50 (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

(4) T47D Cell Alkaline Phosphatase Assay

Purpose:

To identify progestins or antiprogestins by determining a compound's effect on alkaline phosphatase activity in T47D cells.

Methods:

A. Reagents:

Culture Medium:

DMEM:F12 (1:1) (GIBCO, BRL) supplemented with 5% (v/v) charcoal stripped fetal bovine serum (not heat-inactivated), 100 U/ml penicillin, 100 mg/ml streptomycin, and 2 mM GlutaMax (GIBCO, BRL).

Alkaline Phosphatase Assay Buffer:

I. 0.1 M Tris-HCl, pH 9.8, containing 0.2% Triton X-100

II. 0.1 M Tris-HCl, pH 9.8 containing 4 mM p-nitrophenyl phosphate (Sigma).

B. Cell Culture and Treatment:

Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

Note: For high throughput screening, one concentration of each compound was tested at 0.3 mg/ml. Based on an average molecular weight of 300 g/mol for the compounds in the library, the concentration was approximately 1 mM. Subsequently, active compounds were tested in dose response assays to determine $EC_{50}$ or $IC_{50}$ C. Alkaline Phosphatase Enzyme Assay:

At the end of treatment, the medium was removed from the plate. Fifty µl of assay buffer I was added to each well. The plates were shaken in a titer plate shaker for 15 min. Then 150

μl of assay buffer II was added to each well. Optical density measurements were taken at 5 min intervals for 30 min at a test wavelength of 405 nM.

Analysis of Results:

Analysis of Dose-Response Data

For reference and test compounds, a dose response curve was generated for dose (X-axis) vs. the rate of enzyme reaction (slope) (Y-axis). Square root-transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear dose response analyses in both single dose and dose response studies.

Reference Compounds:

Progesterone and trimegestone were reference progestins and RU486 was the reference antiprogestin. All reference compounds were run in full dose response curves and the $EC_{50}$ or $IC_{50}$ values were calculated.

TABLE 8

Estimated $EC_{50}$, standard error (SE), and 95% confidence intervals (CI) for reference progestins from three independent experiments

| Compound | Exp. | EC50 (nM) | SE | 95% CI lower | 95% CI upper |
|---|---|---|---|---|---|
| Progesterone | 1 | 0.839 | 0.030 | 0.706 | 0.996 |
| | 2 | 0.639 | 0.006 | 0.611 | 0.669 |
| | 3 | 1.286 | 0.029 | 1.158 | 1.429 |
| Trimegestone | 1 | 0.084 | 0.002 | 0.076 | 0.091 |
| | 2 | 0.076 | 0.001 | 0.072 | 0.080 |
| | 3 | 0.160 | 0.004 | 0.141 | 0.181 |

TABLE 9

Estimated $IC_{50}$, standard error, and 95% confident interval for the reference antiprogestin RU486 from three independent experiments

| Compound | Exp. | IC 50 (nM) | SE | 95% CI lower | 95% CI upper |
|---|---|---|---|---|---|
| RU486 | 1 | 0.103 | 0.002 | 0.092 | 0.115 |
| | 2 | 0.120 | 0.001 | 0.115 | 0.126 |
| | 3 | 0.094 | 0.007 | 0.066 | 0.134 |

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

All patents, publications, and other documents cited herein are hereby incorporated by reference in their entirety.

What is claimed:

1. A compound of the formula:

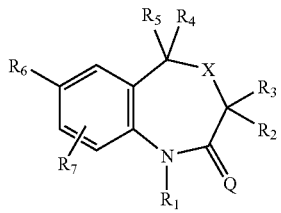

wherein:

$R_1$ is H, $C_{1-3}$ alkyl, or $COR^A$;

$R^A$ is H, $C_{1-4}$ alkyl, $C_{1-4}$ alkoxy, or $C_{1-3}$ aminoalkyl;

$R_2$ and $R_3$ are each independently H, $CF_3$, or $C_{1-3}$ alkyl;

$R_4$ and $R_5$ are each independently H, $C_{1-6}$ alkyl, $C_{2-6}$ alkenyl, $C_{2-6}$ alkynyl, $CF_3$, $CF_2CF_3$, $C_{3-6}$ cycloalkyl, aryl, substituted aryl, heterocycle, substituted heterocycle, or together with the carbon atom to which they are attached form a 3 to 6 membered alkylspirocyclic ring or a 3 to 6 membered heterospirocyclic ring containing one to three heteroatoms within the spirocyclic ring, said heteroatoms being O, S, SO, $SO_2$, or N;

$R_6$ is a 5 or 6 membered heterocyclic ring containing 1 or 3 heteroatoms and 1 to 3 substituents, said heteroatoms being O, S, SO, $SO_2$ or N and said substituents independently being H, halogen, CN, $NO_2$, OH, amino, $C_{1-3}$ alkyl, $C_{1-3}$ alkoxy, $C_{1-3}$ aminoalkyl, C=$NOR^C$, or $NR^C$-$COR^D$;

$R^C$ is H, $C_{1-4}$ alkyl, substituted $C_{1-4}$ alkyl, or $COR^D$;

$R^D$ is H, $C_{1-3}$ alkyl, $C_{1-3}$ alkoxy, or $C_{1-3}$ aminoalkyl;

$R_7$ is H, halogen, CN, $NO_2$, OH, $C_{1-3}$ alkyl, $C_{2-3}$ alkenyl, $C_{2-3}$ alkynyl, $C_{1-3}$ alkoxy, amino, or $C_{1-3}$ aminoalkyl;

Q is O, S, $NR_8$, $CR_9R_{10}$, or $R_{13}R_{14}$;

$R_8$ is CN, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, or substituted heterocyclic, $SO_2CF_3$, $OR^{11}$ or $NR^{11}R^{12}$;

$R_9$ and $R_{10}$ are independently H, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, substituted heterocyclic, $NO_2$, CN, or $CO_2R_{11}$;

or $CR^9R^{10}$ is a six membered ring of the structure:

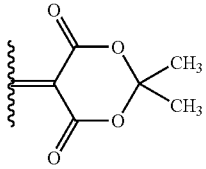

$R_{11}$ and $R_{12}$ are independently each H, $C_{1-6}$ alkyl, substituted $C_{1-6}$ alkyl, aryl, substituted aryl, heterocyclic, substituted heterocyclic, alkyl carbonyl or sulfonyl;

$R_{13}$ and $R_{14}$ are each independently H, $C_{1-3}$ lower alkyl, $C_{1-3}$ lower perfluoroalkyl, aryl, heterocyclic, a 3 to 6 membered alkylspirocyclic ring is a 3 to 6 membered heterospirocyclic ring containing one to three heteroatoms within the spirocyclic ring, said heteroatoms being O, S, SO, $SO_2$ or N;

X is S, $NR^E$, or $CR^ER^F$;

$R^E$ and $R^F$ are each independently H or $C_{1-4}$ alkyl;

provided that when X is $NR^E$, Q is O or S, $R_6$ is a 5 or 6 membered heterocyclic ring, and $R_4$ is cyclopropyl or $C_{1-3}$ alkyl, then $R_5$ is H, $CF_3$, $CF_2CF_3$, $C_{3-6}$ cycloalkyl, aryl, substituted aryl, heterocycle, or a substituted heterocycle;

the alkyl group of said substituted alkyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the alkenyl group of said substituted alkenyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the alkynyl group of said substituted alkynyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the aryl group of said substituted aryl comprises one or more substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

wherein said heterocycle is a stable 4- to 7-membered monocyclic or a stable multicyclic heterocyclic ring which is saturated, partially unsaturated, or unsaturated, and which consists of carbon atoms and from one to four heteroatoms selected from the group consisting of N, O, and S atoms;

the heterocyclic group of said substituted heterocyclic comprises one or more substituents selected from the group consisting of halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

or pharmaceutically acceptable salt thereof.

2. A compound according to claim 1 wherein $R_1$, $R_2$, and $R_3$ are each H.

3. A compound according to claim 1 wherein Q is $NR_8$, $CR_9R_{10}$, or $R_{13}R_{14}$.

4. A compound according to claim 3 wherein $R_8$ is CN, $C_{1-3}$ alkyl, $SO_2CF_3$, $OR_{11}$ or $NR_{11}R_{12}$.

5. A compound according to claim 3 wherein $R_8$ is CN, $SO_2CF_3$, or $OR_{11}$.

6. A compound according to claim 3 wherein $R_9$ and $R_{10}$ are each, independently, H, $C_{1-3}$ alkyl, $NO_2$, CN, or $CO_2R_{11}$; or $CR_9R_{10}$ is a six membered ring as shown by the structure:

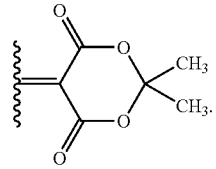

7. A compound according to claim 3 wherein $R_9$ and $R_{10}$ are each, independently, $NO_2$, CN, or $CO_2R_{11}$.

8. A compound according to claim 3 wherein $R_{11}$ and $R_{12}$ are each independently, H, $C_{1-3}$ alkyl, alkyl carbonyl or sulfonyl.

9. A compound according to claim 3 wherein $R_{11}$ and $R_{12}$ are each independently, H or $C_{1-3}$ alkyl.

10. A compound according to claim 3 wherein $R_{13}$ and $R_{14}$ are each, independently, H, $C_{1-3}$ lower alkyl, or $C_{1-3}$ perfluoroalkyl.

11. A compound according to claim 1 wherein:
$R_6$ is a 5 or 6 membered heterocyclic ring containing 1 heteroatom substituted with 1 to 2 substituents from the group including halogen, CN, $NO_2$, OH, and $C_{1-3}$ alkyl, C=NOH, said heteroatoms being O, S, SO, $SO_2$ or N.

12. A compound according to claim 1 wherein:
$R_4$ is H, $C_{1-6}$ alkyl, $CF_3$, $CF_2CF_3$, $C_{2-6}$ alkenyl, $C_{2-6}$ alkynyl, aryl, substituted aryl, heterocycle, or substituted heterocycle;
$R_5$ is aryl, substituted aryl, heterocycle, or substituted heterocycle; or
$R_4$ and $R_5$ together with the carbon to which they are attached are a 3 to 6 membered alkylspirocyclic ring comprising $R_4$ and $R_5$, or a 3 to 6 membered heterospirocyclic ring comprising $R_4$ and $R_5$ and containing one to three heteroatoms within the spirocyclic ring, said heteroatoms being O, S, SO, $SO_2$, or N.

13. A compound according to claim 1 wherein $R_7$ is H, halogen, CN or $NO_2$.

14. A compound according to claim 1 wherein:
$R_1$, $R_2$, and $R_3$ are each H;
$R_4$ is H, $C_{1-6}$ alkyl, $CF_3$, $CF_2CF_3$, $C_{2-6}$ alkenyl, $C_{2-6}$ alkynyl, aryl, substituted aryl, heterocycle, or substituted heterocycle;
$R_5$ is aryl, substituted aryl, heterocycle, or substituted heterocycle; or
$R_4$ and $R_5$ are a 3 to 6 membered alkylspirocyclic ring comprising $R_4$ and $R_5$, a 3 to 6 membered heterospirocyclic ring comprising $R_4$ and $R_5$ and containing one to three heteroatoms within the spirocyclic ring, said heteroatoms being O, S, SO, 502, or N;
$R_8$ is CN, $C_{1-3}$ alkyl, $SO_2CF_3$, $OR_{11}$ or $NR_{11}R_{12}$;
$R_9$ and $R_{10}$ are each, independently, H, $C_{1-3}$ alkyl, $NO_2$, CN, or $CO_2R_{11}$;
or $CR_9R_{10}$ is a six membered ring as shown by the structure:

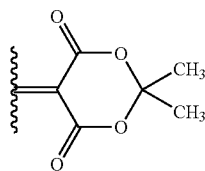

$R_{11}$ and $R_{12}$ are each, independently, H, $C_{1-3}$ alkyl, alkyl carbonyl or sulfonyl; and
$R_{13}$ and $R_{14}$ are each, independently, H, $C_{1-3}$ lower alkyl, or $C_{1-3}$ perfluoroalkyl.

15. A compound according to claim 1 wherein:
$R_7$ is H, halogen, CN, or $NO_2$,
$R_8$ is selected from the group of CN, $SO_2CF_3$, or $OR_{11}$;
$R_9$ and $R_{10}$ are each, independently, $NO_2$, CN, or $CO_2R_{11}$;
$R_{11}$, and $R_{12}$ are each, independently, H or $C_{1-3}$ alkyl; and
$R_{13}$ and $R_{14}$ are each, independently, H, $C_{1-3}$ alkyl, or $C_{1-3}$ perfluoroalkyl.

16. A compound of the formula:

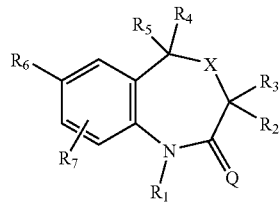

wherein:
$R_1$ is H, $C_{1-3}$ alkyl, or $COR^A$;
$R^A$ is H, $C_{1-4}$ alkyl, $C_{1-4}$ alkoxy, or $C_{1-3}$ aminoalkyl;
$R_2$ and $R_3$ are each independently H, $CF_3$, or $C_{1-3}$ alkyl;
$R_4$ and $R_5$ are each independently H, $C_{1-6}$ alkyl, $C_{2-6}$ alkenyl, $C_{2-6}$ alkynyl, $CF_3$, $CF_2CF_3$, $C_{3-6}$ cycloalkyl, aryl, substituted aryl, heterocycle, substituted heterocycle, or together with the carbon atom to which they are attached form a 3 to 6 membered alkylspirocyclic ring or a 3 to 6 membered heterospirocyclic ring containing one to three heteroatoms within the spirocyclic ring, said heteroatoms being O, S, SO, $SO_2$, or N;
$R_6$ is substituted phenyl containing 1 to 3 substituents, said substituents independently being H, halogen, CN, $NO_2$, OH, amino, $C_{1-3}$ alkyl, $C_{1-3}$ alkoxy, $C_{1-3}$ aminoalkyl, C=$NOR^C$, $COR^D$, or $NR^CCOR^D$; or
$R_6$ is a benzofused heterocyclic ring of the following formula

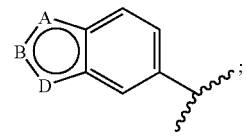

where A, B, and D are each independently CH, N, O, or S;
$R^C$ is H, $C_{1-4}$ alkyl, substituted $C_{1-4}$ alkyl, or $COR^D$;
$R^D$ is H, $C_{1-3}$ alkyl, $C_{1-3}$ alkoxy, or $C_{1-3}$ aminoalkyl;
$R_7$ is H, halogen, CN, $NO_2$, OH, $C_{1-3}$ alkyl, $C_{2-3}$ alkenyl, $C_{2-3}$ alkynyl, $C_{1-3}$ alkoxy, amino, or $C_{1-3}$ aminoalkyl;
Q is O, S, $NR_8$, $CR_9R_{10}$, or $R_{13}R_{14}$;
$R_8$ is CN, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, or substituted heterocyclic, $SO_2CF_3$, $OR^{11}$ or $NR_{11}R_{12}$;
$R_9$ and $R_{10}$ are independently H, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, substituted heterocyclic, $NO_2$, CN, or $CO_2R_{11}$;
or $CR_9R_{10}$ is a six membered ring of the structure:

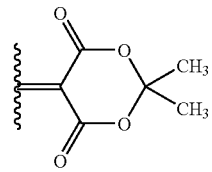

$R_{11}$ and $R_{12}$ are independently each H, $C_{1-6}$ alkyl, substituted $C_{1-6}$ alkyl, aryl, substituted aryl, heterocyclic, substituted heterocyclic, alkyl carbonyl or sulfonyl;

$R_{13}$ and $R_{14}$ are each independently H, $C_{1-3}$ lower alkyl, $C_{1-3}$ lower perfluoroalkyl, aryl, heterocyclic, a 3 to 6 membered alkylspirocyclic ring is a 3 to 6 membered heterospirocyclic ring containing one to three heteroatoms within the spirocyclic ring, said heteroatoms being O, S, SO, $SO_2$ or N;

X is S, $NR^E$, or $CR^E R^F$;

$R^E$ and $R^F$ are each independently H or $C_{1-4}$ alkyl;

the alkyl group of said substituted alkyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the alkenyl group of said substituted alkenyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the alkynyl group of said substituted alkynyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

the aryl group of said substituted aryl comprises one or more substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

wherein said heterocycle is a stable 4- to 7-membered monocyclic or a stable multicyclic heterocyclic ring which is saturated, partially unsaturated, or unsaturated, and which consists of carbon atoms and from one to four heteroatoms selected from the group consisting of N, O, and S atoms;

the heterocyclic group of said substituted heterocyclic comprises one or more substituents selected from the group consisting of halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

or pharmaceutically acceptable salt thereof.

17. A pharmaceutical composition comprising a compound according to claim 1, or a pharmaceutically acceptable salt thereof, and a pharmaceutically acceptable carrier or excipient.

18. A method of inducing contraception comprising administering to a mammal in need thereof a pharmaceutically effective amount of a compound of claim 1.

19. A method according to claim 18 wherein the compound is administered orally.

20. A method of treating a benign or malignant neoplastic disease selected from the group consisting of uterine myometrial fibroids, endometriosis, benign prostatic hypertrophy, carcinomas and adenocarcinomas of the endometrium, ovary, breast, colon, prostate, and pituitary, and meningioma or other hormone-dependent tumors, said method comprising administering to a mammal in need thereof a pharmaceutically effective amount of a compound of claim 1.

21. A method of hormone replacement therapy comprising administering to a mammal in need thereof a pharmaceutically effective amount of a compound of claim 1.

22. A compound according to claim 16, wherein:

$R_6$ is substituted phenyl containing 1 to 2 substituents, where said substituents are halogen, CN, $NO_2$, OH, C=NOH; or $R_6$ is a benzofused heterocyclic ring of the following formula

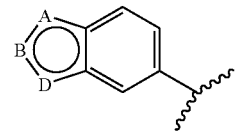

A and D are each independently CH, O, or S;

B is N; and

X is O.

23. A compound according to claim 16, wherein $R_1$, $R_2$, and $R_3$ are each H.

24. A compound according to claim 16, wherein:

$R_6$ is substituted phenyl containing 1 to 2 substituents, where said substituents are selected from halogen, CN, $NO_2$, OH, C=NOH; or $R_6$ is a benzofused heterocyclic ring of the following formula

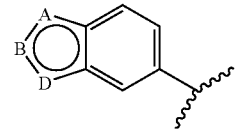

A and D are each independently CH, O, or S; and

B is N.

25. A compound according to claim 16, wherein:

$R_4$ is H, $C_{1-6}$ alkyl, $CF_3$, $CF_2CF_3$, $C_{2-6}$ alkenyl, $C_{2-6}$ alkynyl, aryl, substituted aryl, heterocycle, or substituted heterocycle;

$R_5$ is aryl, substituted aryl, heterocycle, or substituted heterocycle; or $R_4$ and $R_5$ together with the carbon to which they are attached are a 3 to 6 membered alkylspirocyclic ring comprising $R_4$ and $R_5$, or a 3 to 6 membered heterospirocyclic ring comprising $R_4$ and $R_5$ and containing one to three heteroatoms within the spirocyclic ring, said heteroatoms being O, S, SO, $SO_2$, or N.

26. A compound according to claim 16, wherein $R_7$ is H, halogen, CN or $NO_2$.

27. A compound according to claim 16, wherein:

$R_1$, $R_2$, and $R_3$ are each H;

$R_4$ is H, $C_{1-6}$ alkyl, $CF_3$, $CF_2CF_3$, $C_{2-6}$ alkenyl, $C_{2-6}$ alkynyl, aryl, substituted aryl, heterocycle, or substituted heterocycle;

$R_5$ is aryl, substituted aryl, heterocycle, or substituted heterocycle; or $R_4$ and $R_5$ are a 3 to 6 membered alkylspirocyclic ring comprising $R_4$ and $R_5$, a 3 to 6 membered heterospirocyclic ring comprising $R_4$ and $R_5$ and containing one to three heteroatoms within the spirocyclic ring, said heteroatoms being O, S, SO, $SO_2$, or N;

$R_8$ is CN, $C_{1-3}$ alkyl, $SO_2CF_3$, $OR_{11}$ or $NR_{11}R_{12}$;

$R_9$ and $R_{10}$ are each, independently, H, $C_{1-3}$ alkyl, $NO_2$, CN, or $CO_2R_{11}$;

or $CR_9R_{10}$ is a six membered ring as shown by the structure:

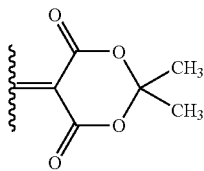

$R_{11}$ and $R_{12}$ are each, independently, H, $C_{1-3}$ alkyl, alkyl carbonyl or sulfonyl; and
$R_{13}$ and $R_{14}$ are each, independently, H, $C_{1-3}$ lower alkyl, or $C_{1-3}$ perfluoroalkyl.

28. A compound according to claim 16, wherein:
$R_7$ is H, halogen, CN, or $NO_2$,
$R_8$ is selected from the group of CN, $SO_2CF_3$, or $OR_{11}$;
$R_9$ and $R_{10}$ are each, independently, $NO_2$, CN, or $CO_2R_{11}$;
$R_{11}$ and $R_{12}$ are each, independently, H or $C_{1-3}$ alkyl; and
$R_{13}$ and $R_{14}$ are each, independently, H, $C_{1-3}$ alkyl, or $C_{1-3}$ perfluoroalkyl.

29. The compound according to claim 16, wherein said compound is 7-(3-chloro-4-fluorophenyl)-4,5,5-trimethyl-1,3,4,5-tetrahydro-2H-1,4-benzodiazepin-2-one or 7-(3-Chloro-4-fluorophenyl)-4,5-dimethyl-2-oxo-2,3-dihydro-H-1,4-benzodiazepin-4-ium.

30. A pharmaceutical composition comprising a compound according to claim 16, or a pharmaceutically acceptable salt thereof, and a pharmaceutically acceptable carrier or excipient.

31. A method of inducing contraception comprising administering to a mammal in need thereof a pharmaceutically effective amount of a compound of claim 16.

32. A method of treating benign or malignant neoplastic disease selected from the group consisting of uterine myometrial fibroids, endometriosis, benign prostatic hypertrophy, carcinomas and adenocarcinomas of the endometrium, ovary, breast, colon, prostate, and pituitary, and meningioma or other hormone-dependent tumors, said method comprising administering to a mammal in need thereof a pharmaceutically effective amount of a compound of claim 16.

33. A method of hormone replacement therapy comprising administering to a mammal in need thereof a pharmaceutically effective amount of a compound of claim 16.

34. A compound of the formula:

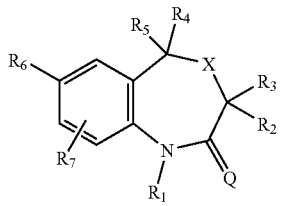

wherein:
$R_1$ is H, $C_{1-3}$ alkyl, or $COR^A$;
$R^A$ is H, $C_{1-4}$ alkyl, $C_{1-4}$ alkoxy, or $C_{1-3}$ aminoalkyl;
$R_2$ and $R_3$ are each independently H, $CF_3$, or $C_{1-3}$ alkyl;
$R_4$ and $R_5$ are each independently H, $C_{1-6}$ alkyl, $C_{2-6}$ alkenyl, $C_{2-6}$ alkynyl, $CF_3$, $CF_2CF_3$, $C_{3-6}$ cycloalkyl, aryl, substituted aryl, heterocycle, substituted heterocycle, or together with the carbon atom to which they are attached form a 3 to 6 membered alkylspirocyclic ring or a 3 to 6 membered heterospirocyclic ring containing one to three heteroatoms within the spirocyclic ring, said heteroatoms being O, S, SO, $SO_2$, or N;
$R_6$ is a 5 or 6 membered heterocyclic ring containing 2 heteroatoms and 1 to 3 substituents, said heteroatoms being O, S, SO, $SO_2$ or N and said substituents independently being H, halogen, CN, $NO_2$, OH, $C_{1-3}$ alkoxy, $C_{1-3}$ aminoalkyl,
$C=NOR^C$, $COR^D$, or $NR^CCOR^D$;
$R_7$ is H, halogen, CN, $NO_2$, OH, $C_{1-3}$ alkyl, $C_{2-3}$ alkenyl, $C_{2-3}$ alkynyl, $C_{1-3}$ alkoxy, amino, or $C_{1-3}$ aminoalkyl;
Q is O, S, $NR_8$, $CR_9R_{10}$, or $R_{13}R_{14}$;
$R_8$ is CN, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, or substituted heterocyclic, $SO_2CF_3$, $OR^{11}$ or $NR^{11}R_{12}$;
$R_9$ and $R_{10}$ are independently H, $C_{1-6}$ alkyl, substituted $C_{1-6}$ alkyl, $C_{3-8}$ cycloalkyl, substituted $C_{3-8}$ cycloalkyl, aryl, substituted aryl, heterocyclic, substituted heterocyclic, $NO_2$, CN, or $CO_2R_{11}$;
or $CR_9R_{10}$ is a six membered ring of the structure:

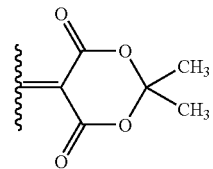

$R_{11}$ and $R_{12}$ are independently each H, $C_{1-6}$ alkyl, substituted $C_{1-6}$ alkyl, aryl, substituted aryl, heterocyclic, substituted heterocyclic, alkyl carbonyl or sulfonyl;
$R_{13}$ and $R_{14}$ are each independently H, $C_{1-3}$ lower alkyl, $C_{1-3}$ lower perfluoroalkyl, aryl, heterocyclic, a 3 to 6 membered alkylspirocyclic ring is a 3 to 6 membered heterospirocyclic ring containing one to three heteroatoms within the spirocyclic ring, said heteroatoms being O, S, SO, $SO_2$ or N;
X is S, $NR^E$, or $CR^ER^F$;
$R^E$ and $R^F$ are each independently H or $C_{1-4}$ alkyl;
provided that when X is $NR^E$, Q is O or S, $R_6$ is a 5 or 6 membered heterocyclic ring, and $R_4$ is cyclopropyl or $C_{1-3}$ alkyl, then $R_5$ is H, $CF_3$, $CF_2CF_3$, $C_{3-6}$ cycloalkyl, aryl, substituted aryl, heterocycle, or a substituted heterocycle;
the alkyl group of said substituted alkyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;
the alkenyl group of said substituted alkenyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;
the alkynyl group of said substituted alkynyl comprises one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;
the aryl group of said substituted aryl comprises one or more substituents selected from the group consisting of halogen, CN, OH, NO$_2$, amino, alkyl, cycloalkyl, alkenyl, alkynyl, alkoxy, aryloxy, substituted alkyloxy, alkylcarbonyl, alkylcarboxy, alkylamino, and arylthio;

wherein said heterocycle is a stable 4- to 7-membered monocyclic or a stable multicyclic heterocyclic ring which is saturated, partially unsaturated, or unsaturated, and which consists of carbon atoms and from one to four heteroatoms selected from the group consisting of N, O, and S atoms;

the heterocyclic group of said substituted heterocyclic comprises one or more substituents selected from the group consisting of halogen, CN, OH, NO$_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

or pharmaceutically acceptable salt thereof.

35. A compound according to claim 34, wherein R$^1$, R$_2$, and R$_3$ are each H.

36. A compound according to claim 34, wherein R$_6$ is a 5 or 6 membered heterocyclic ring containing 2 heteroatoms substituted with 1 to 2 substituents from the group including halogen, CN, NO$_2$, OH, and C$_{1-3}$ alkyl, C═NOH, said heteroatoms being O, S, SO, SO$_2$ or N.

37. A compound according to claim 34, wherein:
R$_4$ is H, C$_{1-6}$ alkyl, CF$_3$, CF$_2$CF$_3$, C$_{2-6}$ alkenyl, C$_{2-6}$ alkynyl, aryl, substituted aryl, heterocycle, or substituted heterocycle;
R$_5$ is aryl, substituted aryl, heterocycle, or substituted heterocycle; or
R$_4$ and R$_5$ together with the carbon to which they are attached are a 3 to 6 membered alkylspirocyclic ring comprising R$_4$ and R$_5$, or a 3 to 6 membered heterospirocyclic ring comprising R$_4$ and R$_5$ and containing one to three heteroatoms within the spirocyclic ring, said heteroatoms being O, S, SO, SO$_2$, or N.

38. A compound according to claim 34, wherein R$_7$ is H, halogen, CN or NO$_2$.

39. A compound according to claim 34, wherein:
R$_1$, R$_2$, and R$_3$ are each H;
R$_4$ is H, C$_{1-6}$ alkyl, CF$_3$, CF$_2$CF$_3$, C$_{2-6}$ alkenyl, C$_{2-6}$ alkynyl, aryl, substituted aryl, heterocycle, or substituted heterocycle;
R$_5$ is aryl, substituted aryl, heterocycle, or substituted heterocycle; or
R$_4$ and R$_5$ are a 3 to 6 membered alkylspirocyclic ring comprising R$_4$ and R$_5$, a 3 to 6 membered heterospirocyclic ring comprising R$_4$ and R$_5$ and containing one to three heteroatoms within the spirocyclic ring, said heteroatoms being O, S, SO, SO$_2$, or N;
R$_8$ is CN, C$_{1-3}$ alkyl, SO$_2$CF$_3$, OR$_{11}$ or NR$_{11}$R$_{12}$;

R$_9$ and R$_{10}$ are each, independently, H, C$_{1-3}$ alkyl, NO$_2$, CN, or CO$_2$R$_{11}$;

or CR$_9$R$_{10}$ is a six membered ring as shown by the structure:

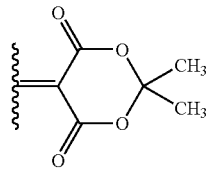

R$_{11}$ and R$_{12}$ are each, independently, H, C$_{1-3}$ alkyl, alkyl carbonyl or sulfonyl; and R$_{13}$ and R$_{14}$ are each, independently, H, C$_{1-3}$ lower alkyl, or C$_{1-3}$ perfluoroalkyl.

40. A compound according to claim 34, wherein:
R$_7$ is H, halogen, CN, or NO$_2$,
R$_8$ is selected from the group of CN, SO$_2$CF$_3$, or OR$_{11}$;
R$_9$ and R$_{10}$ are each, independently, NO$_2$, CN, or CO$_2$R$_{11}$;
R$_{11}$ and R$_{12}$ are each, independently, H or C$_{1-3}$ alkyl; and
R$_{13}$ and R$_{14}$ are each, independently, H, C$_{1-3}$ alkyl, or C$_{1-3}$ perfluoroalkyl.

41. A compound according to claim 34, wherein R$_6$ is a 5 or 6 membered heterocyclic ring containing 2 heteroatoms substituted with 1 to 2 substituents from the group including halogen, CN, NO$_2$, OH, and C$_1$ to C$_3$ alkyl, C═NOH, said heteroatoms being O, S, SO, SO$_2$ or N.

42. A pharmaceutical composition comprising a compound according to claim 34, or a pharmaceutically acceptable salt thereof, and a pharmaceutically acceptable carrier or excipient.

43. A method of inducing contraception comprising administering to a mammal in need thereof a pharmaceutically effective amount of a compound of claim 34.

44. A method of treating or preventing benign or malignant neoplastic disease selected from the group consisting of uterine myometrial fibroids, endometriosis, benign prostatic hypertrophy, carcinomas and adenocarcinomas of the endometrium, ovary, breast, colon, prostate, and pituitary, and meningioma or other hormone-dependent tumors, said method comprising administering to a mammal in need thereof a pharmaceutically effective amount of a compound of claim 34.

45. A method of hormone replacement therapy comprising administering to a mammal in need thereof a pharmaceutically effective amount of a compound of claim 34.

\* \* \* \* \*